US008137911B2

(12) United States Patent
Dahl et al.

(10) Patent No.: US 8,137,911 B2
(45) Date of Patent: Mar. 20, 2012

(54) PREPARATION AND USE OF SINGLE-STRANDED TRANSCRIPTION SUBSTRATES FOR SYNTHESIS OF TRANSCRIPTION PRODUCTS CORRESPONDING TO TARGET SEQUENCES

(75) Inventors: Gary A. Dahl, Madison, WI (US); Jerome J. Jendrisak, Madison, WI (US); Elena K. Davydova, Chicago, IL (US); Lucia B. Rothman-Denes, Chicago, IL (US); Svetalana Y. Gerdes, Madison, WI (US)

(73) Assignee: CellScript, Inc., Madison, WI (US)

( * ) Notice: Subject to any disclaimer, the term of this patent is extended or adjusted under 35 U.S.C. 154(b) by 786 days.

(21) Appl. No.: 10/719,372

(22) Filed: Nov. 21, 2003

(65) Prior Publication Data

US 2004/0171041 A1 Sep. 2, 2004

Related U.S. Application Data

(63) Continuation-in-part of application No. 10/153,219, filed on May 22, 2002.

(60) Provisional application No. 60/428,013, filed on Nov. 21, 2002, provisional application No. 60/292,845, filed on May 22, 2001.

(51) Int. Cl.
*C12Q 1/68* (2006.01)
*C12P 19/34* (2006.01)

(52) U.S. Cl. ........................................ 435/6.1; 435/91.2

(58) Field of Classification Search ................. 435/91.2; 436/6, 91.2
See application file for complete search history.

(56) References Cited

U.S. PATENT DOCUMENTS 5,021,335 A 6/1991 Tecott et al.
5,130,238 A 7/1992 Malek et al.
5,168,038 A 12/1992 Tecott et al.
5,194,370 A 3/1993 Berninger et al.
5,399,491 A 3/1995 Kacian et al.
5,409,818 A 4/1995 Davey et al.
5,437,990 A 8/1995 Burg et al.
5,466,586 A 11/1995 Davey et al.
5,514,545 A 5/1996 Eberwine
5,523,204 A 6/1996 Singer et al.
5,536,649 A 7/1996 Fraiser et al.
5,545,522 A 8/1996 Van Gelder et al.
5,554,517 A 9/1996 Davey et al.
5,591,609 A 1/1997 Auerbach
5,614,389 A 3/1997 Auerbach
5,624,825 A 4/1997 Walker et al.
5,631,147 A 5/1997 Lohman et al.
5,648,211 A 7/1997 Fraiser et al.
5,665,545 A 9/1997 Malek et al.
5,700,667 A 12/1997 Marble et al.
5,716,785 A 2/1998 Van Gelder et al.
5,733,752 A 3/1998 Lohman et al.
5,744,311 A 4/1998 Fraiser et al.
5,756,702 A 5/1998 Lohman et al.
5,773,733 A 6/1998 Tuan
5,786,183 A 7/1998 Ryder et al.
5,830,662 A 11/1998 Soares et al.
5,834,202 A 11/1998 Auerbach
5,849,546 A 12/1998 Sousa et al.
5,849,547 A 12/1998 Cleuziat et al.
5,874,260 A 2/1999 Cleuziat et al.
5,891,636 A 4/1999 Van Gelder et al.
5,916,779 A 6/1999 Pearson et al.
5,958,688 A 9/1999 Eberwine et al.
5,962,272 A 10/1999 Chenchik et al.
5,994,069 A 11/1999 Hall et al.
6,063,603 A 5/2000 Davey et al.
6,063,604 A 5/2000 Wick et al.
6,087,133 A 7/2000 Dattagupta et al.
6,090,591 A 7/2000 Burg et al.
6,124,120 A 9/2000 Lizardi
6,136,535 A 10/2000 Lorincz et al.
6,214,587 B1 4/2001 Dattagupta et al.
6,218,145 B1 4/2001 Bogosian et al.
6,218,151 B1 4/2001 Cleuziat et al.
6,238,868 B1 5/2001 Carrino et al.
6,251,639 B1 6/2001 Kurn
6,280,949 B1 8/2001 Lizardi
6,291,170 B1 9/2001 Van Gelder et al.
6,309,833 B1 10/2001 Edman et al.

(Continued)

FOREIGN PATENT DOCUMENTS

EP 329 822 8/1989

(Continued)

OTHER PUBLICATIONS

Diegelman et al. Nucleic Acids Research, vol. 26, No. 13, pp. 3235-3241, 1998.*
Dai et al. Genes & Development, vol. 12, pp. 2782-2790, Sep. 1998.*
Abravaya et al., J Mol Biol (1990) 211 p. 359-372.
Murakawa et al., DNA 7:287-295, 1988.
Phillips and Eberwine, Methods in Enzymol. Suppl. 10:283-288, 1996.
Ginsberg et al., Ann. Neurol. 45:174-181, 1999.
Ginsberg et al., Ann. Neurol. 48:77-87, 2000.
Van Gelder et al., PNAS 87:1663-1667, 1990.

(Continued)

*Primary Examiner* — Gary Benzion
*Assistant Examiner* — Cynthia Wilder
(74) *Attorney, Agent, or Firm* — Casimir Jones, S.C.

(57) ABSTRACT

The present invention provides methods, compositions and kits for using an RNA polymerase for making transcription products corresponding to a target sequence by obtaining single-stranded DNA transcription substrates that comprise a single-stranded promoter that is operably joined to a single-stranded target sequence. The invention has broad applicability for research, diagnostic and therapeutic applications, such as preparing cDNA corresponding to full-length mRNA, making sense or anti-sense probes, detecting gene- or organism-specific sequences, cloning, cell signaling or making RNA for use in RNAi.

24 Claims, 25 Drawing Sheets

U.S. PATENT DOCUMENTS

| | | | | |
|---|---|---|---|---|
| 6,316,229 | B1 | 11/2001 | Lizardi et al. | |
| 6,326,173 | B1 | 12/2001 | Edman et al. | |
| 6,368,801 | B1 | 4/2002 | Faruqui et al. | |
| 6,410,278 | B1 | 6/2002 | Notomi et al. | |
| 6,448,017 | B1 | 9/2002 | Auerbach | |
| 2002/0058270 | A1 * | 5/2002 | Kurn | 435/6 |

FOREIGN PATENT DOCUMENTS

| | | |
|---|---|---|
| EP | 0427073 | 5/1991 |
| EP | 0427074 | 5/1991 |
| WO | WO 89/06700 | 7/1989 |
| WO | WO 91/18155 | 11/1991 |
| WO | WO 00/11160 | 3/2000 |
| WO | WO 00/28082 | 5/2000 |
| WO | WO 00/56877 | 9/2000 |
| WO | WO 00/75356 | 12/2000 |
| WO | WO 02/14476 | 2/2002 |
| WO | WO 02/16639 | 2/2002 |
| WO | WO 02/065093 | 8/2002 |

OTHER PUBLICATIONS

Eberwine et al., Proc. Natl. Acad. Sci. USA 89:3010-3014, 1992.
Kwoh et al., Proc. Natl. Acad. Sci. USA 86:1173, 1989.
Fahy et al, In: PCR Methods and Applications, pp. 25-33, 1991.
Miller et al., Science (1997) 275 p. 1655-1657.
Makrides, Microbiological Reviews (1996) 60, 512-538.
Ohmichi et al. (Proc. Natl. Acad. Sci. USA 99:54-59, 2002.
Schmidt, W.M. and Mueller, M.W., Nucleic Acids Res. 24:1789-91, 1996.
Schmidt et al., Nucleic Acids Res. 27:e31 (i-iv), 1999.
Zhang et al. (Proc. Natl. Acad. Sci. USA 98:5497-5502, 2001.
Kazmierczak, K.M., et al., EMBO J., 21:5815-5823, 2002.
Butler and Chamberlin, J. Biol. Chem. 257:5772-5778, 1982.
Cermakian, et al., Nuc. Acids Res. 24:648-654, 1996.
Dai et al., Genes Devepmnt. 12:2782-2790, 1998.
Falco, et al., Proc. Natl. Acad. Sci. (USA) 74:520-523, 1977.
Falco, et al., Biol. Chem. 255:4339-4347, 1980.
Falco, et al., Proc. Natl. Acad. Sci. (USA) 75:3220-3224, 1978.
Glucksmann-Kuis, et al., Cell, 70, 491-500, 1992.
Malone, et al., Virology 162:328-336, 1988.
Paule, et al., Nuc. Acids Res. 28:1283-1298, 2000.
Rong, et al., Proc. Natl. Acad. Sci. USA 95:515-519, 1998.
Shadel, et al., J. Biol. Chem. 268:16083-16086, 1993.
Sanders, et al., EMBO Journal 16:3124-3132, 1997.
Dai et al., PNAS USA 94:2174-2179, 1997.
Glucksmann-Kuis, et al., Cell 84:147-154, 1996.
Hedtke, et al., Science 277:809-811, 1997.
Delarue, et al., Protein Engineering 3:461-467, 1990.
Cheetham, et al., Curr. Op. In Struc. Biol. 10:117-123, 2000.
Zhang, et al., Cell 98:811-824, 1999.
Sousa, Trends in Biochem. Sci. 21:186-190, 1996.
Markiewicz, et al., Genes and Dev. 6:2010-2019, 1992.
Gross, et al., Cold Spring Harbor Symp. Quant. Biol. 63:141-156, 1998.
Hochschild, et al., Cell 92:597-600, 1998.
Falco, et al., Virology 95:454-465, 1979.
Roeder, Trends Biochem. Sci. 21:327-335, 1996.
Sousa, et al., Nature 364:593-599, 1993.
Ngo et al., Computational Complexity, Protein Structure Prediction, and the Levinthal Paradox, in the Protein Folding Problem and Tertiary Structure Prediction, 1994, Merz et.
Cramer et al., Science, 292(5523):1863-1876 (2001).
Zivin, et al., J. Mol. Biol. 152:335-356, 1981.
Haynes, et al., Cell 41:597-605, 1985.
Campbell, M. A. cDNA Production. Copyright 2002 Department of Biology, Davidson College, Davidson, NC 28036, retrieved Jan. 17, 2007. <http://bio.davidson.edu/COURSES/genomics/method/cDNAproduction.html>.
Christian et al., Detection of DNA point mutations and mRNA expression levels by rolling circle amplification in individual cells PNAS, Dec. 4, 2001, published on line Nov. 27, 2001, vol. 98, No. 25, pp. 14238-14243.

* cited by examiner

FIG. 1

Bacteriophage N4 vRNAP promoters

```
       -11
       A/G
     A     G
       G:C
       C:G
       X:X'
       X:X'                +1
   3'  C:G A A A/T A C C  5'
      -17
```

Identification of the minimal active domain of N4 vRNAP by proteolytic cleavage.

Purification of cloned vRNAP and mini-vRNAP

Activation of N4 vRNAP transcription by *Eco* SSB at different ssDNA concentrations

| ssDNA, nM | 0.8 | | 4 | | 20 | |
|---|---|---|---|---|---|---|
| *Eco*SSB | + | - | + | - | + | - |

Effect of *Eco* SSB on the state of template DNA and product RNA in vRNAP transcription Effect of *Eco* SSB on transcription of vRNAP and mini-RNAP Determination of mini-vRNAP promoter contacts

A

B

Identification of the transcription start site by catalytic autolabeling

UV crosslinking of mutant mini-vRNAPases to promoter oligonucleotides

Detection of *in vivo* activities of N4 vRNAP and mini-vRNAP

SEQUENCE LISTING

<160> NUMBER OF SEQ ID NOS: 41

<210> SEQ ID NO 1
<211> LENGTH: 10506
<212> TYPE: DNA
<213> ORGANISM: Artificial Sequence
<220> FEATURE:
<223> OTHER INFORMATION: Synthetic

<400> SEQUENCE: 1

```
atgtcagtat ttgatagact ggctgggttc gcagacagcg taaccaatgc aaagcaagtt      60
gacgtctcta ctgcaaccgc ccagaagaaa gctgaacaag gtgtcactac tcctcttgtt     120
tctcctgatg ctgcttatca aatgcaagct gcccgtactg gtaatgttgg ggctaatgca     180
tttgaaccag ggacagtgca atcagatttc atgaatctga ccccaatgca aatcatgaat     240
aagtatgggg ttgagcaagg cttacaactt atcaatgctc gtgctgatgc agggaaccag     300
gtattcaatg attcagttac tacaagaact cctggggaag aactggggga tattgctact     360
ggtgttggcc ttggttttgt taataccctt gggggcattg gtgctcttgg ggcaggctta     420
ctcaacgatg atgcaggtgc tgttgttgct caacaattga gtaagtttaa tgatgctgtt     480
catgctaccc aaagccaggc attacaagat aaacgtaagc tctttgctgc tcgtaactta     540
atgaatgaag tagagagtga acgtcagtat caaacagata agaaagaagg cactaatgac     600
atagtagctt ccttatctaa atttggacgt gattttgtag gttcaattga gaatgctgct     660
caaactgact ctattatttc tgatgggtta gcagaagggg taggttctct attaggtgct     720
ggtcctgtat taaggggtgc atctttactg ggtaaagcag ttgttccagc aaatactctt     780
cgtagtgctg cattggctgg tgctattgat gcaggtactg gtactcagtc actggctcgt     840
attgcctcta ctgtaggtag agctgcaccg ggtatggttg gtgttggtgc aatggaagct     900
ggtggtgcat accaacaaac tgctgatgaa attatgaaga tgagtcttaa agacttagag     960
aagtctcctg tttatcagca acatattaaa gatggtatgt cccctgaaca ggctcgtcgt    1020
cagactgcat ctgaaactgg tcttactgct gctgctattc aattacctat tgctgctgca    1080
accggtcctc tggtatcccg ttttgagatg gctcctttcc gtgctggctc tttaggtgct    1140
gtaggtatga accttgcccg tgaaacagtg gaagaaggtg ttcagggtgc tacaggccaa    1200
ctggctcaga atattgcaca gcaacaaaac attgataaga accaagacct gcttaaaggt    1260
gtcggtacac aggctggttt aggtgctctt tatggctttg gttctgctgg tgttgtacag    1320
gctccggctg gtgctgctcg tttagcaggt gctgcaactg ctcctgtatt gcgtaccaca    1380
atggctggtg ttaaagctgc tggtagtgta gcaggtaagg ttgtttctcc tattaagaat    1440
actttagtag ctcgtggtga acgggttatg aagcagaatg aagaagcatc tcctgttgct    1500
gatgactatg ttgcacaggc agcacaagaa gctatggctc aagcaccaga agcagaagtt    1560
actattcgtg atgctgttga agcaactgat gctactccag aacagaaagt tgcagcacac    1620
cagtatgttt ctgacttaat gaatgctact cgttttaatc ctgaaaatta tcaggaagca    1680
ccagagcata ttcgtaatgc tgtagctggt tctactgacc aagtacaggt tattcagaag    1740
ttagcagact tagttaacac attagatgaa tctaatcctc aagcactgat ggaagctgca    1800
tcttatatgt atgatgctgt ttcagagttt gagcagttca ttaaccgtga ccctgctgca    1860
ctggatagca ttcctaaaga ttctccggct attgagttac tcaaccgtta tacgaatctg    1920
acagctaata ttcagaacac accaaaagta attggtgcac tgaatgttat taatcgaatg    1980
```

```
attaatgaat ctgctcagaa tggttctttg aatgtgactg aagaatccag tccacaggaa   2040

atgcagaacg tagcattagc tgctgaagta gcccctgaaa agctcaatcc agagtctgta   2100

aatgttgttc ttaaacatgc tgctgatggt cgtattaaac tgaataatcg ccagattgct   2160

gccctccaga atgctgctgc aatcctgaag gggcacgggg aatatgatgc agaagctgcc   2220

cgtcttggat tacgtcctca agacattgtg agtaaacaga ttaaaacgga tgagagcaga   2280

actcaggaag gacaatactc tgcgttgcaa catgcgaata ggattcggtc tgcgtataac   2340

tctggtaatt tcgagttggc ctccgcttac ctgaacgact ttatgcagtt cgcccagcac   2400

atgcagaata aggttggagc gttgaatgag catcttgtta cggggaatgc ggataagaat   2460

aagtctgtcc actaccaagc tcttactgct gacagagaat gggttcgtag ccgtaccgga   2520

ttgggggtca atccctatga cactaagtcg gttaaatttg cccagcaagt tgctcttgaa   2580

gcgaaaacgg tagcggatat tgctaatgcc ctcgcttcgg cttacccgga actgaaggtc   2640

agtcatataa aagttactcc attggattca cgtcttaacg ctcctgctgc tgaggtggtc   2700

aaggcattcc gtcaaggcaa tcgagacgtt gcttcttctc aaccgaaagc tgactccgtg   2760

aatcaggtta aagaaactcc tgttacaaaa caggaaccag ttacatctac tgtacagact   2820

aagactcctg ttagtgaatc tgttaaaaca gaacctacta ctaaagagtc tagcccacag   2880

gctataaaag aacctgtgaa ccagtctgaa aaacaggatg ttaaccttac taatgaggac   2940

aacatcaagc aacctactga atctgttaaa gaaactgaaa cttctacaaa agaaagtaca   3000

gttacagaag aattaaaaga aggtattgat gctgtttacc cttcattggt aggtactgct   3060

gattctaaag cagagggtat taagaactat ttcaaattgt cctttacctt accagaagaa   3120

cagaaatccc gtactgttgg ttcagaagca cctctaaaag atgtagccca agctctgtct   3180

tctcgtgctc gttatgaact ctttactgag aaagaaactg ctaaccctgc ttttaatggg   3240

gaagttatta agcgatacaa agaactcatg gaacatgggg aaggtattgc tgatattctt   3300

cgctcccgtc tggctaagtt ccttaacact aaggatgttg gtaaacgttt tgctcaaggt   3360

acagaagcca accgttgggt aggtggtaag ttacttaaca ttgttgagca ggatggggat   3420

acctttaagt acaacgaaca attgctacag actgctgtat tagcaggtct tcaatggaga   3480

cttactgcta ccagcaatac tgctatcaaa gatgcaaaag atgttgctgc tattactggt   3540

attgaccaag ctctgctgcc agaaggttta gtagagcaat ttgatactgg tatgacactc   3600

actgaagcag ttagttccct ggctcagaaa attgagtctt actggggatt atctcgtaat   3660

ccaaatgctc cattgggcta taccaaaggc atccctacag caatggctgc tgaaattctg   3720

gctgcatttg tagagtctac tgatgttgta gagaacatcg tggatatgtc agaaattgac   3780

ccagataaca agaagactat tggtctgtac accattactg aactggattc cttcgaccca   3840

attaatagct tccctactgc tattgaagaa gctgttttag tgaatcctac agagaagatg   3900

ttctttggtg atgacattcc tcctgtagct aatactcagc ttcgtaaccc tgctgttcgt   3960

aatactccag aacagaaggc tgcattgaaa gcagagcagg ctacagagtt ctatgtacac   4020

accccaatgg ttcaattcta tgagacgtta ggtaaagacc gtattctcga actgatgggt   4080

gctggtactc tgaataaaga gttacttaat gataaccatg ctaaatctct ggaaggtaag   4140

aaccgttcag tagaggactc ttacaaccaa ctgttctccg tcattgagca ggtaagagca   4200

cagagcgaag acatctctac tgtacctatt cactatgcat acaatatgac ccgtgttggt   4260

cgtatgcaga tgttaggtaa atacaatcct caatcagcca aactggttcg tgaggccatc   4320

ttacctacta aagctacttt ggatttatcg aaccagaaca atgaagactt ctctgcattc   4380
```

-continued

```
cagttaggtc tggctcaggc attggacatt aaagtccata ctatgactcg tgaggttatg   4440
tctgacgagt tgactaaatt actggaaggt aatctgaaac cagccattga tatgatggtt   4500
gagtttaata ccactggttc cttaccagaa aacgcagttg atgttctgaa tacagcatta   4560
ggagatagga agtcattcgt agcattgatg gctcttatgg agtattcccg ttacttagta   4620
gcagaggata aatctgcatt tgtaactcca ctgtatgtag aagcagatgg tgttactaat   4680
ggtccaatca atgccatgat gctaatgaca ggcggtctgt ttactcctga ctggattcgt   4740
aatattgcca aagggggctt gttcattggt tctccaaata agaccatgaa tgagcatcgc   4800
tctactgctg acaataatga tttatatcaa gcatccacta atgctttgat ggaatcgttg   4860
ggtaagttac gtagtaacta tgcctctaat atgcctattc agtctcagat agacagtctt   4920
ctttctctga tggatttgtt tttaccggat attaatcttg gtgagaatgg tgctttagaa   4980
cttaaacgtg gtattgctaa gaacccactg actattacca tctatggttc tggtgctcgt   5040
ggtattgcag gtaagctggt tagttctgtt actgatgcca tctatgagcg tatgtctgat   5100
gtactgaaag ctcgtgctaa agacccaaat atctctgctg ctatggcaat gtttggtaag   5160
caagctgctt cagaagcaca tgctgaagaa cttcttgccc gtttcctgaa agatatggaa   5220
acactgactt ctactgttcc tgttaaacgt aaaggtgtac tggaactaca atccacaggt   5280
acaggagcca aaggaaaaat caatcctaag acctatacca ttaagggcga gcaactgaag   5340
gcacttcagg aaaatatgct gcacttcttt gtagaaccac tacgtaatgg tattactcag   5400
actgtaggtg aaagtctggt gtactctact gaacaattac agaaagctac tcagattcaa   5460
tctgtagtgc tggaagatat gttcaaacag cgagtacaag agaagctggc agagaaggct   5520
aaagacccaa catggaagaa aggtgatttc cttactcaga aagaactgaa tgatattcag   5580
gcttctctga ataacttagc ccctatgatt gagactggtt ctcagacttt ctacattgct   5640
ggttcagaaa atgcagaagt agcaaatcag gtattagcta ctaaccttga tgaccgtatg   5700
cgtgtaccaa tgagtatcta tgctccagca caggccggtg tagcaggtat tccatttatg   5760
actattggta ctggtgatgg catgatgatg caaactcttt ccactatgaa aggtgcacca   5820
aagaataccc tcaaaatctt tgatggtatg aacattggtt tgaatgacat cactgatgcc   5880
agtcgtaaag ctaatgaagc tgtttacact tcttggcagg gtaaccctat taagaatgtt   5940
tatgaatcat atgctaagtt catgaagaat gtagatttca gcaagctgtc ccctgaagca   6000
ttggaagcaa ttggtaaatc tgctctggaa tatgaccaac gtgagaatgc tactgtagat   6060
gatattgcta acgctgcatc tctgattgaa cgtaacttac gtaatattgc actgggtgta   6120
gatattcgtc ataaggtgct ggataaggta aatctgtcca ttgaccagat ggctgctgta   6180
ggtgctcctt atcagaacaa cggtaagatt gacctcagca atatgacccc tgaacaacag   6240
gctgatgaac tgaataaact ttccgtgaa gagttagaag cccgtaaaca aaaagtcgct   6300
aaggctaggg ctgaagtcaa agaagaaact gtttctgaaa aagaaccagt gaatccagac   6360
tttggtatgg taggccgtga gcataaggca tctggtgttc gtatcctgtc tgctactgct   6420
attcgtaatc tggctaagat tagtaatctg ccatctactc aggcagctac tcttgcggag   6480
attcagaaat cactggcagc taaagactat aagattatct acggtacacc tactcaggtt   6540
gcagagtatg ctcgtcagaa gaatgttact gaattgactt ctcaggaaat ggaagaagct   6600
caggcaggta atatttatgg ctggactaac ttcgatgata agaccattta tctggttagc   6660
ccatctatgg aaaccctcat tcatgaactg gttcatgcct ctaccttcga ggaagtttat   6720
tccttctatc agggtaatga agtaagccct acttctaagc aggctattga gaaccttgaa   6780
```

```
ggtctgatgg aacagttccg ttctctggat atttccaaag attctccaga aatgagagaa   6840
gcatatgctg atgctattgc aactatcgaa ggtcatttga gtaatggatt tgttgaccca   6900
gctatctcta aagctgctgc tcttaatgag tttatggctt gggggttagc taaccgtgct   6960
cttgctgcta aacagaagag aacatcttca ctggttcaaa tggtgaaaga tgtttatcag   7020
gctattaaga aattgatttg ggacgtaaa caagctcctg cattgggaga agatatgttc   7080
tccaatctgc tgtttaactc tgcaattctg atgcgtagcc aacctacaac tcaggcagta   7140
gctaaagatg gcacactgtt ccatagcaaa gcatatggta ataatgaacg tctgtctcag   7200
ttgaaccaga ctttcgataa actggtaact gattaccttc gtactgaccc agttacagaa   7260
gtagaacgtc gtggcaatgt ggctaatgca ttaatgagtg ctactcgact ggttcgtgat   7320
gttcagtctc atggcttcaa tatgactgct caggaacagt ctgtattcca gatggttact   7380
gctgcattag caactgaagc tgcgattgac ccacatgcta tggctcgtgc tcaggaactt   7440
tatacccatg taatgaaaca ccttacggta gagcatttca tggctgaccc tgatagtact   7500
aaccctgctg accgttacta tgctcaacag aaatatgaca ccatctctgg tgctaatctg   7560
gttgaagtag atgccaaagg tagaaccagt ctgttaccta cattcctggg tctggctatg   7620
gttaatgaag aactacgttc aatcattaaa gaaatgcctg tacctaaagc agataagaaa   7680
ttagggaatg atatagatac tctgcttacc aatgcaggta ctcaggtaat ggaatctctg   7740
aaccgtcgta tggctggtga ccagaaagct actaatgttc aggacagtat tgatgctttg   7800
tcagaaacaa tcatggctgc tgctttgaaa cgagagtcct tctatgatgc tgtagcaacc   7860
cctaccggta acttcattga ccgtgctaat cagtacgtaa cggatagcat tgaacggtta   7920
tctgaaactg ttattgagaa ggcagataag gtaattgcta acccttctaa tatagctgct   7980
aaaggtgttg ctcatctggc taaactgact gctgctattg catctgaaaa acagggtgaa   8040
atagtggctc agggtgttat gactgctatg aaccagggta aagtatggca acctttccat   8100
gacttagtta atgacattgt tggccgtact aagactaatg ccaatgtcta tgacttaatc   8160
aaattggtta agagccagat ttctcaagac cgtcagcaat tccgtgagca tttacctaca   8220
gtcattgctg gtaagttctc tcgtaaattg actgataccg aatggtctgc aatgcatact   8280
ggtttaggta aaacagattt agctgttcta cgtgaaacta tgagcatggc tgaaattaga   8340
gatttactct cttcatccaa gaaagtgaaa gatgaaatct ctactctgga aaaagagatt   8400
cagaaccaag caggtagaaa ctggaatctg gttcagaaga aatctaagca actggctcaa   8460
tacatgatta tgggggaagt aggtaataac ctccttcgta atgcccatgc tattagtcgt   8520
ttgttaggtg aacgtattac taatggtcct gtggcagatg tagctgctat tgataagctc   8580
attactttgt actctctgga attgatgaat aagtctgacc gtgacctttt gtcagaattg   8640
gctcaatcag aagtggaagg tatggagttc tccattgctt atatggttgg tcaacgtact   8700
gaagagatgc gtaaagctaa aggtgataac cgtactctgc tgaatcactt taaaggctat   8760
atccctgtag agaaccagca aggtgtgaat ttgattattg ctgacgataa agagtttgct   8820
aagttaaata gccaatcctt tactcgtatt ggtacttatc aggggagcac tggtttccgt   8880
actggttcta aaggttatta cttcagccca gtagctgccc gtgcccctta ctctcagggt   8940
attcttcaga acgttcgtaa tactgctggt ggtgtggata ttggtactgg ctttacgtta   9000
ggcactatgg ttgctgggcg tattactgac aaaccaaccg tagagcgtat taccaaagct   9060
ctggctaaag gtgagcgtgg gcgtgaacca ctgatgccaa tttataacag caaaggtcag   9120
gtagttgctt atgaacaatc cgttgaccct aatatgttga agcacctaaa ccaagacaat   9180
```

```
cactttgcta agatggttgg tgtatggcgt ggtcgtcagg tggaagaggc taaagcacaa   9240

cgttttaatg acattctcat tgagcaatta catgctatgt atgagaaaga cattaaagac   9300

tccagtgcta ataaatctca atatgtaaac ctgttaggta aaattgatga cccagtactg   9360

gctgatgcga ttaacctgat gaacattgag actcgtcata aggccgaaga actcttcggt   9420

aaagatgagt tatgggttcg tagggatatg ctgaatgatg cacttggcta tcgtgctgca   9480

tctattggtg atgtgtggac cggtaactct cgttggtcac ctagcaccct tgatactgtt   9540

aagaagatgt tcctcggtgc attcggtaat aaggcatatc atgtagtaat gaatgctgaa   9600

aataccattc agaacttagt gaaggacgct aagacagtaa ttgttgttaa atctgttgta   9660

gtaccggcag ttaacttcct tgctaacatc taccagatga ttggacgtgg tgttcctgtt   9720

aaagatattg ctgtgaacat tcctcgtaag acgtcagaga ttaatcagta tattaaatct   9780

cgtttacgtc agattgatgc ggaagcagag ctacgtgctg ctgaaggtaa ccctaatctg   9840

gttcgtaaac ttaaaactga gattcaatct attactgata gtcatcgtcg tatgagtatc   9900

tggcctttga ttgaagcagg tgagttctct tctattgctg atgctggtat tagtcgtgat   9960

gacctgttag tagctgaagg taagattcat gagtacatgg aaaaacttgc taataaactt  10020

ccagaaaaag tacgtaatgc tggccgttac gctcttattg ctaaggacac tgctctgttc  10080

cagggtatcc agaaaacagt agagtattca gactttattg ctaaagccat catctatgat  10140

gatttagtga aacgtaagaa aaaatcttct tctgaagcat taggtcaggt aactgaagag  10200

tttattaact atgacagatt gcctggtcgt ttccgtggct atatggaaag tatgggtctg  10260

atgtggttct acaactttaa aattcgttcc attaaagttg ctatgagcat gattagaaac  10320

aacccagtac attctctgat tgctacagta gtacctgctc ctaccatgtt tggtaacgta  10380

ggtctaccaa ttcaggacaa catgctaacc atgctggctg aaggaagact ggattactca  10440

ttaggcttcg gacaaggatt aagagcacct accctcaatc cttggttcaa ccttactcac  10500

taataa                                                             10506
```

<210> SEQ ID NO 2
<211> LENGTH: 3500
<212> TYPE: PRT
<213> ORGANISM: Artificial Sequence
<220> FEATURE:
<223> OTHER INFORMATION: Synthetic

<400> SEQUENCE: 2

```
Met Ser Val Phe Asp Arg Leu Ala Gly Phe Ala Asp Ser Val Thr Asn
1               5                   10                  15

Ala Lys Gln Val Asp Val Ser Thr Ala Thr Ala Gln Lys Lys Ala Glu
            20                  25                  30

Gln Gly Val Thr Thr Pro Leu Val Ser Pro Asp Ala Ala Tyr Gln Met
        35                  40                  45

Gln Ala Ala Arg Thr Gly Asn Val Gly Ala Asn Ala Phe Glu Pro Gly
    50                  55                  60

Thr Val Gln Ser Asp Phe Met Asn Leu Thr Pro Met Gln Ile Met Asn
65                  70                  75                  80

Lys Tyr Gly Val Glu Gln Gly Leu Gln Leu Ile Asn Ala Arg Ala Asp
                85                  90                  95

Ala Gly Asn Gln Val Phe Asn Asp Ser Val Thr Thr Arg Thr Pro Gly
            100                 105                 110

Glu Glu Leu Gly Asp Ile Ala Thr Gly Val Gly Leu Gly Phe Val Asn
        115                 120                 125
```

```
Thr Leu Gly Gly Ile Gly Ala Leu Gly Ala Gly Leu Leu Asn Asp Asp
    130                 135                 140

Ala Gly Ala Val Val Ala Gln Gln Leu Ser Lys Phe Asn Asp Ala Val
145                 150                 155                 160

His Ala Thr Gln Ser Gln Ala Leu Gln Asp Lys Arg Lys Leu Phe Ala
                165                 170                 175

Ala Arg Asn Leu Met Asn Glu Val Glu Ser Glu Arg Gln Tyr Gln Thr
            180                 185                 190

Asp Lys Lys Glu Gly Thr Asn Asp Ile Val Ala Ser Leu Ser Lys Phe
        195                 200                 205

Gly Arg Asp Phe Val Gly Ser Ile Glu Asn Ala Ala Gln Thr Asp Ser
    210                 215                 220

Ile Ile Ser Asp Gly Leu Ala Glu Gly Val Gly Ser Leu Leu Gly Ala
225                 230                 235                 240

Gly Pro Val Leu Arg Gly Ala Ser Leu Leu Gly Lys Ala Val Val Pro
                245                 250                 255

Ala Asn Thr Leu Arg Ser Ala Ala Leu Ala Gly Ala Ile Asp Ala Gly
            260                 265                 270

Thr Gly Thr Gln Ser Leu Ala Arg Ile Ala Ser Thr Val Gly Arg Ala
        275                 280                 285

Ala Pro Gly Met Val Gly Val Gly Ala Met Glu Ala Gly Gly Ala Tyr
    290                 295                 300

Gln Gln Thr Ala Asp Glu Ile Met Lys Met Ser Leu Lys Asp Leu Glu
305                 310                 315                 320

Lys Ser Pro Val Tyr Gln Gln His Ile Lys Asp Gly Met Ser Pro Glu
                325                 330                 335

Gln Ala Arg Arg Gln Thr Ala Ser Glu Thr Gly Leu Thr Ala Ala Ala
            340                 345                 350

Ile Gln Leu Pro Ile Ala Ala Ala Thr Gly Pro Leu Val Ser Arg Phe
        355                 360                 365

Glu Met Ala Pro Phe Arg Ala Gly Ser Leu Gly Ala Val Gly Met Asn
    370                 375                 380

Leu Ala Arg Glu Thr Val Glu Glu Gly Val Gln Gly Ala Thr Gly Gln
385                 390                 395                 400

Leu Ala Gln Asn Ile Ala Gln Gln Gln Asn Ile Asp Lys Asn Gln Asp
                405                 410                 415

Leu Leu Lys Gly Val Gly Thr Gln Ala Gly Leu Gly Ala Leu Tyr Gly
            420                 425                 430

Phe Gly Ser Ala Gly Val Val Gln Ala Pro Ala Gly Ala Ala Arg Leu
        435                 440                 445

Ala Gly Ala Ala Thr Ala Pro Val Leu Arg Thr Thr Met Ala Gly Val
    450                 455                 460

Lys Ala Ala Gly Ser Val Ala Gly Lys Val Val Ser Pro Ile Lys Asn
465                 470                 475                 480

Thr Leu Val Ala Arg Gly Glu Arg Val Met Lys Gln Asn Glu Glu Ala
                485                 490                 495

Ser Pro Val Ala Asp Asp Tyr Val Ala Gln Ala Ala Gln Glu Ala Met
            500                 505                 510

Ala Gln Ala Pro Glu Ala Glu Val Thr Ile Arg Asp Ala Val Glu Ala
        515                 520                 525

Thr Asp Ala Thr Pro Glu Gln Lys Val Ala Ala His Gln Tyr Val Ser
    530                 535                 540

Asp Leu Met Asn Ala Thr Arg Phe Asn Pro Glu Asn Tyr Gln Glu Ala
545                 550                 555                 560
```

```
Pro Glu His Ile Arg Asn Ala Val Ala Gly Ser Thr Asp Gln Val Gln
                565                 570                 575

Val Ile Gln Lys Leu Ala Asp Leu Val Asn Thr Leu Asp Glu Ser Asn
            580                 585                 590

Pro Gln Ala Leu Met Glu Ala Ala Ser Tyr Met Tyr Asp Ala Val Ser
        595                 600                 605

Glu Phe Glu Gln Phe Ile Asn Arg Asp Pro Ala Ala Leu Asp Ser Ile
    610                 615                 620

Pro Lys Asp Ser Pro Ala Ile Glu Leu Leu Asn Arg Tyr Thr Asn Leu
625                 630                 635                 640

Thr Ala Asn Ile Gln Asn Thr Pro Lys Val Ile Gly Ala Leu Asn Val
                645                 650                 655

Ile Asn Arg Met Ile Asn Glu Ser Ala Gln Asn Gly Ser Leu Asn Val
            660                 665                 670

Thr Glu Glu Ser Ser Pro Gln Glu Met Gln Asn Val Ala Leu Ala Ala
        675                 680                 685

Glu Val Ala Pro Glu Lys Leu Asn Pro Glu Ser Val Asn Val Val Leu
    690                 695                 700

Lys His Ala Ala Asp Gly Arg Ile Lys Leu Asn Asn Arg Gln Ile Ala
705                 710                 715                 720

Ala Leu Gln Asn Ala Ala Ala Ile Leu Lys Gly Ala Arg Glu Tyr Asp
                725                 730                 735

Ala Glu Ala Ala Arg Leu Gly Leu Arg Pro Gln Asp Ile Val Ser Lys
            740                 745                 750

Gln Ile Lys Thr Asp Glu Ser Arg Thr Gln Glu Gly Gln Tyr Ser Ala
        755                 760                 765

Leu Gln His Ala Asn Arg Ile Arg Ser Ala Tyr Asn Ser Gly Asn Phe
    770                 775                 780

Glu Leu Ala Ser Ala Tyr Leu Asn Asp Phe Met Gln Phe Ala Gln His
785                 790                 795                 800

Met Gln Asn Lys Val Gly Ala Leu Asn Glu His Leu Val Thr Gly Asn
                805                 810                 815

Ala Asp Lys Asn Lys Ser Val His Tyr Gln Ala Leu Thr Ala Asp Arg
            820                 825                 830

Glu Trp Val Arg Ser Arg Thr Gly Leu Gly Val Asn Pro Tyr Asp Thr
        835                 840                 845

Lys Ser Val Lys Phe Ala Gln Gln Val Ala Leu Glu Ala Lys Thr Val
    850                 855                 860

Ala Asp Ile Ala Asn Ala Leu Ala Ser Ala Tyr Pro Glu Leu Lys Val
865                 870                 875                 880

Ser His Ile Lys Val Thr Pro Leu Asp Ser Arg Leu Asn Ala Pro Ala
                885                 890                 895

Ala Glu Val Val Lys Ala Phe Arg Gln Gly Asn Arg Asp Val Ala Ser
            900                 905                 910

Ser Gln Pro Lys Ala Asp Ser Val Asn Gln Val Lys Glu Thr Pro Val
        915                 920                 925

Thr Lys Gln Glu Pro Val Thr Ser Thr Val Gln Thr Lys Thr Pro Val
    930                 935                 940

Ser Glu Ser Val Lys Thr Glu Pro Thr Thr Lys Glu Ser Ser Pro Gln
945                 950                 955                 960

Ala Ile Lys Glu Pro Val Asn Gln Ser Glu Lys Gln Asp Val Asn Leu
                965                 970                 975

Thr Asn Glu Asp Asn Ile Lys Gln Pro Thr Glu Ser Val Lys Glu Thr
```

```
            980                 985                 990

Glu Thr Ser Thr Lys Glu Ser Thr  Val Thr Glu Glu Leu  Lys Glu Gly
        995                 1000                1005

Ile Asp  Ala Val Tyr Pro Ser  Leu Val Gly Thr Ala  Asp Ser Lys
    1010                 1015                 1020

Ala Glu  Gly Ile Lys Asn Tyr  Phe Lys Leu Ser Phe  Thr Leu Pro
    1025                 1030                 1035

Glu Glu  Gln Lys Ser Arg Thr  Val Gly Ser Glu Ala  Pro Leu Lys
    1040                 1045                 1050

Asp Val  Ala Gln Ala Leu Ser  Ser Arg Ala Arg Tyr  Glu Leu Phe
    1055                 1060                 1065

Thr Glu  Lys Glu Thr Ala Asn  Pro Ala Phe Asn Gly  Glu Val Ile
    1070                 1075                 1080

Lys Arg  Tyr Lys Glu Leu Met  Glu His Gly Glu Gly  Ile Ala Asp
    1085                 1090                 1095

Ile Leu  Arg Ser Arg Leu Ala  Lys Phe Leu Asn Thr  Lys Asp Val
    1100                 1105                 1110

Gly Lys  Arg Phe Ala Gln Gly  Thr Glu Ala Asn Arg  Trp Val Gly
    1115                 1120                 1125

Gly Lys  Leu Leu Asn Ile Val  Glu Gln Asp Gly Asp  Thr Phe Lys
    1130                 1135                 1140

Tyr Asn  Glu Gln Leu Leu Gln  Thr Ala Val Leu Ala  Gly Leu Gln
    1145                 1150                 1155

Trp Arg  Leu Thr Ala Thr Ser  Asn Thr Ala Ile Lys  Asp Ala Lys
    1160                 1165                 1170

Asp Val  Ala Ala Ile Thr Gly  Ile Asp Gln Ala Leu  Leu Pro Glu
    1175                 1180                 1185

Gly Leu  Val Glu Gln Phe Asp  Thr Gly Met Thr Leu  Thr Glu Ala
    1190                 1195                 1200

Val Ser  Ser Leu Ala Gln Lys  Ile Glu Ser Tyr Trp  Gly Leu Ser
    1205                 1210                 1215

Arg Asn  Pro Asn Ala Pro Leu  Gly Tyr Thr Lys Gly  Ile Pro Thr
    1220                 1225                 1230

Ala Met  Ala Ala Glu Ile Leu  Ala Ala Phe Val Glu  Ser Thr Asp
    1235                 1240                 1245

Val Val  Glu Asn Ile Val Asp  Met Ser Glu Ile Asp  Pro Asp Asn
    1250                 1255                 1260

Lys Lys  Thr Ile Gly Leu Tyr  Thr Ile Thr Glu Leu  Asp Ser Phe
    1265                 1270                 1275

Asp Pro  Ile Asn Ser Phe Pro  Thr Ala Ile Glu Glu  Ala Val Leu
    1280                 1285                 1290

Val Asn  Pro Thr Glu Lys Met  Phe Phe Gly Asp Asp  Ile Pro Pro
    1295                 1300                 1305

Val Ala  Asn Thr Gln Leu Arg  Asn Pro Ala Val Arg  Asn Thr Pro
    1310                 1315                 1320

Glu Gln  Lys Ala Ala Leu Lys  Ala Glu Gln Ala Thr  Glu Phe Tyr
    1325                 1330                 1335

Val His  Thr Pro Met Val Gln  Phe Tyr Glu Thr Leu  Gly Lys Asp
    1340                 1345                 1350

Arg Ile  Leu Glu Leu Met Gly  Ala Gly Thr Leu Asn  Lys Glu Leu
    1355                 1360                 1365

Leu Asn  Asp Asn His Ala Lys  Ser Leu Glu Gly Lys  Asn Arg Ser
    1370                 1375                 1380
```

```
Val Glu  Asp Ser Tyr Asn Gln  Leu Phe Ser Val Ile  Glu Gln Val
    1385                 1390                 1395

Arg Ala  Gln Ser Glu Asp Ile  Ser Thr Val Pro Ile  His Tyr Ala
    1400                 1405                 1410

Tyr Asn  Met Thr Arg Val Gly  Arg Met Gln Met Leu  Gly Lys Tyr
    1415                 1420                 1425

Asn Pro  Gln Ser Ala Lys Leu  Val Arg Glu Ala Ile  Leu Pro Thr
    1430                 1435                 1440

Lys Ala  Thr Leu Asp Leu Ser  Asn Gln Asn Asn Glu  Asp Phe Ser
    1445                 1450                 1455

Ala Phe  Gln Leu Gly Leu Ala  Gln Ala Leu Asp Ile  Lys Val His
    1460                 1465                 1470

Thr Met  Thr Arg Glu Val Met  Ser Asp Glu Leu Thr  Lys Leu Leu
    1475                 1480                 1485

Glu Gly  Asn Leu Lys Pro Ala  Ile Asp Met Met Val  Glu Phe Asn
    1490                 1495                 1500

Thr Thr  Gly Ser Leu Pro Glu  Asn Ala Val Asp Val  Leu Asn Thr
    1505                 1510                 1515

Ala Leu  Gly Asp Arg Lys Ser  Phe Val Ala Leu Met  Ala Leu Met
    1520                 1525                 1530

Glu Tyr  Ser Arg Tyr Leu Val  Ala Glu Asp Lys Ser  Ala Phe Val
    1535                 1540                 1545

Thr Pro  Leu Tyr Val Glu Ala  Asp Gly Val Thr Asn  Gly Pro Ile
    1550                 1555                 1560

Asn Ala  Met Met Leu Met Thr  Gly Gly Leu Phe Thr  Pro Asp Trp
    1565                 1570                 1575

Ile Arg  Asn Ile Ala Lys Gly  Gly Leu Phe Ile Gly  Ser Pro Asn
    1580                 1585                 1590

Lys Thr  Met Asn Glu His Arg  Ser Thr Ala Asp Asn  Asn Asp Leu
    1595                 1600                 1605

Tyr Gln  Ala Ser Thr Asn Ala  Leu Met Glu Ser Leu  Gly Lys Leu
    1610                 1615                 1620

Arg Ser  Asn Tyr Ala Ser Asn  Met Pro Ile Gln Ser  Gln Ile Asp
    1625                 1630                 1635

Ser Leu  Leu Ser Leu Met Asp  Leu Phe Leu Pro Asp  Ile Asn Leu
    1640                 1645                 1650

Gly Glu  Asn Gly Ala Leu Glu  Leu Lys Arg Gly Ile  Ala Lys Asn
    1655                 1660                 1665

Pro Leu  Thr Ile Thr Ile Tyr  Gly Ser Gly Ala Arg  Gly Ile Ala
    1670                 1675                 1680

Gly Lys  Leu Val Ser Ser Val  Thr Asp Ala Ile Tyr  Glu Arg Met
    1685                 1690                 1695

Ser Asp  Val Leu Lys Ala Arg  Ala Lys Asp Pro Asn  Ile Ser Ala
    1700                 1705                 1710

Ala Met  Ala Met Phe Gly Lys  Gln Ala Ala Ser Glu  Ala His Ala
    1715                 1720                 1725

Glu Glu  Leu Leu Ala Arg Phe  Leu Lys Asp Met Glu  Thr Leu Thr
    1730                 1735                 1740

Ser Thr  Val Pro Val Lys Arg  Lys Gly Val Leu Glu  Leu Gln Ser
    1745                 1750                 1755

Thr Gly  Thr Gly Ala Lys Gly  Lys Ile Asn Pro Lys  Thr Tyr Thr
    1760                 1765                 1770

Ile Lys  Gly Glu Gln Leu Lys  Ala Leu Gln Glu Asn  Met Leu His
    1775                 1780                 1785
```

```
Phe Phe  Val Glu Pro Leu Arg  Asn Gly Ile Thr Gln  Thr Val Gly
    1790                 1795                 1800

Glu Ser  Leu Val Tyr Ser Thr  Glu Gln Leu Gln Lys  Ala Thr Gln
    1805                 1810                 1815

Ile Gln  Ser Val Val Leu Glu  Asp Met Phe Lys Gln  Arg Val Gln
    1820                 1825                 1830

Glu Lys  Leu Ala Glu Lys Ala  Lys Asp Pro Thr Trp  Lys Lys Gly
    1835                 1840                 1845

Asp Phe  Leu Thr Gln Lys Glu  Leu Asn Asp Ile Gln  Ala Ser Leu
    1850                 1855                 1860

Asn Asn  Leu Ala Pro Met Ile  Glu Thr Gly Ser Gln  Thr Phe Tyr
    1865                 1870                 1875

Ile Ala  Gly Ser Glu Asn Ala  Glu Val Ala Asn Gln  Val Leu Ala
    1880                 1885                 1890

Thr Asn  Leu Asp Asp Arg Met  Arg Val Pro Met Ser  Ile Tyr Ala
    1895                 1900                 1905

Pro Ala  Gln Ala Gly Val Ala  Gly Ile Pro Phe Met  Thr Ile Gly
    1910                 1915                 1920

Thr Gly  Asp Gly Met Met Met  Gln Thr Leu Ser Thr  Met Lys Gly
    1925                 1930                 1935

Ala Pro  Lys Asn Thr Leu Lys  Ile Phe Asp Gly Met  Asn Ile Gly
    1940                 1945                 1950

Leu Asn  Asp Ile Thr Asp Ala  Ser Arg Lys Ala Asn  Glu Ala Val
    1955                 1960                 1965

Tyr Thr  Ser Trp Gln Gly Asn  Pro Ile Lys Asn Val  Tyr Glu Ser
    1970                 1975                 1980

Tyr Ala  Lys Phe Met Lys Asn  Val Asp Phe Ser Lys  Leu Ser Pro
    1985                 1990                 1995

Glu Ala  Leu Glu Ala Ile Gly  Lys Ser Ala Leu Glu  Tyr Asp Gln
    2000                 2005                 2010

Arg Glu  Asn Ala Thr Val Asp  Asp Ile Ala Asn Ala  Ala Ser Leu
    2015                 2020                 2025

Ile Glu  Arg Asn Leu Arg Asn  Ile Ala Leu Gly Val  Asp Ile Arg
    2030                 2035                 2040

His Lys  Val Leu Asp Lys Val  Asn Leu Ser Ile Asp  Gln Met Ala
    2045                 2050                 2055

Ala Val  Gly Ala Pro Tyr Gln  Asn Asn Gly Lys Ile  Asp Leu Ser
    2060                 2065                 2070

Asn Met  Thr Pro Glu Gln Gln  Ala Asp Glu Leu Asn  Lys Leu Phe
    2075                 2080                 2085

Arg Glu  Glu Leu Glu Ala Arg  Lys Gln Lys Val Ala  Lys Ala Arg
    2090                 2095                 2100

Ala Glu  Val Lys Glu Glu Thr  Val Ser Glu Lys Glu  Pro Val Asn
    2105                 2110                 2115

Pro Asp  Phe Gly Met Val Gly  Arg Glu His Lys Ala  Ser Gly Val
    2120                 2125                 2130

Arg Ile  Leu Ser Ala Thr Ala  Ile Arg Asn Leu Ala  Lys Ile Ser
    2135                 2140                 2145

Asn Leu  Pro Ser Thr Gln Ala  Ala Thr Leu Ala Glu  Ile Gln Lys
    2150                 2155                 2160

Ser Leu  Ala Ala Lys Asp Tyr  Lys Ile Ile Tyr Gly  Thr Pro Thr
    2165                 2170                 2175

Gln Val  Ala Glu Tyr Ala Arg  Gln Lys Asn Val Thr  Glu Leu Thr
```

```
    2180                2185                2190

Ser Gln  Glu Met Glu Glu Ala  Gln Ala Gly Asn Ile  Tyr Gly Trp
    2195                2200                2205

Thr Asn  Phe Asp Asp Lys Thr  Ile Tyr Leu Val Ser  Pro Ser Met
    2210                2215                2220

Glu Thr  Leu Ile His Glu Leu  Val His Ala Ser Thr  Phe Glu Glu
    2225                2230                2235

Val Tyr  Ser Phe Tyr Gln Gly  Asn Glu Val Ser Pro  Thr Ser Lys
    2240                2245                2250

Gln Ala  Ile Glu Asn Leu Glu  Gly Leu Met Glu Gln  Phe Arg Ser
    2255                2260                2265

Leu Asp  Ile Ser Lys Asp Ser  Pro Glu Met Arg Glu  Ala Tyr Ala
    2270                2275                2280

Asp Ala  Ile Ala Thr Ile Glu  Gly His Leu Ser Asn  Gly Phe Val
    2285                2290                2295

Asp Pro  Ala Ile Ser Lys Ala  Ala Ala Leu Asn Glu  Phe Met Ala
    2300                2305                2310

Trp Gly  Leu Ala Asn Arg Ala  Leu Ala Ala Lys Gln  Lys Arg Thr
    2315                2320                2325

Ser Ser  Leu Val Gln Met Val  Lys Asp Val Tyr Gln  Ala Ile Lys
    2330                2335                2340

Lys Leu  Ile Trp Gly Arg Lys  Gln Ala Pro Ala Leu  Gly Glu Asp
    2345                2350                2355

Met Phe  Ser Asn Leu Leu Phe  Asn Ser Ala Ile Leu  Met Arg Ser
    2360                2365                2370

Gln Pro  Thr Thr Gln Ala Val  Ala Lys Asp Gly Thr  Leu Phe His
    2375                2380                2385

Ser Lys  Ala Tyr Gly Asn Asn  Glu Arg Leu Ser Gln  Leu Asn Gln
    2390                2395                2400

Thr Phe  Asp Lys Leu Val Thr  Asp Tyr Leu Arg Thr  Asp Pro Val
    2405                2410                2415

Thr Glu  Val Glu Arg Arg Gly  Asn Val Ala Asn Ala  Leu Met Ser
    2420                2425                2430

Ala Thr  Arg Leu Val Arg Asp  Val Gln Ser His Gly  Phe Asn Met
    2435                2440                2445

Thr Ala  Gln Glu Gln Ser Val  Phe Gln Met Val Thr  Ala Ala Leu
    2450                2455                2460

Ala Thr  Glu Ala Ala Ile Asp  Pro His Ala Met Ala  Arg Ala Gln
    2465                2470                2475

Glu Leu  Tyr Thr His Val Met  Lys His Leu Thr Val  Glu His Phe
    2480                2485                2490

Met Ala  Asp Pro Asp Ser Thr  Asn Pro Ala Asp Arg  Tyr Tyr Ala
    2495                2500                2505

Gln Gln  Lys Tyr Asp Thr Ile  Ser Gly Ala Asn Leu  Val Glu Val
    2510                2515                2520

Asp Ala  Lys Gly Arg Thr Ser  Leu Leu Pro Thr Phe  Leu Gly Leu
    2525                2530                2535

Ala Met  Val Asn Glu Glu Leu  Arg Ser Ile Ile Lys  Glu Met Pro
    2540                2545                2550

Val Pro  Lys Ala Asp Lys Lys  Leu Gly Asn Asp Ile  Asp Thr Leu
    2555                2560                2565

Leu Thr  Asn Ala Gly Thr Gln  Val Met Glu Ser Leu  Asn Arg Arg
    2570                2575                2580
```

```
Met Ala Gly Asp Gln Lys Ala Thr Asn Val Gln Asp Ser Ile Asp
    2585                2590                2595

Ala Leu Ser Glu Thr Ile Met Ala Ala Ala Leu Lys Arg Glu Ser
    2600                2605                2610

Phe Tyr Asp Ala Val Ala Thr Pro Thr Gly Asn Phe Ile Asp Arg
    2615                2620                2625

Ala Asn Gln Tyr Val Thr Asp Ser Ile Glu Arg Leu Ser Glu Thr
    2630                2635                2640

Val Ile Glu Lys Ala Asp Lys Val Ile Ala Asn Pro Ser Asn Ile
    2645                2650                2655

Ala Ala Lys Gly Val Ala His Leu Ala Lys Leu Thr Ala Ala Ile
    2660                2665                2670

Ala Ser Glu Lys Gln Gly Glu Ile Val Ala Gln Gly Val Met Thr
    2675                2680                2685

Ala Met Asn Gln Gly Lys Val Trp Gln Pro Phe His Asp Leu Val
    2690                2695                2700

Asn Asp Ile Val Gly Arg Thr Lys Thr Asn Ala Asn Val Tyr Asp
    2705                2710                2715

Leu Ile Lys Leu Val Lys Ser Gln Ile Ser Gln Asp Arg Gln Gln
    2720                2725                2730

Phe Arg Glu His Leu Pro Thr Val Ile Ala Gly Lys Phe Ser Arg
    2735                2740                2745

Lys Leu Thr Asp Thr Glu Trp Ser Ala Met His Thr Gly Leu Gly
    2750                2755                2760

Lys Thr Asp Leu Ala Val Leu Arg Glu Thr Met Ser Met Ala Glu
    2765                2770                2775

Ile Arg Asp Leu Leu Ser Ser Ser Lys Lys Val Lys Asp Glu Ile
    2780                2785                2790

Ser Thr Leu Glu Lys Glu Ile Gln Asn Gln Ala Gly Arg Asn Trp
    2795                2800                2805

Asn Leu Val Gln Lys Lys Ser Lys Gln Leu Ala Gln Tyr Met Ile
    2810                2815                2820

Met Gly Glu Val Gly Asn Asn Leu Leu Arg Asn Ala His Ala Ile
    2825                2830                2835

Ser Arg Leu Leu Gly Glu Arg Ile Thr Asn Gly Pro Val Ala Asp
    2840                2845                2850

Val Ala Ala Ile Asp Lys Leu Ile Thr Leu Tyr Ser Leu Glu Leu
    2855                2860                2865

Met Asn Lys Ser Asp Arg Asp Leu Leu Ser Glu Leu Ala Gln Ser
    2870                2875                2880

Glu Val Glu Gly Met Glu Phe Ser Ile Ala Tyr Met Val Gly Gln
    2885                2890                2895

Arg Thr Glu Glu Met Arg Lys Ala Lys Gly Asp Asn Arg Thr Leu
    2900                2905                2910

Leu Asn His Phe Lys Gly Tyr Ile Pro Val Glu Asn Gln Gln Gly
    2915                2920                2925

Val Asn Leu Ile Ile Ala Asp Asp Lys Glu Phe Ala Lys Leu Asn
    2930                2935                2940

Ser Gln Ser Phe Thr Arg Ile Gly Thr Tyr Gln Gly Ser Thr Gly
    2945                2950                2955

Phe Arg Thr Gly Ser Lys Gly Tyr Tyr Phe Ser Pro Val Ala Ala
    2960                2965                2970

Arg Ala Pro Tyr Ser Gln Gly Ile Leu Gln Asn Val Arg Asn Thr
    2975                2980                2985
```

```
Ala Gly  Gly Val Asp Ile Gly  Thr Gly Phe Thr Leu  Gly Thr Met
    2990                 2995                 3000

Val Ala  Gly Arg Ile Thr Asp  Lys Pro Thr Val Glu  Arg Ile Thr
    3005                 3010                 3015

Lys Ala  Leu Ala Lys Gly Glu  Arg Gly Arg Glu Pro  Leu Met Pro
    3020                 3025                 3030

Ile Tyr  Asn Ser Lys Gly Gln  Val Val Ala Tyr Glu  Gln Ser Val
    3035                 3040                 3045

Asp Pro  Asn Met Leu Lys His  Leu Asn Gln Asp Asn  His Phe Ala
    3050                 3055                 3060

Lys Met  Val Gly Val Trp Arg  Gly Arg Gln Val Glu  Glu Ala Lys
    3065                 3070                 3075

Ala Gln  Arg Phe Asn Asp Ile  Leu Ile Glu Gln Leu  His Ala Met
    3080                 3085                 3090

Tyr Glu  Lys Asp Ile Lys Asp  Ser Ser Ala Asn Lys  Ser Gln Tyr
    3095                 3100                 3105

Val Asn  Leu Leu Gly Lys Ile  Asp Asp Pro Val Leu  Ala Asp Ala
    3110                 3115                 3120

Ile Asn  Leu Met Asn Ile Glu  Thr Arg His Lys Ala  Glu Glu Leu
    3125                 3130                 3135

Phe Gly  Lys Asp Glu Leu Trp  Val Arg Arg Asp Met  Leu Asn Asp
    3140                 3145                 3150

Ala Leu  Gly Tyr Arg Ala Ala  Ser Ile Gly Asp Val  Trp Thr Gly
    3155                 3160                 3165

Asn Ser  Arg Trp Ser Pro Ser  Thr Leu Asp Thr Val  Lys Lys Met
    3170                 3175                 3180

Phe Leu  Gly Ala Phe Gly Asn  Lys Ala Tyr His Val  Val Met Asn
    3185                 3190                 3195

Ala Glu  Asn Thr Ile Gln Asn  Leu Val Lys Asp Ala  Lys Thr Val
    3200                 3205                 3210

Ile Val  Val Lys Ser Val Val  Val Pro Ala Val Asn  Phe Leu Ala
    3215                 3220                 3225

Asn Ile  Tyr Gln Met Ile Gly  Arg Gly Val Pro Val  Lys Asp Ile
    3230                 3235                 3240

Ala Val  Asn Ile Pro Arg Lys  Thr Ser Glu Ile Asn  Gln Tyr Ile
    3245                 3250                 3255

Lys Ser  Arg Leu Arg Gln Ile  Asp Ala Glu Ala Glu  Leu Arg Ala
    3260                 3265                 3270

Ala Glu  Gly Asn Pro Asn Leu  Val Arg Lys Leu Lys  Thr Glu Ile
    3275                 3280                 3285

Gln Ser  Ile Thr Asp Ser His  Arg Arg Met Ser Ile  Trp Pro Leu
    3290                 3295                 3300

Ile Glu  Ala Gly Glu Phe Ser  Ser Ile Ala Asp Ala  Gly Ile Ser
    3305                 3310                 3315

Arg Asp  Asp Leu Leu Val Ala  Glu Gly Lys Ile His  Glu Tyr Met
    3320                 3325                 3330

Glu Lys  Leu Ala Asn Lys Leu  Pro Glu Lys Val Arg  Asn Ala Gly
    3335                 3340                 3345

Arg Tyr  Ala Leu Ile Ala Lys  Asp Thr Ala Leu Phe  Gln Gly Ile
    3350                 3355                 3360

Gln Lys  Thr Val Glu Tyr Ser  Asp Phe Ile Ala Lys  Ala Ile Ile
    3365                 3370                 3375

Tyr Asp  Asp Leu Val Lys Arg  Lys Lys Lys Ser Ser  Ser Glu Ala
```

```
    3380                3385                3390

Leu Gly  Gln Val Thr Glu Glu  Phe Ile Asn Tyr Asp  Arg Leu Pro
    3395                3400                3405

Gly Arg  Phe Arg Gly Tyr Met  Glu Ser Met Gly Leu  Met Trp Phe
    3410                3415                3420

Tyr Asn  Phe Lys Ile Arg Ser  Ile Lys Val Ala Met  Ser Met Ile
    3425                3430                3435

Arg Asn  Asn Pro Val His Ser  Leu Ile Ala Thr Val  Val Pro Ala
    3440                3445                3450

Pro Thr  Met Phe Gly Asn Val  Gly Leu Pro Ile Gln  Asp Asn Met
    3455                3460                3465

Leu Thr  Met Leu Ala Glu Gly  Arg Leu Asp Tyr Ser  Leu Gly Phe
    3470                3475                3480

Gly Gln  Gly Leu Arg Ala Pro  Thr Leu Asn Pro Trp  Phe Asn Leu
    3485                3490                3495

Thr His
    3500
```

<210> SEQ ID NO 3
<211> LENGTH: 3318
<212> TYPE: DNA
<213> ORGANISM: Artificial Sequence
<220> FEATURE:
<223> OTHER INFORMATION: Synthetic

<400> SEQUENCE: 3

```
gaaagtacag ttacagaaga attaaaagaa ggtattgatg ctgtttaccc ttcattggta     60

ggtactgctg attctaaagc agagggtatt aagaactatt tcaaattgtc ctttacctta    120

ccagaagaac agaaatcccg tactgttggt tcagaagcac ctctaaaaga tgtagcccaa    180

gctctgtctt ctcgtgctcg ttatgaactc tttactgaga aagaaactgc taaccctgct    240

tttaatgggg aagttattaa gcgatacaaa gaactcatgg aacatgggga aggtattgct    300

gatattcttc gctcccgtct ggctaagttc cttaacacta aggatgttgg taaacgtttt    360

gctcaaggta cagaagccaa ccgttgggta ggtggtaagt tacttaacat tgttgagcag    420

gatggggata cctttaagta caacgaacaa ttgctacaga ctgctgtatt agcaggtctt    480

caatggagac ttactgctac cagcaatact gctatcaaag atgcaaaaga tgttgctgct    540

attactggta ttgaccaagc tctgctgcca gaaggtttag tagagcaatt tgatactggt    600

atgacactca ctgaagcagt tagttccctg gctcagaaaa ttgagtctta ctggggatta    660

tctcgtaatc caaatgctcc attgggctat accaaaggca tccctacagc aatggctgct    720

gaaattctgg ctgcatttgt agagtctact gatgttgtag agaacatcgt ggatatgtca    780

gaaattgacc cagataacaa gaagactatt ggtctgtaca ccattactga actggattcc    840

ttcgacccaa ttaatagctt ccctactgct attgaagaag ctgttttagt gaatcctaca    900

gagaagatgt tctttggtga tgacattcct cctgtagcta atactcagct tcgtaaccct    960

gctgttcgta atactccaga acagaaggct gcattgaaag cagagcaggc tacagagttc   1020

tatgtacaca ccccaatggt tcaattctat gagacgttag gtaaagaccg tattctcgaa   1080

ctgatgggtg ctggtactct gaataaagag ttacttaatg ataaccatgc taaatctctg   1140

gaaggtaaga accgttcagt agaggactct tacaaccaac tgttctccgt cattgagcag   1200

gtaagagcac agagcgaaga catctctact gtacctattc actatgcata caatatgacc   1260

cgtgttggtc gtatgcagat gttaggtaaa tacaatcctc aatcagccaa actggttcgt   1320
```

```
gaggccatct tacctactaa agctactttg gatttatcga accagaacaa tgaagacttc   1380

tctgcattcc agttaggtct ggctcaggca ttggacatta aagtccatac tatgactcgt   1440

gaggttatgt ctgacgagtt gactaaatta ctggaaggta atctgaaacc agccattgat   1500

atgatggttg agtttaatac cactggttcc ttaccagaaa acgcagttga tgttctgaat   1560

acagcattag gagataggaa gtcattcgta gcattgatgg ctcttatgga gtattcccgt   1620

tacttagtag cagaggataa atctgcattt gtaactccac tgtatgtaga agcagatggt   1680

gttactaatg gtccaatcaa tgccatgatg ctaatgacag gcggtctgtt tactcctgac   1740

tggattcgta atattgccaa agggggcttg ttcattggtt ctccaaataa gaccatgaat   1800

gagcatcgct ctactgctga caataatgat ttatatcaag catccactaa tgctttgatg   1860

gaatcgttgg gtaagttacg tagtaactat gcctctaata tgcctattca gtctcagata   1920

gacagtcttc tttctctgat ggatttgttt ttaccggata ttaatcttgg tgagaatggt   1980

gctttagaac ttaaacgtgg tattgctaag aacccactga ctattaccat ctatggttct   2040

ggtgctcgtg gtattgcagg taagctggtt agttctgtta ctgatgccat ctatgagcgt   2100

atgtctgatg tactgaaagc tcgtgctaaa gacccaaata tctctgctgc tatggcaatg   2160

tttggtaagc aagctgcttc agaagcacat gctgaagaac ttcttgcccg tttcctgaaa   2220

gatatggaaa cactgacttc tactgttcct gttaaacgta aaggtgtact ggaactacaa   2280

tccacaggta caggagccaa aggaaaaatc aatcctaaga cctataccat taagggcgag   2340

caactgaagg cacttcagga aaatatgctg cacttctttg tagaaccact acgtaatggt   2400

attactcaga ctgtaggtga aagtctggtg tactctactg aacaattaca gaaagctact   2460

cagattcaat ctgtagtgct ggaagatatg ttcaaacagc gagtacaaga gaagctggca   2520

gagaaggcta aagacccaac atggaagaaa ggtgatttcc ttactcagaa agaactgaat   2580

gatattcagg cttctctgaa taacttagcc cctatgattg agactggttc tcagactttc   2640

tacattgctg gttcagaaaa tgcagaagta gcaaatcagg tattagctac taaccttgat   2700

gaccgtatgc gtgtaccaat gagtatctat gctccagcac aggccggtgt agcaggtatt   2760

ccatttatga ctattggtac tggtgatggc atgatgatgc aaactctttc cactatgaaa   2820

ggtgcaccaa agaataccct caaaatcttt gatggtatga acattggttt gaatgacatc   2880

actgatgcca gtcgtaaagc taatgaagct gtttacactt cttggcaggg taaccctatt   2940

aagaatgttt atgaatcata tgctaagttc atgaagaatg tagatttcag caagctgtcc   3000

cctgaagcat tggaagcaat tggtaaatct gctctggaat atgaccaacg tgagaatgct   3060

actgtagatg atattgctaa cgctgcatct ctgattgaac gtaacttacg taatattgca   3120

ctgggtgtag atattcgtca taaggtgctg gataaggtaa atctgtccat tgaccagatg   3180

gctgctgtag gtgctcctta tcagaacaac ggtaagattg acctcagcaa tatgacccct   3240

gaacaacagg ctgatgaact gaataaactt ttccgtgaag agttagaagc ccgtaaacaa   3300

aaagtcgcta aggctagg                                                 3318
```

<210> SEQ ID NO 4
<211> LENGTH: 1107
<212> TYPE: PRT
<213> ORGANISM: Artificial Sequence
<220> FEATURE:
<223> OTHER INFORMATION: Synthetic

<400> SEQUENCE: 4

```
Met Glu Ser Thr Val Thr Glu Glu Leu Lys Glu Gly Ile Asp Ala Val
1               5                   10                  15
```

```
Tyr Pro Ser Leu Val Gly Thr Ala Asp Ser Lys Ala Glu Gly Ile Lys
            20                  25                  30

Asn Tyr Phe Lys Leu Ser Phe Thr Leu Pro Glu Glu Gln Lys Ser Arg
        35                  40                  45

Thr Val Gly Ser Glu Ala Pro Leu Lys Asp Val Ala Gln Ala Leu Ser
    50                  55                  60

Ser Arg Ala Arg Tyr Glu Leu Phe Thr Glu Lys Glu Thr Ala Asn Pro
65                  70                  75                  80

Ala Phe Asn Gly Glu Val Ile Lys Arg Tyr Lys Glu Leu Met Glu His
                85                  90                  95

Gly Glu Gly Ile Ala Asp Ile Leu Arg Ser Arg Leu Ala Lys Phe Leu
            100                 105                 110

Asn Thr Lys Asp Val Gly Lys Arg Phe Ala Gln Gly Thr Glu Ala Asn
        115                 120                 125

Arg Trp Val Gly Gly Lys Leu Leu Asn Ile Val Glu Gln Asp Gly Asp
    130                 135                 140

Thr Phe Lys Tyr Asn Glu Gln Leu Leu Gln Thr Ala Val Leu Ala Gly
145                 150                 155                 160

Leu Gln Trp Arg Leu Thr Ala Thr Ser Asn Thr Ala Ile Lys Asp Ala
                165                 170                 175

Lys Asp Val Ala Ala Ile Thr Gly Ile Asp Gln Ala Leu Leu Pro Glu
            180                 185                 190

Gly Leu Val Glu Gln Phe Asp Thr Gly Met Thr Leu Thr Glu Ala Val
        195                 200                 205

Ser Ser Leu Ala Gln Lys Ile Glu Ser Tyr Trp Gly Leu Ser Arg Asn
    210                 215                 220

Pro Asn Ala Pro Leu Gly Tyr Thr Lys Gly Ile Pro Thr Ala Met Ala
225                 230                 235                 240

Ala Glu Ile Leu Ala Ala Phe Val Glu Ser Thr Asp Val Val Glu Asn
                245                 250                 255

Ile Val Asp Met Ser Glu Ile Asp Pro Asp Asn Lys Lys Thr Ile Gly
            260                 265                 270

Leu Tyr Thr Ile Thr Glu Leu Asp Ser Phe Asp Pro Ile Asn Ser Phe
        275                 280                 285

Pro Thr Ala Ile Glu Glu Ala Val Leu Val Asn Pro Thr Glu Lys Met
    290                 295                 300

Phe Phe Gly Asp Asp Ile Pro Pro Val Ala Asn Thr Gln Leu Arg Asn
305                 310                 315                 320

Pro Ala Val Arg Asn Thr Pro Glu Gln Lys Ala Ala Leu Lys Ala Glu
                325                 330                 335

Gln Ala Thr Glu Phe Tyr Val His Thr Pro Met Val Gln Phe Tyr Glu
            340                 345                 350

Thr Leu Gly Lys Asp Arg Ile Leu Glu Leu Met Gly Ala Gly Thr Leu
        355                 360                 365

Asn Lys Glu Leu Leu Asn Asp Asn His Ala Lys Ser Leu Glu Gly Lys
    370                 375                 380

Asn Arg Ser Val Glu Asp Ser Tyr Asn Gln Leu Phe Ser Val Ile Glu
385                 390                 395                 400

Gln Val Arg Ala Gln Ser Glu Asp Ile Ser Thr Val Pro Ile His Tyr
                405                 410                 415

Ala Tyr Asn Met Thr Arg Val Gly Arg Met Gln Met Leu Gly Lys Tyr
            420                 425                 430

Asn Pro Gln Ser Ala Lys Leu Val Arg Glu Ala Ile Leu Pro Thr Lys
```

```
        435                 440                 445

Ala Thr Leu Asp Leu Ser Asn Gln Asn Asn Glu Asp Phe Ser Ala Phe
    450                 455                 460

Gln Leu Gly Leu Ala Gln Ala Leu Asp Ile Lys Val His Thr Met Thr
465                 470                 475                 480

Arg Glu Val Met Ser Asp Glu Leu Thr Lys Leu Leu Glu Gly Asn Leu
                485                 490                 495

Lys Pro Ala Ile Asp Met Met Val Glu Phe Asn Thr Thr Gly Ser Leu
            500                 505                 510

Pro Glu Asn Ala Val Asp Val Leu Asn Thr Ala Leu Gly Asp Arg Lys
        515                 520                 525

Ser Phe Val Ala Leu Met Ala Leu Met Glu Tyr Ser Arg Tyr Leu Val
    530                 535                 540

Ala Glu Asp Lys Ser Ala Phe Val Thr Pro Leu Tyr Val Glu Ala Asp
545                 550                 555                 560

Gly Val Thr Asn Gly Pro Ile Asn Ala Met Met Leu Met Thr Gly Gly
                565                 570                 575

Leu Phe Thr Pro Asp Trp Ile Arg Asn Ile Ala Lys Gly Gly Leu Phe
            580                 585                 590

Ile Gly Ser Pro Asn Lys Thr Met Asn Glu His Arg Ser Thr Ala Asp
        595                 600                 605

Asn Asn Asp Leu Tyr Gln Ala Ser Thr Asn Ala Leu Met Glu Ser Leu
    610                 615                 620

Gly Lys Leu Arg Ser Asn Tyr Ala Ser Asn Met Pro Ile Gln Ser Gln
625                 630                 635                 640

Ile Asp Ser Leu Leu Ser Leu Met Asp Leu Phe Leu Pro Asp Ile Asn
                645                 650                 655

Leu Gly Glu Asn Gly Ala Leu Glu Leu Lys Arg Gly Ile Ala Lys Asn
            660                 665                 670

Pro Leu Thr Ile Thr Ile Tyr Gly Ser Gly Ala Arg Gly Ile Ala Gly
        675                 680                 685

Lys Leu Val Ser Ser Val Thr Asp Ala Ile Tyr Glu Arg Met Ser Asp
    690                 695                 700

Val Leu Lys Ala Arg Ala Lys Asp Pro Asn Ile Ser Ala Ala Met Ala
705                 710                 715                 720

Met Phe Gly Lys Gln Ala Ala Ser Glu Ala His Ala Glu Glu Leu Leu
                725                 730                 735

Ala Arg Phe Leu Lys Asp Met Glu Thr Leu Thr Ser Thr Val Pro Val
            740                 745                 750

Lys Arg Lys Gly Val Leu Glu Leu Gln Ser Thr Gly Thr Gly Ala Lys
        755                 760                 765

Gly Lys Ile Asn Pro Lys Thr Tyr Thr Ile Lys Gly Glu Gln Leu Lys
    770                 775                 780

Ala Leu Gln Glu Asn Met Leu His Phe Phe Val Glu Pro Leu Arg Asn
785                 790                 795                 800

Gly Ile Thr Gln Thr Val Gly Glu Ser Leu Val Tyr Ser Thr Glu Gln
                805                 810                 815

Leu Gln Lys Ala Thr Gln Ile Gln Ser Val Val Leu Glu Asp Met Phe
            820                 825                 830

Lys Gln Arg Val Gln Glu Lys Leu Ala Glu Lys Ala Lys Asp Pro Thr
        835                 840                 845

Trp Lys Lys Gly Asp Phe Leu Thr Gln Lys Glu Leu Asn Asp Ile Gln
    850                 855                 860
```

```
Ala Ser Leu Asn Asn Leu Ala Pro Met Ile Glu Thr Gly Ser Gln Thr
865                 870                 875                 880

Phe Tyr Ile Ala Gly Ser Glu Asn Ala Glu Val Ala Asn Gln Val Leu
                885                 890                 895

Ala Thr Asn Leu Asp Asp Arg Met Arg Val Pro Met Ser Ile Tyr Ala
            900                 905                 910

Pro Ala Gln Ala Gly Val Ala Gly Ile Pro Phe Met Thr Ile Gly Thr
        915                 920                 925

Gly Asp Gly Met Met Met Gln Thr Leu Ser Thr Met Lys Gly Ala Pro
    930                 935                 940

Lys Asn Thr Leu Lys Ile Phe Asp Gly Met Asn Ile Gly Leu Asn Asp
945                 950                 955                 960

Ile Thr Asp Ala Ser Arg Lys Ala Asn Glu Ala Val Tyr Thr Ser Trp
                965                 970                 975

Gln Gly Asn Pro Ile Lys Asn Val Tyr Glu Ser Tyr Ala Lys Phe Met
            980                 985                 990

Lys Asn Val Asp Phe Ser Lys Leu  Ser Pro Glu Ala Leu  Glu Ala Ile
        995                 1000                1005

Gly Lys  Ser Ala Leu Glu Tyr  Asp Gln Arg Glu Asn  Ala Thr Val
    1010                 1015                1020

Asp Asp  Ile Ala Asn Ala Ala  Ser Leu Ile Glu Arg  Asn Leu Arg
    1025                 1030                1035

Asn Ile  Ala Leu Gly Val Asp  Ile Arg His Lys Val  Leu Asp Lys
    1040                 1045                1050

Val Asn  Leu Ser Ile Asp Gln  Met Ala Ala Val Gly  Ala Pro Tyr
    1055                 1060                1065

Gln Asn  Asn Gly Lys Ile Asp  Leu Ser Asn Met Thr  Pro Glu Gln
    1070                 1075                1080

Gln Ala  Asp Glu Leu Asn Lys  Leu Phe Arg Glu Glu  Leu Glu Ala
    1085                 1090                1095

Arg Lys  Gln Lys Val Ala Lys  Ala Arg
    1100                 1105
```

```
<210> SEQ ID NO 5
<211> LENGTH: 3432
<212> TYPE: DNA
<213> ORGANISM: Artificial Sequence
<220> FEATURE:
<223> OTHER INFORMATION: Synthetic

<400> SEQUENCE: 5

atggggggtt ctcatcatca tcatcatcat ggtatggcta gcatgactgg tggacagcaa     60

atgggtcggg atctgtacga cgatgacgat aaggatccga gctcgagatc tgaaagtaca    120

gttacagaag aattaaaaga aggtattgat gctgtttacc cttcattggt aggtactgct    180

gattctaaag cagagggtat taagaactat ttcaaattgt cctttacctt accagaagaa    240

cagaaatccc gtactgttgg ttcagaagca cctctaaaag atgtagccca agctctgtct    300

tctcgtgctc gttatgaact ctttactgag aaagaaactg ctaaccctgc ttttaatggg    360

gaagttatta agcgatacaa agaactcatg gaacatgggg aaggtattgc tgatattctt    420

cgctcccgtc tggctaagtt ccttaacact aaggatgttg gtaaacgttt tgctcaaggt    480

acagaagcca accgttgggt aggtggtaag ttacttaaca ttgttgagca ggatggggat    540

acctttaagt acaacgaaca attgctacag actgctgtat tagcaggtct tcaatggaga    600

cttactgcta ccagcaatac tgctatcaaa gatgcaaaag atgttgctgc tattactggt    660
```

-continued

```
attgaccaag ctctgctgcc agaaggttta gtagagcaat ttgatactgg tatgacactc    720

actgaagcag ttagttccct ggctcagaaa attgagtctt actggggatt atctcgtaat    780

ccaaatgctc cattgggcta taccaaaggc atccctacag caatggctgc tgaaattctg    840

gctgcatttg tagagtctac tgatgttgta gagaacatcg tggatatgtc agaaattgac    900

ccagataaca agaagactat tggtctgtac accattactg aactggattc cttcgaccca    960

attaatagct tccctactgc tattgaagaa gctgttttag tgaatcctac agagaagatg   1020

ttctttggtg atgacattcc tcctgtagct aatactcagc ttcgtaaccc tgctgttcgt   1080

aatactccag aacagaaggc tgcattgaaa gcagagcagg ctacagagtt ctatgtacac   1140

accccaatgg ttcaattcta tgagacgtta ggtaaagacc gtattctcga actgatgggt   1200

gctggtactc tgaataaaga gttacttaat gataaccatg ctaaatctct ggaaggtaag   1260

aaccgttcag tagaggactc ttacaaccaa ctgttctccg tcattgagca ggtaagagca   1320

cagagcgaag acatctctac tgtacctatt cactatgcat acaatatgac ccgtgttggt   1380

cgtatgcaga tgttaggtaa atacaatcct caatcagcca aactggttcg tgaggccatc   1440

ttacctacta aagctacttt ggatttatcg aaccagaaca atgaagactt ctctgcattc   1500

cagttaggtc tggctcaggc attggacatt aaagtccata ctatgactcg tgaggttatg   1560

tctgacgagt tgactaaatt actggaaggt aatctgaaac cagccattga tatgatggtt   1620

gagtttaata ccactggttc cttaccagaa aacgcagttg atgttctgaa tacagcatta   1680

ggagatagga agtcattcgt agcattgatg gctcttatgg agtattcccg ttacttagta   1740

gcagaggata aatctgcatt tgtaactcca ctgtatgtag aagcagatgg tgttactaat   1800

ggtccaatca atgccatgat gctaatgaca ggcggtctgt ttactcctga ctggattcgt   1860

aatattgcca aaggggggctt gttcattggt tctccaaata agaccatgaa tgagcatcgc   1920

tctactgctg acaataatga tttatatcaa gcatccacta atgctttgat ggaatcgttg   1980

ggtaagttac gtagtaacta tgcctctaat atgcctattc agtctcagat agacagtctt   2040

ctttctctga tggatttgtt tttaccggat attaatcttg gtgagaatgg tgctttagaa   2100

cttaaacgtg gtattgctaa gaacccactg actattacca tctatggttc tggtgctcgt   2160

ggtattgcag gtaagctggt tagttctgtt actgatgcca tctatgagcg tatgtctgat   2220

gtactgaaag ctcgtgctaa agacccaaat atctctgctg ctatggcaat gtttggtaag   2280

caagctgctt cagaagcaca tgctgaagaa cttcttgccc gtttcctgaa agatatggaa   2340

acactgactt ctactgttcc tgttaaacgt aaaggtgtac tggaactaca atccacaggt   2400

acaggagcca aaggaaaaat caatcctaag acctatacca ttaagggcga gcaactgaag   2460

gcacttcagg aaaatatgct gcacttcttt gtagaaccac tacgtaatgg tattactcag   2520

actgtaggtg aaagtctggt gtactctact gaacaattac agaaagctac tcagattcaa   2580

tctgtagtgc tggaagatat gttcaaacag cgagtacaag agaagctggc agagaaggct   2640

aaagacccaa catggaagaa aggtgatttc cttactcaga aagaactgaa tgatattcag   2700

gcttctctga ataacttagc ccctatgatt gagactggtt ctcagacttt ctacattgct   2760

ggttcagaaa atgcagaagt agcaaatcag gtattagcta ctaaccttga tgaccgtatg   2820

cgtgtaccaa tgagtatcta tgctccagca caggccggtg tagcaggtat tccatttatg   2880

actattggta ctggtgatgg catgatgatg caaactcttt ccactatgaa aggtgcacca   2940

aagaataccc tcaaaatctt tgatggtatg aacattggtt tgaatgacat cactgatgcc   3000

agtcgtaaag ctaatgaagc tgtttacact tcttggcagg gtaaccctat taagaatgtt   3060
```

```
tatgaatcat atgctaagtt catgaagaat gtagatttca gcaagctgtc ccctgaagca   3120

ttggaagcaa ttggtaaatc tgctctggaa tatgaccaac gtgagaatgc tactgtagat   3180

gatattgcta acgctgcatc tctgattgaa cgtaacttac gtaatattgc actgggtgta   3240

gatattcgtc ataaggtgct ggataaggta aatctgtcca ttgaccagat ggctgctgta   3300

ggtgctcctt atcagaacaa cggtaagatt gacctcagca atatgacccc tgaacaacag   3360

gctgatgaac tgaataaact tttccgtgaa gagttagaag cccgtaaaca aaaagtcgct   3420

aaggctaggt aa                                                        3432
```

<210> SEQ ID NO 6
<211> LENGTH: 1143
<212> TYPE: PRT
<213> ORGANISM: Artificial Sequence
<220> FEATURE:
<223> OTHER INFORMATION: Synthetic

<400> SEQUENCE: 6

```
Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Ser Ser Arg Ser Glu Ser Thr Val Thr Glu Glu Leu Lys Glu Gly
        35                  40                  45

Ile Asp Ala Val Tyr Pro Ser Leu Val Gly Thr Ala Asp Ser Lys Ala
    50                  55                  60

Glu Gly Ile Lys Asn Tyr Phe Lys Leu Ser Phe Thr Leu Pro Glu Glu
65                  70                  75                  80

Gln Lys Ser Arg Thr Val Gly Ser Glu Ala Pro Leu Lys Asp Val Ala
                85                  90                  95

Gln Ala Leu Ser Ser Arg Ala Arg Tyr Glu Leu Phe Thr Glu Lys Glu
            100                 105                 110

Thr Ala Asn Pro Ala Phe Asn Gly Glu Val Ile Lys Arg Tyr Lys Glu
        115                 120                 125

Leu Met Glu His Gly Glu Gly Ile Ala Asp Ile Leu Arg Ser Arg Leu
    130                 135                 140

Ala Lys Phe Leu Asn Thr Lys Asp Val Gly Lys Arg Phe Ala Gln Gly
145                 150                 155                 160

Thr Glu Ala Asn Arg Trp Val Gly Gly Lys Leu Leu Asn Ile Val Glu
                165                 170                 175

Gln Asp Gly Asp Thr Phe Lys Tyr Asn Glu Gln Leu Leu Gln Thr Ala
            180                 185                 190

Val Leu Ala Gly Leu Gln Trp Arg Leu Thr Ala Thr Ser Asn Thr Ala
        195                 200                 205

Ile Lys Asp Ala Lys Asp Val Ala Ala Ile Thr Gly Ile Asp Gln Ala
    210                 215                 220

Leu Leu Pro Glu Gly Leu Val Glu Gln Phe Asp Thr Gly Met Thr Leu
225                 230                 235                 240

Thr Glu Ala Val Ser Ser Leu Ala Gln Lys Ile Glu Ser Tyr Trp Gly
                245                 250                 255

Leu Ser Arg Asn Pro Asn Ala Pro Leu Gly Tyr Thr Lys Gly Ile Pro
            260                 265                 270

Thr Ala Met Ala Ala Glu Ile Leu Ala Ala Phe Val Glu Ser Thr Asp
        275                 280                 285

Val Val Glu Asn Ile Val Asp Met Ser Glu Ile Asp Pro Asp Asn Lys
    290                 295                 300
```

```
Lys Thr Ile Gly Leu Tyr Thr Ile Thr Glu Leu Asp Ser Phe Asp Pro
305                 310                 315                 320

Ile Asn Ser Phe Pro Thr Ala Ile Glu Glu Ala Val Leu Val Asn Pro
                325                 330                 335

Thr Glu Lys Met Phe Phe Gly Asp Asp Ile Pro Pro Val Ala Asn Thr
            340                 345                 350

Gln Leu Arg Asn Pro Ala Val Arg Asn Thr Pro Glu Gln Lys Ala Ala
        355                 360                 365

Leu Lys Ala Glu Gln Ala Thr Glu Phe Tyr Val His Thr Pro Met Val
    370                 375                 380

Gln Phe Tyr Glu Thr Leu Gly Lys Asp Arg Ile Leu Glu Leu Met Gly
385                 390                 395                 400

Ala Gly Thr Leu Asn Lys Glu Leu Leu Asn Asp Asn His Ala Lys Ser
                405                 410                 415

Leu Glu Gly Lys Asn Arg Ser Val Glu Asp Ser Tyr Asn Gln Leu Phe
            420                 425                 430

Ser Val Ile Glu Gln Val Arg Ala Gln Ser Glu Asp Ile Ser Thr Val
        435                 440                 445

Pro Ile His Tyr Ala Tyr Asn Met Thr Arg Val Gly Arg Met Gln Met
    450                 455                 460

Leu Gly Lys Tyr Asn Pro Gln Ser Ala Lys Leu Val Arg Glu Ala Ile
465                 470                 475                 480

Leu Pro Thr Lys Ala Thr Leu Asp Leu Ser Asn Gln Asn Asn Glu Asp
                485                 490                 495

Phe Ser Ala Phe Gln Leu Gly Leu Ala Gln Ala Leu Asp Ile Lys Val
            500                 505                 510

His Thr Met Thr Arg Glu Val Met Ser Asp Glu Leu Thr Lys Leu Leu
        515                 520                 525

Glu Gly Asn Leu Lys Pro Ala Ile Asp Met Met Val Glu Phe Asn Thr
    530                 535                 540

Thr Gly Ser Leu Pro Glu Asn Ala Val Asp Val Leu Asn Thr Ala Leu
545                 550                 555                 560

Gly Asp Arg Lys Ser Phe Val Ala Leu Met Ala Leu Met Glu Tyr Ser
                565                 570                 575

Arg Tyr Leu Val Ala Glu Asp Lys Ser Ala Phe Val Thr Pro Leu Tyr
            580                 585                 590

Val Glu Ala Asp Gly Val Thr Asn Gly Pro Ile Asn Ala Met Met Leu
        595                 600                 605

Met Thr Gly Gly Leu Phe Thr Pro Asp Trp Ile Arg Asn Ile Ala Lys
    610                 615                 620

Gly Gly Leu Phe Ile Gly Ser Pro Asn Lys Thr Met Asn Glu His Arg
625                 630                 635                 640

Ser Thr Ala Asp Asn Asn Asp Leu Tyr Gln Ala Ser Thr Asn Ala Leu
                645                 650                 655

Met Glu Ser Leu Gly Lys Leu Arg Ser Asn Tyr Ala Ser Asn Met Pro
            660                 665                 670

Ile Gln Ser Gln Ile Asp Ser Leu Leu Ser Leu Met Asp Leu Phe Leu
        675                 680                 685

Pro Asp Ile Asn Leu Gly Glu Asn Gly Ala Leu Glu Leu Lys Arg Gly
    690                 695                 700

Ile Ala Lys Asn Pro Leu Thr Ile Thr Ile Tyr Gly Ser Gly Ala Arg
705                 710                 715                 720

Gly Ile Ala Gly Lys Leu Val Ser Ser Val Thr Asp Ala Ile Tyr Glu
```

```
                725                 730                 735

Arg Met Ser Asp Val Leu Lys Ala Arg Ala Lys Asp Pro Asn Ile Ser
            740                 745                 750

Ala Ala Met Ala Met Phe Gly Lys Gln Ala Ala Ser Glu Ala His Ala
        755                 760                 765

Glu Glu Leu Leu Ala Arg Phe Leu Lys Asp Met Glu Thr Leu Thr Ser
    770                 775                 780

Thr Val Pro Val Lys Arg Lys Gly Val Leu Glu Leu Gln Ser Thr Gly
785                 790                 795                 800

Thr Gly Ala Lys Gly Lys Ile Asn Pro Lys Thr Tyr Thr Ile Lys Gly
                805                 810                 815

Glu Gln Leu Lys Ala Leu Gln Glu Asn Met Leu His Phe Phe Val Glu
            820                 825                 830

Pro Leu Arg Asn Gly Ile Thr Gln Thr Val Gly Glu Ser Leu Val Tyr
        835                 840                 845

Ser Thr Glu Gln Leu Gln Lys Ala Thr Gln Ile Gln Ser Val Val Leu
    850                 855                 860

Glu Asp Met Phe Lys Gln Arg Val Gln Glu Lys Leu Ala Glu Lys Ala
865                 870                 875                 880

Lys Asp Pro Thr Trp Lys Lys Gly Asp Phe Leu Thr Gln Lys Glu Leu
                885                 890                 895

Asn Asp Ile Gln Ala Ser Leu Asn Asn Leu Ala Pro Met Ile Glu Thr
            900                 905                 910

Gly Ser Gln Thr Phe Tyr Ile Ala Gly Ser Glu Asn Ala Glu Val Ala
        915                 920                 925

Asn Gln Val Leu Ala Thr Asn Leu Asp Asp Arg Met Arg Val Pro Met
    930                 935                 940

Ser Ile Tyr Ala Pro Ala Gln Ala Gly Val Ala Gly Ile Pro Phe Met
945                 950                 955                 960

Thr Ile Gly Thr Gly Asp Gly Met Met Met Gln Thr Leu Ser Thr Met
                965                 970                 975

Lys Gly Ala Pro Lys Asn Thr Leu Lys Ile Phe Asp Gly Met Asn Ile
            980                 985                 990

Gly Leu Asn Asp Ile Thr Asp Ala  Ser Arg Lys Ala Asn  Glu Ala Val
        995                 1000                1005

Tyr Thr  Ser Trp Gln Gly Asn  Pro Ile Lys Asn Val  Tyr Glu Ser
    1010                1015                1020

Tyr Ala  Lys Phe Met Lys Asn  Val Asp Phe Ser Lys  Leu Ser Pro
    1025                1030                1035

Glu Ala  Leu Glu Ala Ile Gly  Lys Ser Ala Leu Glu  Tyr Asp Gln
    1040                1045                1050

Arg Glu  Asn Ala Thr Val Asp  Asp Ile Ala Asn Ala  Ala Ser Leu
    1055                1060                1065

Ile Glu  Arg Asn Leu Arg Asn  Ile Ala Leu Gly Val  Asp Ile Arg
    1070                1075                1080

His Lys  Val Leu Asp Lys Val  Asn Leu Ser Ile Asp  Gln Met Ala
    1085                1090                1095

Ala Val  Gly Ala Pro Tyr Gln  Asn Asn Gly Lys Ile  Asp Leu Ser
    1100                1105                1110

Asn Met  Thr Pro Glu Gln Gln  Ala Asp Glu Leu Asn  Lys Leu Phe
    1115                1120                1125

Arg Glu  Glu Leu Glu Ala Arg  Lys Gln Lys Val Ala  Lys Ala Arg
    1130                1135                1140
```

<210> SEQ ID NO 7
<211> LENGTH: 3432
<212> TYPE: DNA
<213> ORGANISM: Artificial Sequence
<220> FEATURE:
<223> OTHER INFORMATION: Synthetic

<400> SEQUENCE: 7

```
atggggggtt ctcatcatca tcatcatcat ggtatggcta gcatgactgg tggacagcaa     60
atgggtcggg atctgtacga cgatgacgat aaggatccga gctcgagatc tgaaagtaca    120
gttacagaag aattaaaaga aggtattgat gctgtttacc cttcattggt aggtactgct    180
gattctaaag cagagggtat taagaactat ttcaaattgt cctttacctt accagaagaa    240
cagaaatccc gtactgttgg ttcagaagca cctctaaaag atgtagccca agctctgtct    300
tctcgtgctc gttatgaact ctttactgag aaagaaactg ctaaccctgc ttttaatggg    360
gaagttatta agcgatacaa agaactcatg gaacatgggg aaggtattgc tgatattctt    420
cgctcccgtc tggctaagtt ccttaacact aaggatgttg gtaaacgttt tgctcaaggt    480
acagaagcca accgttgggt aggtggtaag ttacttaaca ttgttgagca ggatggggat    540
acctttaagt acaacgaaca attgctacag actgctgtat tagcaggtct tcaatggaga    600
cttactgcta ccagcaatac tgctatcaaa gatgcaaaag atgttgctgc tattactggt    660
attgaccaag ctctgctgcc agaaggttta gtagagcaat ttgatactgg tatgacactc    720
actgaagcag ttagttccct ggctcagaaa attgagtctt actggggatt atctcgtaat    780
ccaaatgctc cattgggcta taccaaaggc atccctacag caatggctgc tgaaattctg    840
gctgcatttg tagagtctac tgatgttgta gagaacatcg tggatatgtc agaaattgac    900
ccagataaca agaagactat tggtctgtac accattactg aactggattc cttcgaccca    960
attaatagct tccctactgc tattgaagaa gctgttttag tgaatcctac agagaagatg   1020
ttctttggtg atgacattcc tcctgtagct aatactcagc ttcgtaaccc tgctgttcgt   1080
aatactccag aacagaaggc tgcattgaaa gcagagcagg ctacagagtt ctatgtacac   1140
accccaatgg ttcaattcta tgagacgtta ggtaaagacc gtattctcga actgatgggt   1200
gctggtactc tgaataaaga gttacttaat gataaccatg ctaaatctct ggaaggtaag   1260
aaccgttcag tagaggactc ttacaaccaa ctgttctccg tcattgagca ggtaagagca   1320
cagagcgaag acatctctac tgtacctatt cactatgcat acaatatgac ccgtgttggt   1380
cgtatgcaga tgttaggtaa atacaatcct caatcagcca aactggttcg tgaggccatc   1440
ttacctacta aagctacttt ggatttatcg aaccagaaca atgaagactt ctctgcattc   1500
cagttaggtc tggctcaggc attggacatt aaagtccata ctatgactcg tgaggttatg   1560
tctgacgagt tgactaaatt actggaaggt aatctgaaac cagccattga tatgatggtt   1620
gagtttaata ccactggttc cttaccagaa aacgcagttg atgttctgaa tacagcatta   1680
ggagatagga agtcattcgt agcattgatg gctcttatgg agtattcccg ttacttagta   1740
gcagaggata aatctgcatt tgtaactcca ctgtatgtag aagcagatgg tgttactaat   1800
ggtccaatca atgccatgat gctaatgaca ggcggtctgt ttactcctga ctggattcgt   1860
aatattgcca aaggggcctt gttcattggt tctccaaata agaccatgaa tgagcatcgc   1920
tctactgctg acaataatga tttatatcaa gcatccacta atgctttgat ggaatcgttg   1980
ggtaagttac gtagtaacta tgcctctaat atgcctattc agtctcagat agacagtctt   2040
ctttctctga tggatttgtt tttaccggat attaatcttg gtgagaatgg tgctttagaa   2100
```

```
cttaaacgtg gtattgctaa gaacccactg actattacca tcttcggttc tggtgctcgt   2160

ggtattgcag gtaagctggt tagttctgtt actgatgcca tctatgagcg tatgtctgat   2220

gtactgaaag ctcgtgctaa agacccaaat atctctgctg ctatggcaat gtttggtaag   2280

caagctgctt cagaagcaca tgctgaagaa cttcttgccc gtttcctgaa agatatggaa   2340

acactgactt ctactgttcc tgttaaacgt aaaggtgtac tggaactaca atccacaggt   2400

acaggagcca aaggaaaaat caatcctaag acctatacca ttaagggcga gcaactgaag   2460

gcacttcagg aaaatatgct gcacttcttt gtagaaccac tacgtaatgg tattactcag   2520

actgtaggtg aaagtctggt gtactctact gaacaattac agaaagctac tcagattcaa   2580

tctgtagtgc tggaagatat gttcaaacag cgagtacaag agaagctggc agagaaggct   2640

aaagacccaa catggaagaa aggtgatttc cttactcaga aagaactgaa tgatattcag   2700

gcttctctga ataacttagc ccctatgatt gagactggtt ctcagacttt ctacattgct   2760

ggttcagaaa atgcagaagt agcaaatcag gtattagcta ctaaccttga tgaccgtatg   2820

cgtgtaccaa tgagtatcta tgctccagca caggccggtg tagcaggtat tccatttatg   2880

actattggta ctggtgatgg catgatgatg caaactcttt ccactatgaa aggtgcacca   2940

aagaataccc tcaaaatctt tgatggtatg aacattggtt tgaatgacat cactgatgcc   3000

agtcgtaaag ctaatgaagc tgtttacact tcttggcagg gtaaccctat taagaatgtt   3060

tatgaatcat atgctaagtt catgaagaat gtagatttca gcaagctgtc ccctgaagca   3120

ttggaagcaa ttggtaaatc tgctctggaa tatgaccaac gtgagaatgc tactgtagat   3180

gatattgcta acgctgcatc tctgattgaa cgtaacttac gtaatattgc actgggtgta   3240

gatattcgtc ataaggtgct ggataaggta aatctgtcca ttgaccagat ggctgctgta   3300

ggtgctcctt atcagaacaa cggtaagatt gacctcagca atatgacccc tgaacaacag   3360

gctgatgaac tgaataaact tttccgtgaa gagttagaag cccgtaaaca aaaagtcgct   3420

aaggctaggt aa                                                       3432
```

<210> SEQ ID NO 8
<211> LENGTH: 1143
<212> TYPE: PRT
<213> ORGANISM: Artificial Sequence
<220> FEATURE:
<223> OTHER INFORMATION: Synthetic

<400> SEQUENCE: 8

```
Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Ser Ser Arg Ser Glu Ser Thr Val Thr Glu Glu Leu Lys Glu Gly
        35                  40                  45

Ile Asp Ala Val Tyr Pro Ser Leu Val Gly Thr Ala Asp Ser Lys Ala
    50                  55                  60

Glu Gly Ile Lys Asn Tyr Phe Lys Leu Ser Phe Thr Leu Pro Glu Glu
65                  70                  75                  80

Gln Lys Ser Arg Thr Val Gly Ser Glu Ala Pro Leu Lys Asp Val Ala
                85                  90                  95

Gln Ala Leu Ser Ser Arg Ala Arg Tyr Glu Leu Phe Thr Glu Lys Glu
            100                 105                 110

Thr Ala Asn Pro Ala Phe Asn Gly Glu Val Ile Lys Arg Tyr Lys Glu
        115                 120                 125
```

```
Leu Met Glu His Gly Glu Gly Ile Ala Asp Ile Leu Arg Ser Arg Leu
    130                 135                 140

Ala Lys Phe Leu Asn Thr Lys Asp Val Gly Lys Arg Phe Ala Gln Gly
145                 150                 155                 160

Thr Glu Ala Asn Arg Trp Val Gly Gly Lys Leu Leu Asn Ile Val Glu
                165                 170                 175

Gln Asp Gly Asp Thr Phe Lys Tyr Asn Glu Gln Leu Leu Gln Thr Ala
            180                 185                 190

Val Leu Ala Gly Leu Gln Trp Arg Leu Thr Ala Thr Ser Asn Thr Ala
        195                 200                 205

Ile Lys Asp Ala Lys Asp Val Ala Ala Ile Thr Gly Ile Asp Gln Ala
    210                 215                 220

Leu Leu Pro Glu Gly Leu Val Glu Gln Phe Asp Thr Gly Met Thr Leu
225                 230                 235                 240

Thr Glu Ala Val Ser Ser Leu Ala Gln Lys Ile Glu Ser Tyr Trp Gly
                245                 250                 255

Leu Ser Arg Asn Pro Asn Ala Pro Leu Gly Tyr Thr Lys Gly Ile Pro
            260                 265                 270

Thr Ala Met Ala Ala Glu Ile Leu Ala Ala Phe Val Glu Ser Thr Asp
        275                 280                 285

Val Val Glu Asn Ile Val Asp Met Ser Glu Ile Asp Pro Asp Asn Lys
    290                 295                 300

Lys Thr Ile Gly Leu Tyr Thr Ile Thr Glu Leu Asp Ser Phe Asp Pro
305                 310                 315                 320

Ile Asn Ser Phe Pro Thr Ala Ile Glu Glu Ala Val Leu Val Asn Pro
                325                 330                 335

Thr Glu Lys Met Phe Phe Gly Asp Asp Ile Pro Pro Val Ala Asn Thr
            340                 345                 350

Gln Leu Arg Asn Pro Ala Val Arg Asn Thr Pro Glu Gln Lys Ala Ala
        355                 360                 365

Leu Lys Ala Glu Gln Ala Thr Glu Phe Tyr Val His Thr Pro Met Val
    370                 375                 380

Gln Phe Tyr Glu Thr Leu Gly Lys Asp Arg Ile Leu Glu Leu Met Gly
385                 390                 395                 400

Ala Gly Thr Leu Asn Lys Glu Leu Leu Asn Asp Asn His Ala Lys Ser
                405                 410                 415

Leu Glu Gly Lys Asn Arg Ser Val Glu Asp Ser Tyr Asn Gln Leu Phe
            420                 425                 430

Ser Val Ile Glu Gln Val Arg Ala Gln Ser Glu Asp Ile Ser Thr Val
        435                 440                 445

Pro Ile His Tyr Ala Tyr Asn Met Thr Arg Val Gly Arg Met Gln Met
    450                 455                 460

Leu Gly Lys Tyr Asn Pro Gln Ser Ala Lys Leu Val Arg Glu Ala Ile
465                 470                 475                 480

Leu Pro Thr Lys Ala Thr Leu Asp Leu Ser Asn Gln Asn Asn Glu Asp
                485                 490                 495

Phe Ser Ala Phe Gln Leu Gly Leu Ala Gln Ala Leu Asp Ile Lys Val
            500                 505                 510

His Thr Met Thr Arg Glu Val Met Ser Asp Glu Leu Thr Lys Leu Leu
        515                 520                 525

Glu Gly Asn Leu Lys Pro Ala Ile Asp Met Met Val Glu Phe Asn Thr
    530                 535                 540

Thr Gly Ser Leu Pro Glu Asn Ala Val Asp Val Leu Asn Thr Ala Leu
545                 550                 555                 560
```

```
Gly Asp Arg Lys Ser Phe Val Ala Leu Met Ala Leu Met Glu Tyr Ser
                565                 570                 575

Arg Tyr Leu Val Ala Glu Asp Lys Ser Ala Phe Val Thr Pro Leu Tyr
            580                 585                 590

Val Glu Ala Asp Gly Val Thr Asn Gly Pro Ile Asn Ala Met Met Leu
        595                 600                 605

Met Thr Gly Gly Leu Phe Thr Pro Asp Trp Ile Arg Asn Ile Ala Lys
    610                 615                 620

Gly Gly Leu Phe Ile Gly Ser Pro Asn Lys Thr Met Asn Glu His Arg
625                 630                 635                 640

Ser Thr Ala Asp Asn Asn Asp Leu Tyr Gln Ala Ser Thr Asn Ala Leu
                645                 650                 655

Met Glu Ser Leu Gly Lys Leu Arg Ser Asn Tyr Ala Ser Asn Met Pro
            660                 665                 670

Ile Gln Ser Gln Ile Asp Ser Leu Leu Ser Leu Met Asp Leu Phe Leu
        675                 680                 685

Pro Asp Ile Asn Leu Gly Glu Asn Gly Ala Leu Glu Leu Lys Arg Gly
    690                 695                 700

Ile Ala Lys Asn Pro Leu Thr Ile Thr Ile Phe Gly Ser Gly Ala Arg
705                 710                 715                 720

Gly Ile Ala Gly Lys Leu Val Ser Ser Val Thr Asp Ala Ile Tyr Glu
                725                 730                 735

Arg Met Ser Asp Val Leu Lys Ala Arg Ala Lys Asp Pro Asn Ile Ser
            740                 745                 750

Ala Ala Met Ala Met Phe Gly Lys Gln Ala Ala Ser Glu Ala His Ala
        755                 760                 765

Glu Glu Leu Leu Ala Arg Phe Leu Lys Asp Met Glu Thr Leu Thr Ser
    770                 775                 780

Thr Val Pro Val Lys Arg Lys Gly Val Leu Glu Leu Gln Ser Thr Gly
785                 790                 795                 800

Thr Gly Ala Lys Gly Lys Ile Asn Pro Lys Thr Tyr Thr Ile Lys Gly
                805                 810                 815

Glu Gln Leu Lys Ala Leu Gln Glu Asn Met Leu His Phe Phe Val Glu
            820                 825                 830

Pro Leu Arg Asn Gly Ile Thr Gln Thr Val Gly Glu Ser Leu Val Tyr
        835                 840                 845

Ser Thr Glu Gln Leu Gln Lys Ala Thr Gln Ile Gln Ser Val Val Leu
    850                 855                 860

Glu Asp Met Phe Lys Gln Arg Val Gln Glu Lys Leu Ala Glu Lys Ala
865                 870                 875                 880

Lys Asp Pro Thr Trp Lys Lys Gly Asp Phe Leu Thr Gln Lys Glu Leu
                885                 890                 895

Asn Asp Ile Gln Ala Ser Leu Asn Asn Leu Ala Pro Met Ile Glu Thr
            900                 905                 910

Gly Ser Gln Thr Phe Tyr Ile Ala Gly Ser Glu Asn Ala Glu Val Ala
        915                 920                 925

Asn Gln Val Leu Ala Thr Asn Leu Asp Asp Arg Met Arg Val Pro Met
    930                 935                 940

Ser Ile Tyr Ala Pro Ala Gln Ala Gly Val Ala Gly Ile Pro Phe Met
945                 950                 955                 960

Thr Ile Gly Thr Gly Asp Gly Met Met Met Gln Thr Leu Ser Thr Met
                965                 970                 975

Lys Gly Ala Pro Lys Asn Thr Leu Lys Ile Phe Asp Gly Met Asn Ile
```

```
            980                 985                 990

Gly Leu Asn Asp Ile Thr Asp Ala  Ser Arg Lys Ala Asn  Glu Ala Val
        995                 1000                1005

Tyr Thr  Ser Trp Gln Gly Asn  Pro Ile Lys Asn Val  Tyr Glu Ser
    1010                 1015                 1020

Tyr Ala  Lys Phe Met Lys Asn  Val Asp Phe Ser Lys  Leu Ser Pro
    1025                 1030                 1035

Glu Ala  Leu Glu Ala Ile Gly  Lys Ser Ala Leu Glu  Tyr Asp Gln
    1040                 1045                 1050

Arg Glu  Asn Ala Thr Val Asp  Asp Ile Ala Asn Ala  Ala Ser Leu
    1055                 1060                 1065

Ile Glu  Arg Asn Leu Arg Asn  Ile Ala Leu Gly Val  Asp Ile Arg
    1070                 1075                 1080

His Lys  Val Leu Asp Lys Val  Asn Leu Ser Ile Asp  Gln Met Ala
    1085                 1090                 1095

Ala Val  Gly Ala Pro Tyr Gln  Asn Asn Gly Lys Ile  Asp Leu Ser
    1100                 1105                 1110

Asn Met  Thr Pro Glu Gln Gln  Ala Asp Glu Leu Asn  Lys Leu Phe
    1115                 1120                 1125

Arg Glu  Glu Leu Glu Ala Arg  Lys Gln Lys Val Ala  Lys Ala Arg
    1130                 1135                 1140
```

<210> SEQ ID NO 9
<211> LENGTH: 69
<212> TYPE: DNA
<213> ORGANISM: Artificial Sequence
<220> FEATURE:
<223> OTHER INFORMATION: Synthetic

<400> SEQUENCE: 9

```
tcccagacaa aaggttaaga tttcatacag gattggatgc attacttcat ccaaaagaag     60

cggagcttc                                                             69
```

<210> SEQ ID NO 10
<211> LENGTH: 69
<212> TYPE: DNA
<213> ORGANISM: Artificial Sequence
<220> FEATURE:
<223> OTHER INFORMATION: Synthetic

<400> SEQUENCE: 10

```
tgggagagaa aaggttaaga tttgatagag gattggatgg attagttgat ggaaaagaag     60

cggagcttc                                                             69
```

<210> SEQ ID NO 11
<211> LENGTH: 69
<212> TYPE: DNA
<213> ORGANISM: Artificial Sequence
<220> FEATURE:
<223> OTHER INFORMATION: Synthetic

<400> SEQUENCE: 11

```
tccctgtctt ttggttttgt tttctttctg gtttggttgc ttttcttctt ccaaaagaag     60

cggagcttc                                                             69
```

<210> SEQ ID NO 12
<211> LENGTH: 69
<212> TYPE: DNA
<213> ORGANISM: Artificial Sequence
<220> FEATURE:

<223> OTHER INFORMATION: Synthetic

<400> SEQUENCE: 12

```
tcccacacaa aaccttaaca tttcatacac cattccatcc attacttcat ccaaaagaag     60

cggagcttc                                                             69
```

<210> SEQ ID NO 13
<211> LENGTH: 69
<212> TYPE: DNA
<213> ORGANISM: Artificial Sequence
<220> FEATURE:
<223> OTHER INFORMATION: Synthetic

<400> SEQUENCE: 13

```
acccagacaa aaggaaaaga aaacaaacag gaaaggaagc aaaacaacaa ccaaaagaag     60

cggagcttc                                                             69
```

<210> SEQ ID NO 14
<211> LENGTH: 10617
<212> TYPE: DNA
<213> ORGANISM: Artificial Sequence
<220> FEATURE:
<223> OTHER INFORMATION: Synthetic

<400> SEQUENCE: 14

```
atgggggggtt ctcatcatca tcatcatcat ggtatggcta gcatgactgg tggacagcaa     60

atgggtcggg atctgtacga cgatgacgat aaggatccga gctcgagatc tatgtcagta    120

tttgatagac tggctgggtt cgcagacagc gtaaccaatg caaagcaagt tgacgtctct    180

actgcaaccg cccagaagaa agctgaacaa ggtgtcacta ctcctcttgt ttctcctgat    240

gctgcttatc aaatgcaagc tgcccgtact ggtaatgttg ggctaatgc atttgaacca    300

gggacagtgc aatcagattt catgaatctg accccaatgc aaatcatgaa taagtatggg    360

gttgagcaag gcttacaact tatcaatgct cgtgctgatg cagggaacca ggtattcaat    420

gattcagtta ctacaagaac tcctggggaa gaactggggg atattgctac tggtgttggc    480

cttggttttg ttaataccct tgggggcatt ggtgctcttg ggcaggctt actcaacgat    540

gatgcaggtg ctgttgttgc tcaacaattg agtaagttta atgatgctgt tcatgctacc    600

caaagccagg cattacaaga taaacgtaag ctctttgctg ctcgtaactt aatgaatgaa    660

gtagagagtg aacgtcagta tcaaacagat aagaaagaag gcactaatga catagtagct    720

tccttatcta aatttggacg tgattttgta ggttcaattg agaatgctgc tcaaactgac    780

tctattattt ctgatgggtt agcagaaggg gtaggttctc tattaggtgc tggtcctgta    840

ttaaggggtg catctttact gggtaaagca gttgttccag caaatactct tcgtagtgct    900

gcattggctg gtgctattga tgcaggtact ggtactcagt cactggctcg tattgcctct    960

actgtaggta gagctgcacc gggtatggtt ggtgttggtg caatggaagc tggtggtgca   1020

taccaacaaa ctgctgatga aattatgaag atgagtctta aagacttaga gaagtctcct   1080

gtttatcagc aacatattaa agatggtatg tcccctgaac aggctcgtcg tcagactgca   1140

tctgaaactg gtcttactgc tgctgctatt caattaccta ttgctgctgc aaccggtcct   1200

ctggtatccc gttttgagat ggctcctttc cgtgctggct ctttaggtgc tgtaggtatg   1260

aaccttgccc gtgaaacagt ggaagaaggt gttcagggtg ctacaggcca actggctcag   1320

aatattgcac agcaacaaaa cattgataag aaccaagacc tgcttaaagg tgtcggtaca   1380

caggctggtt taggtgctct ttatggcttt ggttctgctg gtgttgtaca ggctccggct   1440
```

```
ggtgctgctc gtttagcagg tgctgcaact gctcctgtat tgcgtaccac aatggctggt   1500
gttaaagctg ctggtagtgt agcaggtaag gttgtttctc ctattaagaa tactttagta   1560
gctcgtggtg aacgggttat gaagcagaat gaagaagcat ctcctgttgc tgatgactat   1620
gttgcacagg cagcacaaga agctatggct caagcaccag aagcagaagt tactattcgt   1680
gatgctgttg aagcaactga tgctactcca gaacagaaag ttgcagcaca ccagtatgtt   1740
tctgacttaa tgaatgctac tcgttttaat cctgaaaatt atcaggaagc accagagcat   1800
attcgtaatg ctgtagctgg ttctactgac caagtacagg ttattcagaa gttagcagac   1860
ttagttaaca cattagatga atctaatcct caagcactga tggaagctgc atcttatatg   1920
tatgatgctg tttcagagtt tgagcagttc attaaccgtg accctgctgc actggatagc   1980
attcctaaag attctccggc tattgagtta ctcaaccgtt atacgaatct gacagctaat   2040
attcagaaca caccaaaagt aattggtgca ctgaatgtta ttaatcgaat gattaatgaa   2100
tctgctcaga atggttcttt gaatgtgact gaagaatcca gtccacagga aatgcagaac   2160
gtagcattag ctgctgaagt agcccctgaa aagctcaatc cagagtctgt aaatgttgtt   2220
cttaaacatg ctgctgatgg tcgtattaaa ctgaataatc gccagattgc tgccctccag   2280
aatgctgctg caatcctgaa gggggcacgg gaatatgatg cagaagctgc ccgtcttgga   2340
ttacgtcctc aagacattgt gagtaaacag attaaaacgg atgagagcag aactcaggaa   2400
ggacaatact ctgcgttgca acatgcgaat aggattcggt ctgcgtataa ctctggtaat   2460
ttcgagttgg cctccgctta cctgaacgac tttatgcagt tcgcccagca catgcagaat   2520
aaggttggag cgttgaatga gcatcttgtt acggggaatg cggataagaa taagtctgtc   2580
cactaccaag ctcttactgc tgacagagaa tgggttcgta gccgtaccgg attgggggtc   2640
aatccctatg acactaagtc ggttaaattt gcccagcaag ttgctcttga agcgaaaacg   2700
gtagcggata ttgctaatgc cctcgcttcg gcttacccgg aactgaaggt cagtcatata   2760
aaagttactc cattggattc acgtcttaac gctcctgctg ctgaggtggt caaggcattc   2820
cgtcaaggca atcgagacgt tgcttcttct caaccgaaag ctgactccgt gaatcaggtt   2880
aaagaaactc ctgttacaaa acaggaacca gttacatcta ctgtacagac taagactcct   2940
gttagtgaat ctgttaaaac agaacctact actaaagagt ctagcccaca ggctataaaa   3000
gaacctgtga accagtctga aaaacaggat gttaacctta ctaatgagga caacatcaag   3060
caacctactg aatctgttaa agaaactgaa acttctacaa aagaaagtac agttacagaa   3120
gaattaaaag aaggtattga tgctgtttac ccttcattgg taggtactgc tgattctaaa   3180
gcagagggta ttaagaacta tttcaaattg tcctttacct taccagaaga acagaaatcc   3240
cgtactgttg gttcagaagc acctctaaaa gatgtagccc aagctctgtc ttctcgtgct   3300
cgttatgaac tctttactga gaaagaaact gctaaccctg cttttaatgg ggaagttatt   3360
aagcgataca aagaactcat ggaacatggg gaaggtattg ctgatattct tcgctcccgt   3420
ctggctaagt tccttaacac taaggatgtt ggtaaacgtt ttgctcaagg tacagaagcc   3480
aaccgttggg taggtggtaa gttacttaac attgttgagc aggatgggga tacctttaag   3540
tacaacgaac aattgctaca gactgctgta ttagcaggtc ttcaatggag acttactgct   3600
accagcaata ctgctatcaa agatgcaaaa gatgttgctg ctattactgg tattgaccaa   3660
gctctgctgc cagaaggttt agtagagcaa tttgatactg gtatgacact cactgaagca   3720
gttagttccc tggctcagaa aattgagtct tactggggat tatctcgtaa tccaaatgct   3780
ccattgggct ataccaaagg catccctaca gcaatggctg ctgaaattct ggctgcattt   3840
```

```
gtagagtcta ctgatgttgt agagaacatc gtggatatgt cagaaattga cccagataac   3900
aagaagacta ttggtctgta caccattact gaactggatt ccttcgaccc aattaatagc   3960
ttccctactg ctattgaaga agctgtttta gtgaatccta cagagaagat gttctttggt   4020
gatgacattc ctcctgtagc taatactcag cttcgtaacc ctgctgttcg taatactcca   4080
gaacagaagg ctgcattgaa agcagagcag gctacagagt tctatgtaca caccccaatg   4140
gttcaattct atgagacgtt aggtaaagac cgtattctcg aactgatggg tgctggtact   4200
ctgaataaag agttacttaa tgataaccat gctaaatctc tggaaggtaa gaaccgttca   4260
gtagaggact cttacaacca actgttctcc gtcattgagc aggtaagagc acagagcgaa   4320
gacatctcta ctgtacctat tcactatgca tacaatatga cccgtgttgg tcgtatgcag   4380
atgttaggta aatacaatcc tcaatcagcc aaactggttc gtgaggccat cttacctact   4440
aaagctactt tggatttatc gaaccagaac aatgaagact tctctgcatt ccagttaggt   4500
ctggctcagg cattggacat taaagtccat actatgactc gtgaggttat gtctgacgag   4560
ttgactaaat tactggaagg taatctgaaa ccagccattg atatgatggt tgagtttaat   4620
accactggtt ccttaccaga aaacgcagtt gatgttctga atacagcatt aggagatagg   4680
aagtcattcg tagcattgat ggctcttatg gagtattccc gttacttagt agcagaggat   4740
aaatctgcat ttgtaactcc actgtatgta gaagcagatg gtgttactaa tggtccaatc   4800
aatgccatga tgctaatgac aggcggtctg tttactcctg actggattcg taatattgcc   4860
aaagggggct tgttcattgg ttctccaaat aagaccatga atgagcatcg ctctactgct   4920
gacaataatg atttatatca agcatccact aatgctttga tggaatcgtt gggtaagtta   4980
cgtagtaact atgcctctaa tatgcctatt cagtctcaga tagacagtct tctttctctg   5040
atggatttgt ttttaccgga tattaatctt ggtgagaatg gtgctttaga acttaaacgt   5100
ggtattgcta agaacccact gactattacc atctatggtt ctggtgctcg tggtattgca   5160
ggtaagctgg ttagttctgt tactgatgcc atctatgagc gtatgtctga tgtactgaaa   5220
gctcgtgcta aagacccaaa tatctctgct gctatggcaa tgtttggtaa gcaagctgct   5280
tcagaagcac atgctgaaga acttcttgcc cgtttcctga aagatatgga aacactgact   5340
tctactgttc ctgttaaacg taaaggtgta ctggaactac aatccacagg tacaggagcc   5400
aaaggaaaaa tcaatcctaa gacctatacc attaagggcg agcaactgaa ggcacttcag   5460
gaaaatatgc tgcacttctt tgtagaacca ctacgtaatg gtattactca gactgtaggt   5520
gaaagtctgg tgtactctac tgaacaatta cagaaagcta ctcagattca atctgtagtg   5580
ctggaagata tgttcaaaca gcgagtacaa gagaagctgg cagagaaggc taaagaccca   5640
acatggaaga aaggtgattt ccttactcag aaagaactga atgatattca ggcttctctg   5700
aataacttag cccctatgat tgagactggt tctcagactt tctacattgc tggttcagaa   5760
aatgcagaag tagcaaatca ggtattagct actaaccttg atgaccgtat gcgtgtacca   5820
atgagtatct atgctccagc acaggccggt gtagcaggta ttccatttat gactattggt   5880
actggtgatg gcatgatgat gcaaactctt tccactatga aaggtgcacc aaagaatacc   5940
ctcaaaatct ttgatggtat gaacattggt ttgaatgaca tcactgatgc cagtcgtaaa   6000
gctaatgaag ctgtttacac ttcttggcag ggtaacccta ttaagaatgt ttatgaatca   6060
tatgctaagt tcatgaagaa tgtagatttc agcaagctgt cccctgaagc attggaagca   6120
attggtaaat ctgctctgga atatgaccaa cgtgagaatg ctactgtaga tgatattgct   6180
aacgctgcat ctctgattga acgtaactta cgtaatattg cactgggtgt agatattcgt   6240
```

```
cataaggtgc tggataaggt aaatctgtcc attgaccaga tggctgctgt aggtgctcct   6300
tatcagaaca acggtaagat tgacctcagc aatatgaccc ctgaacaaca ggctgatgaa   6360
ctgaataaac ttttccgtga agagttagaa gcccgtaaac aaaaagtcgc taaggctagg   6420
gctgaagtca aagaagaaac tgtttctgaa aaagaaccag tgaatccaga ctttggtatg   6480
gtaggccgtg agcataaggc atctggtgtt cgtatcctgt ctgctactgc tattcgtaat   6540
ctggctaaga ttagtaatct gccatctact caggcagcta ctcttgcgga gattcagaaa   6600
tcactggcag ctaaagacta taagattatc tacggtacac ctactcaggt tgcagagtat   6660
gctcgtcaga agaatgttac tgaattgact tctcaggaaa tggaagaagc tcaggcaggt   6720
aatatttatg gctggactaa cttcgatgat aagaccattt atctggttag cccatctatg   6780
gaaaccctca ttcatgaact ggttcatgcc tctaccttcg aggaagttta ttccttctat   6840
cagggtaatg aagtaagccc tacttctaag caggctattg agaaccttga aggtctgatg   6900
gaacagttcc gttctctgga tatttccaaa gattctccag aaatgagaga agcatatgct   6960
gatgctattg caactatcga aggtcatttg agtaatggat ttgttgaccc agctatctct   7020
aaagctgctg ctcttaatga gtttatggct tgggggttag ctaaccgtgc tcttgctgct   7080
aaacagaaga gaacatcttc actggttcaa atggtgaaag atgtttatca ggctattaag   7140
aaattgattt ggggacgtaa acaagctcct gcattgggag aagatatgtt ctccaatctg   7200
ctgtttaact ctgcaattct gatgcgtagc caacctacaa ctcaggcagt agctaaagat   7260
ggcacactgt tccatagcaa agcatatggt aataatgaac gtctgtctca gttgaaccag   7320
actttcgata aactggtaac tgattacctt cgtactgacc cagttacaga agtagaacgt   7380
cgtggcaatg tggctaatgc attaatgagt gctactcgac tggttcgtga tgttcagtct   7440
catggcttca atatgactgc tcaggaacag tctgtattcc agatggttac tgctgcatta   7500
gcaactgaag ctgcgattga cccacatgct atggctcgtg ctcaggaact ttatacccat   7560
gtaatgaaac accttacggt agagcatttc atggctgacc ctgatagtac taaccctgct   7620
gaccgttact atgctcaaca gaaatatgac accatctctg gtgctaatct ggttgaagta   7680
gatgccaaag gtagaaccag tctgttacct acattcctgg gtctggctat ggttaatgaa   7740
gaactacgtt caatcattaa agaaatgcct gtacctaaag cagataagaa attagggaat   7800
gatatagata ctctgcttac caatgcaggt actcaggtaa tggaatctct gaaccgtcgt   7860
atggctggtg accagaaagc tactaatgtt caggacagta ttgatgcttt gtcagaaaca   7920
atcatggctg ctgctttgaa acgagagtcc ttctatgatg ctgtagcaac ccctaccggt   7980
aacttcattg accgtgctaa tcagtacgta acggatagca ttgaacggtt atctgaaact   8040
gttattgaga aggcagataa ggtaattgct aacccttcta atatagctgc taaaggtgtt   8100
gctcatctgg ctaaactgac tgctgctatt gcatctgaaa aacagggtga aatagtggct   8160
cagggtgtta tgactgctat gaaccagggt aaagtatggc aaccttttcca tgacttagtt   8220
aatgacattg ttggccgtac taagactaat gccaatgtct atgacttaat caaattggtt   8280
aagagccaga tttctcaaga ccgtcagcaa ttccgtgagc atttacctac agtcattgct   8340
ggtaagttct ctcgtaaatt gactgatacc gaatggtctg caatgcatac tggtttaggt   8400
aaaacagatt tagctgttct acgtgaaact atgagcatgg ctgaaattag agatttactc   8460
tcttcatcca agaaagtgaa agatgaaatc tctactctgg aaaaagagat tcagaaccaa   8520
gcaggtagaa actggaatct ggttcagaag aaatctaagc aactggctca atacatgatt   8580
atgggggaag taggtaataa cctccttcgt aatgcccatg ctattagtcg tttgttaggt   8640
```

```
gaacgtatta ctaatggtcc tgtggcagat gtagctgcta ttgataagct cattactttg   8700

tactctctgg aattgatgaa taagtctgac cgtgaccttt tgtcagaatt ggctcaatca   8760

gaagtggaag gtatggagtt ctccattgct tatatggttg gtcaacgtac tgaagagatg   8820

cgtaaagcta aaggtgataa ccgtactctg ctgaatcact ttaaaggcta tatccctgta   8880

gagaaccagc aaggtgtgaa tttgattatt gctgacgata aagagtttgc taagttaaat   8940

agccaatcct ttactcgtat tggtacttat caggggagca ctggtttccg tactggttct   9000

aaaggttatt acttcagccc agtagctgcc cgtgcccctt actctcaggg tattcttcag   9060

aacgttcgta atactgctgg tggtgtggat attggtactg gctttacgtt aggcactatg   9120

gttgctgggc gtattactga caaaccaacc gtagagcgta ttaccaaagc tctggctaaa   9180

ggtgagcgtg ggcgtgaacc actgatgcca atttataaca gcaaaggtca ggtagttgct   9240

tatgaacaat ccgttgaccc taatatgttg aagcacctaa accaagacaa tcactttgct   9300

aagatggttg gtgtatggcg tggtcgtcag gtggaagagg ctaaagcaca acgttttaat   9360

gacattctca ttgagcaatt acatgctatg tatgagaaag acattaaaga ctccagtgct   9420

aataaatctc aatatgtaaa cctgttaggt aaaattgatg acccagtact ggctgatgcg   9480

attaacctga tgaacattga gactcgtcat aaggccgaag aactcttcgg taaagatgag   9540

ttatgggttc gtagggatat gctgaatgat gcacttggct atcgtgctgc atctattggt   9600

gatgtgtgga ccggtaactc tcgttggtca cctagcaccc ttgatactgt taagaagatg   9660

ttcctcggtg cattcggtaa taaggcatat catgtagtaa tgaatgctga aaataccatt   9720

cagaacttag tgaaggacgc taagacagta attgttgtta aatctgttgt agtaccggca   9780

gttaacttcc ttgctaacat ctaccagatg attggacgtg gtgttcctgt taaagatatt   9840

gctgtgaaca ttcctcgtaa gacgtcagag attaatcagt atattaaatc tcgtttacgt   9900

cagattgatg cggaagcaga gctacgtgct gctgaaggta accctaatct ggttcgtaaa   9960

cttaaaactg agattcaatc tattactgat agtcatcgtc gtatgagtat ctggcctttg  10020

attgaagcag gtgagttctc ttctattgct gatgctggta ttagtcgtga tgacctgtta  10080

gtagctgaag gtaagattca tgagtacatg gaaaaacttg ctaataaact tccagaaaaa  10140

gtacgtaatg ctggccgtta cgctcttatt gctaaggaca ctgctctgtt ccagggtatc  10200

cagaaaacag tagagtattc agactttatt gctaaagcca tcatctatga tgatttagtg  10260

aaacgtaaga aaaaatcttc ttctgaagca ttaggtcagg taactgaaga gtttattaac  10320

tatgacagat tgcctggtcg tttccgtggc tatatggaaa gtatgggtct gatgtggttc  10380

tacaacttta aaattcgttc cattaaagtt gctatgagca tgattagaaa caacccagta  10440

cattctctga ttgctacagt agtacctgct cctaccatgt ttggtaacgt aggtctacca  10500

attcaggaca acatgctaac catgctggct gaaggaagac tggattactc attaggcttc  10560

ggacaaggat taagagcacc taccctcaat ccttggttca accttactca ctaataa     10617
```

<210> SEQ ID NO 15
<211> LENGTH: 3537
<212> TYPE: PRT
<213> ORGANISM: Artificial Sequence
<220> FEATURE:
<223> OTHER INFORMATION: Synthetic

<400> SEQUENCE: 15

```
Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
```

```
            20                  25                  30

Pro Ser Ser Arg Ser Met Ser Val Phe Asp Arg Leu Ala Gly Phe Ala
        35                  40                  45

Asp Ser Val Thr Asn Ala Lys Gln Val Asp Val Ser Thr Ala Thr Ala
    50                  55                  60

Gln Lys Lys Ala Glu Gln Gly Val Thr Thr Pro Leu Val Ser Pro Asp
65                  70                  75                  80

Ala Ala Tyr Gln Met Gln Ala Ala Arg Thr Gly Asn Val Gly Ala Asn
                85                  90                  95

Ala Phe Glu Pro Gly Thr Val Gln Ser Asp Phe Met Asn Leu Thr Pro
            100                 105                 110

Met Gln Ile Met Asn Lys Tyr Gly Val Glu Gln Gly Leu Gln Leu Ile
        115                 120                 125

Asn Ala Arg Ala Asp Ala Gly Asn Gln Val Phe Asn Asp Ser Val Thr
    130                 135                 140

Thr Arg Thr Pro Gly Glu Glu Leu Gly Asp Ile Ala Thr Gly Val Gly
145                 150                 155                 160

Leu Gly Phe Val Asn Thr Leu Gly Gly Ile Gly Ala Leu Gly Ala Gly
                165                 170                 175

Leu Leu Asn Asp Asp Ala Gly Ala Val Val Ala Gln Gln Leu Ser Lys
            180                 185                 190

Phe Asn Asp Ala Val His Ala Thr Gln Ser Gln Ala Leu Gln Asp Lys
        195                 200                 205

Arg Lys Leu Phe Ala Ala Arg Asn Leu Met Asn Glu Val Glu Ser Glu
    210                 215                 220

Arg Gln Tyr Gln Thr Asp Lys Lys Glu Gly Thr Asn Asp Ile Val Ala
225                 230                 235                 240

Ser Leu Ser Lys Phe Gly Arg Asp Phe Val Gly Ser Ile Glu Asn Ala
                245                 250                 255

Ala Gln Thr Asp Ser Ile Ile Ser Asp Gly Leu Ala Glu Gly Val Gly
            260                 265                 270

Ser Leu Leu Gly Ala Gly Pro Val Leu Arg Gly Ala Ser Leu Leu Gly
        275                 280                 285

Lys Ala Val Val Pro Ala Asn Thr Leu Arg Ser Ala Ala Leu Ala Gly
    290                 295                 300

Ala Ile Asp Ala Gly Thr Gly Thr Gln Ser Leu Ala Arg Ile Ala Ser
305                 310                 315                 320

Thr Val Gly Arg Ala Ala Pro Gly Met Val Gly Val Gly Ala Met Glu
                325                 330                 335

Ala Gly Gly Ala Tyr Gln Gln Thr Ala Asp Glu Ile Met Lys Met Ser
            340                 345                 350

Leu Lys Asp Leu Glu Lys Ser Pro Val Tyr Gln Gln His Ile Lys Asp
        355                 360                 365

Gly Met Ser Pro Glu Gln Ala Arg Arg Gln Thr Ala Ser Glu Thr Gly
    370                 375                 380

Leu Thr Ala Ala Ala Ile Gln Leu Pro Ile Ala Ala Ala Thr Gly Pro
385                 390                 395                 400

Leu Val Ser Arg Phe Glu Met Ala Pro Phe Arg Ala Gly Ser Leu Gly
                405                 410                 415

Ala Val Gly Met Asn Leu Ala Arg Glu Thr Val Glu Glu Gly Val Gln
            420                 425                 430

Gly Ala Thr Gly Gln Leu Ala Gln Asn Ile Ala Gln Gln Gln Asn Ile
        435                 440                 445
```

```
Asp Lys Asn Gln Asp Leu Leu Lys Gly Val Gly Thr Gln Ala Gly Leu
    450                 455                 460

Gly Ala Leu Tyr Gly Phe Gly Ser Ala Gly Val Val Gln Ala Pro Ala
465                 470                 475                 480

Gly Ala Ala Arg Leu Ala Gly Ala Ala Thr Ala Pro Val Leu Arg Thr
                485                 490                 495

Thr Met Ala Gly Val Lys Ala Ala Gly Ser Val Ala Gly Lys Val Val
            500                 505                 510

Ser Pro Ile Lys Asn Thr Leu Val Ala Arg Gly Glu Arg Val Met Lys
        515                 520                 525

Gln Asn Glu Glu Ala Ser Pro Val Ala Asp Asp Tyr Val Ala Gln Ala
    530                 535                 540

Ala Gln Glu Ala Met Ala Gln Ala Pro Glu Ala Glu Val Thr Ile Arg
545                 550                 555                 560

Asp Ala Val Glu Ala Thr Asp Ala Thr Pro Glu Gln Lys Val Ala Ala
                565                 570                 575

His Gln Tyr Val Ser Asp Leu Met Asn Ala Thr Arg Phe Asn Pro Glu
            580                 585                 590

Asn Tyr Gln Glu Ala Pro Glu His Ile Arg Asn Ala Val Ala Gly Ser
        595                 600                 605

Thr Asp Gln Val Gln Val Ile Gln Lys Leu Ala Asp Leu Val Asn Thr
    610                 615                 620

Leu Asp Glu Ser Asn Pro Gln Ala Leu Met Glu Ala Ala Ser Tyr Met
625                 630                 635                 640

Tyr Asp Ala Val Ser Glu Phe Glu Gln Phe Ile Asn Arg Asp Pro Ala
                645                 650                 655

Ala Leu Asp Ser Ile Pro Lys Asp Ser Pro Ala Ile Glu Leu Leu Asn
            660                 665                 670

Arg Tyr Thr Asn Leu Thr Ala Asn Ile Gln Asn Thr Pro Lys Val Ile
        675                 680                 685

Gly Ala Leu Asn Val Ile Asn Arg Met Ile Asn Glu Ser Ala Gln Asn
    690                 695                 700

Gly Ser Leu Asn Val Thr Glu Glu Ser Ser Pro Gln Glu Met Gln Asn
705                 710                 715                 720

Val Ala Leu Ala Ala Glu Val Ala Pro Glu Lys Leu Asn Pro Glu Ser
                725                 730                 735

Val Asn Val Val Leu Lys His Ala Ala Asp Gly Arg Ile Lys Leu Asn
            740                 745                 750

Asn Arg Gln Ile Ala Ala Leu Gln Asn Ala Ala Ala Ile Leu Lys Gly
        755                 760                 765

Ala Arg Glu Tyr Asp Ala Glu Ala Ala Arg Leu Gly Leu Arg Pro Gln
    770                 775                 780

Asp Ile Val Ser Lys Gln Ile Lys Thr Asp Glu Ser Arg Thr Gln Glu
785                 790                 795                 800

Gly Gln Tyr Ser Ala Leu Gln His Ala Asn Arg Ile Arg Ser Ala Tyr
                805                 810                 815

Asn Ser Gly Asn Phe Glu Leu Ala Ser Ala Tyr Leu Asn Asp Phe Met
            820                 825                 830

Gln Phe Ala Gln His Met Gln Asn Lys Val Gly Ala Leu Asn Glu His
        835                 840                 845

Leu Val Thr Gly Asn Ala Asp Lys Asn Lys Ser Val His Tyr Gln Ala
    850                 855                 860

Leu Thr Ala Asp Arg Glu Trp Val Arg Ser Arg Thr Gly Leu Gly Val
865                 870                 875                 880
```

```
Asn Pro Tyr Asp Thr Lys Ser Val Lys Phe Ala Gln Gln Val Ala Leu
                885                 890                 895

Glu Ala Lys Thr Val Ala Asp Ile Ala Asn Ala Leu Ala Ser Ala Tyr
            900                 905                 910

Pro Glu Leu Lys Val Ser His Ile Lys Val Thr Pro Leu Asp Ser Arg
        915                 920                 925

Leu Asn Ala Pro Ala Ala Glu Val Val Lys Ala Phe Arg Gln Gly Asn
    930                 935                 940

Arg Asp Val Ala Ser Ser Gln Pro Lys Ala Asp Ser Val Asn Gln Val
945                 950                 955                 960

Lys Glu Thr Pro Val Thr Lys Gln Glu Pro Val Thr Ser Thr Val Gln
                965                 970                 975

Thr Lys Thr Pro Val Ser Glu Ser Val Lys Thr Glu Pro Thr Thr Lys
            980                 985                 990

Glu Ser Ser Pro Gln Ala Ile Lys  Glu Pro Val Asn Gln  Ser Glu Lys
        995                 1000                 1005

Gln Asp  Val Asn Leu Thr Asn  Glu Asp Asn Ile Lys  Gln Pro Thr
    1010                 1015                 1020

Glu Ser  Val Lys Glu Thr Glu  Thr Ser Thr Lys Glu  Ser Thr Val
    1025                 1030                 1035

Thr Glu  Glu Leu Lys Glu Gly  Ile Asp Ala Val Tyr  Pro Ser Leu
    1040                 1045                 1050

Val Gly  Thr Ala Asp Ser Lys  Ala Glu Gly Ile Lys  Asn Tyr Phe
    1055                 1060                 1065

Lys Leu  Ser Phe Thr Leu Pro  Glu Glu Gln Lys Ser  Arg Thr Val
    1070                 1075                 1080

Gly Ser  Glu Ala Pro Leu Lys  Asp Val Ala Gln Ala  Leu Ser Ser
    1085                 1090                 1095

Arg Ala  Arg Tyr Glu Leu Phe  Thr Glu Lys Glu Thr  Ala Asn Pro
    1100                 1105                 1110

Ala Phe  Asn Gly Glu Val Ile  Lys Arg Tyr Lys Glu  Leu Met Glu
    1115                 1120                 1125

His Gly  Glu Gly Ile Ala Asp  Ile Leu Arg Ser Arg  Leu Ala Lys
    1130                 1135                 1140

Phe Leu  Asn Thr Lys Asp Val  Gly Lys Arg Phe Ala  Gln Gly Thr
    1145                 1150                 1155

Glu Ala  Asn Arg Trp Val Gly  Gly Lys Leu Leu Asn  Ile Val Glu
    1160                 1165                 1170

Gln Asp  Gly Asp Thr Phe Lys  Tyr Asn Glu Gln Leu  Leu Gln Thr
    1175                 1180                 1185

Ala Val  Leu Ala Gly Leu Gln  Trp Arg Leu Thr Ala  Thr Ser Asn
    1190                 1195                 1200

Thr Ala  Ile Lys Asp Ala Lys  Asp Val Ala Ala Ile  Thr Gly Ile
    1205                 1210                 1215

Asp Gln  Ala Leu Leu Pro Glu  Gly Leu Val Glu Gln  Phe Asp Thr
    1220                 1225                 1230

Gly Met  Thr Leu Thr Glu Ala  Val Ser Ser Leu Ala  Gln Lys Ile
    1235                 1240                 1245

Glu Ser  Tyr Trp Gly Leu Ser  Arg Asn Pro Asn Ala  Pro Leu Gly
    1250                 1255                 1260

Tyr Thr  Lys Gly Ile Pro Thr  Ala Met Ala Ala Glu  Ile Leu Ala
    1265                 1270                 1275

Ala Phe  Val Glu Ser Thr Asp  Val Val Glu Asn Ile  Val Asp Met
```

```
    1280                1285                1290

Ser Glu  Ile Asp Pro Asp Asn  Lys Lys Thr Ile Gly  Leu Tyr Thr
    1295                1300                1305

Ile Thr  Glu Leu Asp Ser Phe  Asp Pro Ile Asn Ser  Phe Pro Thr
    1310                1315                1320

Ala Ile  Glu Glu Ala Val Leu  Val Asn Pro Thr Glu  Lys Met Phe
    1325                1330                1335

Phe Gly  Asp Asp Ile Pro Pro  Val Ala Asn Thr Gln  Leu Arg Asn
    1340                1345                1350

Pro Ala  Val Arg Asn Thr Pro  Glu Gln Lys Ala Ala  Leu Lys Ala
    1355                1360                1365

Glu Gln  Ala Thr Glu Phe Tyr  Val His Thr Pro Met  Val Gln Phe
    1370                1375                1380

Tyr Glu  Thr Leu Gly Lys Asp  Arg Ile Leu Glu Leu  Met Gly Ala
    1385                1390                1395

Gly Thr  Leu Asn Lys Glu Leu  Leu Asn Asp Asn His  Ala Lys Ser
    1400                1405                1410

Leu Glu  Gly Lys Asn Arg Ser  Val Glu Asp Ser Tyr  Asn Gln Leu
    1415                1420                1425

Phe Ser  Val Ile Glu Gln Val  Arg Ala Gln Ser Glu  Asp Ile Ser
    1430                1435                1440

Thr Val  Pro Ile His Tyr Ala  Tyr Asn Met Thr Arg  Val Gly Arg
    1445                1450                1455

Met Gln  Met Leu Gly Lys Tyr  Asn Pro Gln Ser Ala  Lys Leu Val
    1460                1465                1470

Arg Glu  Ala Ile Leu Pro Thr  Lys Ala Thr Leu Asp  Leu Ser Asn
    1475                1480                1485

Gln Asn  Asn Glu Asp Phe Ser  Ala Phe Gln Leu Gly  Leu Ala Gln
    1490                1495                1500

Ala Leu  Asp Ile Lys Val His  Thr Met Thr Arg Glu  Val Met Ser
    1505                1510                1515

Asp Glu  Leu Thr Lys Leu Leu  Glu Gly Asn Leu Lys  Pro Ala Ile
    1520                1525                1530

Asp Met  Met Val Glu Phe Asn  Thr Thr Gly Ser Leu  Pro Glu Asn
    1535                1540                1545

Ala Val  Asp Val Leu Asn Thr  Ala Leu Gly Asp Arg  Lys Ser Phe
    1550                1555                1560

Val Ala  Leu Met Ala Leu Met  Glu Tyr Ser Arg Tyr  Leu Val Ala
    1565                1570                1575

Glu Asp  Lys Ser Ala Phe Val  Thr Pro Leu Tyr Val  Glu Ala Asp
    1580                1585                1590

Gly Val  Thr Asn Gly Pro Ile  Asn Ala Met Met Leu  Met Thr Gly
    1595                1600                1605

Gly Leu  Phe Thr Pro Asp Trp  Ile Arg Asn Ile Ala  Lys Gly Gly
    1610                1615                1620

Leu Phe  Ile Gly Ser Pro Asn  Lys Thr Met Asn Glu  His Arg Ser
    1625                1630                1635

Thr Ala  Asp Asn Asn Asp Leu  Tyr Gln Ala Ser Thr  Asn Ala Leu
    1640                1645                1650

Met Glu  Ser Leu Gly Lys Leu  Arg Ser Asn Tyr Ala  Ser Asn Met
    1655                1660                1665

Pro Ile  Gln Ser Gln Ile Asp  Ser Leu Leu Ser Leu  Met Asp Leu
    1670                1675                1680
```

```
Phe Leu Pro Asp Ile Asn Leu Gly Glu Asn Gly Ala Leu Glu Leu
    1685                1690                1695

Lys Arg Gly Ile Ala Lys Asn Pro Leu Thr Ile Thr Ile Tyr Gly
    1700                1705                1710

Ser Gly Ala Arg Gly Ile Ala Gly Lys Leu Val Ser Ser Val Thr
    1715                1720                1725

Asp Ala Ile Tyr Glu Arg Met Ser Asp Val Leu Lys Ala Arg Ala
    1730                1735                1740

Lys Asp Pro Asn Ile Ser Ala Ala Met Ala Met Phe Gly Lys Gln
    1745                1750                1755

Ala Ala Ser Glu Ala His Ala Glu Glu Leu Leu Ala Arg Phe Leu
    1760                1765                1770

Lys Asp Met Glu Thr Leu Thr Ser Thr Val Pro Val Lys Arg Lys
    1775                1780                1785

Gly Val Leu Glu Leu Gln Ser Thr Gly Thr Gly Ala Lys Gly Lys
    1790                1795                1800

Ile Asn Pro Lys Thr Tyr Thr Ile Lys Gly Glu Gln Leu Lys Ala
    1805                1810                1815

Leu Gln Glu Asn Met Leu His Phe Phe Val Glu Pro Leu Arg Asn
    1820                1825                1830

Gly Ile Thr Gln Thr Val Gly Glu Ser Leu Val Tyr Ser Thr Glu
    1835                1840                1845

Gln Leu Gln Lys Ala Thr Gln Ile Gln Ser Val Val Leu Glu Asp
    1850                1855                1860

Met Phe Lys Gln Arg Val Gln Glu Lys Leu Ala Glu Lys Ala Lys
    1865                1870                1875

Asp Pro Thr Trp Lys Lys Gly Asp Phe Leu Thr Gln Lys Glu Leu
    1880                1885                1890

Asn Asp Ile Gln Ala Ser Leu Asn Asn Leu Ala Pro Met Ile Glu
    1895                1900                1905

Thr Gly Ser Gln Thr Phe Tyr Ile Ala Gly Ser Glu Asn Ala Glu
    1910                1915                1920

Val Ala Asn Gln Val Leu Ala Thr Asn Leu Asp Asp Arg Met Arg
    1925                1930                1935

Val Pro Met Ser Ile Tyr Ala Pro Ala Gln Ala Gly Val Ala Gly
    1940                1945                1950

Ile Pro Phe Met Thr Ile Gly Thr Gly Asp Gly Met Met Met Gln
    1955                1960                1965

Thr Leu Ser Thr Met Lys Gly Ala Pro Lys Asn Thr Leu Lys Ile
    1970                1975                1980

Phe Asp Gly Met Asn Ile Gly Leu Asn Asp Ile Thr Asp Ala Ser
    1985                1990                1995

Arg Lys Ala Asn Glu Ala Val Tyr Thr Ser Trp Gln Gly Asn Pro
    2000                2005                2010

Ile Lys Asn Val Tyr Glu Ser Tyr Ala Lys Phe Met Lys Asn Val
    2015                2020                2025

Asp Phe Ser Lys Leu Ser Pro Glu Ala Leu Glu Ala Ile Gly Lys
    2030                2035                2040

Ser Ala Leu Glu Tyr Asp Gln Arg Glu Asn Ala Thr Val Asp Asp
    2045                2050                2055

Ile Ala Asn Ala Ala Ser Leu Ile Glu Arg Asn Leu Arg Asn Ile
    2060                2065                2070

Ala Leu Gly Val Asp Ile Arg His Lys Val Leu Asp Lys Val Asn
    2075                2080                2085
```

```
Leu Ser  Ile Asp Gln Met Ala  Ala Val Gly Ala Pro  Tyr Gln Asn
    2090                 2095                 2100

Asn Gly  Lys Ile Asp Leu Ser  Asn Met Thr Pro Glu  Gln Gln Ala
    2105                 2110                 2115

Asp Glu  Leu Asn Lys Leu Phe  Arg Glu Glu Leu Glu  Ala Arg Lys
    2120                 2125                 2130

Gln Lys  Val Ala Lys Ala Arg  Ala Glu Val Lys Glu  Glu Thr Val
    2135                 2140                 2145

Ser Glu  Lys Glu Pro Val Asn  Pro Asp Phe Gly Met  Val Gly Arg
    2150                 2155                 2160

Glu His  Lys Ala Ser Gly Val  Arg Ile Leu Ser Ala  Thr Ala Ile
    2165                 2170                 2175

Arg Asn  Leu Ala Lys Ile Ser  Asn Leu Pro Ser Thr  Gln Ala Ala
    2180                 2185                 2190

Thr Leu  Ala Glu Ile Gln Lys  Ser Leu Ala Ala Lys  Asp Tyr Lys
    2195                 2200                 2205

Ile Ile  Tyr Gly Thr Pro Thr  Gln Val Ala Glu Tyr  Ala Arg Gln
    2210                 2215                 2220

Lys Asn  Val Thr Glu Leu Thr  Ser Gln Glu Met Glu  Glu Ala Gln
    2225                 2230                 2235

Ala Gly  Asn Ile Tyr Gly Trp  Thr Asn Phe Asp Asp  Lys Thr Ile
    2240                 2245                 2250

Tyr Leu  Val Ser Pro Ser Met  Glu Thr Leu Ile His  Glu Leu Val
    2255                 2260                 2265

His Ala  Ser Thr Phe Glu Glu  Val Tyr Ser Phe Tyr  Gln Gly Asn
    2270                 2275                 2280

Glu Val  Ser Pro Thr Ser Lys  Gln Ala Ile Glu Asn  Leu Glu Gly
    2285                 2290                 2295

Leu Met  Glu Gln Phe Arg Ser  Leu Asp Ile Ser Lys  Asp Ser Pro
    2300                 2305                 2310

Glu Met  Arg Glu Ala Tyr Ala  Asp Ala Ile Ala Thr  Ile Glu Gly
    2315                 2320                 2325

His Leu  Ser Asn Gly Phe Val  Asp Pro Ala Ile Ser  Lys Ala Ala
    2330                 2335                 2340

Ala Leu  Asn Glu Phe Met Ala  Trp Gly Leu Ala Asn  Arg Ala Leu
    2345                 2350                 2355

Ala Ala  Lys Gln Lys Arg Thr  Ser Ser Leu Val Gln  Met Val Lys
    2360                 2365                 2370

Asp Val  Tyr Gln Ala Ile Lys  Lys Leu Ile Trp Gly  Arg Lys Gln
    2375                 2380                 2385

Ala Pro  Ala Leu Gly Glu Asp  Met Phe Ser Asn Leu  Leu Phe Asn
    2390                 2395                 2400

Ser Ala  Ile Leu Met Arg Ser  Gln Pro Thr Thr Gln  Ala Val Ala
    2405                 2410                 2415

Lys Asp  Gly Thr Leu Phe His  Ser Lys Ala Tyr Gly  Asn Asn Glu
    2420                 2425                 2430

Arg Leu  Ser Gln Leu Asn Gln  Thr Phe Asp Lys Leu  Val Thr Asp
    2435                 2440                 2445

Tyr Leu  Arg Thr Asp Pro Val  Thr Glu Val Glu Arg  Arg Gly Asn
    2450                 2455                 2460

Val Ala  Asn Ala Leu Met Ser  Ala Thr Arg Leu Val  Arg Asp Val
    2465                 2470                 2475

Gln Ser  His Gly Phe Asn Met  Thr Ala Gln Glu Gln  Ser Val Phe
```

```
    2480                2485                2490

Gln Met  Val Thr Ala Ala Leu  Ala Thr Glu Ala Ala  Ile Asp Pro
    2495                2500                2505

His Ala  Met Ala Arg Ala Gln  Glu Leu Tyr Thr His  Val Met Lys
    2510                2515                2520

His Leu  Thr Val Glu His Phe  Met Ala Asp Pro Asp  Ser Thr Asn
    2525                2530                2535

Pro Ala  Asp Arg Tyr Tyr Ala  Gln Gln Lys Tyr Asp  Thr Ile Ser
    2540                2545                2550

Gly Ala  Asn Leu Val Glu Val  Asp Ala Lys Gly Arg  Thr Ser Leu
    2555                2560                2565

Leu Pro  Thr Phe Leu Gly Leu  Ala Met Val Asn Glu  Glu Leu Arg
    2570                2575                2580

Ser Ile  Ile Lys Glu Met Pro  Val Pro Lys Ala Asp  Lys Lys Leu
    2585                2590                2595

Gly Asn  Asp Ile Asp Thr Leu  Leu Thr Asn Ala Gly  Thr Gln Val
    2600                2605                2610

Met Glu  Ser Leu Asn Arg Arg  Met Ala Gly Asp Gln  Lys Ala Thr
    2615                2620                2625

Asn Val  Gln Asp Ser Ile Asp  Ala Leu Ser Glu Thr  Ile Met Ala
    2630                2635                2640

Ala Ala  Leu Lys Arg Glu Ser  Phe Tyr Asp Ala Val  Ala Thr Pro
    2645                2650                2655

Thr Gly  Asn Phe Ile Asp Arg  Ala Asn Gln Tyr Val  Thr Asp Ser
    2660                2665                2670

Ile Glu  Arg Leu Ser Glu Thr  Val Ile Glu Lys Ala  Asp Lys Val
    2675                2680                2685

Ile Ala  Asn Pro Ser Asn Ile  Ala Ala Lys Gly Val  Ala His Leu
    2690                2695                2700

Ala Lys  Leu Thr Ala Ala Ile  Ala Ser Glu Lys Gln  Gly Glu Ile
    2705                2710                2715

Val Ala  Gln Gly Val Met Thr  Ala Met Asn Gln Gly  Lys Val Trp
    2720                2725                2730

Gln Pro  Phe His Asp Leu Val  Asn Asp Ile Val Gly  Arg Thr Lys
    2735                2740                2745

Thr Asn  Ala Asn Val Tyr Asp  Leu Ile Lys Leu Val  Lys Ser Gln
    2750                2755                2760

Ile Ser  Gln Asp Arg Gln Gln  Phe Arg Glu His Leu  Pro Thr Val
    2765                2770                2775

Ile Ala  Gly Lys Phe Ser Arg  Lys Leu Thr Asp Thr  Glu Trp Ser
    2780                2785                2790

Ala Met  His Thr Gly Leu Gly  Lys Thr Asp Leu Ala  Val Leu Arg
    2795                2800                2805

Glu Thr  Met Ser Met Ala Glu  Ile Arg Asp Leu Leu  Ser Ser Ser
    2810                2815                2820

Lys Lys  Val Lys Asp Glu Ile  Ser Thr Leu Glu Lys  Glu Ile Gln
    2825                2830                2835

Asn Gln  Ala Gly Arg Asn Trp  Asn Leu Val Gln Lys  Lys Ser Lys
    2840                2845                2850

Gln Leu  Ala Gln Tyr Met Ile  Met Gly Glu Val Gly  Asn Asn Leu
    2855                2860                2865

Leu Arg  Asn Ala His Ala Ile  Ser Arg Leu Leu Gly  Glu Arg Ile
    2870                2875                2880
```

```
Thr Asn  Gly Pro Val Ala Asp  Val Ala Ala Ile Asp  Lys Leu Ile
    2885                 2890                 2895

Thr Leu  Tyr Ser Leu Glu Leu  Met Asn Lys Ser Asp  Arg Asp Leu
    2900                 2905                 2910

Leu Ser  Glu Leu Ala Gln Ser  Glu Val Glu Gly Met  Glu Phe Ser
    2915                 2920                 2925

Ile Ala  Tyr Met Val Gly Gln  Arg Thr Glu Glu Met  Arg Lys Ala
    2930                 2935                 2940

Lys Gly  Asp Asn Arg Thr Leu  Leu Asn His Phe Lys  Gly Tyr Ile
    2945                 2950                 2955

Pro Val  Glu Asn Gln Gln Gly  Val Asn Leu Ile Ile  Ala Asp Asp
    2960                 2965                 2970

Lys Glu  Phe Ala Lys Leu Asn  Ser Gln Ser Phe Thr  Arg Ile Gly
    2975                 2980                 2985

Thr Tyr  Gln Gly Ser Thr Gly  Phe Arg Thr Gly Ser  Lys Gly Tyr
    2990                 2995                 3000

Tyr Phe  Ser Pro Val Ala Ala  Arg Ala Pro Tyr Ser  Gln Gly Ile
    3005                 3010                 3015

Leu Gln  Asn Val Arg Asn Thr  Ala Gly Gly Val Asp  Ile Gly Thr
    3020                 3025                 3030

Gly Phe  Thr Leu Gly Thr Met  Val Ala Gly Arg Ile  Thr Asp Lys
    3035                 3040                 3045

Pro Thr  Val Glu Arg Ile Thr  Lys Ala Leu Ala Lys  Gly Glu Arg
    3050                 3055                 3060

Gly Arg  Glu Pro Leu Met Pro  Ile Tyr Asn Ser Lys  Gly Gln Val
    3065                 3070                 3075

Val Ala  Tyr Glu Gln Ser Val  Asp Pro Asn Met Leu  Lys His Leu
    3080                 3085                 3090

Asn Gln  Asp Asn His Phe Ala  Lys Met Val Gly Val  Trp Arg Gly
    3095                 3100                 3105

Arg Gln  Val Glu Glu Ala Lys  Ala Gln Arg Phe Asn  Asp Ile Leu
    3110                 3115                 3120

Ile Glu  Gln Leu His Ala Met  Tyr Glu Lys Asp Ile  Lys Asp Ser
    3125                 3130                 3135

Ser Ala  Asn Lys Ser Gln Tyr  Val Asn Leu Leu Gly  Lys Ile Asp
    3140                 3145                 3150

Asp Pro  Val Leu Ala Asp Ala  Ile Asn Leu Met Asn  Ile Glu Thr
    3155                 3160                 3165

Arg His  Lys Ala Glu Glu Leu  Phe Gly Lys Asp Glu  Leu Trp Val
    3170                 3175                 3180

Arg Arg  Asp Met Leu Asn Asp  Ala Leu Gly Tyr Arg  Ala Ala Ser
    3185                 3190                 3195

Ile Gly  Asp Val Trp Thr Gly  Asn Ser Arg Trp Ser  Pro Ser Thr
    3200                 3205                 3210

Leu Asp  Thr Val Lys Lys Met  Phe Leu Gly Ala Phe  Gly Asn Lys
    3215                 3220                 3225

Ala Tyr  His Val Val Met Asn  Ala Glu Asn Thr Ile  Gln Asn Leu
    3230                 3235                 3240

Val Lys  Asp Ala Lys Thr Val  Ile Val Val Lys Ser  Val Val Val
    3245                 3250                 3255

Pro Ala  Val Asn Phe Leu Ala  Asn Ile Tyr Gln Met  Ile Gly Arg
    3260                 3265                 3270

Gly Val  Pro Val Lys Asp Ile  Ala Val Asn Ile Pro  Arg Lys Thr
    3275                 3280                 3285
```

```
Ser Glu  Ile Asn Gln Tyr Ile  Lys Ser Arg Leu Arg  Gln Ile Asp
    3290                 3295                 3300

Ala Glu  Ala Glu Leu Arg Ala  Ala Glu Gly Asn Pro  Asn Leu Val
    3305                 3310                 3315

Arg Lys  Leu Lys Thr Glu Ile  Gln Ser Ile Thr Asp  Ser His Arg
    3320                 3325                 3330

Arg Met  Ser Ile Trp Pro Leu  Ile Glu Ala Gly Glu  Phe Ser Ser
    3335                 3340                 3345

Ile Ala  Asp Ala Gly Ile Ser  Arg Asp Asp Leu Leu  Val Ala Glu
    3350                 3355                 3360

Gly Lys  Ile His Glu Tyr Met  Glu Lys Leu Ala Asn  Lys Leu Pro
    3365                 3370                 3375

Glu Lys  Val Arg Asn Ala Gly  Arg Tyr Ala Leu Ile  Ala Lys Asp
    3380                 3385                 3390

Thr Ala  Leu Phe Gln Gly Ile  Gln Lys Thr Val Glu  Tyr Ser Asp
    3395                 3400                 3405

Phe Ile  Ala Lys Ala Ile Ile  Tyr Asp Asp Leu Val  Lys Arg Lys
    3410                 3415                 3420

Lys Lys  Ser Ser Ser Glu Ala  Leu Gly Gln Val Thr  Glu Glu Phe
    3425                 3430                 3435

Ile Asn  Tyr Asp Arg Leu Pro  Gly Arg Phe Arg Gly  Tyr Met Glu
    3440                 3445                 3450

Ser Met  Gly Leu Met Trp Phe  Tyr Asn Phe Lys Ile  Arg Ser Ile
    3455                 3460                 3465

Lys Val  Ala Met Ser Met Ile  Arg Asn Asn Pro Val  His Ser Leu
    3470                 3475                 3480

Ile Ala  Thr Val Val Pro Ala  Pro Thr Met Phe Gly  Asn Val Gly
    3485                 3490                 3495

Leu Pro  Ile Gln Asp Asn Met  Leu Thr Met Leu Ala  Glu Gly Arg
    3500                 3505                 3510

Leu Asp  Tyr Ser Leu Gly Phe  Gly Gln Gly Leu Arg  Ala Pro Thr
    3515                 3520                 3525

Leu Asn  Pro Trp Phe Asn Leu  Thr His
    3530                 3535
```

<210> SEQ ID NO 16
<211> LENGTH: 32
<212> TYPE: DNA
<213> ORGANISM: Artificial Sequence
<220> FEATURE:
<223> OTHER INFORMATION: Synthetic

<400> SEQUENCE: 16
ggcattactt catccaaaag aagcggagct tc 32

<210> SEQ ID NO 17
<211> LENGTH: 37
<212> TYPE: DNA
<213> ORGANISM: Artificial Sequence
<220> FEATURE:
<223> OTHER INFORMATION: Synthetic

<400> SEQUENCE: 17
ggccatccat tacttcatcc aaaagaagcg gagcttc 37

<210> SEQ ID NO 18
<211> LENGTH: 23
<212> TYPE: DNA

<213> ORGANISM: Artificial Sequence
<220> FEATURE:
<223> OTHER INFORMATION: Synthetic

<400> SEQUENCE: 18
ggatccaaaa gaagcggagc ttc 23

<210> SEQ ID NO 19
<211> LENGTH: 32
<212> TYPE: DNA
<213> ORGANISM: Artificial Sequence
<220> FEATURE:
<223> OTHER INFORMATION: Synthetic

<400> SEQUENCE: 19
ggcattactt catccaaaag aagctgagct tc 32

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
ggcattactt catccaaaag aagcggagc 29

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggaggctcct cggagtctcc tttt 24

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
ggactacctt cgggtagtcc ttttt 25

<210> SEQ ID NO 23
<211> LENGTH: 33
<212> TYPE: DNA
<213> ORGANISM: Artificial Sequence
<220> FEATURE:
<223> OTHER INFORMATION: Synthetic

<400> SEQUENCE: 23
agaagggggc tactaagccc tcttcttatt ttt 33

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
aagctgctcc gcagctttt 19

<210> SEQ ID NO 25
<211> LENGTH: 35
<212> TYPE: DNA
<213> ORGANISM: Artificial Sequence
<220> FEATURE:
<223> OTHER INFORMATION: Synthetic

<400> SEQUENCE: 25
aaggctatcc ctacgggggt agcctttatt ttttt 35

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
gccctccttg tgagggcttt tt 22

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
tccataagtt gcgaagcaac 20

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
tccaaaagaa gcggagcttc tt 22

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
accaaaagct gcggagcagc 20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
tccaaaagaa gcggagcttc 20

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
atccaaaaga agcggagctt c 21

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
atccaaaaga agcggagct 19

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
atccaaaaga agcggagc 18

<210> SEQ ID NO 34
<211> LENGTH: 17
<212> TYPE: DNA
<213> ORGANISM: Artificial Sequence
<220> FEATURE:
<223> OTHER INFORMATION: Synthetic

<400> SEQUENCE: 34
atccaaaaga agcggag 17

<210> SEQ ID NO 35
<211> LENGTH: 16
<212> TYPE: DNA
<213> ORGANISM: Artificial Sequence
<220> FEATURE:
<223> OTHER INFORMATION: Synthetic

<400> SEQUENCE: 35
atccaaaaga agcgga 16

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
atccaaaaga agcggagctt ctt 23

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atccaaaaga agcggagctt cttt 24

<210> SEQ ID NO 38
<211> LENGTH: 25
<212> TYPE: DNA

```
<213> ORGANISM: Artificial Sequence
<220> FEATURE:
<223> OTHER INFORMATION: Synthetic

<400> SEQUENCE: 38

atccaaaaga agcggagctt ctttt                                           25


<210> SEQ ID NO 39
<211> LENGTH: 26
<212> TYPE: DNA
<213> ORGANISM: Artificial Sequence
<220> FEATURE:
<223> OTHER INFORMATION: Synthetic

<400> SEQUENCE: 39

atccaaaaga agcggagctt cttttg                                          26


<210> SEQ ID NO 40
<211> LENGTH: 14
<212> TYPE: PRT
<213> ORGANISM: Artificial Sequence
<220> FEATURE:
<223> OTHER INFORMATION: Synthetic

<400> SEQUENCE: 40

Arg Gly Ile Ala Lys Asn Pro Leu Thr Ile Thr Ile Tyr Gly
1               5                   10


<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Arg Gly Ile Ala Ala Asn Pro Leu Thr Ile Thr Ile Phe Gly
1               5                   10
```

PREPARATION AND USE OF SINGLE-STRANDED TRANSCRIPTION SUBSTRATES FOR SYNTHESIS OF TRANSCRIPTION PRODUCTS CORRESPONDING TO TARGET SEQUENCES

CROSS-REFERENCE TO RELATED APPLICATION

This application is a Continuation in Part of U.S. patent application Ser. No. 10/153,219, filed May 22, 2002, which claims priority to U.S. Provisional Patent Application Ser. No. 60/292,845, filed May 22, 2001. This application also claims priority to U.S. Provisional Patent Application Ser. No. 60/428,013, filed Nov. 21, 2002. The entire disclosure of all referenced priority applications is specifically incorporated herein by reference.

STATEMENT REGARDING FEDERALLY SPONSORED RESEARCH OR DEVELOPMENT

The government may own rights in the present invention pursuant to grant number R01 A1 12575 from the National Institute of Health.

FIELD OF THE INVENTION

The present invention relates generally to methods, compositions and kits for using an RNA polymerase for making transcription products corresponding to a target sequence by obtaining single-stranded DNA transcription substrates that comprise a single-stranded promoter that is operably joined to a single-stranded target sequence. The invention has broad applicability for research, diagnostic and therapeutic applications, such as preparing cDNA corresponding to full-length mRNA, making sense or anti-sense probes, detecting gene- or organism-specific sequences, cloning, cell signaling or making RNA for use in RNAi.

BACKGROUND OF THE INVENTION

Description of Related Art

Transcription of DNA into mRNA is regulated by the promoter region of the DNA. The promoter region contains a sequence of bases that signals RNA polymerase to associate with the DNA, and to initiate the transcription of mRNA using one of the DNA strands as a template to make a corresponding complementary strand of RNA. RNA polymerases from different species typically recognize promoter regions comprised of different sequences. In order to express a protein-encoding gene in a host cell, either the promoter driving transcription of the protein-encoding gene must be recognized by a host RNA polymerase, or an RNA polymerase which recognizes the promoter driving transcription of the protein-encoding gene must be provided to the host cell (U.S. Pat. No. 6,218,145).

There are many reasons for which it is beneficial to obtain cDNA and transcribe one or more target nucleic acid sequences. For example, in vitro transcription is frequently used in methods to make probes corresponding to mRNA sequences in samples in order to profile the expression of genes in cells of a particular type versus another type or versus a similar type in response to different conditions or stimuli. Contemporary gene expression profiling is typically performed by simultaneously hybridizing labeled probes prepared from one or more samples to arrays or microarrays having sequences for up to hundreds or thousands of different genes attached to a surface. In some cases, the expression or lack of expression of particular genes may correlate with or be indicative of the presence or status of a disease state, such as, but not limited to, a cancer.

Examples of methods that involve in vitro transcription for making probes for gene expression profiling are described in: Murakawa et al., *DNA* 7:287-295, 1988; Phillips and Eberwine, *Methods in Enzymol. Suppl.* 10:283-288, 1996; Ginsberg et al., *Ann. Neurol.* 45:174-181, 1999; Ginsberg et al., *Ann. Neurol.* 48:77-87, 2000; VanGelder et al. *Proc. Natl. Acad. Sci. USA* 87:1663-1667, 1990; Eberwine et al., *Proc. Natl. Acad. Sci. USA* 89:3010-3014, 1992; U.S. Pat. Nos. 5,021,335; 5,168,038; 5,545,522; 5,514,545; 5,716,785; 5,891,636; 5,958,688; 6,291,170; and PCT Patent Applications WO 00/75356 and WO 02/065093.

Still other methods use in vitro transcription as part of a process for amplifying and detecting one or more target nucleic acid sequences in order to detect the presence of a pathogen, such as a viral or microbial pathogen, that is a causative agent for a disease or to detect a gene sequence that is related to a disease or the status of a disease for medical purposes. Examples of methods that use in vitro transcription for this purpose include U.S. Pat. Nos. 5,130,238; 5,194,370; 5,399,491; 5,409,818; 5,437,990; 5,466,586; 5,554,517; 5,665,545; 6,063,603; 6,090,591; 6,100,024; 6,410,276;.Kwoh et al., *Proc. Natl. Acad. Sci. USA* 86:1173, 1989; Fahy et al, In: PCR Methods and Applications, pp. 25-33, 1991; PCT Patent Application Nos. WO 89/06700 and WO 91/18155; and European Patent Application Nos. 0427073 A2 and 0427074 A2.

Most DNA-dependent RNA polymerases read double-stranded DNA, limiting RNA synthesis to systems in which a double-stranded DNA template is available. The synthesis of RNA using single-stranded DNA is not as common. All of the methods referenced above for making probes for gene expression profiling or for amplifying and detecting one or more target nucleic acid sequences require, at a minimum, the use of a double-stranded transcription promoter, and in most cases, also require the use of a double-stranded DNA as a template. Synthesizing RNA using a single-stranded DNA template immobilized on a solid support is described in U.S. Pat. No. 5,700,667, but transcription of the single-stranded template still required formation of a double-stranded promoter region for binding of the RNA polymerase.

In contrast to the methods in the art, the present invention provides methods, compositions and kits for transcription of target nucleic acid sequences using RNA polymerases that bind single-stranded DNA promoters and read single-stranded DNA templates.

BRIEF SUMMARY OF THE INVENTION

The invention provides methods of use for a various novel deletion mutants of bacteriophage N4-coded, virion RNA polymerases (mini-vRNAPs) and compositions and kits therefore. The novel polymerases are described by an isolated nucleic acid comprising a region encoding a polypeptide having the amino sequence set forth in SEQ ID NO:2, SEQ ID NO:4, SEQ ID NO:6, SEQ ID NO:8 or SEQ ID NO:15. The nucleic acid may comprise the nucleic acid sequence of SEQ ID NO:1, SEQ ID NO:3, SEQ ID NO:5, SEQ ID NO:7 or SEQ ID NO:14. The vRNAP and mini-vRNA polymerase transcribe nucleic acid operatively linked to an N4 promoter such as a P2 promoter of SEQ ID NO:16, SEQ ID NO:19, SEQ ID NO:27, SEQ ID NO:28 or SEQ ID NO:29. The promoter of SEQ ID NO:16 or SEQ ID NO:28 is preferred.

The current invention can use a polypeptide encoded by an isolated polynucleotide comprising a sequence identical or complementary to at least 14 contiguous nucleotides of SEQ ID NO:1. The polynucleotide may comprise at least 20, 25, 30,35, 40, 45, 50, 60, 75, 100, 150, 200, 250, 300, 400, 600, 800, 1000, 2000, 3000, 3300 or more contiguous nucleotides of SEQ ID NO:1. The polynucleotide may comprise all contiguous nucleotides of SEQ ID NO:3 or all contiguous nucleotides of SEQ ID NO:1. Similarly, the polynucleotide may comprise at least 20, 25, 30, 35, 40, 45, 50, 60, 75, 100, 150, 200, 250, 300, 400, 600, 800, 1000, 2000, 3000, 3300 or more nucleotides complementary to at least 20, 25, 30, 35, 40, 45, 50, 60, 75, 100, 150, 200, 250, 300, 400, 600, 800, 1000, 2000, 3000, 3300 or more contiguous nucleotides of SEQ ID NO:1.

A purified N4 virion RNA polymerase of the current invention can comprise at least 20 contiguous amino acids of SEQ ID NO:2. It is preferred that the polymerase contain at least 25, 30, 35, 40, 45, 50, 60, 75, 100, 150, 200, 250, 300, 400, 600, 800, 1000 or more contiguous amino acids of SEQ ID NO:2.

In another aspect, the current invention can use a polypeptide encoded by an isolated nucleic acid comprising a region encoding at least 6 contiguous amino acids of SEQ ID NO:2, wherein the polypeptide has RNA polymerase activity under appropriate reaction conditions. It is preferred that this polypeptide comprises at least 10, 15, 20, 25, 30, 35, 40, 45, 50, 60, 75, 100, 150, 200, 250, 300, 400, 600, 800, 1000 or more contiguous amino acids of SEQ ID NO:2, SEQ ID NO:4, SEQ ID NO:6, SEQ ID NO:8, or SEQ ID NO:15. The encoded polypeptide may have at least one hexahistidine tag or other tag, or the encoded polypeptide may lack a tag. The polypeptide may be a mutant of the peptide found in SEQ ID NO:2 or SEQ ID NO:4, such as an enzyme possessing an amino acid substitution at position Y678.

An embodiment of the current invention comprises a method of making RNA. This method comprises: (a) obtaining a N4 virion RNA polymerase (i.e. the polypeptide); (b) obtaining DNA wherein the DNA preferably contains a N4 virion RNA polymerase promoter sequence; (c) admixing the RNA polymerase and the DNA; and (d) culturing the RNA polymerase and the DNA under conditions effective to allow RNA synthesis. Optionally, the method may comprise synthesizing polynucleotides containing modified ribonucleotides or deoxyribonucleotides. The DNA is preferably single-stranded DNA or denatured double-stranded DNA. Step (c) may occur in a host cell such as an *E. coli* host cell.

The amino acid sequence of the RNA polymerase is preferably the sequence essentially as set forth in SEQ ID NO:2, SEQ ID NO:4, SEQ ID NO:6, SEQ ID NO:8, SEQ ID NO:15, or a mutant form of the polymerase of SEQ ID NO:4 or SEQ ID NO:6. The mutation may be, for example, at position number Y678. The RNA transcript may contain derivatized nucleotides.

An aspect of the current invention comprises using an N4 vRNAP promoter to direct transcription. The promoter is preferentially an N4 promoter set forth in SEQ ID NO:16, SEQ ID NO:19, SEQ ID NO:20, SEQ ID NO:27, SEQ ID NO:28 or SEQ ID NO:29. The P2 promoter of SEQ ID NO:16 or SEQ ID NO:28 is preferred. The promoter sequence may be upstream of the transcription initiation site. The promoter may comprise a set of inverted repeats forming a hairpin with a 2-7 base pair long stem and 3-5 base loop having purines in the central and/or next to the central position of the loop.

The preferred conditions of the transcription method claimed herein includes a pH in step (c) of between 6 and 9, with a pH of between 7.5 and 8.5 more preferred. $Mg^{+2}$ or $Mn^{+2}$, preferably $Mg^{+2}$ may be admixed. Preferred temperatures for the reaction are 25° C. to 50° C. with the range of 30° C. to 45° C. being more preferred and the range of 32° C. to 42° C. being most preferred. The admixing may occur in vivo or in vitro.

An aspect of the current invention also includes translation of the RNA after transcription. A reporter gene such as an α-peptide of β-galactosidase may be used. It is preferred the transcription comprises admixing an *E. coli* single-stranded binding protein (EcoSSB), a SSB protein homologous to EcoSSB or another naturally occurring or chimeric SSB protein homologous to EcoSSB with the polymerase and DNA. Yet another aspect of the current invention is the transcription method in which no EcoSSB is admixed with the RNA polymerase and DNA; the product of this method is a DNA/RNA hybrid.

The DNA admixed with the RNA polymerase of the current invention may be single-stranded linear DNA or single-stranded circular DNA such as bacteriophage M13 DNA. The DNA may be denatured DNA, such as single-stranded, double-stranded linear or double-stranded circular denatured DNA. The DNA may also be double-stranded DNA under certain conditions. The RNA may be pure RNA or may contain modified nucleotides. Mixed RNA-DNA oligonucleotides may also be synthesized with the Y678F mutant mini-vRNAP (SEQ ID NO:8) of the current invention.

The synthesized RNA may comprise a detectable label such as a fluorescent tag, biotin, digoxigenin, 2'-fluoro nucleoside triphosphate, or a radiolabel such as a $^{35}S$ or $^{32}P$-label. The synthesized RNA may be adapted for use as a probe for blotting experiments or in-situ hybridization. Nucleoside triphosphates (NTPs) or derivatized NTPs may be incorporated into the RNA, and may optionally have a detectable label. Deoxynucleoside triphosphates may be incorporated into the RNA.

The RNA may be adapted for use for NMR structural determination. Short RNAs such as those between 10 and 1000 bases or between 10 and 300 bases may be used. The RNA may be adapted for use in spliceosome assembly, splicing reactions or for antisense or RNA interference experiments. Also, the RNA may be adapted for use in probing for a complementary nucleotide sequence or for use as a probe in RNase protection studies.

Yet another aspect of the current invention comprises delivering RNA into a cell after transcription of the RNA. The delivery may be by microinjection, transfection, electroporation, or other methods in the art. Another aspect of the invention comprises amplifying the RNA after transcription.

Another embodiment of the current invention comprises a method of making RNA comprising: (a) obtaining a N4 virion RNA polymerase; (b) obtaining a single-stranded DNA oligonucleotide wherein the oligonucleotide contains a N4 virion RNA polymerase promoter sequence; (c) admixing the RNA polymerase and the oligonucleotide; and (d) culturing the RNA polymerase and the oligonucleotide under conditions effective to allow RNA synthesis. The polymerase preferentially has the amino sequence set forth in SEQ ID NO:4, SEQ ID NO:6 or SEQ ID NO:8. In this embodiment, it is preferred that the DNA has between 20 and 200 bases.

Yet another embodiment of the invention comprises a method of making RNA comprising: (a) obtaining a N4 virion RNA polymerase; (b) obtaining a single-stranded DNA wherein the DNA contains a N4 virion RNA polymerase promoter sequence; (c) obtaining a ribonucleoside triphosphate (XTP) or a derivatized ribonucleoside triphosphate; (d) admixing the RNA polymerase, the DNA and the XTP; and (e) culturing the RNA polymerase and the oligonucleotide under conditions effective to allow RNA synthesis wherein the RNA is a derivatized RNA. The RNA polymerase preferentially has the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8.

Another embodiment of the invention comprises a method for making transcription product corresponding to a target nucleic acid sequence, the method comprising: (a) obtaining an RNA polymerase that can transcribe RNA using a single-stranded promoter; (b) obtaining a single-stranded DNA wherein the single-stranded DNA comprises a target nucleic sequence that is present in or complementary to at least a portion of a target nucleic acid in a sample; (c) obtaining a ssDNA transcription substrate by operably joining to the single-stranded DNA a single-stranded promoter sequence that binds the RNA polymerase; (d) obtaining nucleoside triphosphates (NTPs) that are substrates for the RNA polymerase and that are complementary to the canonical nucleic acid bases; (e) admixing the RNA polymerase, the ssDNA transcription substrate and the NTPs; and (f) incubating the RNA polymerase and the ssDNA transcription substrate under conditions effective to allow synthesis of transcription product. The RNA polymerase preferentially has the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8.

Yet another embodiment of the invention comprises a method for obtaining additional rounds of synthesis of transcription product corresponding to a target nucleic acid sequence, the method comprising: (a) obtaining an RNA polymerase that can transcribe RNA using a single-stranded promoter; (b) obtaining a first transcription product by transcription of a first ssDNA transcription substrate corresponding to a target nucleic acid sequence; (c) obtaining a reverse transcriptase; (d) reverse transcribing the first transcription product; (e) obtaining first-strand cDNA complementary to the first transcription product; (f) obtaining a second ssDNA transcription substrate by operably joining to the first-strand cDNA a single-stranded promoter sequence that binds the RNA polymerase; (g) admixing the RNA polymerase and the second ssDNA transcription substrate; and (e) incubating the RNA polymerase and the second ssDNA transcription substrate under conditions effective to allow synthesis of a second transcription product. This method for obtaining additional rounds of synthesis of transcription product can be repeated to obtain synthesis of still more transcription products. The RNA polymerase preferentially has the amino sequence set forth in SEQ ID NO:4, SEQ ID NO:6 or SEQ ID NO:8.

Another embodiment of the invention comprises a method for in vivo or in vitro protein synthesis comprising: (a) obtaining an RNA polymerase having the amino sequence set forth in SEQ ID NO:4, SEQ ID NO:6 or a mutant thereof; (b) obtaining DNA wherein the DNA contains a N4 virion RNA polymerase promoter sequence; (c) admixing the RNA polymerase and the DNA; (d) culturing the RNA polymerase and the DNA under conditions effective to allow RNA synthesis; and (e) culturing the RNA in vivo or in vitro under conditions effective to allow protein synthesis. Step (e) may comprise using a two plasmid system or a one plasmid system in which a reporter gene and the RNA polymerase gene are located on the same plasmid.

Another embodiment of the invention provides for a method that comprises a target nucleic acid sequence compriseing a 3'-portion that encodes a first sequence, a 5'-portion that encodes a second sequence that is complementary to the first sequence, and a middle portion that joins the 3'portion and the 5'portion, wherein the middle portion comprises a sequence that is not complementary to either the 3'-portion or the 5'portion and wherein the transcription product comprises a hairpin RNA corresponding to a target nucleic acid sequence in a target nucleic acid, wherein the hairpin RNA is SiRNA has RNA interference activity in a cell.

Another embodiment of the invention provides for a method of cloning a target nucleic acid, the method comprising:

a) obtaining a single-stranded DNA wherein the single-stranded DNA comprises a target nucleic acid sequence that is present in or complementary to the target nucleic acid;
b) joining to the single-stranded DNA a single-stranded polynucleotide comprising a single-stranded origin of replication and a marker gene;
c) making a circular ssDNA molecule by covalently joining the 3'-end and the 5'-end of the product of step (b);
d) transforming the circular ssDNA molecule into a host cell, in which the marker gene is expressible, wherein the host cell is capable of replicating the circular ssDNA molecule; and
e) growing the host cell under conditions that support the expression of the marker gene.

Still another embodiment of the invention provides for a method for detecting an analyte in a sample, the method comprising:

a) obtaining a transcription signaling system comprising a ssDNA comprising:
   i) a promoter sequence that binds an RNA polymerase that can transcribe RNA using a single-stranded promoter, and
   ii) a signal sequence that is operably joined to the promoter sequence;
b) joining the transcription signaling system to an analyte-binding substance;
c) contacting the analyte-binding substance to which the transcription signaling system is joined with a sample under conditions effective to allow binding of an analyte to the analyte-binding substance and forming a specific binding pair;
d) removing the specific binding pair from the sample;
e) incubating the specific-binding pair with an RNA polymerase that can transcribe RNA using a single-stranded promoter under conditions effective to allow synthesis of a transcription product; and
f) detecting the transcription product.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Bacteriophage N4 vRNAP promoters on single-stranded templates. These promoters are characterized by conserved sequences and a 5 bp stem, 3 base loop hairpin structure.

FIG. 2A shows a schematic of the N4 vRNAP protein with three motifs: the T/DxxGR motif found in DNA-dependent polymerases, the P-loop, an ATP/GTP-binding motif present in some nucleotide-binding proteins, and motif B ($Rx_3Kx_{6-7}YG$), one of three motifs common to the Pol I and Pol α DNA polymerases and the T7-like RNA polymerases. FIG. 2B shows the mini-vRNAP.

FIG. 3A, SDS-PAGE analysis of the products of vRNAP digestion with trypsin. FIG. 3B N-terminal sequencing of the three initial proteolytic fragments indicated that the stable active polypeptide (mini-vRNAP) corresponds to the middle ⅓ of vRNAP, the region containing the three motifs described in FIG. 2A.

DETAILED DESCRIPTION OF THE INVENTION

Figure 2:
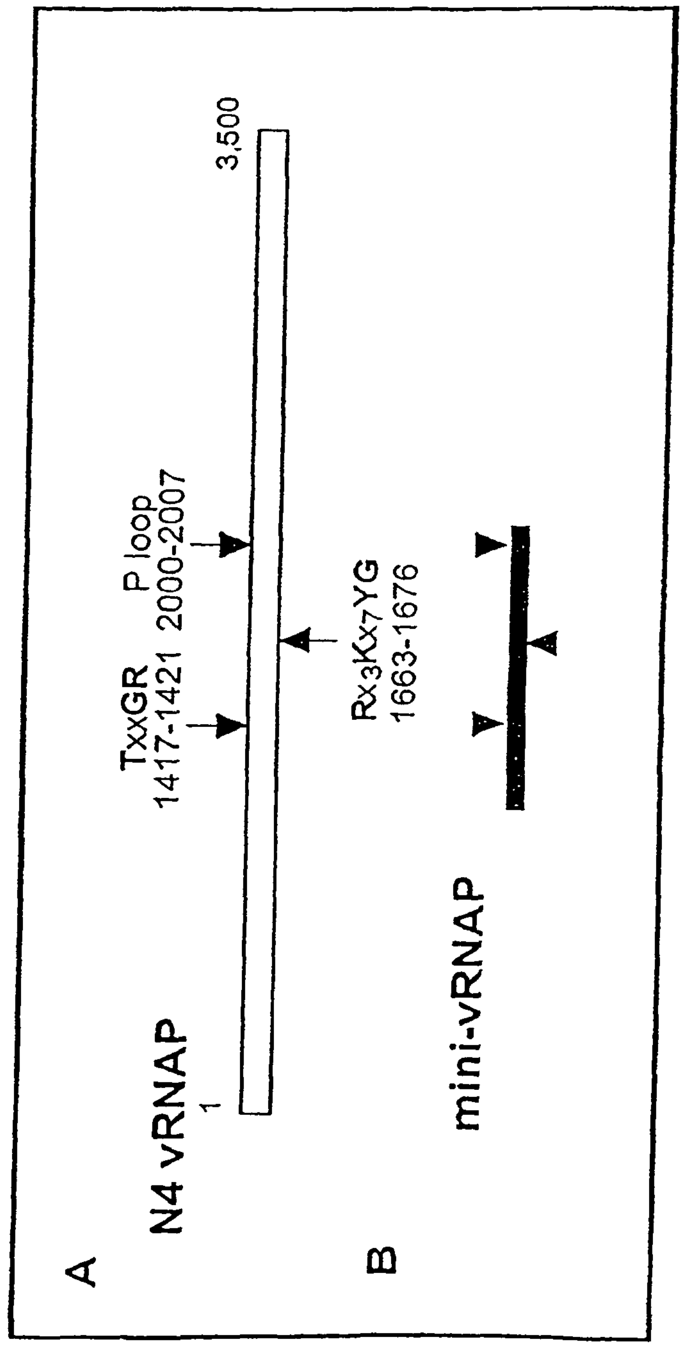
FIG. 2A and FIG. 2B—N4 vRNAP and generation of mini-vRNAP.

Methods are provided for using various deletion mutants of bacteriophage N4-coded, virion RNA polymerases (mini-vRNAPs), which have been developed, cloned and expressed in *E. coli*, and purified in active form. In the presence of *E. coli* SSB protein, mini-vRNAPs efficiently transcribe single-stranded DNA (ssDNA) transcription substrates that comprise a single-stranded DNA target sequence as a template if the template is operably joined to a sequence comprising a single-stranded 17-base promoter. The enzymes efficiently incorporate derivatized nucleoside triphosphates, and a specific amino acid mutant of mini-vRNAP (Y678F) also incorporates other nucleotides, such as 2'-deoxynucleoside triphosphates, with greater efficiency. Methods, compositions and kits are provided for making ssDNA transcription substrates for synthesis of transcription products corresponding to a target sequence and for obtaining additional rounds of transcription by using transcription products synthesized in earlier rounds for obtaining additional ssDNA transcription substrates. Methods are provided for obtaining replicable clones, including expression clones, of target sequences by using oligos comprising a single-stranded origin of replication and a sequence encoding a selectable or screenable marker for obtaining circular ssDNA, which is used to transform a host cell. Other methods are provided for obtaining signaling systems for analytes by using mini-vRNAP to transcribe ssDNA comprising a promoter and a signal sequence, which ssDNA is joined to an analyte-binding substance.

DESCRIPTION OF ILLUSTRATIVE EMBODIMENTS

The present invention relates to novel methods, compositions, and kits for synthesizing RNA corresponding to one or multiple target nucleic acid sequences in or from a sample. The target sequence can comprise at least a portion of one or more target nucleic acids comprising either RNA or DNA from any source. By way of example, but not of limitation, the target nucleic acid sequences that are transcribed using a method of the invention can comprise first-strand cDNA corresponding to from one to substantially all mRNA molecules in a sample. Alternatively, the target nucleic acid sequence that is transcribed using a method of the invention can comprise a specific sequence in genomic DNA of a particular organism. The present invention overcomes deficiencies in the art by providing a stable RNA polymerase that uses single-stranded DNA transcription substrate that comprises both a sense promoter and a template for transcription and provides a unique system to synthesize RNAs of a desired sequence. Thus, in contrast to other methods currently used in the art, the methods of the present invention do not require synthesis of double-stranded DNA, use of a proto-promoter, or annealing of a promoter-complementary oligonucleotide for transcription. The RNA polymerase and mini-vRNA polymerase can be used to synthesize RNA for use as probes for expression studies using arrays or microarrays or in RNase protection studies of DNAs or RNAs, in situ hybridization studies, and in Southern and Northern blot analysis, for the synthesis of defined RNA:DNA hybrids, for NMR structure determination of RNAs, for in vitro studies of spliceosome assembly, splicing reactions and antisense or RNA interference experiments, for in vitro translation or microinjection, and for nucleic acid amplification. The present invention allows for the synthesis of derivatized RNA and can use ssDNA in the form of single-stranded oligonucleotides, denatured DNA or DNA cloned into M13 templates.

I. RNA POLYMERASES a. Structure and Promoter Recognition of DNA-Dependent RNA Polymerases

Inspection of the sequences of phage, archaebacterial, eubacterial, eukaryotic and viral DNA-dependent RNA polymerases has revealed the existence of two enzyme families. The eubacterial, eukaryotic, archaebacterial, chloroplast and the vaccinia virus RNA polymerases are complex multisubunit enzymes (5-14 subunits) composed of two large subunits, one to several subunits of intermediate molecular weight (30-50-kDa) and none to several subunits of small molecular weight (<30-kDa) (Archambault and Friesen, *Microbiol. Rev.* 57:703-724, 1993; Record et al., *Cell and Molecular Biology* 1:792-821, 1995. Eubacterial RNA polymerases are the simplest with an $\alpha_2\beta\beta'$ core structure. Sequence comparison of the genes coding for the different subunits of these enzymes has revealed: 1-sequence homology in eight segments (A to H) between β' and the largest subunit of other RNA polymerases, 2-sequence homology in nine segments (A to I) between β and the next largest subunit of other RNA polymerases, 3-sequence homology in 3 segments (1.1, 1.2 and 2) between a and a subunit in RNA polymerases I, II and III (Puhler, et al., *Proc. Natl. Acad. Sci. USA* 86:4569-4573, 1989; Sweetser, et al., *Proc. Natl. Acad. Sci. USA* 84:1192-1196, 1987). Not surprisingly, the crystal structures of yeast RNAP II and *E. coli* RNAP core revealed remarkable similarities (Zhang, et al., *Cell* 98:811-824, 1999; Cramer, et al., *Sciencexpress*, www.sciencexpress.org. 19 Apr. 2001).

In contrast, members of the phage T7-like (T3, SP6) family of RNA polymerases consist of a single (~100 kDa) polypeptide which catalyzes all functions required for accurate transcription (Cheetham, et al., *Curr. Op. In Struc. Biol.* 10:117-123, 2000). The heterodimeric bacteriophage N4 RNAP II, nuclear-coded mitochondrial, and Arabidopsis chloroplast RNA polymerases show sequence similarity to the phage RNA polymerases (Cermakian, et al., *Nuc. Acids Res.* 24:648-654, 1996; Hedtke, et al., *Science* 277:809-811, 1997; Zehring, et al., *J. Biol. Chem.* 258:8074-8080, 1983). Three sequence motifs—A and C, which contain the two aspartic acids required for catalysis, and motif B—are conserved in polymerases that use DNA as a template (Delarue, et al., *Protein Engineering* 3:461-467, 1990). The crystal structure of T7 RNAP resembles a "cupped right hand" with "palm," "fingers" and "thumb" subdomains (Sousa, et al., *Nature* 364:593-599, 1993). The two catalytic aspartates are present in the "palm" of the structure. This structure is shared by the polymerase domains of *E. coli* DNA polymerase I and HIV reverse transcriptase (Sousa, *Trends in Biochem. Sci.* 21:186-190, 1996). Genetic, biochemical and structural information indicates that T7 RNA polymerase contains additional structures dedicated to nascent RNA binding, promoter recognition, dsDNA unwinding and RNA:DNA hybrid unwinding (Cheetham, et al., *Curr. Op. In Struc. Biol.* 10:117-123, 2000; Sousa, *Trends in Biochem. Sci.* 21:186-190, 1996).

Both Class I and Class II RNA polymerases recognize specific sequences, called promoters, on B form double-stranded DNA. Eubacterial promoters (except those recognized by $\sigma^{54}$) are characterized by two regions of sequence homology: the −10 and the −35 hexamers (Gross, et al., *Cold Spring Harbor Symp. Quant. Biol.* 63:141-156, 1998). Specificity of promoter recognition is conferred to the core enzyme by the σ subunit, which makes specific interactions with the −10 and −35 sequences through two distinct DNA binding domains (Gross, et al., *Cold Spring Harbor Symp. Quant. Biol.* 63:141-156, 1998). This modular promoter structure is also present at the promoters for eukaryotic RNA polymerases I, II and III. Transcription factors TFIIIA and TFIIIC direct recognition of RNAP III to two separate sequences (boxes A and C, separated by defined spacing) at the 5S gene promoter, while transcription factors TFIIIB and TFIIIC direct recognition of this enzyme to blocks A and B, separated by variable distance (31-74 bp) at the tRNA promoters (Paule, et al., *Nuc. Acids Res.* 28:1283-1298, 2000). Sequences important for RNAP I transcription initiation at the human rRNA promoters are also restricted to two regions: the "core" region located at −40 to +1 and the "upstream" region present at −160 to −107 (Paule, et al., *Nuc. Acids Res.* 28:1283-1298, 2000). Assembly of the initiation complex at RNAP II promoters requires several general transcription factors (TFIIA, TFIIB, TFIID, TFIIE, TFIIF and TFIIH). Recognition involves three core elements: the TATA box located at position −30 and recognized by TBP, the initiator element located near −1, and the downstream promoter element near +30 (Roeder, *Trends Biochem. Sci.* 21:327-335, 1996).

Promoters for the T7-like and mitochondrial RNAPases are simpler. The T7-type RNAP promoters span a continuous highly conserved 23 bp region extending from position −17 to +6 relative to the start site of transcription (+1) (Rong, et al., *Proc. Natl. Acad. Sci. USA* 95:515-519, 1998). The yeast mitochondrial RNAP promoters are even smaller, extending from −8 to +1 (Shadel, et al., *J. Biol. Chem.* 268:16083-16086, 1993). One exception are the promoters for N4 RNAP II, which are restricted to two blocks of conserved sequence: a/tTTTA at +1 and AAGACCTG present 18-26 bp upstream of +1 (Abravaya, et al., *J. Mol. Biol.* 211:359-372, 1990).

The activity of the multisubunit class of RNA polymerases is enhanced by activators at weak promoters. Transcription activators generally bind at specific sites on double-stranded DNA upstream of the −35 region (with the exception of the T4 sliding clamp activator), or at large distances in the cases of enhancers (Sanders, et al., *EMBO Journal* 16:3124-3132, 1997). Activators modulate transcription by increasing the binding (formation of closed complex) or isomerization (formation of open complex) steps of transcription through interactions with the α or σ subunits of RNAP (Hochschild, et al., *Cell* 92:597-600, 1998). An exception is N4SSB, the activator of *E. coli* RNAP$\sigma^{70}$ at the bacteriophage N4 late promoters, which activates transcription through direct interactions with the β' subunit of RNAP in the absence of DNA binding (Miller, et al., *Science* 275:1655-1657, 1997).

Proteins that bind to ssDNAs with high affinity but without sequence specificity have been purified and characterized from several prokaryotes, eukaryotes, and their viruses (Chase, et al., *Ann. Rev. Biochem.* 55:130-136, 1986). These proteins (SSBs), which are required for replication, recombination and repair, bind stoichiometrically and, in many cases, cooperatively to ssDNA to cover the transient single-stranded regions of DNA that normally arise in vivo as a result of replication, repair and recombination. Binding to DNA results in the removal of hairpin structures found on ssDNA, providing an extended conformation for proteins involved in DNA metabolism. Several lines of evidence suggest that single-stranded DNA binding proteins play a more dynamic role in cellular processes. Genetic and biochemical evidence indicates that these proteins are involved in a multitude of protein-protein interactions including transcription activation (Rothman-Denes, et al., *Genes Devepmnt.* 12:2782-2790, 1999).

b. The Bacteriophage N4 Virion RNA Polymerase

Figure 1:
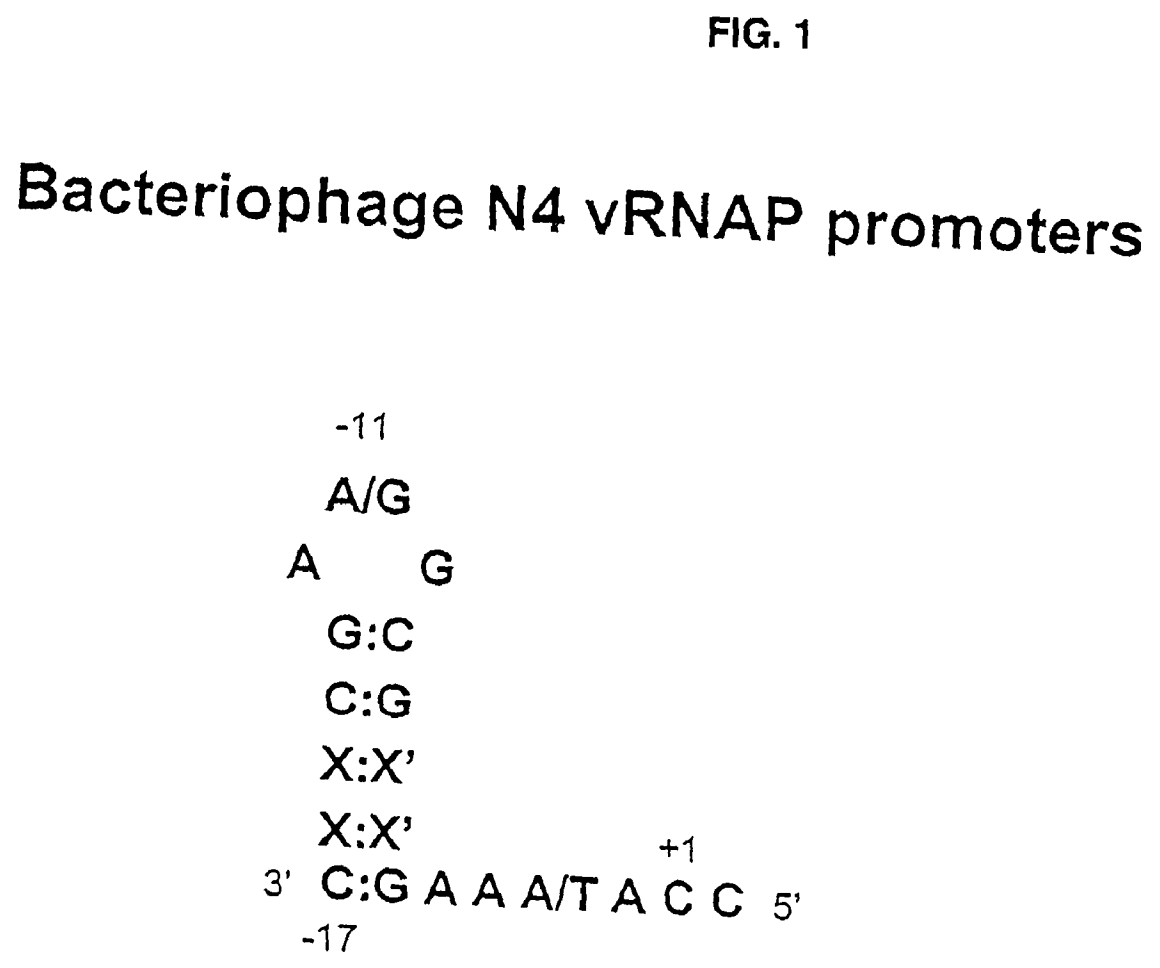

Bacteriophage N4 virion RNA polymerase (N4 vRNAP) is present in N4 virions and is injected into the *E. coli* cell at the beginning of infection, where it is responsible for transcription of the N4 early genes (Falco, et al., *Proc. Natl. Acad. Sci. (USA)* 74:520-523, 1977; Falco, et al., *Virology* 95:454-465, 1979; Malone, et al., *Virology* 162:328-336, 1988). The N4 vRNAP gene maps to the late region of the N4 genome (Zivin, et al., *J. Mol. Biol.* 152:335-356, 1981). N4 vRNAP purified from virions is composed of a single polypeptide with an apparent molecular mass of approximately 320,000 kDa (Falco, et al., *Biol. Chem.* 255:4339-4347, 1980). In contrast to other DNA-dependent RNAPases, N4 vRNAP recognizes promoters on single-stranded templates (Falco, et al., *Proc. Natl. Acad. Sci. (USA)* 75:3220-3224, 1978). These promoters are characterized by conserved sequences and a 5 bp stem, 3 base loop hairpin structure (FIG. 1) (Haynes, et al., *Cell* 41:597-605, 1985; Glucksmann, et al., *Cell* 70:491-500, 1992). In vivo, *E. coli* gyrase and single-stranded binding protein are required for transcription by N4 vRNAP (Falco, et al., *J. Biol. Chem.* 255:4339-4347, 1980; Markiewicz, et al., *Genes and Dev.* 6:2010-2019, 1992).

Sequencing of the N4 vRNAP gene revealed an ORF coding for a protein 3,500 amino acids in length (SEQ ID NO:1-2). Inspection of the sequence revealed no extensive homology to either the multisubunit or the T7-like families of RNA polymerases. However, three motifs are present (FIG. 2A): the T/DxxGR motif found in DNA-dependent polymerases, and Motif B ($Rx_3Kx_{6-7}YG$), one of three motifs common to the Pol I and Pol αDNA polymerases and the T7-like RNA polymerases.

c. Transcription Using N4 vRNAP

RNA synthesis requires RNA polymerase, a DNA template, an activated precursor (the ribonucleoside triphosphates ATP, GTP, UTP and CTP (XTP)), and divalent metal ions such as $Mg^{+2}$ or $Mn^{+2}$. The metal ion $Mg^{+2}$ is strongly preferred. Synthesis of RNA begins at the promoter site on the DNA. This site contains a sequence which the RNA polymerase recognizes and binds. The RNA synthesis proceeds until a termination site is reached. N4 vRNAP termination signals comprise a hairpin loop that forms in the newly synthesized RNA which is followed by a string of uracils (poly U). The sequence of the terminator signals for vRNAP present in the N4 genome include SEQ ID NOS:21-26. These N4 vRNAP termination signals possess all of the characteristics of eubacterial sequence-dependent terminators. The ribonucleoside triphosphate may be derivatized with, for example, biotin. Derivatized XTPs can be used for the preparation of derivatized RNA. Exemplary methods for making derivatized XTPs are disclosed in detail in Rashtchian et al., "Nonradioactive Labeling and Detection of Biomolecules," C. Kessler, Ed., Springer-Verlag, New York, pp. 70-84, 1992, herein incorporated by reference.

Single-stranded DNA of varying lengths can be used as a template for RNA synthesis using the N4 vRNAP or mini-vRNAP. Oligonucleotides and polynucleotides of intermediate length may be used. One particular single-stranded DNA that may be used is M13 DNA. M13 genomic DNA exists temporarily inside infected *E. coli* cells as a double-stranded DNA plasmid and is packaged as a small, single-stranded circular DNA into phage particles. M13 phage particles are secreted by an infected cell and single-stranded DNA can be purified from these particles for use as a transcription template. Initially M13 phage vectors required a working knowledge of phage biology and were primarily used for creating single-strand DNA molecules for DNA sequencing. M13-derived cloning vectors called "phagemids" take advantage of M13 replication to produce single-strand molecules, but can be propagated as conventional Co1E1-based replicating double-strand plasmids.

EcoSSB is essential for N4 vRNAP transcription in vivo (Falco et al., *Proc. Natl. Acad. Sci. (USA)* 75:3220-3224, 1978; Glucksmann, et al., *Cell* 70:491-500, 1992, herein incorporated by reference). EcoSSB is a specific activator of N4 vRNAP on single-stranded and supercoiled double-stranded DNA templates. EcoSSB, unlike other SSBs, does not melt the N4 vRNAP promoter hairpin structure (Glucksmann-Kuis, et al., *Cell* 84:147-154, 1996). EcoSSB has a high specificity for N4 vRNAP and mini-vRNAP resulting from EcoSSB's ability to stabilize the template-strand hairpin, whereas the nontemplate strand hairpin is destabilized. Other single-stranded DNA binding proteins destabilize the template-strand hairpin (Glucksmann-Kuis, et al., *Cell* 84:147-154, 1996; Dai et al., *Genes Devepmnt.* 12:2782-2790, 1998). EcoSSB mediates template recycling during transcription by N4 vRNAP (Davidova, E K and Rothman-Denes, L B, *Proc. Natl. Acad. Sci. USA* 100:9250-9255, 2003, incorporated herein by reference). When EcoSSB is not used in N4 vRNAP transcription in vitro, a DNA:RNA hybrid is formed, preventing template reutilization.

II. GENES AND DNA SEGMENTS

Important aspects of the present invention concern isolated DNA segments and recombinant vectors encoding N4 vRNAP or more particularly mini-vRNAP or a mutant of mini-vRNAP and the creation and use of recombinant host cells through the application of DNA technology, that express a wild type, polymorphic or mutant vRNAP. Other aspects of the present invention concern isolated nucleic acid segments and recombinant vectors encoding vRNAP. Sequences of SEQ ID NO:1, 3, 5, 7, 14 and biologically functional equivalents thereof are used in the current invention. Single-stranded DNA oligonucleotides and polynucleotides can be used as DNA templates.

The present invention concerns isolated nucleic acid segments that are capable of expressing a protein, polypeptide or peptide that has RNA polymerase activity. As used herein, the term "nucleic acid segment" refers to a nucleic acid molecule that has been isolated free of total genomic DNA of a particular species. Therefore, a nucleic acid segment encoding vRNAP refers to a nucleic acid segment that contains wild-type, polymorphic or mutant vRNAP coding sequences yet is isolated away from, or purified free from, total bacterial or N4 phage genomic DNA. Included within the term "nucleic acid segment," are nucleic acid segments and smaller fragments of such segments, and also recombinant vectors, including, for example, plasmids, cosmids, phage, viruses, and the like.

Similarly, a nucleic acid segment comprising an isolated or purified vRNAP gene refers to a nucleic acid segment including vRNAP protein, polypeptide or peptide coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those of skill in the art, this functional term includes both genomic sequences, cDNA sequences and engineered segments that express, or may be adapted to express, proteins, polypeptides, domains, peptides, vRNAPs and mutants of vRNAP encoding sequences.

"Isolated substantially away from other coding sequences" means that the gene of interest, in this case the vRNAP, or more particularly mini-vRNAP genes, forms the significant part of the coding region of the nucleic acid segment, and that the nucleic acid segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

The term "a sequence essentially as set forth in SEQ ID NO:2 means, for example, that the sequence substantially corresponds to a portion of SEQ ID NO:2 and has relatively few amino acids that are not identical to, or a biologically functional equivalent of, the amino acids of SEQ ID NO:2. This applies with respect to all peptide and protein sequences herein, such as those of SEQ ID NO:4, 6, 8 and 15.

The term "biologically functional equivalent" is well understood in the art and is further defined in detail herein. Accordingly, sequences that have about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO:2 will be sequences that are "essentially as set forth in SEQ ID NO:2," provided the biological activity of the protein is maintained. In particular embodiments, the biological activity of a vRNAP protein, polypeptide or peptide, or a biologically functional equivalent, comprises transcription. A preferred transcriptional activity that may be possessed by a vRNAP protein, polypeptide or peptide, or a biologically finctional equivalent, is RNA synthesis using single-stranded N4 vRNAP promoter-containing DNA as a template.

In certain other embodiments, the invention concerns isolated nucleic acid segments and recombinant vectors that include within their sequence a nucleic acid sequence essentially as set forth in SEQ ID NO:1. The term "essentially as set forth in SEQ ID NO:1 is used in the same sense as described above and means that the nucleic acid sequence substantially corresponds to a portion of SEQ ID NO:1 and has relatively few codons that are not identical, or finctionally equivalent, to the codons of SEQ ID NO:1. Again, nucleic acid segments that encode proteins, polypeptide or peptides exhibiting RNAP activity will be most preferred.

The term "functionally equivalent codon" is used herein to refer to codons that encode the same amino acid, such as the six codons for arginine and serine, and also refers to codons that encode biologically equivalent amino acids. For optimization of expression of vRNAP in human cells, the following codons are used, with preference of use from left to right: Alanine Ala A GCC GCT GCA GCG; Cysteine Cys C TGC TGT; Aspartic acid Asp D GAG GAT; Glutamic acid Glu E GAG GAA; Phenylalanine Phe F TTC TTT; Glycine Gly G GGC GGG GGA GGT; Histidine His H CAC CAT; Isoleucine Ile I ATC ATT ATA; Lysine Lys K AAG AAA; Leucine Leu L CTG CTC TTG CTT CTA TTA; Methionine Met M ATG; Asparagine Asn N AAC AAT; Proline Pro P CCC CCT CCA CCG; Glutamine Gln Q CAG CAA; Arginine Arg R CGC AGG CGG AGA CGA CGT; Serine Ser S AGC TCC TCT AGT TCA TCG; Threonine Thr T ACC ACA ACT ACG; Valine Val V GTG GTC GTT GTA; Tryptophan Trp W TGG; Tyrosine Tyr Y TAC TAT. Thus, the most preferred codon for alanine is "GCC," and the least is "GCG." Codon usage for various organisms and organelles can be found at the website http://www.kazusa.orjp/codon/, incorporated herein by reference, allowing one of skill in the art to optimize codon usage for expression in various organisms using the disclosures herein. Thus, it is contemplated that codon usage may be optimized for other animals, as well as other organisms such as a prokaryote (e.g., an eubacteria), an archaea, an eukaryote (e.g., a protist, a plant, a fungus, an animal), a virus and the like, as well as organelles that contain nucleic acids, such as mitochondria or chloroplasts, based on the preferred codon usage as would be known to those of ordinary skill in the art.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99%; and any range derivable therein, such as, for example, about 50% to about 80%, and more preferably about 81% and about 90%; or even more preferably, between about 91% and about 99%; of nucleotides that are identical to the nucleotides of SEQ ID NO:1 will be sequences that are "essentially as set forth in SEQ ID NO:1".

a. Nucleic Acid Hybridization

The nucleic acid sequences disclosed herein also have a variety of uses. Contiguous sequences from vRNAP nucleic acid sequences can be used, for example, as templates to synthesize vRNAP.

Naturally, the present invention also encompasses DNA segments that are complementary, or essentially complementary, to the sequence set forth in SEQ ID NO:1, 3, 5, 7 and 14. Nucleic acid sequences that are "complementary" are those that are capable of base-pairing according to the standard Watson-Crick complementary rules. As used herein, the term "complementary sequences" means nucleic acid sequences that are complementary, as may be assessed by the same nucleotide comparison set forth above, or as defined as being capable of hybridizing to the nucleic acid segment of SEQ ID NO:1 under stringent conditions such as those described herein.

As used herein, a "DNA/RNA hybrid" is understood to mean that a single strand of RNA is hybridized to a single strand of DNA.

The term "appropriate reaction conditions" as described herein mean that temperature, pH, buffer, and other parameters are adjusted to optimize the reaction rate and yield.

As used herein, "hybridization," "hybridizes" or "capable of hybridizing" is understood to mean the forming of a double or triple stranded molecule or a molecule with partial double or triple stranded nature. The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suit a particular application. For example, in other embodiments, hybridization may be achieved under conditions of 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 MM $MgCl_2$, at temperatures ranging from approximately 40° C. to about 72° C.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a contiguous stretch of nucleotides identical to or complementary to SEQ ID NO:1, 3, 5, 7 or 14. Nucleic acid fragments for use as a DNA transcription template may also be prepared. These fragments may be short or of intermediate lengths, such as, for example, about 8, about 10 to about 14, or about 15 to about 20 nucleotides, and that are chromosome-sized pieces, up to about 35,000, about 30,000, about 25,000, about 20,000, about 15,000, about 10,000, or about 5,000 base pairs in length, as well as DNA segments with total lengths of about 1,000, about 500, about 200, about 100 and about 50 base pairs in length (including all intermediate lengths of these lengths listed above, i.e., any range derivable therein and any integer derivable therein such a range) are also contemplated to be useful.

For example, it will be readily understood that "intermediate lengths," in these contexts, means any length between the quoted ranges, such as 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 130, 140, 150, 160, 170, 180, 190, including all integers through the 200-500; 500-1,000; 1,000-2,000; 2,000-3,000; 3,000-5,000; 5,000-10,000 ranges, up to and including sequences of about 12,001, 12,002, 13,001, 13,002, 15,000, 20,000 and the like.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

The use of a hybridization probe of between 17 and 100 nucleotides in length, or in some aspect of the invention even up to 1-2 Kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having complementary sequences over stretches of 20 to 30 nucleotides, or even longer where desired. Such fragments may be readily prepared by, for example, directly synthesizing the fragment by chemical means or by introducing selected sequences into recombinant vectors for recombinant production.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

b. Nucleic Acid Amplification

Nucleic acid used as a template for amplification is isolated from cells contained in the biological sample, according to standard methodologies (Sambrook et al., In: Molecular Cloning: A Laboratory Manual 2 rev.ed., Cold Spring Harbor: Cold Spring Harbor Laboratory Press, 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label, or even via a system using electrical or thermal impulse signals (Affymax technology).

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, each incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products, and the process is repeated.

A reverse transcriptase PCR amplification procedure may be performed in order to quantify the amount of mRNA amplified. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Q-beta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence, which can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification method described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double-stranded DNA molecules are heat denatured again. In either case, the single-stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single-stranded DNA, which is then converted to double-stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, In: PCR Protocols: A Guide To Methods And Applications, Academic Press, N.Y., 1990, incorporated herein by reference).

Methods based on ligation of two (or more) oligonucleotides in the presence of nucleic acid having the sequence of the resulting "di-oligonucleotide," thereby amplifying the di-oligonucleotide, may also be used in the amplification step of the present invention.

c. Nucleic Acid Detection

In certain embodiments, it will be advantageous to employ nucleic acid sequences of the present invention such as all or part of SEQ ID NO:1, 3, 5, 7, 14 or a mutant thereof in combination with an appropriate means, such as a label, for hybridization assays, RNase protection and Northern hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In embodiments wherein nucleic acids are amplified, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., In: Molecular Cloning: A Laboratory Manual 2 rev.ed., Cold Spring Harbor: Cold Spring Harbor Laboratory Press, 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of an *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase Protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences are hybridized to complementary target regions derived from test samples. The test target generally comprises DNA (either genomic DNA or DNA amplified by cloning in plasmids or by PCR), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

Nuclease S1 analysis of reaction products can be used to measure RNA. An exemplary procedure for S1 analysis involves hybridization reaction with the RNA of interest (0.005-0.1 mg) and an excess of S1 probe which comprises a labeled oligonucleotide complementary to 20-80 or more sequential nucleotides of a specific RNA in S1 hybridization buffer (80% formamide, 0.4 M NaCl, 1 mM EDTA, 40 mM Pipes, pH 6.4). After denaturation for 4 min at 94° C., overnight hybridization at 30° C. and precipitation with ethanol, the S1 probe/RNA mixture is resuspended in S1 buffer (0.26 M NaCl, 0.05 M sodium acetate, pH 4.6, and 4.5 mM zinc sulfate). The sample is divided into two volumes and 100 units of S1 nuclease (Sigma Chemical Company) is added to one tube. The samples are incubated for 60 minutes at 37° C.; then EDTA (10 mM final concentration) and 15 g polyl-polyC RNA are added and the sample is extracted with phenol/chloroform and precipitated in ethanol. The samples are then subjected to polyacrylamide gel electrophoresis.

One method to produce a radiolabeled RNA probe with high specific activity includes admixing a radiolabeled NTP during transcription. Suitable isotopes for radiolabeling include $^{35}$S- and $^{32}$P-labeled UTP, GTP, CTP or ATP. For optimal results, a gel-purified radiolabeled RNA probe which is preferentially 300-500 bases in length, with a specific activity of 1-3×10 8 cpm/μg should be generated using the RNA polymerase of the current invention. In order to produce this in vitro transcript, it is often advisable to use a high specific activity (e.g., [α-$^{32}$P]CTP at 3,000 Ci/mmol) NTP. To prevent background hybridization, it is important to remove plasmid template DNA by digestion which can be done with, for example, RQ1 RNase-Free DNase followed by phenol:chloroform:isoamyl alcohol extraction and ethanol precipitation.

Another method for producing radiolabeled probes includes using a riboprobe system which can produce high specific activity, radiolabeled RNA probes or microgram quantities of in vitro transcript. Riboprobes are useful with radiolabeled RNA probes in many applications including RNase protection, Northern hybridization, S1 analysis and in situ hybridization assays. The principle components of an in vitro transcription are the riboprobe, an RNA polymerase, a DNA template which includes a phage RNA polymerase promoter and ribonucleotide triphosphates.

d. Cloning vRNAP Genes

The present invention contemplates cloning vRNAP, or more particularly mini-vRNAP genes. A technique often employed by those skilled in the art of protein production today is to obtain a so-called "recombinant" version of the protein, to express it in a recombinant cell and to obtain the protein, polypeptide or peptide from such cells. These techniques are based upon the "cloning" of a nucleic acid molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, such as, for example, from a phage, bacteria, yeast, fungus, mouse, rat, monkey or human. The screening protocol may utilize nucleotide segments or probes that are designed to hybridize to cDNA or genomic sequences of vRNAPs from protists. Additionally, antibodies designed to bind to the expressed vRNAP proteins, polypeptides, or peptides may be used as probes to screen an appropriate viral, eubacterial, archaebacterial or eukaryotic DNA expression library. Alternatively, activity assays may be employed. The operation of such screening protocols are well known to those of skill in the art and are described in detail in the scientific literature, for example, in Sambrook et al., In: Molecular Cloning: A Laboratory Manual 2 rev.ed., Cold Spring Harbor: Cold Spring Harbor Laboratory Press, 1989, incorporated herein by reference. Moreover, as the present invention encompasses the cloning of genomic segments as well as cDNA molecules, it is contemplated that suitable genomic cloning methods, as known to those in the art, may also be used.

Encompassed by the invention are DNA segments encoding relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2, 4, 6, 8 or 15 and also larger polypeptides up to and including proteins corresponding to the full-length sequences set forth in SEQ ID NO:2 and SEQ ID NO:15, and any range derivable therein and any integer derivable in such a range. In addition to the "standard" DNA and RNA nucleotide bases, modified bases are also contemplated for use in particular applications of the present invention.

III. RECOMBINANT VECTORS, PROMOTORS, HOST CELLS AND EXPRESSION

Recombinant vectors form an important further aspect of the present invention. The term "expression vector or construct" means any type of genetic construct containing a nucleic acid coding for a gene product in which part or all of the nucleic acid encoding sequence is capable of being transcribed. The transcript may be translated into a proteinaceous molecule, but it need not be, such as in the case of mini-vRNAP transcribing an RNA using a single-stranded DNA template. Thus, in certain embodiments, expression includes both transcription of a single-stranded DNA and translation of an RNA into the protein product. In other embodiments, expression only includes transcription of the nucleic acid. A recombinant vector can also be used for delivery of the RNA of the current invention.

Particularly useful vectors are contemplated to be those vectors in which the coding portion of the DNA segment, whether encoding a full length protein or smaller polypeptide or peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

One particularly useful vector is pBAD. The pBAD expression vectors allow for greater control of bacterial expression of recombinant proteins and allow tight regulation for turning expression on or off. pBAD vectors allow for dose dependent induction for modulation of expression levels. The pBAD expression system helps overcome two of the most common problems of heterologous protein expression in bacteria: toxicity of the recombinant protein to the host and insolubility of the recombinant protein when it is expressed at high, uncontrolled levels. In both cases, a tightly-regulated expression system is critical for maximizing recombinant protein yields. The pBAD expression system is based on the araBAD operon which controls the arabinose metabolic pathway in *E. coli* and allows for precise modulation of heterologous expression to levels that are optimal for recovering high yields of the protein of interest (Guzman et al., *J. Bact.* 177:4121-4130, 1995).

a. Promoters

Any promoters normally found in a host cell in the native state can be used in the present invention to drive expression of N4 vRNA or mini-vRNA polymerase. Also, promoters not normally found in the host cell in the native state that are recognized by a native, normally native host cell RNA polymerase, or non-native RNA polymerase expressed in the cell can be used in the present invention to drive expression of the RNA polymerase. Other promoters may be selected from a nucleic acid sequence database accessible to those of skill in the art, e.g., GenBank, or the promoter can be isolated by a screening method. A promoter recognized by the host cell can be operably linked to the gene or genes encoding the N4 RNA polymerase. The operable linkage can be constructed using any known techniques for DNA manipulation, as referred to herein.

Promoters are described as either constitutive or inducible. Constitutive promoters actively drive expression of genes under their control. Inducible promoters, in contrast, are activated in response to specific environmental stimuli. Both constitutive and inducible promoters can be used in the present invention for expressing non-host genes in a host cell.

Inducible promoters include, but are not limited to, trp, tac, lac, ara, reca, λPr, and λP1. These promoters and others that can be used in the present invention for expression of the N4 vRNA or mini-vRNA polymerase, in embodiments in which the host cell is *E. coli*, are described by Makrides, *Microbiological Reviews* 60, 512-538, 1996, herein incorporated by reference. Further, in embodiments of the present invention wherein the host cell is a microbe other than *E. coli*, such as *Saccharomyces, Bacillus*, and *Pseudomonas*, any inducible promoter known to those skilled in the art to be active in the host cell can be used to drive expression of the heterologous RNA polymerase. (U.S. Pat. No. 6,218,145).

The promoter may be in the form of the promoter that is naturally associated with N4 vRNA or mini-vRNA polymerase, as may be obtained by isolating the 5' non-coding sequences located upstream of the coding segment or exon, for example, using recombinant cloning and/or PCR technology, in connection with the compositions disclosed herein (PCR technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with N4 vRNA or mini-vRNA polymerase in its natural environment. Such promoters may include promoters normally associated with other genes, and/or promoters isolated from any other bacterial, viral, eukaryotic, protist, or mammalian cell, and/or promoters made by the hand of man that are not "naturally occurring," i e., containing different elements from different promoters, or mutations that increase, decrease, or alter expression.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. In: Molecular Cloning: A Laboratory Manual 2 rev.ed., Cold Spring Harbor: Cold Spring Harbor Laboratory Press, 1989, incorporated herein by reference. The promoters employed may be constitutive, or inducible, and can be used under the appropriate conditions to direct high level expression of the introduced DNA segment, such as is advantageous in the large-scale production of recombinant proteins, polypeptides or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase promoter, the spacing between promoter elements can be increased to 50 base pairs apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the *Rous sarcoma* virus long terminal repeat can be used to obtain high-level expression of the instant nucleic acids. The use of other viral or mammalian cellular or bacterial phage promoters which are well-known in the art to achieve expression are contemplated as well, provided that the levels of expression are sufficient for a given purpose.

In certain embodiments of the invention, promoter sequences may be used that that are recognized specifically by a DNA-dependent RNA polymerase, such as, but not limited to, those described by Chamberlin and Ryan, In: The Enzymes. San Diego, Calif., Academic Press, 15:87-108, 1982, and by Jorgensen et al., *J. Biol. Chem.* 266:645-655, 1991. These promoters can be used to express a wild-type or mutant form of a miniV RNA polymerase of the invention. Several RNA polymerase promoter sequences are especially useful, including, but not limited to, promoters derived from SP6 (e.g., Zhou and Doetsch, *Proc. Nat. Acad. Sci. USA* 90:6601-6605, 1993), T7 (e.g., Martin, and Coleman, *Biochemistry* 26:2690-2696, 1987) and T3 (e.g., McGraw et al., *Nucl. Acid. Res.* 13:6753-6766, 1985). An RNA polymerase promoter sequence derived from *Thermus thermophilus* can also be used (see, e.g., Wendt et al., *Eur. J. Biochem.* 191:467-472, 1990; Faraldo et al., *J. Bact.* 174:7458-7462, 1992; Hartmann et al., *Biochem.* 69:1097-1104, 1987; Hartmann et al., *Nucl. Acids Res.* 19:5957-5964, 1991). The length of the promoter sequence will vary depending upon the promoter chosen. For example, the T7 RNA polymerase promoter can be only about 25 bases in length and act as a functional promoter, while other promoter sequences require 50 or more bases to provide a functional promoter.

In other embodiments of the invention, a promoter is used that is recognized by an RNA polymerase from a T7-like bacteriophage. The genetic organization of all T7-like phages that have been examined has been found to be essentially the same as that of T7. Examples of T7-like phages according to the invention include, but are not limited to *Escherichia coli* phages T3, ϕI, ϕII, W31, H, Y, A1, 122, cro, C21, C22, and C23; *Pseudomonas putida* phage gh-1; *Salmonella typhimurium* phage SP6; *Serratia marcescens* phages IV; *Citrobacter* phage ViIII; and *Klebsiella* phage No. 11 (Hausmann, *Current Topics in Microbiology and Immunology* 75:77-109, 1976; Korsten et al., *J. Gen. Virol.* 43:57-73, 1975; Dunn, et al., *Nature New Biology* 230:94-96, 1971; Towle, et al., *J. Biol. Chem.* 250:1723-1733, 1975; Butler and Chamberlin, *J. Biol. Chem.* 257:5772-5778, 1982).

When a T7 RNA polymerase promoter, or another T7-like RNA polymerase promoter is used to express a wild-type or mutant form of a gene for a miniV RNA polymerase of the invention, the gene can be expressed in a host cell which expresses the T7 RNA polymerase, or the corresponding T7-like RNA polymerase for the promoter used, wherein the RNA polymerase for the promoter is expressed either constitutively, or more preferably, from an inducible promoter. By way of example, a T7 RNA polymerase expression system, such as, but not limited to, the expression systems disclosed in, for example, U.S. Pat. Nos. 5,693,489 and 5,869,320, the disclosures of which are incorporated herein by reference in their entirety.

b. Enhancers

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB, http://www.epd.isb-sib.ch/) could also be used to drive expression.

Eukaryotic cells can support cytoplasmic transcription from certain bacterial promoters if the appropriate bacterial polymerase is provided, either as part of the delivery complex or as an additional genetic expression construct.

Turning to the expression of the proteinaceous molecules after transcription using the vRNAP, mini-vRNAP, or mutants thereof of the present invention, once a suitable clone or clones have been obtained, whether they be cDNA based or genomic, one may proceed to prepare an expression system.

The engineering of DNA segment(s) for expression in a prokaryotic or eukaryotic system may be performed by techniques generally known to those of skill in recombinant expression. It is believed that virtually any expression system may be employed in the expression of the proteinaceous molecules of the present invention.

Both cDNA and genomic sequences are suitable for eukaryotic expression, as the host cell will generally process the genomic transcripts to yield functional mRNA for translation into proteinaceous molecules. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

c. Antisense, RNAi and Ribozymes

In some embodiments of the invention the vRNA polymerase can be used to synthesize antisense RNA, RNAi or interference RNA or ribozymes.

The term "antisense nucleic acid" is intended to refer to the oligonucleotides complementary to the base sequences of DNA and RNA. Antisense oligonucleotides, when introduced into a target cell, specifically bind to their target nucleic acid and interfere with transcription, RNA processing, transport, translation, and/or stability. Targeting double-stranded (ds) DNA with oligonucleotides leads to triple-helix formation; targeting RNA will lead to double-helix formation. An antisense nucleic acid may be complementary to SEQ ID NO:1, 3, 5, 7 or 14, complementary to a mini-vRNAP encoding sequence or to mini-vRNAP non-coding sequences. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries (splice junctions) of a gene. It is contemplated that the most effective antisense constructs may include regions complementary to intron/exon splice junctions. Thus, antisense constructs with complementary regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vivo to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., *Science* 260:1510-1513, 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Sequences for ribozymes may be included in the DNA template to eliminate undesired 5' end sequences in RNAs generated through T7 RNA polymerase transcription.

Ribozymes are RNA-protein complexes that cleave nucleic acids in a site-specific fashion. Ribozymes have specific catalytic domains that possess endonuclease activity (Kim and Cech, *Proc. Natl. Acad. Sci. USA* 84:8788-8792, 1987; Gerlach et al., *Nature* 328:802-805, 1987; Forster and Symons, *Cell* 49:211-220, 1987). For example, a large number of ribozymes accelerate phosphoester transfer reactions with a high degree of specificity, often cleaving only one of several phosphoesters in an oligonucleotide substrate (Cech et al., *Cell* 27:487-496, 1981; Michel and Westhof, *J. Mol. Biol.* 216:585-610, 1990; Reinhold-Hurek and Shub, *Nature* 357:173-176, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, *Nature* 338:217-244, 1989; Cech et al., *Cell* 27:487-496, 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., *Proc. Natl. Acad. Sci. USA* 88:10591-10595, 1991; Sarver et al., *Science* 247:1222-1225, 1990; Sioud et al., *J. Mol. Biol.* 223:831-835, 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, *Annu. Rev. Biochem.* 61:641-671, 1992). Examples of ribozymes include sequences from the Group I self-splicing introns including tobacco ringspot virus (Prody, et al., *Science* 231:1577-1580, 1986), avocado sunblotch viroid (Palukaitis, et al., *Virology* 99:145-151, 1979; Symons, *Nucl. Acids Res.* 9:6527-6537, 1981), and Lucerne transient streak virus (Forster and Symons, *Cell* 49:211-220, 1987). Sequences from these and related viruses are referred to as hammerhead ribozymes based on a predicted folded secondary structure.

Other suitable ribozymes include sequences from RNase P with RNA cleavage activity (Yuan, et al., *Proc. Natl. Acad. Sci. USA* 89:8006-8010, 1992; Yuan and Altman, *Science,* 263:1269-1273, 1994), hairpin ribozyme structures (Berzal-Herranz, et al., *Genes and Devel.* 6:129-134, 1992; Chowrira et al., *Biochemistry* 32:1088-1095, 1993) and hepatitis δ virus based ribozymes (Perrotta and Been, *Biochemistry* 31:16-21, 1992). The general design and optimization of ribozyme directed RNA cleavage activity has been discussed in detail (Haseloff and Gerlach, *Nature* 334:585-591, 1988; Symons, *Annu. Rev. Biochem.* 61:641-671, 1992; Chowrira, et al., *J. Biol. Chem.* 269:25856-25864, 1994; and Thompson, et al., *Nature Medicine* 1:277-278, 1995).

The other variable on ribozyme design is the selection of a cleavage site on a given target RNA. Ribozymes are targeted to a given sequence by virtue of annealing to a site by complementary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., *Gene* 113:157-163, 1992; Thompson, et al., *Nature Medicine* 1:277-278, 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., *J. Biol. Chem.* 269:25856-25864 (1994) and Lieber and Strauss, *Mol. Cell. Biol.* 15: 540-551 (1995), each incorporated by reference. The identification of operative and preferred sequences for use in ribozymes is simply a matter of preparing and testing a given sequence, and is a routinely practiced "screening" method known to those of skill in the art.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

d. Host Cells

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryotic host cell for replication of many vector copies. Bacterial cells used as host cells for vector replication and/or expression include DH5α, BL 21, JM109, and KC8, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells. Appropriate yeast cells include *Saccharomyces cerevisiae, Saccharomyces pombe*, and *Pichia pastoris.*

Examples of eukaryotic host cells for replication and/or expression of a vector include HeLa, NIH3T3, Jurrat, 293, Cos, CHO, Saos, BHK, C127 and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and/or their polypeptides, proteins, or peptides.

It is proposed that vRNAP, or more particularly mini-vRNAP may be co-expressed with other selected proteinaceous molecules such as EcoSSB and other proteins of interest, wherein the proteinaceous molecules may be co-expressed in the same cell or vRNAP gene may be provided to a cell that already has another selected proteinaceous molecule. Co-expression may be achieved by co-transfecting the cell with two distinct recombinant vectors, each bearing a copy of either of the respective DNAs. Alternatively, a single recombinant vector may be constructed to include the coding regions for both of the proteinaceous molecules, which could then be expressed in cells transfected with the single vector. In either event, the term "co-expression" herein refers to the expression of both the vRNAP gene and the other selected proteinaceous molecules in the same recombinant cell.

As used herein, the terms "engineered" and "recombinant" cells or host cells are intended to refer to a cell into which an exogenous DNA segment or gene, such as a cDNA or gene encoding vRNAP, mini-vRNAP or a mutant thereof, has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant vRNAP, whether mutant or wild-type, in accordance with the present invention one would prepare an expression vector that comprises a wild-type, or mutant vRNAP proteinaceous molecule-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of the chosen promoter. The "upstream" promoter directs transcription of the DNA and promotes expression of the encoded recombinant protein, polypeptide or peptide. This is the meaning of "recombinant expression" in this context.

Many standard techniques are available to construct expression vectors containing the appropriate nucleic acids and transcriptional/translational control sequences in order to achieve protein, polypeptide or peptide expression in a variety of host expression systems. Cell types available for expression include, but are not limited to, bacteria, such as *E. coli* and *B. subtilis*, transformed with recombinant bacteriophage DNA, plasmid DNA or cosmid DNA expression vectors.

Certain examples of prokaryotic hosts are *E. coil* strain RR1, *E. coli* LE392, *E. coli* B, *E. coli* X 1776 (ATCC No. 31537) as well as *E. coli* W31 10 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication origin, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors; and pGEX vectors, for use in generating glutathione S-transferase (GST) soluble proteins for later purification and separation or cleavage.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant proteinaceous molecule may be induced, e.g., by adding IPTG or any appropriate inducer to the media or by switching incubation to a higher temperature, depending on the regulated promoter used. After culturing the bacteria for a further period, generally of between 2 and 24 hours, the cells are collected by centrifugation and washed to remove residual media.

The bacterial cells are then lysed, for example, by disruption in a cell homogenizer, by sonication or cell press and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant proteinaceous molecule is expressed in the inclusion bodies, as is the case in many instances, these can be washed in any of several solutions to remove some of the contaminating host proteins, then solubilized in solutions containing high concentrations of urea (e.g., 8M) or chaotropic agents such as guanidine hydrochloride in the presence of reducing agents, such as β-mercaptoethanol or DTT (dithiothreitol).

Under some circumstances, it may be advantageous to incubate the proteinaceous molecule for several hours under conditions suitable for the proteinaceous molecule to undergo a refolding process into a conformation which more closely resembles that of the native proteinaceous molecule. Such conditions generally include low proteinaceous molecule concentrations, less than 500 mg/ml, low levels of reducing agent, concentrations of urea less than 2 M and often the presence of reagents such as a mixture of reduced and oxidized glutathione which facilitate the interchange of disulfide bonds within the proteinaceous molecule.

The refolding process can be monitored, for example, by SDS-PAGE, or with antibodies specific for the native molecule (which can be obtained from animals vaccinated with the native molecule or smaller quantities of recombinant proteinaceous molecule). Following refolding, the proteinaceous molecule can then be purified further and separated from the refolding mixture by chromatography on any of several supports including ion exchange resins, gel permeation resins or on a variety of affinity columns.

For expression in *Saccharomyces*, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoter sequences in yeast vectors include the promoters for 3-phosphoglycerate kinase or other glycolytic enzymes, such as enolase, glyceraldehyde-3-phosphate protein, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector downstream of the sequence desired to be expressed to provide polyadenylation of the mRNA and termination.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more RNAP coding sequences.

Different host cells have characteristic and specific mechanisms for the post-translational processing and modification of proteinaceous molecules. Appropriate cells lines or host systems can be chosen to ensure the correct modification and processing of the foreign proteinaceous molecule expressed.

A number of viral-based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing an RNA in infected hosts.

Specific initiation signals may also be used for more efficient translation using the vRNAP of the current invention. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the proteinaceous molecule at a position prior to transcription termination.

For long-term, high-yield production of a recombinant vRNAP protein, polypeptide or peptide, stable expression is preferred. For example, cell lines that stably express constructs encoding a vRNAP protein, polypeptide or peptide may be engineered. Rather than using expression vectors that contain viral origins of replication, host cells can be transformed with vectors controlled by appropriate expression control elements (e.g., promoter, enhancer sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in $tk^-$, $hgprt^-$ or $aprt^-$ cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Large scale suspension culture of bacterial cells in stirred tanks is a common method for production of recombinant proteinaceous molecules. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor for microbial fermentation relies on a gas stream to both mix and oxygenate the culture. The gas stream enters a riser section of the reactor and drives circulation. Gas disengages at the culture surface, causing denser liquid free of gas bubbles to travel downward in the downcorner section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the vRNAP proteins, polypeptides or peptides of the invention may be "overexpressed," i.e., expressed in increased levels relative to its natural expression in cells. Such overexpression may be assessed by a variety of methods, including radio-labeling and/or proteinaceous molecule purification. However, simple and direct methods are preferred, for example, those involving SDS/PAGE and proteinaceous composition staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific proteinaceous molecule in relation to the other proteins produced by the host cell and, e.g., visible on a gel.

IV. METHODS OF GENE TRANSFER

In order to mediate the effect of transgene expression in a cell, it will be necessary to transfer the expression constructs (e.g., a therapeutic construct) of the present invention into a cell. Such transfer may employ viral or non-viral methods of gene transfer. This section provides a discussion of methods and compositions of gene or nucleic acid transfer, including transfer of antisense sequences.

The vRNAP genes are incorporated into a viral vector to mediate gene transfer to a cell. Additional expression constructs encoding EcoSSB and other therapeutic agents as described herein may also be transferred via viral transduction using infectious viral particles, for example, by transformation with an adenovirus vector of the present invention. Alternatively, a retrovirus, bovine papilloma virus, an adeno-associated virus (AAV), a lentiviral vector, a vaccinia virus, a polyoma virus, or an infective virus that has been engineered to express a specific binding ligand may be used. Similarly, nonviral methods which include, but are not limited to, direct delivery of DNA such as by injection, electroporation, calcium phosphate precipitation, liposome mediated transfection, and microprojectile bombardment may be employed. Thus, in one example, viral infection of cells is used in order to deliver therapeutically significant genes to a cell. Typically, the virus simply will be exposed to the appropriate host cell under physiologic conditions, permitting uptake of the virus.

Microinjection can be used for delivery into a cell. Microinjection involves the insertion of a substance such as RNA into a cell through a microelectrode. Typical applications include the injection of drugs, histochemical markers (such as horseradish peroxidase or lucifer yellow) and RNA or DNA in molecular biological studies. To extrude the substances through the very fine electrode tips, either hydrostatic pressure (pressure injection) or electric currents (ionophoresis) is employed.

V. PROTEINACEOUS COMPOSITIONS

In certain embodiments, the present invention concerns novel compositions or methods comprising at least one proteinaceous molecule. The proteinaceous molecule may have a sequence essentially as set forth in SEQ ID NO:2, 4, 6, 8 or 15. The proteinaceous molecule may be a vRNAP or more preferably a mini-vRNAP, or a delivery agent. The proteinaceous molecule may also be a mutated mini-vRNAP.

As used herein, a "proteinaceous molecule," "proteinaceous composition," "proteinaceous compound," "proteinaceous chain" or "proteinaceous material" generally refers to, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to the following, beginning with the corresponding abbreviation: Aad 2-Aminoadipic acid; EtAsn N-Ethylasparagine; Baad 3-Aminoadipic acid; Hyl Hydroxylysine; Bala β-alanine, β-Amino-propionic acid; AHyl allo-Hydroxylysine; Abu 2-Aminobutyric acid; 3Hyp 3-Hydroxyproline; 4Abu 4-Aminobutyric acid, piperidinic; 4Hyp 4-Hydroxy-proline acid; Acp 6-Aminocaproic acid; Ide Isodesmosine; Ahe 2-Amino-heptanoic acid; AIle allo-Isoleucine; Aib 2-Aminoisobutyric acid; MeGly N-Methylglycine, sarcosine; Baib 3-Aminoisobutyric acid; MeIle N-Methylisoleucine; Apm 2-Aminopimelic acid; MeLys 6-N-Methyllysine; Dbu 2,4-Diaminobutyric acid; MeVal N-Methylvaline; Des Desmosine; Nva Norvaline; Dpm 2,2'-Diaminopimelic acid; Nle Norleucine; Dpr 2,3-Diaminopropionic acid; Orn Ornithine EtGly N-Ethylglycine.

In certain embodiments the proteinaceous composition comprises at least one protein, polypeptide or peptide, such as vRNAP or mini-vRNAP. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments, a proteinaceous compound may be purified. Generally, "purified" will refer to a specific or desired protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. A mini-vRNAP antibody may comprise all or part of an antibody that specifically recognizes mini-vRNAP. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, $F(ab')_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that the high viscosity will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. Organisms that may be used include, but are not limited to, a bovine, a reptilian, an amphibian, a piscine, a rodent, an avian, a canine, a feline, a fungal, a plant, or a prokaryotic organism, with a selected animal or human subject being preferred. The "autologous protein, polypeptide or peptide" may then be used as a component of a composition intended for application to the selected animal or human subject. In certain aspects, the autologous proteins or peptides are prepared, for example from whole plasma of the selected donor. The plasma is placed in tubes and placed in a freezer at about −80° C. for at least about 12 hours and then centrifuged at about 12,000 times g for about 15 minutes to obtain the precipitate. The precipitate, such as fibrinogen may be stored for up to about one year.

VI. PROTEIN PURIFICATION

To prepare a composition comprising a vRNAP or mini-vRNAP, it is desirable to purify the components or variants thereof Purification of the mini-vRNAP (SEQ ID NO:4) can be done in two step using affinity columns. The mini-vRNAP of SEQ ID NO:6 has been modified to comprise a His tag such that purification can be done in a single step when using metal affinity columns such as those which employ nickel, cobalt or zinc. The full length vRNAP of SEQ ID NO:15 is also His tagged for purification.

According to one embodiment of the present invention, purification of a peptide comprising vRNAP can be utilized ultimately to operatively link this domain with a selective agent. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is affinity chromatography.

A tag may be used for protein or peptide purification and detection such as hexahistidine (6-His, HHHHHH), FLAG (DYKDDDDK), hemaglutinin (HA, YPYDVPDYA) and c-myc (EQKLISEEDL). Other tags also have been generated, most of which are very small, comprising only a few amino acids, and are therefore likely to have little to no effect on the conformation of the mature protein or peptide. These small tags do not require any special conformation to be recognized by antibodies. Systems for protein purification using these tags include NTA resin (6-His) or the FLAG fusion system marketed by IBI (FLAG) where the fusion protein is affinity-purified on an antibody column.

Certain aspects of the present invention concern the purification, and in particular embodiments, the substantial purification, of an encoded protein or peptide, such as a vRNAP. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition, such as the vRNAP, that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification" number. The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

Ion exchange chromatography is a preferred method of separation. Using columns resins such as the metal affinity chromatography resin TALON are also preferred. TALON resin has an enhanced resolving power for polyhistidine-tagged proteins. This results in greater purity with less effort. TALON employs cobalt, an electropositive metal with a remarkably high affinity for polyhistidine-tagged proteins and a low affinity for other proteins. Often, no discernible binding of host proteins occurs and a separate wash step is not required. The binding properties of cobalt allow protein elution under mild pH conditions that protect protein integrity.

Further concentration of the proteins can be done on an anion exchange column, such as the MonoQ column, a high resolution, anion exchange column. This column works at pressures less than 5 MPa, has a high capacity and gives very high chromatographic resolution.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography, a particularly efficient method of purifying peptides, is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature). Tags, as described herein above, can be used in affinity chromatography.

The matrix should be a substance that itself does not adsorb molecules to any significant extent and that has a broad range of chemical, physical and thermal stability. The ligand should be coupled in such a way as to not affect its binding properties. The ligand also should provide relatively tight binding, and it should be possible to elute the substance without destroying the sample or the ligand. One of the most common forms of affinity chromatography is immunoaffinity chromatography. The generation of antibodies that would be suitable for use in accordance with the present invention is discussed below.

An affinity column may have an N4 promoter which the vRNAP or mini-vRNAP proteins recognize attached to a matrix. This column would be suitable for use for the purification of polymerases with no additional tags such as histidine tags.

VII. SEPARATION, QUANTITATION, AND IDENTIFICATION METHODS

Following synthesis of the RNA, it may be desirable to separate the amplification products of several different lengths from each other and from the template and the excess primer.

a. Gel Electrophoresis

In one embodiment, amplification products are separated by agarose, agarose-acrylamide or polyacrylamide gel electrophoresis using standard methods.

b. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography. In yet another alternative, labeled cDNA products, such as biotin-labeled or antigen-labeled, can be captured with beads bearing avidin or antibody, respectively.

c. Microfluidic Techniques

Microfluidic techniques include separation on a platform such as microcapillaries, designed by ACLARA BioSciences Inc., or the LabChip™ "liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR apparatus for collection and amplification of nucleic acids from a specimen. U.S. Pat. Nos. 5,304,487 to Wilding et al., and 5,296,375 to Kricka et al., discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

d. Capillary Electrophoresis

In some embodiments, it may be desirable to provide an additional, or alternative means for analyzing the amplified genes. In these embodiments, micro capillary arrays are contemplated to be used for the analysis.

Microcapillary array electrophoresis generally involves the use of a thin capillary or channel which may or may not be filled with a particular separation medium. Electrophoresis of a sample through the capillary provides a size based separation profile for the sample. Microcapillary array electrophoresis generally provides a rapid method for size-based sequencing, PCR product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Rectangular capillaries are known as an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

e. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods known in the art can be found summarized in *Methods in Enzymology, Vol.* 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry).

Two ionization/desorption techniques are electrospray/ionspray (ES) and matrix-assisted laser desorption/ionization (MALDI). As a mass analyzer, a quadrupole is most frequently used. The determination of molecular weights in femtomole amounts of sample is very accurate due to the presence of multiple ion peaks, which all could be used for the mass calculation.

MALDI mass spectrometry, in contrast, can be particularly attractive when a time-of-flight (TOF) configuration is used as a mass analyzer. Since, in most cases, no multiple molecular ion peaks are produced with this technique, the mass spectra, in principle, look simpler compared to ES mass spectrometry. DNA molecules up to a molecular weight of 410,000 Daltons could be desorbed and volatilized. More recently, the use of infra red lasers (IR) in this technique (as opposed to UV-lasers) has been shown to provide mass spectra of larger nucleic acids such as synthetic DNA, restriction enzyme fragments of plasmid DNA, and RNA transcripts up to a size of 2180 nucleotides.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

f. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed. The distance between donor and acceptor dyes at which energy transfer efficiency is 50% is referred to as the Forster distance ($R_O$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label.

Homogeneous methods employing energy transfer or other mechanisms of fluorescence quenching for detection of nucleic acid amplification have also been described. Higuchi et al., *Biotechnology* 10:413-417 (1992) disclose methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs known in the art and may be used in the present invention. These include, for example, fluorescein isothiocyanate (FITC)/tetramethylrhodamine isothiocyanate (TRITC), FITC/Texas Red (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms, it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and may be routinely used to link the donor and acceptor dyes at their respective sites in the detector nucleic acid.

g. In Vitro Studies

The synthesized RNA of the current invention may be used for in vitro studies of spliceosome assembly, splicing reactions, or antisense experiments.

The spliceosome is a large, multisubunit complex consisting of small, nuclear ribonucleoprotein particles (snRNPs). There are a total of 5 snRNAs: U1, U2, U4, U5, and U6 which are small and uridine rich. Each snRNP has 1 or 2 of these RNAs. In addition to catalyzing the splicing reaction, the spliceosome retains intermediate products, positions splice sites for precise joining of the exons, and prevents exons from diffusing away after cleavage and before ligation. Spliceosome catalysis involves concerted cleavage/ligation reactions in which the 2'-OH of branch site A attacks the 5' splice site to form a 2'-5' phosphodiester bond with the first nucleotide of the intron. The resulting 3'-OH at the end of the 5' exon attacks the 3' splice site to release the lariat form of the intron and join the two exons together with a normal 3'-5' phosphodiester bond. At least 50 different proteins are involved in spliceosome assembly and function. In the group I and group II introns, splicing is improved (in velocity and accuracy) by protein factors.

VIII. METHODS FOR MAKING TRANSCRIPTION PRODUCTS CORRESPONDING TO A TARGET NUCLEIC ACID SEQUENCE

In one aspect, the invention comprises a method for making a transcription product corresponding to a target nucleic acid sequence, the method comprising: (a) obtaining an RNA polymerase that can transcribe RNA using a single-stranded promoter; (b) obtaining a single-stranded DNA wherein the single-stranded DNA comprises a target nucleic sequence that is present in or complementary to at least a portion of a target nucleic acid in a sample; (c) obtaining a ssDNA transcription substrate by operably joining to the single-stranded DNA a single-stranded polynucleotide comprising a promoter sequence that binds the RNA polymerase; (d) obtaining nucleoside triphosphates (NTPs) that are substrates for the RNA polymerase and that are complementary to the canonical nucleic acid bases; (e) admixing the RNA polymerase, the ssDNA transcription substrate and the NTPs; and (f) incubating the RNA polymerase and the ssDNA transcription substrate under conditions effective to allow synthesis of transcription product.

In yet another embodiment, the invention comprises a method for obtaining additional rounds of synthesis of a transcription product corresponding to a target nucleic acid sequence, the method comprising: (a) obtaining a first transcription product by transcription of a first ssDNA transcription substrate corresponding to a target nucleic acid sequence; (b) obtaining a reverse transcriptase; (c) reverse transcribing the first transcription product; (d) obtaining first-strand cDNA complementary to the first transcription product; (e) obtaining a second ssDNA transcription substrate by operably joining to the first-strand cDNA a single-stranded polynucleotide comprising a promoter sequence that binds an RNA polymerase that can transcribe RNA using a single-stranded promoter; (f) obtaining an RNA polymerase that can transcribe RNA using a single-stranded promoter; (g) obtaining nucleoside triphosphates (NTPs) that are substrates for the RNA polymerase; (h) admixing the RNA polymerase, the second ssDNA transcription substrate and the NTPs; and (i) incubating the RNA polymerase and the second ssDNA transcription substrate under conditions effective to allow synthesis of a second transcription product. This method for obtaining additional rounds of synthesis of transcription product can be repeated in a stepwise manner to obtain synthesis of still more transcription products. Alternatively, in other embodiments, the invention comprises continuous transcription, wherein additional ssDNA transcription substrates are obtained continuously by reverse transcription of transcription products to obtain first-strand cDNA and operable joining of a promoter to the first-strand cDNA, and wherein, the additional ssDNA transcriptional substrates are used to make more transcription products.

The invention comprises use of any polymerase that synthesizes a transcription product using a single-stranded transcription promoter and a single-stranded DNA template to which the promoter is operably or functionally joined or linked. An RNA polymerase that synthesizes a transcription product using a ssDNA transcription substrate comprising a ssDNA transcription promoter that is operably joined to a target sequence has not previously been known in the art for making a transcription product corresponding to a target sequence. A preferred RNA polymerase of the invention is an N4 mini-vRNAP enzyme or a mutant form of an N4 mini-vRNAP enzyme. The RNA polymerase preferentially has the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8. The vRNAP and mini-vRNA polymerase transcribe nucleic acid operatively linked to an N4 promoter such as a P2 promoter of SEQ ID NO:16, SEQ ID NO:19, SEQ ID NO:27, SEQ ID NO:28 or SEQ ID NO:29. The promoter of SEQ ID NO:16 or SEQ ID NO:28 is preferred.

Other preferred promoters of the invention comprise single-stranded pseudopromoters or synthetic promoters that are recognized by an RNA polymerase (RNAP) so as to function in a method of the invention. A "pseudopromoter" or "synthetic promoter" of the present invention can be any single-stranded sequence that is identified and/or selected to be functional as a promoter for in vitro transcription by an RNA polymerase that binds the promoter with specificity and functions as a promoter for the RNA polymerase in a transcription reaction. A promoter comprising a pseudopromoter or synthetic promoter of the invention can be made as described by Ohmichi et al. (*Proc. Natl. Acad. Sci. USA* 99:54-59, 2002), which is incorporated herein by reference. If a pseudopromoter or synthetic promoter is used as a promoter in a method or assay of the invention, then the corresponding RNA polymerase for which the pseudopromoter or synthetic promoter was identified and/or selected is used in the method. By way of example, but not of limitation, a target probe with a promoter comprising a ssDNA pseudopromoter can be obtained and used in a method or assay of the invention that uses *E. coli* RNAP or a T7-type phage RNAP, such as, but not limited to, T7 RNAP, T3 RNAP, or SP6 RNAP, as described by Ohmichi et al. (*Proc. Natl. Acad. Sci. USA* 99:54-59, 2002) and incorporated herein by reference. By "T7-type RNAPs" we mean T7, T3, ϕ, ϕIIH, W31, gh1, Y, A1122, SP6 and mitochondrial RNAPs. Mutant RNAPs, such as, but not limited to, T7 RNAP Y639F mutant enzyme, T3 RNAP Y573F mutant enzyme, SP6 RNAP Y631F mutant enzyme, T7 RNAP having altered amino acids at both positions 639 and 784, T3 RNAP having altered amino acids at both positions 573 and 785, or SP6 RNAP having altered amino acids at both positions 631 and 779, or other mutant forms of an RNAP that functions in a method of the invention can also be used in embodiments of methods or assays of the invention with single-stranded pseudopromoters obtained as described by Ohmichi et al. (*Proc. Natl. Acad. Sci. USA* 99:54-59, 2002).

A. Supplemental Definitions and Methods

1. Transcription Product

The term "transcription product" as used herein can mean RNA or, in view of the ability of certain polymerases of the invention, such as the Y678F mutant polymerase having SEQ ID NO:8, to use deoxynucleotide substrates, a transcription product can also comprise DNA or a mixture of both RNA and DNA. A transcription product does not necessarily have perfect sequence complementarity or identity to the target sequence. For example, a transcription product can include nucleotide analogs such as deoxyinosine or deoxyuridine, intentional sequence alterations, such as sequence alterations introduced through a primer comprising a sequence that is hybridizable, but not complementary, to the target sequence, and/or sequence errors that occur during transcription.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include, but are not limited to: (1) modification of the $T_m$; (2) changing the susceptibility of the polynucleotide to one or more nucleases; (3) providing a moiety for attachment of a label; (4) providing a label or a quencher for a label; or (5) providing a moiety, such as biotin, for attaching to another molecule which is in solution or bound to a surface.

2. Sample/Target/Target Nucleic Acid/Target Sequence

A "sample" or a "biological sample" according to the present invention is used in its broadest sense. A sample is any specimen that is collected from or is associated with a biological or environmental source, or which comprises or contains biological material, whether in whole or in part, and whether living or dead.

Biological samples may be plant or animal, including human, fluid (e.g., blood or blood fractions, urine, saliva, sputum, cerebral spinal fluid, pleural fluid, milk, lymph, or semen), swabs (e.g., buccal or cervical swabs), solid (e.g., stool), microbial cultures (e.g., plate or liquid cultures of bacteria, fungi, parasites, protozoans, or viruses), or cells or tissue (e.g., fresh or paraffin-embedded tissue sections, hair follicles, mouse tail snips, leaves, or parts of human, animal, plant, microbial, viral, or other cells, tissues, organs or whole organisms, including subcellular fractions or cell extracts), as well as liquid and solid food and feed products and ingredients such as dairy items, vegetables, meat and meat by-products, and waste. Biological samples may be obtained from all of the various families of domestic plants or animals, as well as wild animals or plants.

Environmental samples include environmental material such as surface matter, soil, water, air, or industrial samples, as well as samples obtained from food and dairy processing instruments, apparatus, equipment, utensils, disposable and non-disposable items. These examples are not to be construed as limiting the sample types applicable to the present invention.

In short, a sample comprises a specimen from any source that contains or may contain a naturally occurring target nucleic acid.

A sample on which the assay method of the invention is carried out can be a raw specimen of biological material, such as serum or other body fluid, tissue culture medium or food material. More typically, the method is carried out on a sample that is a processed specimen, derived from a raw specimen by various treatments to remove materials that would interfere with detection of a target nucleic acid or an amplification product thereof. Methods for processing raw samples to obtain a sample more suitable for the assay methods of the invention are well known in the art.

An "analyte" means a substance whose presence, concentration or amount in a sample is being determined in an assay. An analyte is sometimes referred to as a "target substance" or a "target molecule" or a "target analyte" of an assay. An analyte may also be referred to more specifically. Embodiments of the present invention pertain to analytes that are naturally occurring nucleic acids, and the analyte may be referred to as a "target nucleic acid" or a "target polynucleotide" or a "target oligonucleotide" or a "target sequence," depending on the particular case. A composition, kit, or method of the invention can be used for an "analyte-specific reagent" to detect a target nucleic acid analyte or another analyte or analyte-binding substance in a sample.

With respect to the present invention, an analyte is often associated with a biological entity that is present in a sample if and only if the analyte is present. Such biological entities include viroids (analyte is, e.g., a nucleic acid or a segment thereof); viruses (analyte is, e.g., a viral genome, or a segment of viral genome); other microorganisms (analyte is, e.g., a segment of the genome or the RNA of the microorganism); abnormal cells, such as cancer cells (analyte is, e.g., an oncogene); or an abnormal gene (analyte is, e.g., a gene segment which includes the altered bases which render the gene abnormal, or a messenger RNA segment which includes altered bases as a result of having been transcribed from the abnormal gene).

From the description of analyte, it is apparent that the present invention has widespread applicability, including in applications in which nucleic acid probe hybridization assays are often employed. Thus, among other applications, the invention is useful in diagnosing diseases in plants and animals, including humans; and in testing products, such as food, blood, and tissue cultures, for contaminants.

A "target" of the present invention is a biological organism or material that is the reason or basis for which a biological assay or a diagnostic assay is performed. By way of example, but not of limitation, an assay of the present invention may be performed to detect a target that is a virus which is indicative of a present disease or a risk of future disease (e.g., HIV which is believed to result in AIDS), or a target that is a gene which is indicative of antibiotic resistance (e.g., an antibiotic resistance gene in an infectious pathogenic bacterium), or a target that is a gene which, if absent, may be indicative of disease (e.g., a deletion in an essential gene). In developing assays according to the present invention, it is important to identify target analytes that yield assay results that are sufficiently specific, accurate, and sensitive to be meaningful related to the presence or condition of the target.

A target analyte that is a "target polynucleotide" or a "target nucleic acid" comprises at least one nucleic acid molecule or portion of at least one nucleic acid molecule, whether the molecule or molecules is or are DNA, RNA, or both DNA and RNA, and wherein each the molecule has, at least in part, a defined nucleotide sequence. The target polynucleotide may also have at least partial complementarity with other molecules used in an assay, such as, but not limited to, primers, splice template oligos, ligation splint oligos, capture probes or detection probes. The target polynucleotide may be single- or double-stranded. A target polynucleotide of the present invention may be of any length. However, it must comprise a polynucleotide sequence of sufficient sequence specificity and length so as to be useful for its intended purpose. By way of example, but not of limitation, a target nucleic acid that is to be detected using a sequence-complementary detection probe must have a sequence of sufficient sequence specificity and length so as remain hybridized by the detection probe under assay hybridization conditions wherein sequences that are not target polynucleotides are not hybridized. A target polynucleotide having sufficient sequence specificity and length for an assay of the present invention may be identified, using methods known to those skilled in the art, by comparison and analysis of nucleic acid sequences known for a target and for other sequences which may be present in the sample. For example, sequences for nucleic acids of many viruses, bacteria, humans (e.g., for genes and messenger RNA), and many other biological organisms can be searched using public or private databases, and sequence comparisons, folded structures, and hybridization melting temperatures (i.e., $T_m$'s) may be obtained using computer software known to those knowledgeable in the art.

The terms "source of target nucleic acid" or "source of target polynucleotide" refers to any sample that contains a naturally occurring target nucleic acid, RNA or DNA.

Thus, a method of the present invention can be carried out on nucleic acid from a variety of sources, including unpurified nucleic acids, or nucleic acids purified using any appropriate method in the art, such as, but not limited to, various "spin" columns, cationic membranes and filters, or salt precipitation techniques, for which a wide variety of products are commercially available (e.g., MasterPure™ DNA & RNA Purification Kits from Epicentre Technologies, Madison, Wis., USA). Methods of the present invention can also be carried out on nucleic acids isolated from viroids, viruses or cells of a specimen and deposited onto solid supports as described by Gillespie and Spiegelman (*J. Mol. Biol.* 12:829-842, 1965), including solid supports on dipsticks and the inside walls of microtiter plate wells. The method can also be carried out with nucleic acid isolated from specimens and deposited on solid support by "dot" blotting (Kafatos, et al., *Nucl. Acids Res.* 7:1541-1552, 1979); White, and Bancroft, *J. Biol. Chem.* 257:8569-8572, 1982); Southern blotting (Southern, E., *J. Mol. Biol.* 98:503-517, 1975); "northern" blotting (Thomas, *Proc. Natl. Acad. Sci. USA* 77:5201-5205, 1980); and electroblotting (Stellwag, and Dahlberg, *Nucl. Acids Res.* 8:299-317, 1980). The method can also be carried out for nucleic acids spotted on membranes, on slides, or on chips as arrays or microarrays, or the method can be carried out to prepare probes for detecting or quantifying nucleic acids present in a sample based on hybridization to nucleic acids spotted or synthesized on one of these surfaces. Nucleic acid of specimens can also be assayed by the method of the present invention applied to water phase hybridization (Britten, and Kohne, *Science* 161:527-540, 1968) and water/organic interphase hybridizations (Kohne, et al., *Biochemistry* 16:5329-5341, 1977). Water/organic interphase hybridizations have the advantage of proceeding with very rapid kinetics but are not suitable when an organic phase-soluble linking moiety, such as biotin, is joined to the nucleic acid affinity molecule.

The methods of the present invention can also be carried out on amplification products obtained by amplification of a naturally occurring target nucleic acid, provided that the target sequence in the target nucleic acid is amplified by the method used only if the target nucleic acid is present in the sample. Suitable amplification methods include, but are not limited to, PCR, RT-PCR, NASBA, TMA, 3SR, LCR, LLA, SDA (e.g., Walker et al., *Nucleic Acids Res.* 20:1691-1696, 1992), RCA, Multiple Displacement Amplification (Molecular Staging), ICAN™ or UCAN™ (TAKARA), Loop-AMP (EIKEN), and SPIA™ or Ribo-SPIA™ (NuGEN Technologies). There are various reasons for using a nucleic acid that is a product of another amplification method as a target nucleic acid for an assay of the present invention, such as, but not limited to, for obtaining more sensitive detection of targets, greater specificity, or to decrease the time required to obtain an assay result.

The methods of the invention can also be carried out on nucleic acids isolated from specimens and deposited onto solid supports by dot-blotting, or by adsorption onto walls of microtiter plate wells or solid support materials on dipsticks, on membranes, on slides, or on chips as arrays or microarrays.

Still further, the methods of the invention are applicable to detecting cellular nucleic acids in whole cells from a specimen, such as a fixed or paraffin-embedded section, or from microorganisms immobilized on a solid support, such as replica-plated bacteria or yeast. In some embodiments, the methods of the invention can be used to make a transcription product corresponding to a target sequence to detect target nucleic acids in living cells.

A target nucleic acid can be a nucleic acid from any source in purified or unpurified form. For example, a target nucleic acid comprising DNA, can be dsDNA or ssDNA such as mitochondrial DNA, chloroplast DNA, chromosomes, plasmids or other episomes, the genomes of bacteria, yeasts, viruses, viroids, mycoplasma, molds, or other microorganisms, or genomes of fungi, plants, animals, or humans. Target nucleic acids comprising RNA can be tRNA, mRNA, rRNA, mitochondrial RNA, chloroplast RNA, micro RNA, or other RNA molecules, without limit. Target nucleic acids can also be mixtures of DNA and RNA, including, but not limited to, mixtures of the above nucleic acids or fragments thereof, or DNA-RNA hybrids. The target nucleic acid can be only a minor fraction of a complex mixture such as a biological sample and can be obtained from various biological materials by procedures known in the art. Numerous methods for purification of a particular target nucleic are known in the art, if further purification is necessary.

The term "target nucleic acid sequence" or "target sequence" refers to the particular nucleotide sequence of the target nucleic acid(s) that is/are to be transcribed to make a transcription product. A "target sequence" comprises one or more sequences within one or more target nucleic acids. A target sequence can also have "complexing sequences" which are added during processes of methods of the invention for the purpose of facilitating joining of a target sequence to a polynucleotide comprising a single-stranded transcription promoter in order to obtain a ssDNA transcription substrate of the invention. A complexing sequence can provide a complementary sequence to which an oligonucleotide (e.g., a primer and/or splice template) used in a method of the invention can anneal or complex. A complexing sequence usually comprises a "tail" sequence that is added by means such as those discussed herein, including, but not limited to, non-templated addition of dCMP residues to first-strand cDNA by reverse transcriptase pausing at cap structures of mRNA (in the presence or absence of manganese cations) and/or controlled ribonucleotide tailing using TdT. If a complexing sequence is added to a target sequence during a process of a method of the invention, it is desirable that a complexing sequence is chosen that does not to affect the specificity of the transcription products made using the resulting transcription substrate comprising the target sequence.

A target nucleic acid can be either single-stranded or double-stranded RNA, DNA, or mixed RNA and DNA. A target nucleic acid is sometimes referred to more specifically by the type of nucleic acid. By way of example, but not of limitation, a target nucleic acid can be a "target RNA" or an "RNA target," or a "target mRNA," or a "target DNA" or a "DNA target." Similarly, the target sequence can be referred to as "a target RNA sequence" or a "RNA target sequence", or as a "target mRNA sequence" or a "target DNA sequence," or the like. In some embodiments, the target sequence comprises one or more entire target nucleic acids, such as, one or all full-length mRNA molecules in a particular sample. In other embodiments, the target sequence comprises only a portion of one or more target nucleic acid molecules. When the target nucleic acid is originally single-stranded, the term "target sequence" is also meant to refer to the sequence complementary to the "target sequence." When the "target nucleic acid" is originally double-stranded, the term "target sequence" may refer to both the sense strand of the sequence or its complement, or both, depending on the intended purpose of the method. The target sequence may be known or not known, in terms of its actual sequence. In some instances, the terms "target sequence," "target nucleic acid," "target polynucleotide," and variations thereof are used interchangeably.

3. cDNA/First-Strand cDNA/Second-Strand cDNA/Reverse Transcriptase/RnaseH

In some important embodiments of the invention, the target sequence of a transcription substrate comprises cDNA. In general, "cDNA" refers to "complementary DNA" that is synthesized by primer extension using a DNA polymerase, including, but not limited to, an RNA-dependent DNA polymerase or reverse transcriptase, using at least a portion of a target nucleic acid as a template, and which cDNA is "homologous to" or "base pairs with" at least a portion of the target nucleic acid template. In some embodiments of the invention, which are preferred embodiments, cDNA is obtained by reverse transcription primer extension using a reverse transcriptase and a target nucleic acid comprising messenger RNA (mRNA) obtained from a biological sample as a template, and which cDNA is homologous to the mRNA. Methods in the art related to making cDNA from mRNA involve synthesis of double-stranded cDNA comprising first-strand cDNA and second-strand cDNA, which usually are synthesized sequentially using different methods. However herein, we often refer to "first-strand cDNA" even when a method of the invention results in synthesis of only one strand of DNA that is complementary to the mRNA (i.e., the term "first-strand cDNA" is not intended to imply that there is also a second-strand cDNA). In some embodiments, the terms "first-strand cDNA" or "cDNA" refer to a single-stranded DNA molecule obtained by reverse transcription of any RNA molecule, even if it is not mRNA. In other embodiments, the terms "first-strand cDNA" or "cDNA" refer to a single-stranded DNA molecule obtained by primer extension using a target nucleic acid comprising either a single-stranded DNA or one strand of a double-stranded DNA as a template for a DNA polymerization reaction.

An "RNA-dependent DNA polymerase" or "reverse transcriptase" is an enzyme that can synthesize a complementary DNA copy ("cDNA") from an RNA template. All known reverse transcriptases also have the ability to make a complementary DNA copy from a DNA template; thus, they are both RNA- and DNA-dependent DNA polymerases. A "template" is the nucleic acid molecule that is copied by a nucleic acid polymerase. The synthesized copy is complementary to the template. Both RNA and DNA are always synthesized in the 5'-to-3' direction and the two strands of a nucleic acid duplex always are aligned so that the 5' ends of the two strands are at opposite ends of the duplex (and, by necessity, so then are the 3' ends). A primer is required for both RNA and DNA templates to initiate synthesis by a DNA polymerase. Examples of reverse transcriptases that can be used in methods of the present invention include, but are not limited to, AMV reverse transcriptase, MMLV reverse transcriptase, Tth DNA polymerase, rBst DNA polymerase large fragment, also called IsoTherm™ DNA Polymerase (Epicentre Technologies, Madison, Wis., USA), and BcaBEST™ DNA polymerase (Takara Shuzo Co, Kyoto, Japan). In some cases, a mutant form of a reverse transcriptase, such as, an MMLV reverse transcriptase that lacks RNase H activity is used. In still other embodiments, IsoTherm™ DNA polymerase is most suitable. In other embodiments, a wild-type enzyme is preferred.

In embodiments of the invention that obtain a transcription substrate in which a ssDNA target sequence comprising first-strand cDNA is synthesized using a reverse transcriptase and a primer that is complementary to and anneals to the 3'-end of a target nucleic acid comprising mRNA, the primer can comprise oligo(dT) or modified oligo(dT), or it can comprise an oligo d(T) anchor primer, wherein one (or a small number) of the 3'-nucleotides of the anchor primer comprise either a specific base for a specific mRNA or a randomized nucleotide (i.e., synthesized with a mixture of all four nucleotides) for priming all mRNA molecules in a sample, or the primer can comprise an oligonucleotide having a specific sequence that is complementary to the sequence of a specific mRNA molecule, or in some cases, it can comprise an oligonucleotide having a random sequence (i.e., synthesized using a mixture of all four nucleotides for every position of the primer).

If a target nucleic acid is RNA, such as mRNA, and it is desirable to remove the RNA that is annealed to first-strand cDNA following reverse transcription using a promoter primer, this can be accomplished by one of several means. By way of example, but not of limitation, the RNA can be removed by treatment with RNase H, by treatment with a base, such as, but not limited to sodium or potassium hydroxide, or the RNA can be removed from the hybrid by heat denaturation. In preferred embodiments for some applications, the RNA is removed by an RNase H activity of a reverse transcriptase that is used for reverse transcription (or primer extension), such as, but not limited to, MMLV reverse transcriptase. Alternatively, in some embodiments, the RNA is dissociated from the first-strand cDNA by incubating the hybrid or performing the reverse transcription in the presence of a single-strand binding (SSB) protein of the invention, such as, but not limited to *E. coli* SSB (EcoSSB).

In some embodiments of the invention, especially in embodiments for obtaining additional rounds of transcription products, a separate RNase H enzyme is also used, whether or not the reverse transcriptase has RNase H activity. If RNase H activity is desirable in an embodiment for obtaining multiple rounds of transcription, but a separate RNase H enzyme is not added, MMLV reverse transcriptase (wild-type RNase H-positive) can be used. AMV reverse transcriptase can be used in some embodiments for obtaining multiple rounds of transcription in which a separate RNase H enzyme is also added. Kacian et al. (U.S. Pat. No. 5,399,491) disclose information related to the effects of adding different amounts of a separate RNase H enzyme to transcription-mediated amplification assays that use either MMLV or AMV reverse transcriptase, which reference and information is incorporated herein by reference and made a part of the present disclosure.

"Ribonuclease H" or "RNase H" is an enzyme that degrades the RNA portion of an RNA:DNA duplex. An RNase H can be an endonuclease or an exonuclease. Most wild-type reverse transcriptase enzymes have an RNase H activity in addition to their polymerase activity. However, other sources of the RNase H are available without an associated polymerase activity. The degradation may result in separation of RNA from an RNA:DNA complex. Alternatively, the RNase H may simply cut the RNA at various locations such that portions of the RNA melt off or permit enzymes to unwind portions of the RNA. When used in an embodiment of the invention, RNaseH enzymes that can be used include, but are not limited to, *E. coli* RNase H, *Thermus thermophilus* RNase H, and *Thermus flavus* RNase H (U.S. Pat. Nos. 5,268,289; 5,459,055; and 5,500,370, incorporated herein by reference). The latter two enzymes, which are thermostable and, therefore, maintain more consistent activity in reactions and are more easily stored and shipped, are preferred in most embodiments in which a separate RNase H enzyme is used. Other RNase H enzymes that can be used are those that are described by Sagawa et al. in PCT Patent Publication No. WO 02/16639; and in PCT Patent Publications Nos. WO 00/56877 and AU 00/29742, all of which are incorporated herein by reference. In other embodiments, it is desirable to use a less thermally stable enzyme, such as *E. coli* RNase H, because it is easier to inactivate the enzyme in a reaction mixture.

Kacian et al. disclosed in U.S. Pat. No. 5,399,491, incorporated herein by reference, that the number, distribution, and position of putative RNase H cut sites determine, in part, the usefulness of a given primer and that amplification can be improved by inclusion of intentional mismatches or insertion of sequences in order to affect the number, distribution, and position of putative RNase H cut sites. Thus, in preferred processes of the invention for removing RNA from RNA:DNA hybrids following reverse transcription to make first-strand cDNA, the RNA target sequence is determined and then analyzed to determine where RNase H degradation will cause cuts or removal of sections of RNA from the duplex upon synthesis of first-strand cDNA. The processes of the invention include conducting experiments to determine the effect on amplification of the target sequence of the degradation of the RNA target sequence by RNase H present in the reverse transcriptase and/or separate RNase H enzyme(s) used, including, but not limited to, AMV reverse transcriptase, and both RNase H-plus and RNase H-minus MMLV reverse transcriptase, and *E. coli* RNase H or thermostable RNase H enzymes that are stable for more than 10 minutes at 70° C. (U.S. Pat. Nos. 5,268,289; 5,459,055; and 5,500,370, incorporated herein by reference), such as, but not limited to, Hybridase™ thermostable RNase H (Epicentre Technologies, Madison, Wis. USA), Tth RNase H, and Tfl RNase H, or by different combinations of a reverse transcriptase and a separate RNase H.

In selecting a primer, including a promoter primer of the invention, for use in reverse transcription of an RNA target sequence to make first-strand cDNA, it is preferable that the primer be selected so that it will hybridize to a section of RNA which is substantially nondegraded by the RNase H present in the reaction mixture. If there is substantial degradation, the cuts in the RNA strand in the region of the primer may stop or inhibit DNA synthesis and prevent extension of the primer. Thus, it is desirable to select a primer that will hybridize with a sequence of the RNA target, located so that when the RNA is subjected to RNase H, there is no substantial degradation that would prevent formation of the primer extension product.

4. Transcription Substrate

As used herein, a "transcription substrate" or a "ssDNA transcription substrate" according to the present invention comprises a ssDNA comprising a target sequence that is operably joined to a transcription promoter, wherein an RNA polymerase can bind to the transcription promoter with specificity and synthesize a transcription product corresponding to the target sequence under suitable transcription conditions. In order to be operably joined to the target sequence, the transcription promoter is 3'-of the target sequence. A transcription substrate of the invention can also have additional nucleic acid sequences that are 5'-of and/or 3'-of the transcription promoter sequence, but a transcription substrate is not required to have such additional other sequences. By way of example, but not of limitation, a transcription substrate can have a transcription initiation site 5'-of the promoter sequence. Also, in some embodiments of the invention, a transcription substrate can have one or more transcription termination sequences, one or more sites for DNA cleavage to permit controlled linearization of a circular first-strand cDNA that is a transcription substrate, one or more origins ("ori's") of replication (preferably an ori for a single-stranded replicon, such as, but not limited to, a phage M13 replicon), a selectable or screenable marker, such as, but not limited to an antibiotic-resistance gene or a beta-galactosidase gene, respectively, or one or more transposon recognition sequences, such as outer end ("OE") or mosaic end ("ME") sequences for a Tn5-type transposon,) that can be recognized and used by a transposase for in vitro or in vivo transposition, or one or more sites that are recognized by a recombinase (such as, but not limited to, the cre-lox system), and/or other sequences and genetic elements for a particular purpose, including, but not limited to, sequences that are transcribed by the RNA polymerase so as to provide additional regions of complementarity in the RNA transcription products for annealing of primers for reverse transcription in order to make cDNA for additional rounds of transcription. As described herein above, a "transcription substrate" of the present invention is single-stranded, whereas double-stranded DNA molecules, having at a minimum double-stranded promoters and usually also double-stranded templates, are used in other methods in the art.

Since a transcription substrate of the present invention is single-stranded, the terms "3'-of" and "5'-of" are used herein with respect to the present invention to refer to the position or orientation of a particular nucleic acid sequence or genetic element, such as, but not limited to, a transcription promoter, relative to other sequences or genetic elements within the DNA strand comprising the ssDNA transcription substrate. Thus, although the synthesis of RNA in a 5'-to-3' direction during transcription is thought of as proceeding in a "downstream" direction, the transcription promoter on the ssDNA transcription substrate is referred to herein as being 3'-of the target sequence. Those with knowledge in the art will understand these terms in the context of nucleic acid chemistry and structure, particularly related to the 3'- and 5'-positions of sugar moieties of canonical nucleic acid nucleotides. By way of example, a transcription promoter that is "3'-of the target sequence" on a linear transcription substrate refers a promoter sequence that is at or closer to the 3'-end of the transcription substrate relative to the target sequence on the same strand. If a first nucleic acid sequence is 3'-of a second sequence on one strand, the complement of the first sequence will be 5'-of the complement of the second sequence on the complementary strand. The description of the invention will be understood with respect to the relative 5' or 3' position and orientation of a sequence or genetic element within a particular nucleic acid strand, unless explicitly stated to the contrary.

5. Nucleic Acids Polynucleotides and Analogs Thereof

A "nucleic acid" or "polynucleotide" of the invention is a polymer molecule comprising a series of "mononucleosides," also referred to as "nucleosides," in which the 3'-position of the pentose sugar of one nucleoside is linked by an internucleoside linkage, such as, but not limited to, a phosphodiester bond, to the 5'-position of the pentose sugar of the next nucleoside. A nucleoside linked to a phosphate group is referred to as a "nucleotide." The nucleotide that is linked to the 5'-position of the next nucleotide in the series is referred to as "5' of" or the "5' nucleotide" and the nucleotide that is linked to the 3'-position of the 5' nucleotide is referred to as "3' of" or the "3' nucleotide." The pentose sugar of the nucleic acid can be ribose, in which case, the nucleic acid or polynucleotide is referred to as "RNA," or it can be 2'-deoxyribose, in which case, the nucleic acid or polynucleotide is referred to as "DNA." Alternatively, especially if the nucleic acid is synthesized chemically, the nucleic acid can be composed of both DNA and RNA mononucleotides. In both RNA and DNA, each pentose sugar is covalently linked to one of four common "nucleic acid bases" (each also referred to as a "base"). Three of the predominant naturally-occurring bases that are linked to the sugars (adenine, cytidine and guanine) are common for both DNA and RNA, while one base is different; DNA has the additional base thymine, while RNA has the additional base uridine. Those in the art commonly think of a small polynucleotide as an "oligonucleotide." The term "oligonucleotide" as used herein is defined as a molecule comprised of two or more deoxyribonucleotides or ribonucleotides, preferably about 10 to 200 nucleotides, but there is no defined limit to the length of an oligonucleotide. The exact size will depend on many factors, which in turn depends on the ultimate function or use of the oligonucleotide.

In order to accomplish the goals of the invention, there is no limit to the composition of the nucleic acids or polynucleotides of the invention including any splice template oligos, primers, including promoter primers, promoter ligation oligos, ligation splint oligos, detection probes, such as, but not limited to molecular beacons (U.S. Pat. Nos. 5,925,517 and 6,103,476 of Tyagi et al. and 6,461,817 of Alland et al., which are incorporated herein by reference), capture probes, oligonucleotides, or other nucleic acids used or detected in the assays or methods, so long as each of the nucleic acid functions for its intended use. By way of example, but not of limitation, the nucleic acid bases in the mononucleotides may comprise guanine, adenine, uracil, thymine, or cytidine, or alternatively, one or more of the nucleic acid bases may comprise xanthine, allyamino-uracil, hypoxanthine, 2-aminoadenine, 6-methyl and other alkyl adenines, 2-propyl and other alkyl adenines, 5-halouracil, 5-halo cytosine, 5-propynyl uracil, 5-propynyl cytosine, 7-deazaadenine, 7-deazaguanine, 7-deaza-7-methyl-adenine, 7-deaza-7-methyl-guanine, 7-deaza-7-propynyl-adenine, 7-deaza-7-propynyl-guanine and other 7-deaza-7-alkyl or 7-aryl purines, N2-alkyl-guanine, N2-alkyl-2-amino-adenine, purine 6-aza uracil, 6-aza cytosine and 6-aza thymine, 5-uracil (pseudo uracil), 4-thiouracil, 8-halo adenine, 8-amino-adenine, 8-thiol adenine, 8-thiolalkyl adenines, 8-hydroxyl adenine and other 8-substituted adenines and 8-halo guanines, 8-amino-guanine, 8-thiol guanine, 8-thiolalkyl guanines, 8-hydroxyl guanine and other 8-substituted guanines, other aza and deaza uracils, other aza and deaza thymidines, other aza and deaza cytosine, aza and deaza adenines, aza and deaza guanines or 5-trifluoromethyl uracil and 5-trifluorocytosine. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show the broad range of bases which may be used for a particular purpose in a method.

In some embodiments of the invention, a molecule comprising a "peptide nucleic acid" (PNA) or a molecule comprising both a nucleic acid and a PNA, as described in U.S. Pat. Nos. 5,539,082; 5,641,625; 5,700,922; 5,705,333; 5,714,331; 5,719,262; 5,736,336; 5,773,571; 5,786,461; 5,817,811; 5,977,296; 5,986,053; 6,015,887; and 6,020,126 (and references therein), can also be used. In general, a PNA molecule is a nucleic acid analog consisting of a backbone comprising, for example, N-(2-aminoethyl)glycine units, to each of which a nucleic acid base is linked through a suitable linker, such as, but not limited to an aza, amido, ureido, or methylene carbonyl linker. The nucleic acid bases in PNA molecules bind complementary single-stranded DNA or RNA according to Watson-Crick base-pairing rules. However, the $T_m$'s for PNA/DNA or PNA/RNA duplexes or hybrids are higher than the $T_m$'s for DNA/DNA, DNA/RNA, or RNA/RNA duplexes. PNA provides tighter binding and greater binding stability than a nucleic acid of similar base sequence (e.g., see U.S. Pat. No. 5,985,563). Also, since PNA is not naturally occurring, PNA molecules are highly resistant to protease and nuclease activity. PNA can be prepared according to methods know in the art, such as, but not limited to, methods described in the above-mentioned patents, and references therein.

When a molecule comprising both a nucleic acid and a peptide nucleic acid (PNA) is used in the invention, modified bases can be used in one or both parts. For example, binding affinity can be increased by the use of certain modified bases in both the nucleotide subunits that make up the 2'-deoxyoligonucleotides of the invention and in the peptide nucleic acid subunits. Such modified bases may include 5-propynylpyrimidines, 6-azapyrimidines, and N-2, N-6 and O-6 substituted purines including 2-aminopropyl-adenine. Other modified pyrimidine and purine base are also expected to increase the binding affinity of macromolecules to a complementary strand of nucleic acid.

With respect to nucleic acids or polynucleotides of the invention, one or more of the sugar moieties can comprise ribose or 2'-deoxyribose, or alternatively, one or more of the sugar moieties can be some other sugar moiety, such as, but not limited to, 2'-fluoro-2'-deoxyribose or 2'-O-methyl-ribose, which provide resistance to some nucleases, or 2'-amino-2'-deoxyribose or 2'-azido-2'-deoxyribose, which can be used to label transcription products by reacting them with visible, fluorescent, infrared fluorescent or other detectable dyes or chemicals having an electrophilic, photoreactive or other reactive chemical moiety.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenate, or phosphorodiselenate linkages, which are resistant to some nucleases.

A variety of methods are known in the art for making nucleic acids having a particular sequence or that contain particular nucleic acid bases, sugars, internucleoside linkages, chemical moieties, and other compositions and characteristics. Any one or any combination of these methods can be used to make a nucleic acid, polynucleotide, or oligonucleotide for the present invention. The methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et al., Molecular Cloning: A Laboratory Approach Second Edition, 1989, Cold Spring Harbor Laboratory Press, Cold Spring Harbor, N.Y. and Sambrook and Russell, Molecular Cloning, A Laboratory Manual, Third Edition, 2001, Cold Spring Harbor Laboratory Press,) such as, but not limited to a plasmid, bacteriophage (e.g., M13 or lamba), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillus stearothermophilus* (rBst), or *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or SP6 or T7 R&DNA™ Polymerase (Epicentre Technologies, Madison, Wis. USA), or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) other compositions, such as, but not limited to, a ribozyme ligase to join RNA molecules; and/or (11) any combination of any of the above or other techniques known in the art. Oligonucleotides and polynucleotides, including chimeric (i.e., composite) molecules and oligonucleotides with modified bases, sugars, or internucleoside linkages are commercially available (e.g., TriLink Biotechnologies, San Diego, Calif., USA or Integrated DNA Technologies, Coralville, Iowa).

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

6. Ligation/Ligase

"Ligation" refers to the joining of a 5'-phosphorylated end of one nucleic acid molecule to a 3'-hydroxyl end of the same or another nucleic acid molecule by an enzyme called a "ligase." Alternatively, in some embodiments of the invention, ligation is effected by a type I topoisomerase moiety attached to one end of a nucleic acid (see U.S. Pat. No. 5,766,891, incorporated herein by reference). The terms "ligating," "ligation," and "ligase" are often used in a general sense herein and are meant to comprise any suitable method and composition for joining a 5'-end of one nucleic acid to a 3'-end of the same or another nucleic acid. Different ligases are preferred in different embodiments of the invention, as discussed elsewhere herein.

In general, if a nucleic acid to be ligated comprises RNA, a ligase such as, but not limited to, T4 RNA ligase, a ribozyme ligase, Tsc RNA Ligase (Prokaria Ltd., Reykjavik, Iceland), or another ligase can be used for non-homologous joining of the ends. T4 DNA ligase can also be used to ligate RNA molecules when a 5'-phosphoryl end is adjacent to a 3'-hydroxyl end annealed to a complementary sequence (e.g., see U.S. Pat. No. 5,807,674 of Tyagi, incorporated herein by reference).

If the nucleic acids to be joined comprise DNA and the 5'-phosphorylated and the 3'-hydroxyl ends are ligated when the ends are annealed to a complementary DNA so that the ends are adjacent (such as, when a "ligation splint" is used), then enzymes such as, but not limited to, T4 DNA ligase, Ampligase® DNA Ligase (Epicentre Technologies, Madison, Wis. USA), Tth DNA ligase, Tfl DNA ligase, or Tsc DNA Ligase (Prokaria Ltd., Reykjavik, Iceland) can be used. However, the invention is not limited to the use of a particular ligase and any suitable ligase can be used. Still further, Faruqui discloses in U.S. Pat. No. 6,368,801 that T4 RNA ligase can efficiently ligate DNA ends of nucleic acids that are adjacent to each other when hybridized to an RNA strand. Thus, T4 RNA ligase is a suitable ligase of the invention in embodiments in which DNA ends are ligated on a ligation splint oligo comprising RNA or modified RNA, such as, but not limited to modified RNA that contains 2'-F-dCTP and 2'-F-dUTP made using the DuraScribe™ T7 Transcription Kit (Epicentre Technologies, Madison, Wis. USA) or the N4 mini-vRNAP Y678F mutant enzyme described herein. With respect to ligation on an homologous ligation template, especially ligation using a "ligation splint" or a "ligation splint oligo" (as discussed elsewhere herein), a region, portion, or sequence that is "adjacent" to another sequence directly abuts that region, portion, or sequence.

In other embodiments comprising intramolecular ligation of linear ssDNA, ligation can be effected in the absence of a ligation splint using a ligase that can catalyze non-homologous ligation of ssDNA, such as, but not limited to, ThermoPhage™ RNA Ligase II (Prokaria Ltd., Reykjavik, Iceland), which is derived from phage TS2126 that infects Thermus scotoductus.

7. DNA Polymerases/Strand-Displacing DNA Polymerases/Strand Displacement/Rolling Circle Replication A "DNA-dependent DNA polymerase" is an enzyme that synthesizes a complementary DNA ("cDNA") copy from a DNA template. Examples are DNA polymerase I from *E. coli* and bacteriophage T7 DNA polymerase. All known DNA-dependent DNA polymerases require a complementary primer to initiate synthesis. It is known that under suitable conditions a DNA-dependent DNA polymerase may synthesize (i.e., "reverse transcribe") a complementary DNA copy from an RNA template, a process that is also referred to as "reverse transcription."

Some DNA polymerases are able to displace the strand complementary to the template strand as a new DNA strand is synthesized by the polymerase. This process is called "strand displacement" and the DNA polymerases that have this activity are referred to herein as "strand-displacing DNA polymerases." The template for strand displacement DNA synthesis using a method of the invention can be a linear or circular ssDNA. If the DNA template is a single-stranded circle, primed DNA synthesis procedes around and around the circle, with continual displacement of the strand ahead of the replicating strand, a process called "rolling circle replication." Rolling circle replication results in synthesis of tandem copies of the circular template. The suitability of a DNA polymerase for use in an embodiment of the invention that comprises strand displacement on linear templates or rolling circle replication can be readily determined by assessing its ability to carry out rolling circle replication. By way of example, but not of limitation, the ability of a polymerase to carry out rolling circle replication can be determined by using the polymerase in a rolling circle replication assay such as those described by Fire and Xu (*Proc. Natl. Acad. Sci. USA* 92:4641-4645, 1995), incorporated herein by reference. It is preferred that a DNA polymerase be a strand displacing DNA polymerase and lack a 5'-to-3' exonuclease activity for strand displacement polymerization reactions using both linear or circular templates since a 5'-to-3' exonuclease activity, if present, might result in the destruction of the synthesized strand. It is also preferred that DNA polymerases for use in the disclosed strand displacement synthesis methods are highly processive. The ability of a DNA polymerase to strand-displace can vary with reaction conditions, in addition to the particular enzyme used. Strand displacement and DNA polymerase processivity can also be assayed using methods described in Kong et al. (*J. Biol. Chem.* 268:1965-1975, 1993 and references cited therein, all of which are incorporated herein by reference).

Preferred strand displacing DNA polymerases of the invention are rBst DNA polymerase large fragment (also called IsoTherm™ DNA Polymerase (Epicentre Technologies, Madison, Wis. USA), BcaBEST™ DNA polymerase (Takara Shuzo Co., Kyoto, Japan), ϕ29 DNA polymerase (U.S. Pat. Nos. 5,576,204 and 5,001,050 to Blanco et al., incorporated herein by reference), SequiTherm™ DNA polymerase (Epicentre Technologies, Madison, Wis. USA), and MMLV reverse transcriptase. Other strand-displacing DNA polymerases which can be used include, but are not limited to, phage M2 DNA polymerase (Matsumoto et al., *Gene* 84:247, 1989), phage ϕPRD1 DNA polymerase (Jung et al., *Proc. Natl. Acad. Sci. USA* 84: 8287, 1987), VENT® DNA polymerase (Kong et al., *J. Biol. Chem.* 268:1965-1975, 1993), Klenow fragment of DNA polymerase I (Jacobsen et al., *Eur. J. Biochem.* 45:623-627, 1974), T5 DNA polymerase (Chatterjee et al., *Gene* 97:13-19, 1991), PRD1 DNA polymerase (Zhu and Ito, *Biochim. Biophys. Acta* 1219: 267-276, 1994), modified T7 DNA polymerase (Tabor and Richardson, *J. Biol. Chem.* 262:15,330-15,333, 1987); Tabor and Richardson, *J. Biol. Chem.* 264:6447-6458, 1989); Sequenase™ (U.S. Biochemicals, Cleveland, Ohio, USA), and T4 DNA polymerase holoenzyme (Kaboord and Benkovic, *Curr. Biol.* 5:149-157, 1995), all of which references, are incorporated herein by reference. Strand displacing DNA polymerases are also useful in some embodiments of the invention for strand displacement replication of linear first-strand cDNA, and in other embodiments, for rolling circle replication of circular first-strand cDNA. IsoTherm™ DNA polymerase (rBst DNA polymerase large fragment; Epicentre) is most preferred because, in addition to having strand-displacing DNA polymerase activity, it can also be used as a reverse transcriptase for synthesis of first-strand cDNA from RNA target nucleic acids (e.g., U.S. Pat. No. 6,030,814 of Jendrisak et al., incorporated herein by reference). BcaBEST™ DNA polymerase (Takara Shuzo Co., Kyoto, Japan) can also be used as a reverse transcriptase as well as a strand-displacing DNA polymerase.

Strand displacement can be facilitated through the use of a strand displacement factor, such as helicase. It is considered that any DNA polymerase that can perform rolling circle replication in the presence of a strand displacement factor is suitable for use in embodiments of the invention that comprise strand displacement or rolling circle replication, even if the DNA polymerase does not perform rolling circle replication in the absence of such a factor. Strand displacement factors useful in rolling circle replication include, but are not limited to, BMRF1 polymerase accessory subunit (Tsurumi et al., *J. Virology* 67:7648-7653, 1993), adenovirus DNA-binding protein (Zijderveld and van der Vliet, *J. Virology* 68:1158-1164, 1994), herpes simplex viral protein ICP8 (Boehmer and Lehman, *J. Virology* 67:711-715, 1993); Skaliter and Lehman, *Proc. Natl. Acad. Sci. USA* 91:10,665-

10,669, 1994), single-stranded DNA binding proteins (SSB; Rigler and Romano, *J. Biol. Chem.* 270:8910-8919, 1995), and calf thymus helicase (Siegel et al., *J. Biol. Chem.* 267:13, 629-13,635, 1992), all of which are incorporated herein by reference.

8. Hybridize/Hybridization

The terms "hybridize" and "hybridization" refer to the formation of complexes between nucleotide sequences that are sufficiently complementary to form complexes via Watson-Crick base pairing. With respect to the present invention, nucleic acid sequences that "hybridize" or "anneal" with each other should form "hybrids" or "complexes" that are sufficiently stable to serve the intended purpose. By way of example, but not of limitation, where a primer or splice template oligo hybridizes or anneals with a target nucleic acid in a sample or with a "tailed" target sequence, respectively, each respective complex or hybrid should be sufficiently stable to serve the respective priming functions required for a DNA polymerase to copy the target sequence by primer extension of the annealed primer or to extend the 3'-end of the target sequence using the annealed splice template oligo as a template, respectively.

9. Reaction Conditions

Appropriate reaction media and conditions for carrying out the methods of the present invention are those that permit nucleic acid transcription and other reactions according to the methods of the present invention. For example, the conditions below can be used for in vitro transcription with N4 vRNAP, mini-vRNAP, and mini-vRNAP Y678F enzymes of the invention. An in vitro transcription reaction is prepared by setting up a reaction mixture containing the following final concentrations of components, added in the order given: 0.1 micromolar of a N4 vRNAP promoter-containing DNA oligo; 1.0 micromolar EcoSSB Protein; 1× transcription buffer comprising 40 mM Tris-HCl (pH 7.5), 6 mM $MgCl_2$, 2 mM spermidine, and 10 mM NaCl; 1 mM DTT; 0.5 mM of each NTP (ATP, CTP, GTP and UTP); deionized RNase-free water so the final volume will be 50 microliters after addition of an RNAP; and 0.1 micromolar of N4 vRNAP, mini-vRNAP or mini-vRNAP Y678F enzyme. In some embodiments of the invention, 2'-F-dUTP and 2'-F-dCTP are used at a final concentration of 0.5 mM each in place of UTP and CTP in order to obtain synthesis of modified RNA which is resistant to ribonuclease A-type enzymes. Other modified nucleoside triphosphates can also be used in place of or in addition to the canonical NTPs for specific applications. The reaction mixture is then incubated at 37° C. to permit synthesis of RNA from the template. The reaction can be followed by gel electrophoresis on a PAGE gel.

The invention is not limited to these reaction conditions or concentrations of reactants. Those with skill in the art will know that other suitable reaction conditions under which an RNA polymerase of the invention can be used can be found by simple experimentation, and any of these reaction conditions are also included within the scope of the invention. Such media and conditions are known to persons of skill in the art, and are described in various publications, such as U.S. Pat. No. 5,679,512 and PCT Pub. No. WO99/42618, incorporated herein by reference. For example, a buffer maybe Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{+2}$ or $Mn^{+2}$, at a final concentration of free ions that is within the range of from about 0.01 to about 10 mM, and most preferably from about 1 to 6 mM. The reaction medium can also include other salts, such as KCl, that contribute to the total ionic strength of the medium. For example, the range of a salt such as KCl is preferably from about 0 to about 100 mM, more preferably from about 0 to about 75 mM, and most preferably from about 0 to about 50 mM. The reaction medium can further include additives that could affect performance of the reactions, but that are not integral to the activity of the enzyme components of the methods. Such additives include proteins such as BSA, and non-ionic detergents such as NP40 or Triton. Reagents, such as DTT, that are capable of maintaining activities enzyme with sulfhydryl groups can also be included. Such reagents are known in the art. Where appropriate, an RNase inhibitor, such as, but not limited to a placental ribonuclease inhibitor (e.g., RNasin®, Promega Corporation, Madison, Wis. USA) or an antibody RNase inhibitor, that does not inhibit the activity of an RNase employed in the method can also be included. Any aspect of the methods of the present invention can occur at the same or varying temperatures. Preferably, the reactions are performed isothermally, which avoids the cumbersome thermocycling process. The reactions are carried out at a temperature that permits hybridization of the oligonucleotides of the present invention to the target sequence and/or first-strand cDNA of a method of the invention and that does not substantially inhibit the activity of the enzymes employed. The temperature can be in the range of preferably about 25° C. to about 85° C., more preferably about 30° C. to about 75° C., and most preferably about 37° C. to about 70° C. In the processes that include RNA transcription, the temperature for the transcription steps is lower than the temperature(s) for the preceding steps. In these processes, the temperature of the transcription steps can be in the range of preferably about 25° C. to about 85° C., more preferably about 30° C. to about 75° C., and most preferably about 37° C. to about 55° C.

As disclosed in U.S. Pat. Nos. 6,048,696 and 6,030,814, as well as in German Patent No. DE4411588C1, all of which are incorporated herein by reference and made part of the present invention, it is preferred in many embodiments to use a final concentration of about 0.25 M, about 0.5 M, about 1.0 M, about 1.5 M, about 2.0 M, about 2.5 M or between about 0.25 M and 2.5 M betaine (trimethylglycine) in DNA polymerase or reverse transcriptase reactions in order to decrease DNA polymerase stops and increase the specificity of reactions which use a DNA polymerase.

Nucleotide and/or nucleotide analogs, such as deoxyribonucleoside triphosphates, that can be employed for synthesis of reverse transcription or primer extension products in the methods of the invention are provided in an amount that is determined to be optimal or useful for a particular intended use.

The oligonucleotide components of reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Promoter splice template oligos, splice templates, promoter ligation oligos, ligation splint oligos, promoter primers, blocker sequence oligos, and strand-displacement primers, and the like, can each be provided at about or at least about any of the following concentrations: 50 nM, 100 nM, 500 nM, 1000 nM, 2500 nM, 5000 nM, or 10,000 nM, but higher or lower concentrations can also be used. By way of example, but not of limitation, a concentration of one or more oligonucleotides may be desirable for production of one or more target nucleic acid sequences that are used in another application or process.

The invention is not limited to a particular concentration of an oligonucleotide, so long as the concentration is effective in a particular method of the invention.

In some embodiments, the foregoing components are added simultaneously at the initiation of the process. In other embodiments, components are added in any order prior to or after appropriate time points during the process, as required and/or permitted by the reaction. Such time points can readily be identified by a person of skill in the art. The enzymes used for nucleic acid reactions according to the methods of the present invention are generally added to the reaction mixture following a step for denaturation of a double-stranded target nucleic acid in or from a sample, and/or following hybridization of primers and/or oligos of a reaction to a denatured double-stranded or single-stranded target nucleic acid, as determined by their thermal stability and/or other considerations known to the person of skill in the art.

The reactions can be stopped at various time points, and resumed at a later time. The time points can readily be identified by a person of skill in the art. Methods for stopping the reactions are known in the art, including, for example, cooling the reaction mixture to a temperature that inhibits enzyme activity. Methods for resuming the reactions are also known in the art, including, for example, raising the temperature of the reaction mixture to a temperature that permits enzyme activity. In some embodiments, one or more of the components of the reactions is replenished prior to, at, or following the resumption of the reactions. Alternatively, the reaction can be allowed to proceed (i.e., from start to finish) without interruption.

10. Detection and Identification of Reaction Products

In some embodiments, the detection of the product is indicative of the presence of the target sequence. Quantitative analysis, including analysis in real time, can also be performed in some embodiments. Direct and indirect detection methods (including quantification) are well known in the art. For example, by comparing the amount of product amplified from a test sample containing an unknown amount of a polynucleotide containing a target sequence to the product of a reference sample that has a known quantity of a polynucleotide that contains the target sequence, the amount of target sequence in the test sample can be determined. The methods of the present invention can also be extended to analysis of sequence alterations and sequencing of the target nucleic acid. The amplified nucleic acid can be sequenced using any suitable procedure. Many such procedures are known. Preferred forms of sequencing for use with amplified sequences produced from some embodiments are nanosequencing methods described by Jalanko et al., *Clinical Chemistry* 38:39-43, 1992; Nikiforov et al., *Nucleic Acids Research* 22:4167-4175, 1994; and Kobayashi et al., *Molecular and Cellular Probes* 9:175-182, 1995, and primer extension sequencing, as described in PCT Application WO 97/20948, all of which references are included herein by reference. Further, detection could be effected by, for example, examination of translation products from RNA products.

B. Methods for Obtaining a ssDNA Comprising a Target Sequence

1. General Aspects and Methods for Obtaining a Target Sequence

An initial step in obtaining a target sequence is rendering the target nucleic acid single-stranded. If the target nucleic acid is a double-stranded DNA (dsDNA), the initial step is target denaturation. The denaturation step may be thermal denaturation or any other method known in the art, such as alkali treatment.

In some embodiments of the invention in which the target nucleic acid in a sample is DNA, the ssDNA target sequence comprises either ssDNA that is present in a biological sample or ssDNA that is obtained by denaturation of dsDNA in the sample.

In other embodiments, the ssDNA target sequence comprises ssDNA that is obtained as a result of a "primer extension reaction," meaning an in vitro or in vivo DNA polymerization reaction using either ssDNA or denatured dsDNA that is present in the sample as a template and an oligonucleotide as a primer under DNA polymerization reaction conditions. A "primer" is an oligonucleotide (oligo), generally with a free 3'-OH group, for which at least the 3'-portion of the oligo is complementary to a portion of the template and which oligo "binds" (or "complexes" or "anneals" or "hybridizes"), by hydrogen bonding and other molecular forces, to the template to give a primer/template complex for initiation of synthesis by a DNA polymerase, and which is extended (i.e., "primer extended") by the addition of covalently bonded bases linked at its 3'-end which are complementary to the template in the process of DNA synthesis. The result is a primer extension product. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer.

In some embodiments, the target nucleic acid in the sample or the primer extension product, or both, are made into smaller DNA fragments by methods known in the art in order to generate a DNA target sequence. In some embodiments using samples containing DNA target nucleic acids, a ssDNA target sequence and/or a transcription substrate is obtained using a strand displacement method, such as but not limited to, a methods described in PCT Patent Publication Nos. WO 02/16639; WO 00/56877; and AU 00/29742; of Takara Shuzo Company, Kyoto, Japan; U.S. Pat. Nos. 5,523,204; 5,536,649; 5,624,825; 5,631,147; 5,648,211; 5,733,752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214,587 of Gen-Probe, Inc.; U.S. Pat. No. 6,063,604 of Wick et al.; U.S. Pat. No. 6,251,639 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi, all of which are incorporated herein by reference. In still other embodiments, the ssDNA target sequence is obtained from a rolling circle replication reaction. The 3'-end of the DNA target sequence can be defined, if it need be defined, by using any suitable method known in the art, such as, but not limited to, a method discussed in the section herein entitled "Methods for Defining the 5'- and 3'-Ends of Target Sequences That Comprise Only a Portion of a Larger RNA or DNA Target Nucleic Acid."

If the target nucleic acid is RNA, the initial step for obtaining a target sequence comprises synthesis of a single-stranded first-strand cDNA by reverse transcription of the RNA target, meaning an in vitro reaction that utilizes an RNA present in a sample as a template and a nucleic acid oligonucleotide that is complementary to at least a portion of a sequence of the RNA template as a primer in order to synthesize ssDNA using an RNA-dependent DNA polymerase (i.e., reverse transcriptase) under reaction conditions. Techniques for the synthesis of cDNA from RNA are known in the art. In some embodiments, a first-strand cDNA for use in methods of the invention is synthesized in situ in cells or tissue in a tissue section using methods similar to those described in U.S. Pat. Nos. 5,168,038; 5,021,335; and 5,514,545, which are incorporated herein by reference. Thus, the first-strand cDNA is synthesized by contacting the cells or tissue in the tissue section under hybridizing conditions with a primer, wherein the primer hybridizes to one or more target sequences in the cell or tissue. The present invention comprises a method for making a transcription substrate comprising first-strand cDNA that is complementary to a target sequence in cells or tissue in a tissue section, the method comprising: (a) contacting the cells or tissue in the tissue section under hybridizing conditions with a promoter primer, the promoter primer comprising (i) a 5'-portion comprising a ssDNA transcription promoter for an RNA polymerase that synthesize RNA using a ssDNA transcription substrate, and (ii) a 3'-end that is complementary to a target sequence in a target nucleic acid; and (b) contacting the cells or tissue containing the promoter primer in the tissue section with a reverse transcriptase under reverse transcription conditions so as to obtain a first-strand cDNA that is complementary to the target sequence; and (c) obtaining first-strand cDNA, wherein the first-strand cDNA comprises a ssDNA transcription substrate for the an RNA polymerase that binds to the promoter.

An oligonucleotide primer can be complementary to a specific known sequence in the RNA target in a sample, or an oligonucleotide primer can comprise a mixture of all possible or many possible sequences, such as, but not limited to, a primer comprising a random hexamer priming sequence. Random primers can be made by using an oligonucleotide synthesizer by including nucleotide reagents that are complementary to each of the four canonical bases (i.e., all four nucleotides) during the chemical synthesis of each nucleotide position of the oligonucleotide that is complementary to the target sequence. In embodiments of the invention using samples containing mRNA targets, the ssDNA target sequence comprises first-strand cDNA that is made by reverse transcription of the mRNA using an oligonucleotide primer comprising either a specific sequence which is complementary to a known sequence of a specific mRNA or, if the mRNA has a poly(A) tail at its 3'-end, an oligo(dT) primer or an oligo(dT) anchor primer. In other embodiments of the invention, a promoter primer is used, which serves both to prime synthesis of the first-strand cDNA target sequence and to join a transcription promoter to the target sequence.

2. Methods for Defining the 5'- and 3'-Ends of Target Sequences That Comprise Only a Portion of a Larger RNA or DNA Target Nucleic Acid When a method of the invention is used to obtain a transcription product corresponding to the complete sequence(s) of one or a multitude of nucleic acid molecules, such as, but not limited to the complete sequences (excluding the cap structure) of substantially all polyadenylated mRNA molecules in a sample, it is not necessary to devise methods to define the 5'- and 3'-ends of the sequences. However, if a method of the invention is used to obtain a transcription product corresponding to a target sequence that comprises only a portion of a larger RNA or DNA nucleic acid in a sample, then methods are needed to delimit the target sequence that becomes the transcription template.

There are two general approaches for delimiting the ends of the target sequence that becomes the transcription template sequence. In the first direct approach, methods are used to determine the size and end sequences of a target nucleic acid molecule or molecules present in the sample itself. In the second indirect approach, instead of changing the size and end sequences of the target nucleic acid molecules present in a sample, methods are used to determine the size and end sequences of one or more first-strand cDNA molecules that is/are synthesesized by reverse transcription or primer extension, respectively, of RNA or of at least one strand of DNA in a sample.

With respect to the direct approach, a number of methods are known in the art for cleaving a nucleic acid molecule at or near a specific sequence, and any of the methods which delimit the size and end sequences of a target nucleic acid for an application of the present invention can be used. By way of example, but not of limitation, a DNA in a sample comprising a dsDNA molecule or a ssDNA molecule to which an appropriate complementary DNA oligo is annealed can be digested with a restriction endonuclease, provided a restriction site that would provide a suitable 5'-end and/or 3'-end sequence is present. Alternatively, one or more DNA oligonucleotides having a double-stranded segment that contains a FokI restriction enzyme site and a single-stranded segment that binds to the desired cleavage site on a first-strand cDNA can be used. As is well known in the art, this type of oligonucleotide can be used with the restriction enzyme FokI to cut a single-stranded DNA at almost any desired sequence (Szybalski, W., *Gene* 40:169-173, 1985; Podhajska A. J. and Szybalski W., *Gene* 40:175, 1985, incorporated herein by reference).

By way of further example, but not of limitation, a ssRNA target nucleic acid present in a sample can be cleaved using a ribonuclease H in regions to which complementary oligonucleotides comprising at least three-to-four deoxynucleotides are annealed. Alternatively, a linear DNA oligonucleotide can be annealed to an RNA in a sample at a location that encodes a recognition site of a restriction enzyme that can cut RNA:DNA heteroduplexes. Cutting the target RNA:DNA oligo with the enzyme will then generate a defined end. Alternatively, an RNA or DNA oligo or polynucleotide with a sequence complementary to the region of an RNA target sequence that is intended to become a transcription substrate can be annealed to the RNA and the sequences of the RNA to which the oligo or polynucleotide is not annealed can be digested using a single-strand-specific ribonuclease, such as RNase A or RNase T1. Still further, either RNA or DNA nucleic acids of known sequence can be cleaved at specific sites using a 5'-nuclease or Cleavase™ enzyme and specific oligonucleotides, as described by Kwiatkowski, et al., (*Molecular Diagnosis* 4:353-364, 1999) and in U.S. Pat. No. 6,001,567 and related patents assigned to Third Wave Technologies (Madison, Wis. USA), which are incorporated herein by reference.

In general, with respect to the second indirect approach, the 5'-end of the primer that is used for reverse transcription of RNA in a sample or for primer extension of at least one strand of DNA in a sample defines the 5'-end of the first-strand cDNA target sequence. Thus, a sample target nucleic acid that is reverse transcribed or primer extended to make a first-strand cDNA target sequence need not have a defined 3'-end.

In order to generate a defined 3'-end on a first-strand cDNA (i.e., corresponding to the 5'-end of the target sequence), a number of methods can be used to obtain a target sequence of the present invention. By way of example, but not of limitation, if a specific sequence is present in the first-strand cDNA that corresponds to a restriction endonuclease site that would provide a suitable 3'-end sequence, a complementary DNA oligo can be annealed to this sequence and the site can be cleaved with the restriction enzyme. The complementary DNA oligo used to provide the double-stranded restriction site can optionally have a 2', 3'-dideoxynucleotide or another terminator nucleotide at its 3'-end so that it cannot be extended by a DNA polymerase. Alternatively, the 3'-end of the target sequence can be defined using a DNA oligonucleotide having a double-stranded segment that contains a FokI restriction enzyme site and a single-stranded segment that binds to the desired cleavage site on a first-strand cDNA (Szybalski, W., *Gene* 40:169-173, 1985; Podhajska A. J. and Szybalski W., *Gene* 40:175, 1985). Still further, a 5'-nuclease can be used to cleave a first-strand cDNA at a defined 3'-end as discussed above.

In addition to the above methods, the 3'-end of a first-strand cDNA can also be limited by other methods. A preferred method of the invention is to use a "blocking oligo" or a "blocker sequence," as disclosed by Laney, et al. in U.S. Pat. No. 5,679,512, and by Kurn in U.S. Pat. No. 6,251,639, both of which are incorporated herein by reference. The "blocker sequence" or "blocker oligo" is a polynucleotide, which is usually a synthetic polynucleotide that is single-stranded and comprises a sequence that is hybridizable, and preferably complementary, to a segment of target nucleic acid, wherein the blocking oligo anneals to the target nucleic acid so as to block further primer extension of the 3'-end of first-strand cDNA at a desired position. Some embodiments of strand displacement methods of the present invention for obtaining a ssDNA transcription substrate comprise use of a blocking oligo. The blocking oligo comprises nucleotides that bind to the target nucleic acid with an affinity, preferably a high affinity, such that the blocker sequence resists displacement by DNA polymerase in the course of primer extension, in preferably more than about 30%, more preferably more than about 50%, even more preferably more than about 75%, and most preferably more than about 90%, of primer extension events. The length and composition of the blocker polynucleotide should be such that excessive random non-specific hybridization is avoided under the conditions of the methods of the present invention. The length of the blocker polynucleotide is preferably from about 3 to about 30 nucleotides, more preferably from about 5 to about 25 nucleotides, even more preferably from about 8 to about 20 nucleotides, and most preferably from about 10 to about 15 nucleotides. In other embodiments, the blocker polynucleotide is at least about any of the following: 3, 5, 8, 10, 15; and less than about any of the following: 20, 25, 30, 35. It is understood that the length can be greater or less as appropriate under the reaction conditions of the methods of this invention. The complementarity of the blocker polynucleotide is preferably at least about 25%, more preferably at least about 50%, even more preferably at least about 75%, and most preferably at least about 90%, to its intended binding sequence on the target nucleic acid. In some embodiments, the blocker sequence that hybridizes to a DNA target nucleic acid is attached to the DNA such that displacement of the blocker sequence by the polymerase that affects primer extension is substantially, or at least sufficiently, inhibited. Suitable methods for achieving such attachment include techniques known in the art, such as using a cytosine analog that contains a G-clamp heterocycle modification as described by Flanagan et al., (*Proc. Natl. Acad. Sci. USA* 96:3513-3518, 1999); and locked nucleic acids as described, e.g., by Kumar et al., (*Bioorg. Med. Chem. Lett.* 8:2219-2222, 1998; and by Wahlestedt et al. (*Proc. Natl. Acad. Sci. USA* 97:5633-5638, 2000), all of which are incorporated herein by reference. Other suitable methods include using, where appropriate, sequences with a high GC content and/or cross-linking. Any of these methods for obtaining enhanced attachment may be used alone or in combination. Alternatively, a molecule comprising a peptide nucleic acid ("PNA") can be used.

Still further, another method that can be used to limit the 3'-end of a first-strand cDNA is to use a thermocycler with short DNA synthesis elongation cycles during reverse transcription or primer extension to synthesize first-strand cDNA. The length of the primer extension product can be somewhat controlled by the length of the DNA synthesis cycle. Conditions can be determined to define an approximate chain length of first-strand cDNA by controlling the temperature and time interval of DNA synthesis before denaturing the growing first-strand cDNA from the template by raising the temperature.

Further, the 3'-end of a first-strand cDNA that is to become the template sequence for a transcription reaction can be defined by first amplifying the target nucleic acid sequence using any suitable amplification method that delimits the end sequence. By way of example, but not of limitation, it can be prepared using PCR, RT-PCR, NASBA, TMA, 3SR, Ligation Chain Reaction (LCR), Linked Linear Amplification (Bio-Rad), SDA, RCA, ICAN™ (Takara: Sagawa et al. in PCT Patent Publication No. WO 02/16639; and in PCT Patent Publications Nos. WO 00/56877 and AU 00/29742; or a strand-displacement method of Kurn (U.S. Pat. No. 6,251,639), all of which are incorporated herein by reference.

If a 3'-end of a target sequence need not be at an exact location, and can be random or imprecise, which is the case in some embodiments of the invention, there are a number of other methods that can be used for making smaller fragments of a DNA molecule, whether for a target nucleic acid, a target sequence, or otherwise. By way of example, but not of limitation, a target nucleic acid can be fragmented by physical means, such as by movement in and out of a syringe needle or other orifice or by sonication, preferably with subsequent end repair, such as using a T4 DNA polymerase or a kit, such as the End-It™ DNA End Repair Kit (Epicentre Technologies, Madison, Wis. USA). Still another method that can be used is to incorporate dUMP randomly into the first-strand cDNA during reverse transcription or primer extension by using dUTP in place of a portion of the TTP in the reaction. The dUMP will be incorporated randomly in place of TMP at a frequency based on the ratio of dUTP to TTP. Then, the first-strand cDNA can be cleaved at sites of dUMP incorporation by treatment (e.g., see U.S. Pat. No. 6,048,696, incorporated herein by reference) with uracil-N-glycosylase (UNG) and endonuclease IV (endo IV), which are available from Epicentre Technologies (Madison, Wis. USA). UNG hydrolyzes the N-glycosidic bond between the deoxyribose sugar and uracil in single- and double-stranded DNA that contains uracil in place of thymidine. It has no activity on uracil residues in RNA or on dUTP. Endo IV cleaves the phosphodiester linkage at the abasic site. It may be useful to use a thermolabile UNG (e.g., HK™-UNG from Epicentre Technologies, Madison, Wis., USA) for some applications. (Also, incorporation of dUMP at specific sites within a synthetic oligonucleotide or, for example, within a promoter primer of the invention between the 3'-target-sequence-complementary portion and the promoter sequence, introduces specific cleavage sites which can be used at any time to cleave a resulting nucleic acid which contains the site by treatment with UNG and endo IV.) Still further, in some cases, the 3'-end of a first-strand cDNA can be defined by treatment with exonuclease III (Henikoff, S., *Gene* 28:351, 1984). In still other cases, the 3'-end of a first-strand cDNA that is annealed to a DNA target nucleic acid can be incubated with T4 DNA polymerase or unmodified T7 DNA polymerase (Epicentre Technologies, Madison, Wis.) in the absence or the presence of dNTPs in the reaction; these enzymes have the 3'-to-5' exonuclease activity in the absence of dNTPs, but the polymerase activity predominates in the presence of dNTPs. These are only some of the methods that can be used to define the 3'-ends of a first-strand cDNA, and the invention is not limited to these methods, which are presented only as examples.

C. Methods for Obtaining a Transcription Substrate

1. Introduction

The invention includes a number of embodiments for obtaining a transcription substrate. In a first general embodiment, a ssDNA transcription substrate is obtained by using a promoter splice template oligo, comprising an anti-sense transcription promoter in its 5'-portion, as a template for DNA polymerase- or reverse transcriptase-catalyzed extension of the 3'-end of first-strand cDNA that is complementary to a target sequence. This first general embodiment results in a transcription substrate with a sense transcription promoter 3'-of a target sequence. In a second general embodiment, a ssDNA transcription substrate is obtained by ligating a promoter ligation oligo, comprising a sense transcription promoter, to the 3'-end of a target sequence. In this embodiment, the target sequence can comprise first-strand cDNA that is complementary to a DNA or RNA target sequence or, if the target nucleic acid is DNA and the 3'-end of the target sequence is suitably delimited, the promoter ligation oligo can be ligated directly onto the 3'-end of the target sequence. In a third general embodiment, a ssDNA transcription substrate is obtained by synthesizing first-strand cDNA by a reverse transcription or primer extension of a promoter primer comprising a sense transcription promoter in its 5'-portion and a sequence complementary to the target sequence at its 3'-end and then ligating the resulting linear first-strand cDNA to obtain a circular ssDNA transcription substrate comprising a promoter-containing circular first-strand cDNA. A linear ssDNA transcription substrate resulting from the first or second general embodiments can also be ligated to make a circular ssDNA transcription substrate. In still other embodiments, any of the above circular ssDNA transcription substrates is linearized 3'-of a sense transcription promoter sequence to obtain a linear ssDNA transcription substrate having the promoter 3'-of the target sequence.

In still another embodiment, a ssDNA transcription substrate comprising second-strand cDNA is obtained by (a) synthesizing first-strand cDNA using a reverse transcriptase or a DNA polymerase and a primer comprising an anti-sense transcription promoter in its 5'-portion and a sequence complementary to the target sequence at its 3'-end; (b) ligating the resulting linear first-strand cDNA to obtain a circular first-strand cDNA having an anti-sense transcription promoter; and (c) obtaining a linear second-strand cDNA comprising a ssDNA transcription substrate by DNA synthesis using the circular first-strand cDNA as a template, a primer with a 3'-end complementary to a sequence on first-strand cDNA and a DNA polymerase, preferably a strand-displacing DNA polymerase that results in strand-displacement DNA synthesis of the linear transcription substrate. In this embodiment, the transcription product of the transcription substrate comprises an anti-sense transcription product.

In yet another embodiment, a ssDNA transcription substrate comprising second-strand cDNA is obtained by (a) synthesizing linear first-strand cDNA having an anti-sense promoter 3'-of a target sequence using a primer, a reverse transcriptase or DNA polymerase, and a splice template oligo having sense promoter in its 5'-portion and a sequence complementary to the target sequence at its 3'-end; (b) ligating the resulting linear first-strand cDNA to obtain a circular first-strand cDNA having an anti-sense transcription promoter; and (c) obtaining a linear second-strand cDNA comprising a ssDNA transcription substrate by DNA synthesis using the circular first-strand cDNA as a template, a primer with a 3'-end complementary to a sequence on the first-strand cDNA and a DNA polymerase, preferably a strand-displacing DNA polymerase that results in strand-displacement DNA synthesis of the linear transcription substrate. In this embodiment, the transcription product of the transcription substrate comprises an anti-sense transcription product.

In still another embodiment, a ssDNA transcription substrate comprising second-strand cDNA is obtained by (a) synthesizing linear first-strand cDNA using a primer and a reverse transcriptase or DNA polymerase; (b) ligating an oligonucleotide comprising an anti-sense promoter to the 3'-end of the first-strand cDNA target sequence; (c) ligating the resulting linear first-strand cDNA having an anti-sense promoter to obtain a circular first-strand cDNA having an anti-sense transcription promoter; and (c) synthesizing a linear second-strand cDNA, comprising a ssDNA transcription substrate, by DNA synthesis using the circular first-strand cDNA as a template, a primer with a 3'-end complementary to a sequence on first-strand cDNA and a DNA polymerase, preferably a strand-displacing DNA polymerase that results in strand-displacement DNA synthesis of the linear transcription substrate. In this embodiment, the transcription product of the transcription substrate comprises an anti-sense transcription product.

In all of the above embodiments for obtaining a transcription substrate comprising second-strand cDNA, the transcription substrate, including the promoter sequence, is nevertheless single-stranded, rather than double-stranded as used in the prior art.

In addition, the invention also comprises embodiments in which a linear ssDNA transcription substrate comprising second-strand cDNA is obtained without attaching either a sense or an anti-sense promoter sequence to the target sequence of the first-strand cDNA. By way of example, but not of limitation, a splice template oligo or a ligation oligo can be used to attach a primer-binding sequence to the 3'-end of a target sequence comprising first-strand cDNA. The splice template oligo or ligation oligo does not comprise a complete sense or anti-sense promoter sequence, although the splice template oligo or ligation oligo can (but need not) comprise part of a sequence that is complementary to a sense or anti-sense promoter, respectively. If the splice template oligo or ligation oligo comprises part of a promoter sequence, the first-strand cDNA will have a portion of an anti-sense promoter sequence on its 3'-end, providing an annealing site for a primer comprising a sense promoter sequence that can be used for synthesis of a ssDNA transcription substrate comprising second-strand cDNA. If the splice template oligo or ligation oligo does not comprise part of a promoter sequence, then the respective oligo will have another sequence that provides an annealing site for another primer that has a complete sense promoter of the invention, thereby permitting synthesis of ssDNA transcription substrate comprising second-strand cDNA by primer extension.

The embodiments of processes for obtaining a transcription substrate for methods of the invention described above are provided only as examples, and are not intended to limit the present invention. The description above and herein will reveal and make evident to those with knowledge in the art numerous other embodiments of methods and processes for obtaining a transcription substrate for use in making a transcription product corresponding to a target nucleic acid sequence in a method of the invention, and the invention includes all of those methods and processes for obtaining a transcription substrate for use in the methods.

In embodiments in which the target sequences comprise mRNA, whether of a single species of mRNA or all of the mRNA in a particular sample, the transcription products can subsequently be used for a variety of applications. By way of example, but not of limitation, transcription products can be used for in vitro or in vivo translation, for use as RNAi to silence one or more genes in vivo, for spotting on a surface to make expression arrays or microarrays, or for making hybridization probes for arrays or microarrays for gene expression profiling or other uses. In still other embodiments, methods of the invention can be used to make first-strand cDNA from mRNA, which in turn can be used for techniques such as random amplification of cDNA ends (RACE) or to make hybridization probes.

2. Obtaining a ssDNA Transcription Substrate using a Splice Template Oligo or Promoter Splice Template Oligo a. Definitions and Methods for Using Splice Template Oligos A "splice template" or "splice template oligo" is an oligonucleotide that complexes with a single-stranded target nucleic acid and is used as a template to extend the 3'-terminus of the target sequence in order to add a specific sequence. The 3'-portion of a splice template is sufficiently complementary to the 3'-terminus of the target sequence that is to be extended to anneal thereto. A DNA- or RNA-dependent DNA polymerase is then used to extend the target nucleic acid molecule using the sequence in the 5'-portion of the splice template oligo as a template. The extension product of the primer-extended molecule has the specific sequence at its 3'-terminus that is complementary to the sequence in the 5'-portion of the splice template oligo.

A preferred embodiment of a splice template of the present invention is a "promoter splice template" or a "promoter splice template oligo." A promoter splice template oligo comprises a sequence in its 3'-portion that is sufficiently complementary to the 3'-end of the target sequence to anneal thereto and a sequence in it 5'-portion that is complementary to a sequence comprising a single-stranded transcription promoter of the invention. Thus, a promoter splice template oligo can provide a template for synthesis of a sequence comprising a transcription promoter at the 3'-end of first-strand cDNA obtained either by reverse transcriptase primer extension of a target sequence comprising an RNA target nucleic acid, such as, but not limited to, an mRNA target, or by DNA polymerase primer extension of a target sequence comprising DNA. If the promoter splice template is annealed to the end of first-strand cDNA made by primer extension of a target nucleic acid, and the promoter splice template comprises a sequence that is complementary to a functional transcription promoter (i.e., the promoter splice template has an anti-sense promoter sequence), then the first-strand cDNA will have a sense promoter and will therefore comprise a ssDNA transcription substrate of the invention. In one embodiment, which is a preferred embodiment, transcription of a ssDNA transcription substrate results in synthesis of transcription products having a sequence identical to that of the target sequence.

However, the invention also comprises other embodiments. Thus, in one embodiment, if the 3'-end of a DNA target nucleic acid in a sample has a defined 3'-end and is itself primer-extended on a promoter splice template oligo comprising an anti-sense promoter sequence (i.e., the target sequence is used directly without being copied using a DNA polymerase to obtain first-strand cDNA), then the transcription products made using the ssDNA transcription substrate will be complementary to the target nucleic acid (i.e., the transcription products can comprise anti-sense RNA or "aRNA"). In another embodiment, if the splice template comprises a sense promoter sequence, primer extension of first-strand cDNA annealed to the promoter splice template results in first-strand cDNA having an anti-sense (i.e., non-functional) promoter. However, if this linear anti-sense-promoter-containing first-strand cDNA is circularized using a ligase under ligation conditions, and replicated by rolling circle replication using a strand displacement primer and a strand-displacing DNA polymerase, the resulting second-strand cDNA will comprise a ssDNA transcription substrate with functional sense promoters. Transcription of this transcription substrate results in synthesis of transcription products that are complementary to the target sequence (i.e., antisense transcription products or aRNA).

If the 3' terminus of a splice template is not blocked and is complementary to the target nucleic acid, the splice template itself may also act as a primer and be primer-extended by the DNA polymerase using the target nucleic acid molecule as a template. Since an RNA polymerase of the present invention can bind to a promoter in a ssDNA transcription substrate and initiate and synthesize RNA therefrom, in most embodiments of the present invention, the 3'-terminus of a splice template, including a promoter splice template oligo, is blocked in any of a variety of ways, including, but not limited to, using a terminal 2',3'-dideoxynucleotide or a 3'-terminal sequence that is non-complementary to the target, or in other ways well known to those skilled in the art. It is also possible to block the 3'-end using a label, or a small molecule that is a member of a specific binding pair, such as biotin.

Some embodiments of the invention comprise methods that use a promoter splice template oligo for obtaining a ssDNA transcription substrate for making a transcription product corresponding to a target nucleic acid sequence, wherein the ssDNA transcription substrate comprises a promoter-containing first-strand cDNA and wherein the promoter-containing first-strand cDNA comprises (i) a transcription promoter for an RNA polymerase that synthesizes RNA from a ssDNA promoter-containing template under transcription conditions and (ii) a target nucleic acid sequence, at least a portion of which target sequence either comprises, or, is complementary to, at least a portion of a nucleic acid sequence in a target nucleic acid present in a sample, and wherein the transcription promoter is 3'-of the target sequence in the ssDNA transcription substrate.

With respect to embodiments that use a promoter splice template oligo, one embodiment of the invention comprises a method for obtaining a ssDNA transcription substrate of the invention for making a transcription product corresponding to a target sequence in a target nucleic acid comprising single-stranded DNA or RNA, the method comprising:

a. obtaining a primer for synthesis of a first-strand cDNA, the primer comprising a sequence that is complementary to the 3'-end of the target sequence that is to be transcribed;

b. optionally, obtaining a blocking oligo, the blocking oligo comprising a sequence that anneals tightly to a sequence on the target nucleic acid so as to delimit the 3'-end of a primer extension product of the primer using the target nucleic acid as a template, wherein the blocking oligo is not displaced by the primer extension product, and wherein the blocking oligo is not itself capable of being primer-extended by a DNA polymerase;

c. annealing the primer and the blocking oligo, if used, to the target nucleic acid;

d. primer-extending the primer annealed to the target nucleic acid with a DNA polymerase under DNA synthesis conditions so as to obtain a linear first-strand cDNA that is complementary to the target sequence to which the primer is annealed;

e. optionally, removing the target nucleic acid that is annealed to the linear first-strand cDNA;

f. optionally, adding one or more tail sequences to the 3'-end of the first-strand cDNA obtained by primer extension of the primer;

g. obtaining a promoter splice template oligo, wherein the promoter splice template oligo comprises (i) a 3'-end that is sufficiently homologous to the 3'-end of the linear first-strand cDNA to hybridize therewith, and (ii) a 5'-portion that comprises a sequence that is complementary to transcription promoter for an RNA polymerase that can synthesize RNA using a ssDNA transcription substrate;

h. annealing the promoter splice template oligo to the linear first-strand cDNA, including the tail, if present;

i. primer-extending the first-strand cDNA including the tail, if present, with a DNA polymerase under DNA polymerization conditions so as to obtain a promoter-containing first-strand cDNA that has a 3'-portion that is complementary to the portion of the promoter splice template oligo that is not hybridizable to the first-strand cDNA including the tail, if present;

j. removing or dissociating the promoter splice template oligo from the promoter-containing first-strand cDNA, the promoter-containing first-strand cDNA comprising a ssDNA transcription substrate; and k. obtaining the ssDNA transcription substrate.

As discussed elsewhere herein, a target nucleic acid of the invention can be DNA or RNA of any type. By way of example, but not of limitation, a target sequence can comprise a target nucleic acid comprising a single species of mRNA or a target sequence can comprise a target nucleic acid comprising all of the mRNA in a sample.

In synthesizing first-strand cDNA from mRNA, when the reverse transcriptase reaches the 5'-end of the mRNA, it can add a non-templated dCMP residue to the 3'-end of full-length first-strand cDNA. The two dCMP residues, including the dG-templated dCMP resulting from an mRNA G[5']ppp [5']G cap structure, provide an annealing site for a splice template oligo or a promoter splice template oligo that comprises a sequence that has at least two G nucleotide residues at or near its 3'-end. Thus, when annealed to the 3'-end of "tailed" first-strand cDNA, the splice template oligo or promoter splice template oligo serves as a template for primer extension of first-strand cDNA. If a promoter splice template oligo is used, a sequence comprising a transcription promoter sequence is added to the 3'-end. The present invention differs from the method of Chenchik et al. (U.S. Pat. No. 5,962,272, incorporated herein by reference) in a number of ways. By way of example, a template switch oligonucleotide of Chenchik et al. has at least one ribonucleotide at its 3'-end portion, and uses the 3'-end of the template switch oligonucleotide to prime synthesis of second-strand cDNA strand. In contrast, since a transcription substrate of the present invention comprises ssDNA, a promoter splice template oligo of the present invention is not used to prime synthesis of second-strand cDNA and the 3'-terminal nucleotide of the promoter splice template oligo is preferably a terminator nucleotide such as, but not limited to, a dideoxynucleotide.

In some embodiments of methods of the invention for making a transcription substrate using a splice template oligo or promoter splice template oligo, three to four non-templated dCMP residues are added to the 3'-end of the target sequence in first-strand cDNA by using a reverse transcriptase in the presence manganese cations and/or two to four rNMP residues are added to the 3'-end by controlled ribonucleotide tailing using terminal deoxynucleotidyl transferase (Schmidt, W. M. and Mueller, M. W., *Nucleic Acids Res.* 24:1789-91, 1996; Ibid, *Nucleic Acids Res.* 27:e31 (i-iv), 1999, both incorporated herein by reference). These additional three to four dCMP residues and/or two to four rNMP residues on the 3'-end of the target sequence in first-strand cDNA provide a site with an even greater degree of homology (compared to Chenchik's method) for annealing to the 3'-end of the splice template oligo or promoter splice template oligo. By way of example, but not of limitation, the splice template oligo or promoter splice template oligo can have two to four nucleotides that are complementary to corresponding rNMP residues at the 3'-end of first-strand cDNA from controlled ribonucleotide tailing and the splice template oligo or promoter splice template oligo can have three to four G nucleotide residues that are complementary to the dCMP residues at or near the 3'-end of first-strand cDNA, providing additional nucleotides for annealing to the splice template oligo. A promoter splice template oligo annealed to the 3'-end of first-strand cDNA serves as a template for extension of first-strand cDNA by an enzyme with DNA polymerase activity, with concomitant synthesis of a sequence comprising a transcription promoter sequence at its 3'-end. The DNA polymerase used for primer extension of the first-strand cDNA can be a DNA-dependent DNA polymerase or an RNA-dependent DNA polymerase (i.e., reverse transcriptase), depending on whether the composition of the splice template oligo or promoter splice template oligo is DNA or RNA, respectively. Preferably, a DNA polymerase with both DNA-dependent and RNA-dependent DNA polymerase activity is used. By way of example, but not of limitation, preferred DNA polymerases of the invention include MMLV reverse transcriptase (including both RNase H-containing enzyme and mutant forms of the enzyme which lack substantial RNase H activity, depending on the particular application and method of the invention used), AMV reverse transcriptase, and rBst DNA polymerase large fragment (Epicentre Technologies, Madison, Wis. USA). Since no synthesis of a second cDNA strand is needed or performed to prepare transcription substrates for the RNA polymerases of the invention, the 3'-terminal nucleotide of the splice template oligo or promoter splice template oligo is preferably a terminator nucleotide such as, but not limited to, a dideoxynucleotide. In some embodiments, the target sequence used comprises full-length first-strand cDNA prepared from mRNA in a sample.

Figure 18:
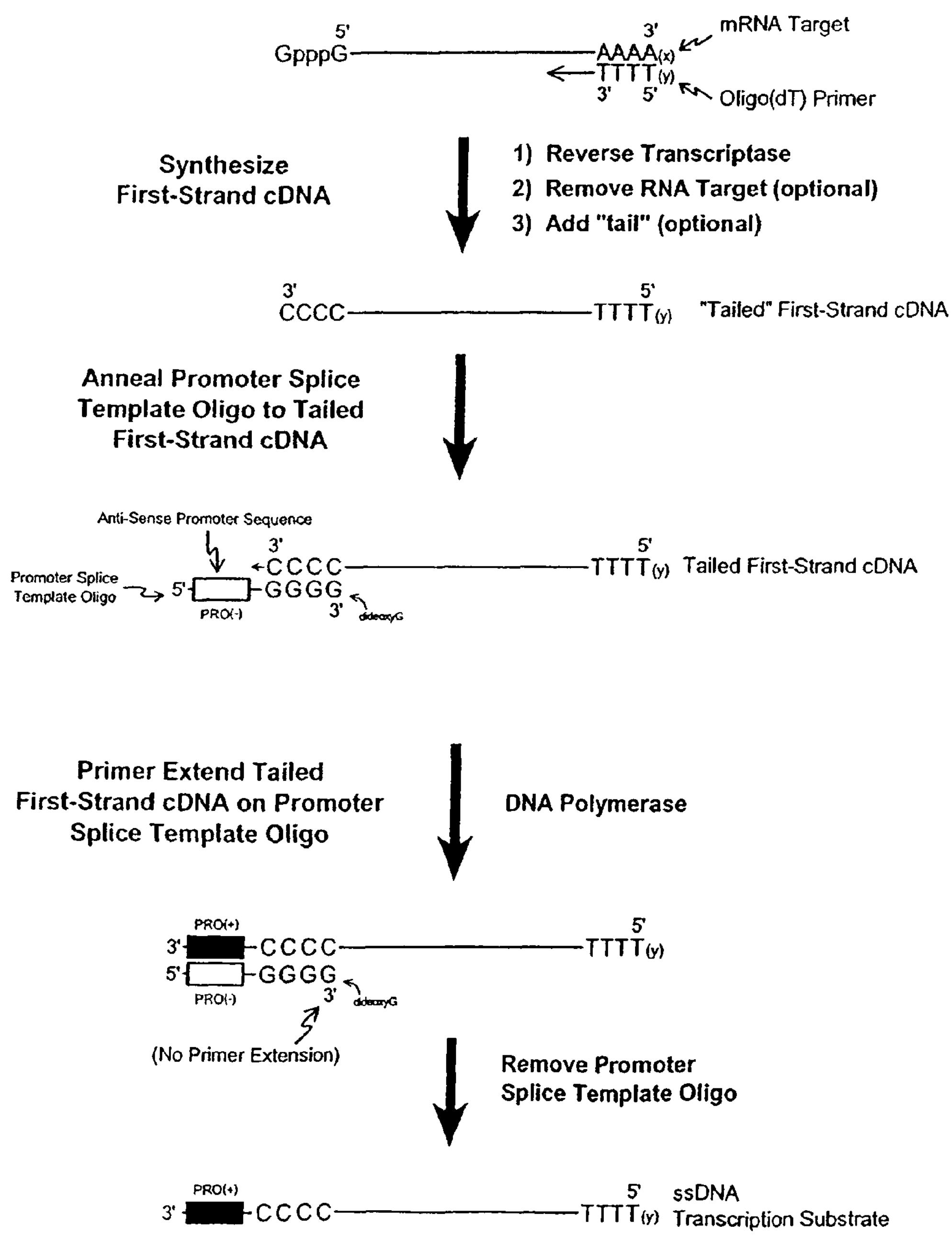
FIG. 18—Schematic of an embodiment of the invention for obtaining a ssDNA transcription substrate using a promoter splice template oligo.

Thus, one embodiment of the invention that uses a promoter splice template oligo is a method for making a transcription product corresponding to a target sequence comprising a target nucleic acid comprising mRNA in a sample (FIG. 18), the method comprising:

a. obtaining target nucleic acid comprising mRNA;

b. obtaining a primer for synthesis of a first-strand cDNA that is complementary to the mRNA, the primer chosen from among: (i) an oligo(dT) primer, and (ii) an oligo(dT) anchor primer; (iii) a primer that is complementary to a specific sequence at the 3'-end of an mRNA, and (iv) a primer in a mixture of primers, the primer comprising a sequence of nucleotides, each of which nucleotides comprises a random nucleotide base that is complementary to any of the four canonical nucleotide bases;

c. annealing the primer to the target mRNA;

d. primer-extending (or reverse transcribing) the primer annealed to the target mRNA with a DNA polymerase (reverse transcriptase) under DNA synthesis (reverse transcription) conditions so as to obtain a linear first-strand cDNA that is complementary to the target mRNA to which the primer was annealed;

e. optionally, adding a tail to the first-strand cDNA using one or more methods;

f. optionally, removing the target mRNA that is annealed to the linear first-strand cDNA;

g. obtaining a promoter splice template oligo, wherein the promoter splice template oligo comprises (i) a 3'-end that is sufficiently homologous to the 3'-end of the linear first-strand cDNA, including the tail, if present, to hybridize therewith, and (ii) a 5'-portion that comprises a sequence that is complementary to transcription promoter for an RNA polymerase that can synthesize RNA using a ssDNA transcription substrate;

h. annealing the promoter splice template oligo to the linear first-strand cDNA, including the tail, if present;

i. primer-extending the first-strand cDNA with a DNA polymerase under DNA polymerization conditions so as to obtain a promoter-containing first-strand cDNA that has a 3'-portion that is complementary to the portion of the promoter splice template oligo that is not hybridizable to the first-strand cDNA including the tail, if present;

j. removing or dissociating the promoter splice template oligo from the promoter-containing first-strand cDNA, the promoter-containing first-strand cDNA comprising a ssDNA transcription substrate;

k. obtaining the ssDNA transcription substrate;

l. contacting the ssDNA transcription substrate from step j with an RNA polymerase that transcribes the ssDNA transcription substrate using the promoter under transcription conditions so as to obtain transcription products; and m. obtaining the transcription products;

Thus a general embodiment of the invention comprises a method for using a promoter splice template oligo to make a transcription product corresponding to a target sequence in a target nucleic acid, the method comprising:

a. obtaining a ssDNA transcription substrate by primer extension of the 3'-end of a target sequence using a promoter splice template oligo as a template;

b. contacting the ssDNA transcription substrate with an RNA polymerase that transcribes the ssDNA transcription substrate using the transcription promoter under transcription conditions so as to obtain transcription products; and c. obtaining the transcription products.

The methods described above for obtaining a ssDNA transcription substrate using a promoter splice template oligo and for making a transcription product corresponding to a target sequence can be performed in a stepwise manner, or, under suitable reaction conditions, they can be performed continuously in a single reaction mixture.

Figure 19:
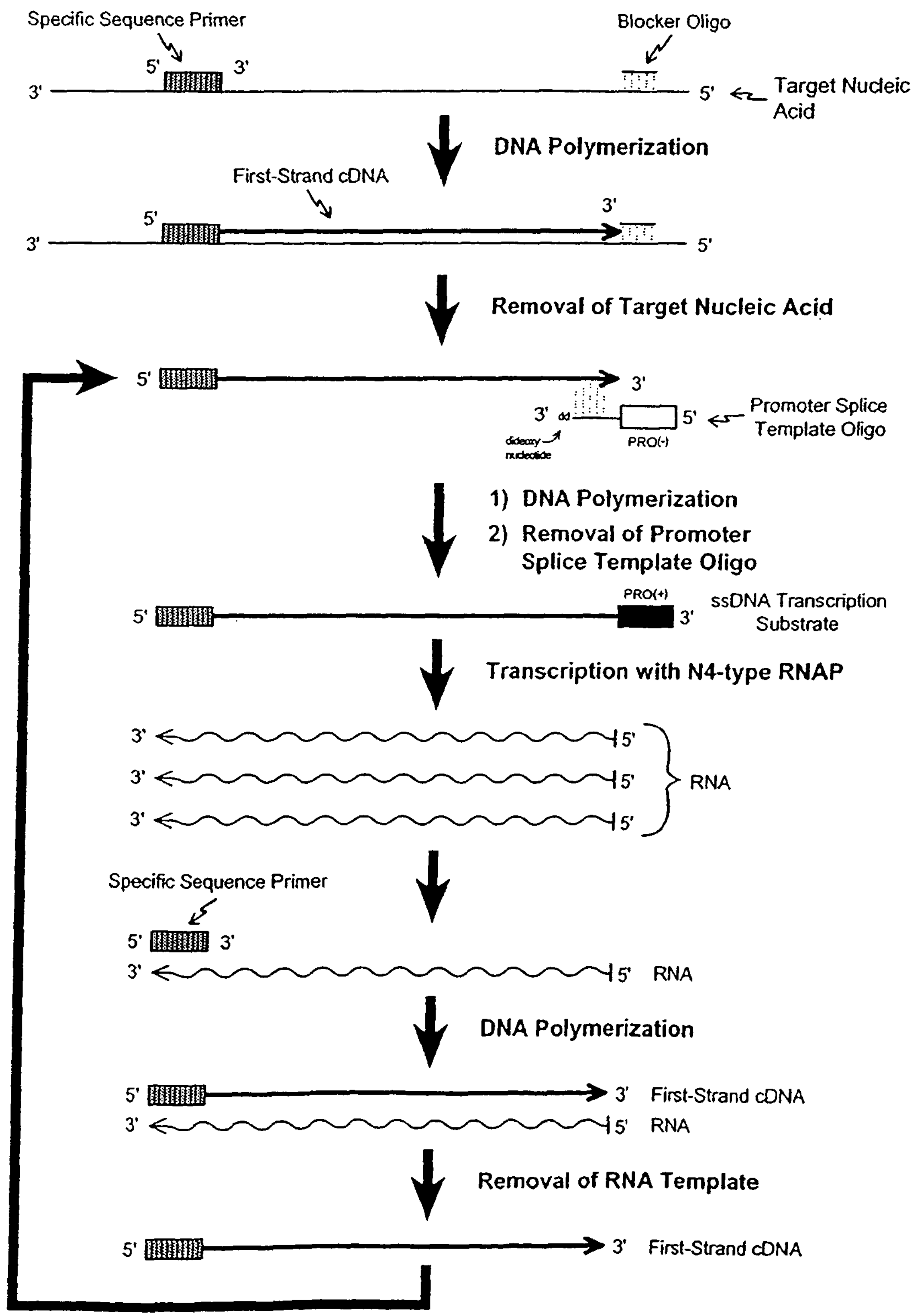
FIG. 19—Schematic of an embodiment of a continuous transcription assay of the invention that utilizes a promoter splice template oligo and a blocker oligo.

Thus, one embodiment of the invention that uses a promoter splice template oligo comprises a method for obtaining additional rounds of transcription of a target sequence comprising a target nucleic acid (FIG. 19), the method comprising:

a. obtaining transcription products from step c of the method above;

b. obtaining a primer for synthesis of a first-strand cDNA, the primer comprising a sequence that is complementary to the 3'-end of the transcription products comprising the target sequence that is to be transcribed;

c. annealing the primer to the transcription products;

d. primer-extending the primer annealed to the transcription products with a DNA polymerase under DNA synthesis conditions so as to obtain a linear first-strand cDNA that is complementary to the transcription products to which the primer was annealed;

e. optionally, removing the transcription products that are annealed to the linear first-strand cDNA;

f. obtaining a promoter splice template, wherein the promoter splice template comprises a 3'-end that is sufficiently homologous to the 3'-end of the linear first-strand cDNA to hybridize therewith, and a 5'-portion that comprises a sequence that is complementary to a transcription promoter for an RNA polymerase that can synthesize RNA using a ssDNA transcription substrate;

g. annealing the promoter splice template to the linear first-strand cDNA;

h. primer-extending the first-strand cDNA with a DNA polymerase under DNA polymerization conditions so as to obtain a promoter-containing first-strand cDNA that has a 3'-portion that is complementary to the portion of the promoter splice template oligo that is not hybridizable to the first-strand cDNA including the tail, if present;

i. removing or dissociating the promoter splice template oligo from the promoter-containing first-strand cDNA, the promoter-containing first-strand cDNA comprising a ssDNA transcription substrate;

j. obtaining the ssDNA transcription substrate;

k. contacting the ssDNA transcription substrate from step j with an RNA polymerase that transcribes the ssDNA transcription substrate using the promoter under transcription conditions so as to obtain additional transcription products; and l. obtaining the additional transcription products; and m. optionally, repeating steps a through m to obtain additional rounds of transcription to obtain transcription products.

Another embodiment of the invention comprises a method for obtaining a ssDNA transcription substrate of the invention for making a transcription product corresponding to a target nucleic acid sequence; wherein the ssDNA transcription substrate comprises a promoter-containing second-strand cDNA and wherein the promoter-containing second-strand cDNA comprises (i) a transcription promoter for an RNA polymerase that synthesizes RNA from a ssDNA promoter-containing template under transcription conditions and (ii) a target nucleic acid sequence, at least a portion of which target sequence either comprises or is complementary to at least a portion of a nucleic acid sequence in a target nucleic acid present in a sample, and wherein the transcription promoter is 3'-of the target sequence in the ssDNA transcription substrate; the method comprising:

(a) annealing to a single-stranded target nucleic acid (i) a primer, the primer being complementary to the 3'-end of the single-stranded target nucleic acid sequence, and, optionally, (ii) a blocking oligo that anneals to the target nucleic acid at a sequence that delimits the 5'-end of the target sequence in the target nucleic acid; and (b) extending the primer by reverse transcription or primer extension with a DNA polymerase so as to obtain a first-strand cDNA that is complementary to the target nucleic acid sequence; and (c) optionally, tailing the first-strand cDNA by adding one or more tail sequences to the 3'-end of the first-strand cDNA obtained by reverse transcription or primer extension using the primer; and (d) annealing to the 3'-end of the first-strand cDNA a promoter splice template oligo, wherein the promoter splice template oligo comprises: (i) a 3'-portion that is hybridizable to the 3'-end of the first-strand cDNA including the tail, if present, and (ii) a 5'-portion comprising a sequence that encodes a transcription promoter for an RNA polymerase that can synthesize RNA using a ssDNA transcription substrate; and (e) extending the first-strand cDNA including the tail, if present, by reverse transcription or primer extension with a DNA polymerase so as to obtain an anti-sense-promoter-containing first-strand cDNA that has a 3'-portion that is complementary to the portion of the promoter splice template oligo that is not hybridizable to the target nucleic acid sequence including the tail, if present; and (f) removing or dissociating the target nucleic acid from the anti-sense-promoter-containing first-strand cDNA; and (g) circularizing the promoter-containing first-strand cDNA with a ligase under ligation reaction conditions; and (h) annealing to the circular anti-sense-promoter-containing first-strand cDNA a strand-displacement primer, wherein the strand-displacement primer is complementary to a sequence on the anti-sense-promoter-containing first-strand cDNA; and (i) incubating the circular anti-sense-promoter-containing first-strand cDNA to which the strand-displacement primer is annealed with a strand-displacing DNA polymerase under strand-displacing DNA polymerization conditions so as to obtain linear promoter-containing second-strand cDNA, wherein the linear promoter-containing second-strand cDNA comprises a ssDNA transcription substrate; and (j) obtaining the ssDNA transcription substrate.

Those embodiments of the invention in which a promoter splice template is used to generate a ssDNA transcription substrate comprising promoter-containing second-strand cDNA will be better understood by reading of the invention specification pertaining to DNA polymerases, particularly, pertaining to strand-displacing DNA polymerases and rolling circle replication. Circularization of anti-sense-promoter-containing first-strand cDNA permits generation of a linear ssDNA comprising sense-promoter-containing second-strand cDNA and positions the transcription promoter 3'-of the target sequence, thereby permitting transcription of target sequence using an RNA polymerase of the present invention. Transcription of a ssDNA transcription substrate comprising second-strand cDNA by an RNA polymerase of the invention results in synthesis of anti-sense RNA with respect to the target nucleic acid sequence, whereas transcription of a ssDNA transcription substrate comprising first-strand cDNA by an RNA polymerase of the invention results in synthesis of sense RNA with respect to the target nucleic In still another embodiment of the invention, a splice template oligo is used to add a sense promoter sequence for a T7-type RNAP to the 3'-end of a first-strand cDNA primer extension product comprising a target sequence. This embodiment is similar in most respects to embodiments for using a promoter splice template oligo to add a single-stranded sense promoter for an N4 mini-vRNAP to the 3'-end of a first-strand cDNA comprising a target sequence. However, since T7-type RNAPs, including, without limitation, T7, T3 and SP6 RNAP, generally use double-stranded promoter sequences for transcription, in this embodiment an operable promoter comprises both a sense promoter sequence and an anti-sense promoter sequence, which sequences are annealed to form a complex. As defined herein, a "sense promoter sequence" for a double-stranded promoter means the promoter sequence of an operable double-stranded promoter that is joined to the 3'-end of the template strand that is transcribed, and an "anti-sense promoter sequence" is a sequence that is complementary to the sense promoter sequence. Promoter sequences for many RNA polymerases are well known in the art and suitable sense and anti-sense promoter sequences can be identified. By way of example, but not of limitation, suitable sense and anti-sense promoter sequences for T7 RNAP can be found in writings by J F Milligan et al. (Nucleic Acids Res., 15: 8783-8798, 1987) and by F W Studier et al. (In: Methods in Enzymology, Vol. 185, pp. 60-89, 1990, edited by D V Goeddel, Academic Press, Inc., San Diego, Calif.), both incorporated herein by reference.

Thus, this embodiment of the invention comprises a method for obtaining a substrate for transcription by a T7-type RNAP that uses a double-stranded promoter, the method comprising: (a) obtaining a single-stranded target nucleic acid comprising a target sequence; (b) obtaining a primer that anneals to the 3'-end of the target sequence; (c) annealing the primer to the target sequence under annealing conditions; (d) synthesizing first-strand cDNA by primer extension of the primer annealed to the 3'-end of the target sequence using a DNA polymerase or reverse transcriptase under polymerization conditions; (e) optionally, tailing the first-strand cDNA; (f) obtaining a splice template oligo, the splice template oligo comprising an anti-sense sequence of a double-stranded promoter and wherein the 3'-end portion of the splice template oligo anneals to the 3'-end of the first-strand cDNA including the tail sequence, if present; (g) annealing the splice template oligo first-strand cDNA; (h) primer extending the 3'-end of the first-strand cDNA using the annealed splice template oligo as a template using a DNA polymerase or reverse transcriptase under polymerization conditions; (i) obtaining a ssDNA "pro-transcription substrate," the pro-transcription substrate comprising the primer-extended first-strand cDNA having at its 3'-end a sense strand promoter sequence; (j) annealing to the pro-transcription substrate an anti-sense promoter oligo, the anti-sense promoter oligo comprising an the anti-sense promoter sequence that is complementary to the sense strand promoter sequence of the pro-transcription substrate; (k) obtaining a "transcription substrate complex," the transcription substrate complex comprising the complex between the pro-transcription substrate and the anti-sense promoter oligo. The transcription substrate complex can be used to make a transcription product using a T7-type RNAP that binds to the double-stranded promoter in the transcription substrate complex and that uses the single-stranded template attached thereto as a template for transcription under transcription conditions. In another embodiment, the ssDNA pro-transcription substrate is circularized using a ligase under ligation conditions prior to annealing an anti-sense promoter oligo, thereby obtaining a "circular transcription substrate complex." Transcription of a circular transcription substrate complex using a T7-type RNAP under transcription conditions comprises "rolling circle transcription," which, unless a transcription termination sequence is present in the circular transcription substrate, makes concatameric transcription products. The methods of the present invention differ from the methods disclosed in PCT Patent Application No. WO 02/065093 which synthesize double-stranded templates for use as transcription substrates.

b. Composition of Promoter Splice Template Oligos and Splice Template Oligos

In most embodiments of the present invention, a splice template oligo or a promoter splice template oligo comprises DNA nucleotides, but a promoter splice template oligo or a splice template oligo can comprise DNA and/or RNA nucleotides and/or modified DNA and/or RNA nucleotides. In some embodiments, a promoter splice template oligo or a splice template oligo can comprise modified RNA having 2'-F-dCMP and 2'-F-dUMP nucleotides in place of CMP and UMP (e.g., made using Epicentre's DuraScribe™ T7 Transcription Kit or N4 mini-vRNAP Y678F enzyme, as described elsewhere herein). The presence of 2'-fluoro-pyrimidines in the oligo makes it resistant to RNaseA-type ribonucleases. As discussed above, since no synthesis of a second cDNA strand is needed or performed to prepare transcription substrates for the RNA polymerases of the invention, the 3'-terminal nucleotide of the promoter splice template oligo or a splice template oligo is preferably a terminator nucleotide such as, but not limited to, a dideoxynucleotide. In some embodiments, 3 or 4 of the internucleotide linkages at the 5'-end of a promoter splice template oligo or a splice template oligo can comprise phosphorothioate linkages or other modified linkages, as discussed elsewhere herein, in order to protect the oligos from degradation by some exonucleases that can be present in a sample (e.g., Nikiforov et al., *PCR Methods and Applications* 3:285-291, 1994, incorporated herein by reference).

In some embodiments, such as in those embodiments in which the ssDNA transcription substrate comprises a second-strand cDNA that is generated by strand displacement during rolling circle replication using anti-sense-promoter-containing first-strand cDNA as a template, a promoter splice template oligo can also comprise a sequence that encodes a primer-binding site for a strand-displacement primer, which primer-binding site is generally 5'-of the sense promoter sequence in the promoter splice template oligo, thus resulting in a primer binding site 3'-of the anti-sense transcription promoter sequence in anti-sense-promoter-containing first-strand cDNA. However, a sequence in the splice template oligo that encodes a primer-binding-site is not required. Alternatively, one or more rolling circle strand displacement primers that prime at one or more other sites on the anti-sense-promoter-containing first-strand cDNA rolling circle replication template can be used. In some embodiments, a sequence that encodes a primer-binding site in the promoter splice template oligo is not desirable because this sequence will be replicated in the rolling circle replication product in addition to the anti-sense sequence of the target nucleic acid sequence.

In general, a splice template oligo that does not comprise a sense or anti-sense promoter sequence is used in conjunction with alternative methods or processes for incorporating a transcription promoter into a ssDNA transcription template, as discussed elsewhere herein. By way of example, but not of limitation, a splice template oligo that does not comprise a sense or anti-sense promoter sequence can be used to add a sequence for a primer-binding site or to add other sequences or genetic elements for other applications in conjunction with use of a promoter primer to incorporate a transcription promoter into a ssDNA transcription template.

3. Obtaining ssDNA Transcription Substrates by Ligation of a Promoter Ligation Oligo to a Target Sequence a. Definitions and Methods for Using Promoter Ligation Oligos A "promoter ligation oligo" is a ssDNA comprising all or substantially all of a sequence for a single-stranded transcription promoter of the invention that is joined to a ssDNA polynucleotide comprising a target sequence in order to make a transcription substrate of the invention. A promoter ligation oligo comprising a sense transcription promoter can be phosphorylated at its 5'-end or it can be phosphorylated during the processes of the methods of the invention using a polynucleotide kinase (PNK), such as, but not limited to T4 PNK, and ATP under suitable reaction conditions. In other embodiments, the promoter ligation oligo can have a bound topoisomerase moiety, or it can be ligated using a topoisomerase during the processes of the methods of the invention.

In some embodiments, the 5'-phosphorylated promoter ligation oligo comprising a sense promoter is ligated to the 3'-hydroxyl end of a ssDNA polynucleotide comprising a target sequence. In other embodiments, the 3'-hydroxyl end of a promoter ligation oligo comprising a sense promoter sequence is ligated to the 5'-end of a ssDNA polynucleotide comprising a target sequence, and then the 5'-end of the promoter ligation oligo is phosphorylated and ligated to the 3'-hydroxyl end of the target sequence to make a circular ssDNA transcription substrate. In still other embodiments, a DNA oligo that encodes all or substantially all a sequence that is complementary to a transcription promoter (i.e., it comprises an anti-sense promoter) is ligated to either the 3'-end or the 5'-end of a target sequence, with the nucleic acid having a 5'-end that is ligated being phosphorylated. In some embodiments in which a promoter ligation oligo comprising an anti-sense promoter is used, the molecule to which the promoter ligation oligo is ligated to make a circular ssDNA template for rolling circle replication, which in turn, makes a single-stranded second-strand DNA that comprises a ssDNA transcription substrate for an RNA polymerase of the invention. In still other embodiments, a linear ssDNA comprising an anti-sense promoter 3'-of the target sequence can be used to make a linear ssDNA transcription substrate by strand displacement amplification.

A "ligation splint" or a "ligation splint oligo" is an oligo that is used to provide an annealing site or a "ligation template" for joining two ends of one nucleic acid (i.e., "intramolecular joining") or two ends of two nucleic acids (i.e., "intermolecular joining") using a ligase or another enzyme with ligase activity. The ligation splint holds the ends adjacent to each other and "creates a ligation junction" between the 5'-phosphorylated and a 3'-hydroxylated ends that are to be ligated. For example, when a ligation splint oligo is used to join a sense promoter ligation oligo to the 3'-end of a first-strand cDNA comprising a target sequence, the ligation splint oligo has a sequence complementary to the 3'-end of the target sequence, including a "tailed" target sequence, if any, and a second adjacent sequence that is complementary to the 5'-end of a the 5'-phosphorylated promoter ligation oligo. Ligases that can be used to ligate suitable ends that are annealed to a ligation splint comprising DNA include, but are not limited to, Ampligase® DNA Ligase (EPICENTRE Technologies, Madison, Wis.), Tth DNA ligase, Tfl DNA ligase, Tsc DNA ligase (Prokaria, Ltd., Reykjavik, Iceland), or T4 DNA ligase. These ligases can be used for both intermolecular and intramolecular ligations when a ligation splint comprising DNA is used to bring the respect ends adjacent. If a ligation splint comprising RNA is used, T4 DNA ligase can be used to join the ends that are annealed to the ligation splint. In some embodiments, a ligase that catalyzes non-homologous intramolecular ligation of a 5'-phosphorylated end with a 3'-hydroxyl end can be used in methods of the invention for circularization of single-stranded DNA without a ligation splint. By way of example, but not of limitation, a ligation splint is not required for ligation of a ssDNA using ThermoPhage™ RNA Ligase II (Prokaria, Ltd., Reykjavik, Iceland).

Some embodiments of the invention comprise methods that use a promoter ligation oligo for obtaining a ssDNA transcription substrate for making a transcription product corresponding to a target nucleic acid sequence, wherein the ssDNA transcription substrate comprises a promoter-containing first-strand cDNA and wherein the promoter-containing first-strand cDNA comprises a transcription promoter for an RNA polymerase that synthesizes RNA from a ssDNA promoter-containing template under transcription conditions and a target nucleic acid sequence, at least a portion of which target sequence either comprises, or, is complementary to, at least a portion of a nucleic acid sequence in a target nucleic acid present in a sample, and wherein the transcription promoter is 3'-of the target sequence in the ssDNA transcription substrate.

With respect to embodiments that use a promoter ligation oligo, one embodiment of the invention comprises a method for obtaining a ssDNA transcription substrate of the invention for making a transcription product corresponding to a target sequence in a target nucleic acid comprising single-stranded DNA or RNA, the method comprising:

a. obtaining a primer for synthesis of a first-strand cDNA, the primer comprising a sequence that is complementary to the 3'-end of the target sequence that is to be transcribed;

b. optionally, obtaining a blocking oligo, the blocking oligo comprising a sequence that anneals tightly to a sequence on the target nucleic acid so as to delimit the 3'-end of a primer extension product of the primer using the target nucleic acid as a template, wherein the blocking oligo is not displaced by the primer extension product, and wherein the blocking oligo is not itself capable of being primer-extended by a DNA polymerase;

c. annealing the primer and the blocking oligo, if used, to the target nucleic acid;

d. primer-extending the primer annealed to the target nucleic acid with a DNA polymerase under DNA synthesis conditions so as to obtain a linear first-strand cDNA that is complementary to the target sequence to which the primer is annealed;

e. optionally, removing the target nucleic acid that is annealed to the linear first-strand cDNA;

f. optionally, adding one or more tail sequences to the 3'-end of the first-strand cDNA obtained by primer extension of the primer;

g. obtaining a promoter ligation oligo, wherein the promoter ligation oligo comprises a_sense transcription promoter for an RNA polymerase that synthesizes RNA from a ssDNA promoter-containing template under transcription conditions, wherein the promoter ligation oligo is either phosphorylated at its 5'-terminus, or is subsequently phosphorylated using a polynucleotide kinase and ATP;

h. obtaining a ligation splint oligo, wherein the ligation splint oligo has a sequence that is complementary to the 5'-end of the promoter ligation oligo and the 3'-end of the first-strand cDNA, wherein the 5'-end of the promoter ligation oligo is adjacent to the 3'-end of the first-strand cDNA when annealed to the ligation splint oligo;

i. incubating under annealing conditions: (i) the first-strand cDNA; (ii) the promoter ligation oligo; and (iii) the ligation splint oligo;

j. ligating using a ligase or a topoisomerase under ligation conditions, the 5'-end of the promoter ligation oligo to the 3'-end of the first-strand cDNA, which ends are annealed to the ligation splint oligo, so as to obtain a promoter-containing first-strand cDNA, the promoter-containing first-strand cDNA comprising a ssDNA transcription substrate;

k. optionally, removing or dissociating the ligation splint oligo; and l. obtaining the ssDNA transcription substrate.

For methods of the invention that use a promoter ligation oligo, a target nucleic acid can be DNA or RNA. By way of example, but not of limitation, a target sequence can comprise a target nucleic acid comprising a single species of mRNA or it can comprise all of the mRNA in a sample. If the target nucleic acid comprises mRNA, an initial step of the method is reverse transcription of mRNA to obtain a target sequence comprising first-strand cDNA. In these embodiments, the transcription promoter is added to the 3'-end of a target sequence comprising first-strand cDNA by ligation using a ligase under ligation conditions. By way of example, but not of limitation, a ssDNA transcription substrate of the invention can be prepared by ligating a sense-strand promoter ligation oligo, which has been phosphorylated at its 5'-end using T4 polynucleotide kinase or another suitable polynucleotide kinase and ATP under suitable reaction conditions, to the 3'-end of a target sequence comprising first-strand cDNA that has additional nucleotides which have been added (e.g., see U.S. Pat. No.5,962,272 and Schmidt and Mueller, *Nucleic Acids Res.* 27:e31 [i-iv], 1999, both incorporated herein by reference). The tail at the 3'-end of the first-strand cDNA is not required, but in those embodiments in which it is used, a tail provides a region of homology for a ligation splint oligo. In some embodiments of this aspect of the invention, a ligation splint oligo, which has a 5'-portion that is complementary to the 5'-end of a phosphorylated sense-strand promoter oligo and a second 3'-portion that is complementary to the 3'-end of a target sequence, such as, but not limited to, “tailed” target sequence, is used to provide an annealing site that will keep the two ends adjacent to one another for ligation. In most embodiments of this method, the promoter ligation oligo comprises ssDNA or modified ssDNA, wherein the modified nucleotides, if present, do not affect the ability of the transcription promoter to function fully as a promoter for in vitro transcription. In some embodiments, the 3'-terminal nucleotide of a ligation splint is a dideoxynucleotide or another termination nucleotide, so that the ligation splint cannot serve as a primer for polymerases in the reaction.

Figure 20:
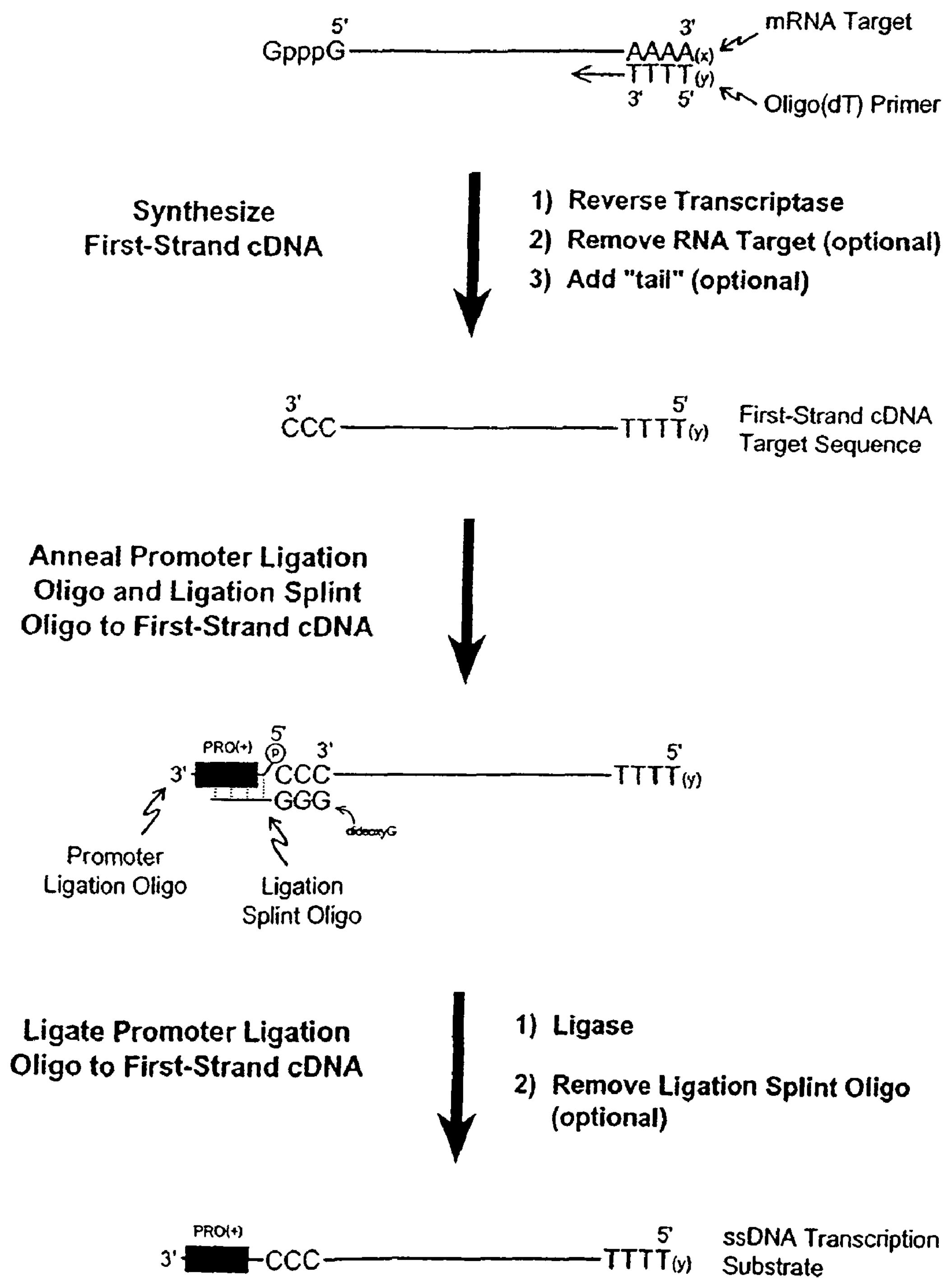
FIG. 20—Schematic of an embodiment of the invention for obtaining a ssDNA transcription substrate using a promoter ligation oligo.

Thus, one embodiment of the invention for using a promoter ligation oligo is a method for making a transcription product corresponding to a target sequence comprising a target nucleic acid comprising mRNA (FIG. 20), the method comprising a. obtaining a target nucleic acid comprising mRNA;

b. obtaining a primer for synthesis of a first-strand cDNA that is complementary to the mRNA, the primer chosen from among: (i) an oligo(dT) primer, and (ii) an oligo(dT) anchor primer; (iii) a primer that is complementary to a specific sequence at the 3'-end of an mRNA, and (iv) a primer in a mixture of primers, the primer comprising a sequence of nucleotides, each of which nucleotides comprises a random nucleotide base that is complementary to any of the four canonical nucleotide bases;

c. annealing the primer to the target mRNA;

d. primer-extending (or reverse transcribing) the primer annealed to the target mRNA with a DNA polymerase (reverse transcriptase) under DNA synthesis (reverse transcription) conditions so as to obtain a linear first-strand cDNA that is complementary to the target mRNA to which the primer was annealed;

e. optionally, adding a tail to the first-strand cDNA using one or more methods;

f. optionally, removing the target mRNA that is annealed to the linear first-strand cDNA;

g. obtaining a promoter ligation oligo, wherein the promoter ligation oligo comprises a_sense transcription promoter for an RNA polymerase that synthesizes RNA from a ssDNA promoter-containing template under transcription conditions, wherein the promoter ligation oligo is either phosphorylated at its 5'-terminus, or is subsequently phosphorylated using a polynucleotide kinase and ATP;

h. obtaining a ligation splint oligo, wherein the ligation splint oligo has a sequence that is complementary to the 5'-end of the promoter ligation oligo and the 3'-end of the first-strand cDNA, wherein the 5'-end of the promoter ligation oligo is adjacent to the 3'-end of the first-strand cDNA when annealed to the ligation splint oligo;

i. incubating under annealing conditions the first-strand cDNA, the promoter ligation oligo, and the ligation splint oligo;

j. ligating using a ligase or a topoisomerase moiety under ligation conditions, the 5'-end of the promoter ligation oligo to the 3'-end of the first-strand cDNA, which ends are annealed to the ligation splint oligo, so as to obtain a promoter-containing first-strand cDNA, the promoter-containing first-strand cDNA comprising a ssDNA transcription substrate;

k. optionally, removing or dissociating the ligation splint oligo;

l. obtaining the ssDNA transcription substrate.

Thus, a general embodiment of the invention comprises a method for using a promoter ligation oligo for making a transcription product corresponding to a target sequence in a target nucleic acid, the method comprising:

a. obtaining a ssDNA transcription substrate by carrying out steps a through l of the method above;

b. contacting the ssDNA transcription substrate with an RNA polymerase that transcribes the ssDNA transcription substrate using the transcription promoter under transcription conditions so as to obtain transcription products; and c. obtaining the transcription products.

The methods described above for obtaining a ssDNA transcription substrate using a promoter ligation oligo and for making a transcription product corresponding to a target sequence can be performed in a stepwise manner, or, under suitable reaction conditions, they can be performed continuously in a single reaction mixture.

Figure 21:
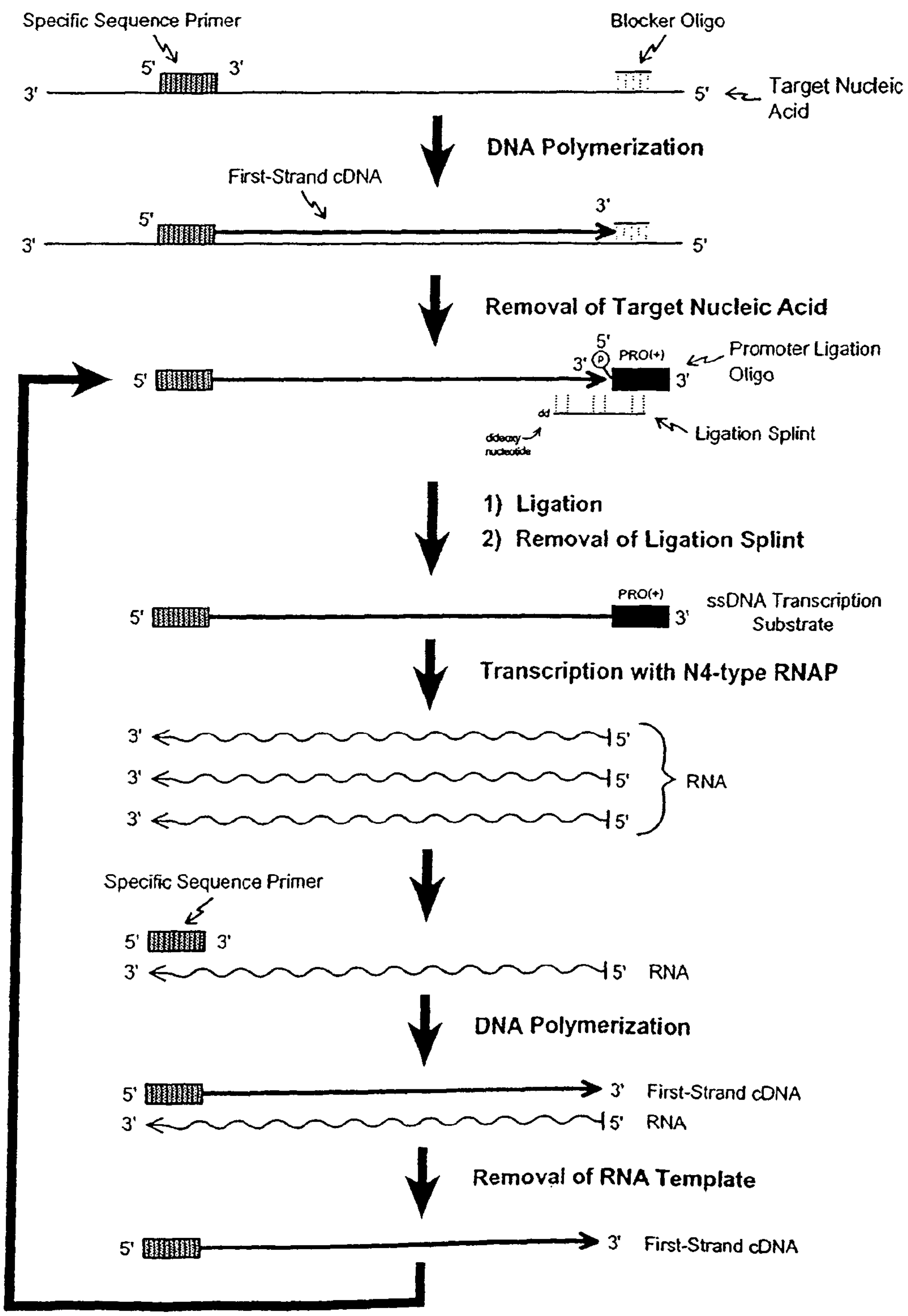
FIG. 21—Schematic of an embodiment of a continuous transcription assay that uses a promoter ligation oligo and a blocker oligo.

Thus, one embodiment of the invention that uses a promoter ligation oligo comprises a method for obtaining additional rounds of transcription of a target sequence in a target nucleic acid (FIG. 21), the method comprising:

a. obtaining the transcription products from step c of the method above;

b. obtaining a primer for synthesis of a first-strand cDNA, the primer comprising a sequence that is complementary to the 3'-end of the transcription products comprising the target sequence that is to be transcribed;

c. annealing the primer to the target nucleic acid;

d. primer-extending the primer annealed to the transcription products with a DNA polymerase under DNA synthesis conditions so as to obtain a linear first-strand cDNA that is complementary to the transcription products to which the primer was annealed;

e. optionally, removing the transcription products that are annealed to the linear first-strand cDNA;

f. optionally, adding one or more tail sequences to the 3'-end of the first-strand cDNA obtained by primer extension of the primer;

g. obtaining a promoter ligation oligo, wherein the promoter ligation oligo comprises a_sense transcription promoter for an RNA polymerase that synthesizes RNA from a ssDNA promoter-containing template under transcription conditions, wherein the promoter ligation oligo is either phosphorylated at its 5'-terminus, or is subsequently phosphorylated using a polynucleotide kinase and ATP;

h. obtaining a ligation splint oligo, wherein the ligation splint oligo has a sequence that is complementary to the 5'-end of the promoter ligation oligo and the 3'-end of the first-strand cDNA, wherein the 5'-end of the promoter ligation oligo is adjacent to the 3'-end of the first-strand cDNA when annealed to the ligation splint oligo;

i. incubating under annealing conditions the first-strand cDNA, the promoter ligation oligo and the ligation splint oligo;

j. ligating using a ligase or a topoisomerase moiety under ligation conditions, the 5'-end of the promoter ligation oligo to the 3'-end of the first-strand cDNA, which ends are annealed to the ligation splint oligo, so as to obtain a promoter-containing first-strand cDNA, the promoter-containing first-strand cDNA comprising a ssDNA transcription substrate;

k. optionally, removing or dissociating the ligation splint oligo;

l. obtaining the ssDNA transcription substrate;

m. contacting the ssDNA transcription substrate from step l with an RNA polymerase that transcribes the ssDNA transcription substrate using the promoter under transcription conditions so as to obtain transcription products; and n. obtaining the additional transcription products; and o. optionally, repeating steps a through o to obtain additional rounds of transcription to obtain transcription products.

In other embodiments for obtaining a ssDNA transcription substrate of the invention, a promoter ligation oligo comprising a sense transcription promoter is ligated to a 5'-phosphorylated end of a target nucleic acid sequence comprising DNA or to a first-strand cDNA prepared by reverse transcription or primer extension of a target sequence in a target nucleic acid. In these embodiments of the invention, the resulting first-strand cDNA having a sense transcription promoter at its 5'-end is then circularized by ligation with a ligase under ligation reaction conditions in order to bring the promoter in proper juxtaposition with the 3'-end of the target sequence for transcription of the target sequence by an RNA polymerase of the invention, thereby obtaining a circular ssDNA transcription substrate of the invention. In this embodiment, the ligation splint oligo comprises a 5'-portion and a 3'-portion, wherein the 5'-portion is complementary to the 5'-end of the DNA or first-strand cDNA target sequence and the 3'-portion is complementary to the 3'-end of the promoter ligation oligo. In yet another embodiment, a circular ssDNA transcription substrate can be linearized 3'-of the transcription promoter using methods discussed elsewhere herein in order to obtain a linear ssDNA transcription substrate of the invention.

In other embodiments of the invention for obtaining a ssDNA transcription substrate, a promoter ligation oligo that comprises an anti-sense transcription promoter is ligated using a ligase under ligation reaction conditions to either the 3'-end or the 5'-end of a ssDNA target sequence or a first-strand cDNA made by primed reverse transcription or primer extension of a target sequence in a target nucleic acid, wherein either the promoter ligation oligo or the first-strand cDNA target sequence, respectively, is 5'-phosphorylated. By way of example, but not of limitation, in one embodiment, a 5'-phosphorylated promoter ligation oligo, which comprises an anti-sense transcription promoter, is ligated in a first ligation reaction using a ligation splint oligo, to the 3'-end of the first-strand cDNA target sequence, generating a linear first-strand cDNA with an anti-sense promoter (i.e., a non-functional complement of a functional promoter). The anti-sense-promoter-containing first-strand cDNA is then phosphorylated at its 5'-end and ligated using a ligase in a second ligation reaction to generate a circular anti-sense-promoter-containing first-strand cDNA molecule. A similar circular DNA molecule can be made following ligation of an anti-sense-promoter ligation oligo to the 5'-end of first-strand cDNA, followed by 5'-phosphorylation, and a second ligation reaction, thereby generating the similar circular first-strand cDNA with an anti-sense transcription promoter. These circular molecules can be used as templates for rolling circle replication using a strand-displacing DNA polymerase of the invention and one or more strand displacement primers that is/are complementary to one or more sequences in the circular molecules. Strand displacement replication of these circular anti-sense-promoter-containing first-strand cDNA molecules using one or more strand displacement primers generates linear second-strand cDNA that is released by strand displacement into the reaction mixture as ssDNA that has a sense (i.e., functional) transcription promoter for an RNA polymerase of the invention. Thus, these linear single-stranded promoter-containing second-strand cDNA molecules comprise ssDNA transcription substrates of the invention. Transcription of these ssDNA transcription substrates by an RNA polymerase of the invention results in synthesis of anti-sense transcription products corresponding to the target sequence. In some embodiments of this method for obtaining a ssDNA transcription substrate of the invention, a ligation splint oligo is used in the second ligation reaction to ligate linear anti-sense-promoter-containing first-strand cDNA to generate circular anti-sense-promoter-containing first-strand cDNA, whereas in other embodiments, the linear single-stranded cDNA is ligated in the second ligation reaction without a ligation splint oligo using a ligase, such as, but not limited to, ThermoPhage™ RNA Ligase II (Prokaria, Reykjavik, Iceland). In still other embodiments ligation splint oligos are used in both the first and second ligation reactions, and both ligation reactions are carried out simultaneously to form circular first-strand cDNA in one step. Primer extension with a second-strand cDNA synthesis primer using the circular first-strand cDNA as a template for a strand displacing DNA polymerase of the invention generates linear ssDNA having tandem repeats of sense transcription promoters and the target sequence, which can be used as a transcription substrate of the invention. In other embodiments, circular first-strand cDNA can be linearized to form a linear first-strand cDNA that can be replicated by strand displacement replication methods in order to generate a linear ssDNA second-strand cDNA transcription substrate of the invention. In some embodiments of this aspect of the method, an anti-sense promoter ligation oligo also has, in addition to an anti-sense transcription promoter, at least one additional sequence that comprises a primer binding site that is complementary to a strand displacement primer in order to provide a priming site outside of the target sequence for making second-strand cDNA. This primer-binding site can be used for primed rolling circle replication of the circular transcription substrate or, following linearization of the circular first-strand cDNA strand displacement template as described elsewhere herein, the primer binding site can be used for strand displacement replication of the linear ssDNA transcription substrate. However, in some embodiments it is not desirable to add another sequence (i.e., the primer-binding site) that is replicated along with the target sequence.

In some embodiments, remaining linear nucleic acids, such as, but not limited to, ligation splint oligos, are removed during the reaction using the gene 6 exonuclease of phage T7. This exonuclease digests DNA starting from the 5'-end of a double-stranded structure. It has been used successfully for the generation of single-stranded DNA after PCR amplification (Holloway et al., *Nucleic Acids Res.* 21:3905-3906, 1993; Nikiforov et al., *PCR Methods and Applications* 3:285-291, 1994, incorporated herein by reference). The gene 6 exonuclease of phage T7 can be added after ligation, together with the rolling circle DNA polymerase to remove unligated oligos. To protect the ssDNA transcription substrate from degradation, a strand displacement primer for rolling circle replication can contain 3 or 4 phosphorothioate linkages at the 5'-end, to make this molecule resistant to the exonuclease (Nikiforov et al., *PCR Methods and Applications* 3:285-291, 1994). The exonuclease degrades unprotected linear molecules as they become associated with the rolling circle DNA product. Based on this description, those with knowledge in the art will understand and know other embodiments of the invention in which this process of the invention for removing single-stranded DNA oligos can be used to advantage, and the invention comprises all such embodiments.

From the above description, those with knowledge in the art will understand other embodiments of methods and processes of the invention for making linear or circular ssDNA transcription substrates, all of which are included herein.

b. Composition of Promoter Ligation Oligos and Ligation Splint Oligos

In most embodiments, a promoter ligation oligo of the invention comprises DNA or modified DNA nucleotides. In addition to the sequence of the transcription promoter, the promoter ligation oligo can also comprise additional nucleic acid sequences that are 3'-of or 5'-of the transcription promoter, which may be included for a particular purpose. By way of example, but not of limitation, a promoter ligation oligo can have an additional sequence that is 3'-of or 5'-of the transcription promoter that serves as a priming site for synthesis of a second-strand cDNA. In some embodiments, the promoter ligation oligo can contain phosphorothioate linkages between the nucleotides at its 5'-end (e.g., between 3 or 4 of the nucleotides) in order to protect it from degradation by some exonucleases. The 5'-terminus of the promoter ligation oligo either has a 5'-phosphoryl group or it is phosphorylated using a polynucleotide kinase, such as, but not limited to, T4 PNK and ATP during the processes of a method of the invention. Promoter ligation oligos can be synthesized on an oligo synthesizer, which is usually preferred, or enzymatically, using methods discussed elsewhere herein.

A "ligation splint" or a "ligation splint oligo" is an oligonucleotide that is used to provide an annealing site or a "ligation template" on which a 5'-phosphorylated end and a 3'-hydroxyl end of one or two different nucleic acids, such as, but not limited to, a promoter ligation oligo and a first-strand cDNA target nucleic acid sequence, can hybridize so as to bring the two ends adjacent to one another in a ligation reaction for joining by a ligase (or a topoisomerase or other enzyme with ligase activity). A ligation splint comprises a sufficient number and composition of nucleotides, and is present in sufficient concentration, so that the complementary sequences of both the 5'- and 3'-ends remain annealed to the ligation splint under ligation conditions so to permit ligation of the ends to occur. Thus, in most embodiments, the ligation splint comprises at least about 4 nucleotides up to about 20 nucleotides, but the invention is not limited to a specific number of nucleotides. An appropriate sequence (and $T_m$) size, and concentration for a ligation splint can be determined empirically by those with knowledge in the art. In most embodiments of the present invention, it is preferable that the 3'-terminal nucleotide of a ligation splint is a dideoxynucleotide or another termination nucleotide, so that the ligation splint oligo cannot serve as a primer for polymerases in the reaction. In most embodiments in which there are multiple rounds of transcription of a target nucleic acid sequence, the other nucleotides in a ligation splint oligo comprise deoxynucleotides. However, in some embodiments, the other nucleotides can comprise ribonucleotides and/or purine ribonucleotides and 2'-fluoro-pyrimidine nucleotides, which confer resistance to RNase A-type nucleases. The composition of a ligation splint oligo will also depend on the ligase and ligation conditions used. By way of example, Ampligase® Thermostable Ligase (Epicentre Technologies, Madison, Wis. USA) will only ligate the 5'-phosphoryl and 3'-hydroxyl ends of DNA that is annealed to a DNA ligation splint and will not ligate DNA ends annealed to RNA. However, T4 RNA ligase has been reported to efficiently ligate DNA ends that are annealed to an RNA ligaton splint (Faruqui et al., U.S. Pat. No. 6,368,801, incorporated herein by reference). Ligation splint oligos can be synthesized on an oligo synthesizer, which is usually preferred, or enzymatically, using methods discussed elsewhere herein.

c. Ligases and Ligation Methods for Attaching a Promoter Ligation Oligo to a Target Sequence The invention is not limited to a specific ligase. However, when a promoter ligation oligo is used, preferably the ligase is not active in ligating blunt ends and is highly selective for ligation of a deoxynucleotide having a 5'-phosphate and a deoxynucleotide having 3'-hydroxyl group when these respective 5'- and 3'-nucleotides are adjacent to each other when annealed to a ligation splint. Ampligase® Thermostable DNA Ligase (Epicentre Technologies, Madison, Wis., USA), Tth DNA ligase, Tfl DNA ligase, and Tsc DNA Ligase (Prokaria Ltd., Reykjavik, Iceland) are NAD-dependent DNA ligases that are not active on blunt ends and that ligate the 5'-phosphate and 3'-hydroxyl termini of DNA ends that are adjacent to one another when annealed to a complementary DNA molecule, and are suitable ligases in embodiments of the invention that use a ligation splint oligo comprising DNA. However, the invention is not limited to the use of a particular ligase and any suitable ligase can be used. For example, T4 DNA ligase can be used in embodiments of the invention that use a ligation splint. Still further, Faruqui discloses in U.S. Pat. No. 6,368,801 that T4 RNA ligase can efficiently ligate DNA ends of nucleic acids that are adjacent to each other when hybridized to an RNA strand. Thus, T4 RNA ligase is a suitable ligase of the invention in embodiments in which DNA ends are ligated on a ligation splint oligo comprising RNA or modified RNA, such as, but not limited to modified RNA that contains 2'-F-dCTP and 2'-F-dUTP made using the DuraScribe™ T7 Transcription Kit (Epicentre Technologies, Madison, Wis. USA) or the N4 mini-vRNAP Y678F mutant enzyme described herein. If a promoter ligation oligo is initially ligated to the 5'-end of a target sequence, the promoter sequence can be operably joined to the 3'-end of the target sequence by first phosphorylating the 5'-end using a polynucleotide kinase, such as, but not limited to, T4 polynucleotide kinase, and then ligating the linear ssDNA to form a circular ssDNA using a ligase that catalyzes non-homologous intramolecular ligation, such as, but not limited ThermoPhage™ RNA Ligase II (Prokaria, Ltd., Reykjavik, Iceland). The invention is also not limited to the use of a ligase for covalently joining the 5'-end to the 3'-end of the same or different nucleic acid molecules in the various embodiments of the invention. By way of example, other ligation methods such as, but not limited to, topoisomerase-mediated ligation (e.g., U.S. Pat. No. 5,766,891, incorporated herein by reference) can be used.

4. Obtaining ssDNA Transcription Substrates Using a Promoter Primer a. Methods for Using Promoter Primers A "promoter primer" is a primer, generally with a free 3'-OH group, that comprises a sequence that is complementary to a target sequence at its 3'-end and which encodes a transcription promoter in its 5'-portion. A promoter primer can have a sequence at its 3'-end that is complementary to a specific known sequence in a target nucleic acid, in which case it is referred to as a "specific-sequence promoter primer." However, other embodiments of promoter primers can also be used in methods of the invention. An "oligo(dT) promoter primer" has an oligo(dT) sequence at its 3'-end, and is used mainly in embodiments of the invention which pertain to mRNA molecules having polyadenylated [i.e., poly(A) tails], although an oligo(dT) promoter primer can also be used in embodiments in which another target nucleic acid is tailed with poly(A) or poly(dA). An "anchored oligo d(T) promoter primer, in addition to having an oligo(dT) sequence in its 3'-portion, also has one (or a small number) of nucleotides 3'-of the oligo(dT) sequence, called "anchor nucleotides," which anneal to the 3'-portion of the mRNA target sequence just prior to the poly(A) sequence. Thus, the anchor nucleotides serve to "anchor" the mRNA-complementary portion of the anchored oligo(dT) promoter primer to the beginning of the protein-coding sequence of the mRNA target sequence. The anchor nucleotides can comprise either a specific base for a specific mRNA or a randomized nucleotide (i.e., synthesized with a mixture of all four nucleotides) for priming all mRNA molecules in a sample. A "random-sequence promoter primer" has a random sequence, such as, but not limited to a random hexamer sequence, at its 3'-end. In most cases, a random-sequence promoter primer comprises a mixture of primers with all possible sequences (e.g., all possible hexamers) in its target sequence-complementary portion. Random-sequence promoter primers can be made by including all four canonical nucleotide reagents during the chemical synthesis of each of the nucleotide positions of the random sequence (e.g., the hexamer sequence) of the target sequence-complementary portion of the primer. A random-sequence promoter primer can be used in those embodiments of the invention in which it is desired to amplify all target nucleic acid sequences in a sample, or to amplify all target nucleic acid sequences in a random manner, such as for making a library of all target nucleic acid sequences. However, although all sequences may be amplified, use of a random-sequence promoter primer does not necessarily generate only full-length copies of target nucleic acids (e.g., full-length cDNA copies of mRNA molecules from a cell). Thus, embodiments of the invention which use random-sequence promoter primers are usually used when full-length copies of a target nucleic acid sequence are not required, such as, for obtaining hybridization probes for some applications.

In embodiments of the invention in which a transcription substrate of the invention comprises first-strand cDNA obtained by reverse transcription or primer extension of a promoter primer using a target nucleic acid as a template, the transcription promoter in the promoter primer comprises a sense promoter sequence that is located in the 5'-portion of the promoter primer. Thus, the transcription promoter in the linear first-strand cDNA obtained by reverse transcriptase- or DNA polymerase-catalyzed extension of the promoter primer using the target nucleic acid as a template is not operable as a promoter for transcription of the target sequence since the promoter is not operably joined to the 3'-end of the target sequence. A method of the present invention solves this problem by operably joining the single-stranded sense transcription promoter in the 5'-portion of the linear first-strand cDNA to the 3'-end of the target sequence using a ligase or another joining means, thus forming a circular ssDNA transcription substrate for an RNA polymerase that can bind the single-stranded promoter and transcribe the target sequence joined thereto.

Figure 22:
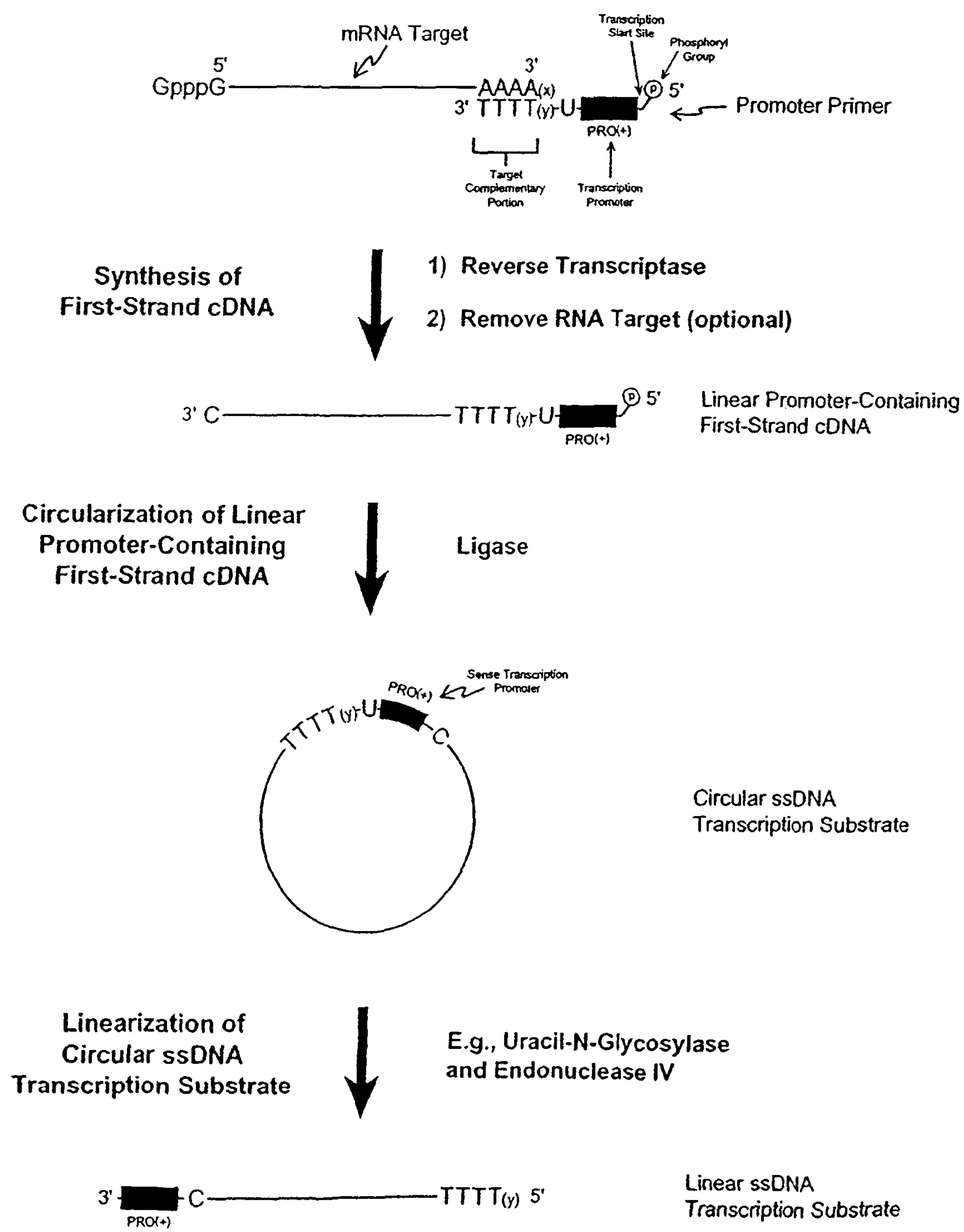
FIG. 22—Embodiments of the invention for obtaining both circular and linear ssDNA transcription substrates using a promoter primer.

Thus, in one embodiment of the invention, a promoter primer having a sequence complementary to a target sequence at its 3'-end and a transcription promoter in its 5'-portion is used to obtain a ssDNA transcription substrate of the invention (FIG. 22). After annealing to a target nucleic acid, the promoter primer is used to prime first-strand cDNA synthesis using a DNA polymerase or reverse transcriptase under suitable reaction conditions in order to obtain linear first-strand cDNA.

The linear promoter-containing first-strand cDNA is then ligated using a ligase under suitable ligation conditions, or using another joining method, such as, but not limited to a topoisomerase (e.g., see U.S. Pat. No. 5,766,891, incorporated herein by reference), under suitable joining conditions, so as to obtain a circular promoter-containing first-strand cDNA. By ligation of the phosphorylated 5'-end of linear first-strand cDNA to its 3'-end, the transcription promoter is joined to the target sequence so that in vitro transcription using an RNA polymerase of the invention under transcription conditions will synthesize transcription products corresponding to the target sequence.

In the example in FIG. 22, the target sequence comprises target nucleic acid comprising all mRNA molecules in a sample and the transcription products that are made by transcription of the transcription substrate comprise RNA that is essentially the same as the sense mRNA. Thus, in this embodiment, the circular first-strand cDNA comprises a ssDNA transcription substrate of the invention, which embodiment is useful for many applications. If there is no sequence in the circular ssDNA transcription substrate that results in termination of transcription, transcription continues around and around the circular ssDNA transcription substrate multiple times and generates concatemers of sense transcription products (i.e., comprising tandem copies of the same nucleic acid sequence as an mRNA target nucleic acid sequence in the sample), which concatemers are useful for certain applications of the invention.

In some embodiments of the invention, one or more transcription termination sequences is/are incorporated into the promoter primer between the target sequence-complementary 3'-region and the transcription promoter 5'-portion in order to permit synthesis of single-copy rather than concatemeric sense transcription products. For example, if a transcription termination sequence is present in the promoter primer, the transcription product can correspond in length to a single copy of an mRNA target nucleic acid sequence following in vitro transcription of the circular ssDNA transcription substrate using an RNA polymerase of the invention. Transcription termination sequences are known in the art and those with knowledge in the art will know how to find information about the sequences, as well as experimental methods for identifying additional termination sequences that can be used. By way of example, but not of limitation, information about transcription termination sequences can be found in a book entitled "RNA Polymerases and the Regulation of Transcription," edited by Reznikoff, W. S., et al., (Elsevier Science Publishing Co., Inc., New York, 1987) and in Section 17 of a book by Miller, J. H. entitled "A Short Course in Bacterial Genetics. A Laboratory Handbook for *Escherichia coli* and Related Bacteria" (Cold Spring Harbor Laboratory Press, Cold Spring Harbor, N.Y., 1992), both incorporated herein by reference.

In still other embodiments, the circular ssDNA transcription substrate is linearized prior to use for in vitro transcription in order to form a "linear ssDNA transcription substrate." By way of example, but not of limitation, the circular transcription substrate can be linearized by treatment with uracil-N-gycosylase ("UNG") and endonuclease IV ("endo IV") (e.g., see methods in U.S. Pat. No. 6,048,696, which is incorporated herein by reference) if the promoter primer is synthesized to have a dUMP nucleotide between the target sequence-complementary 3'-region and the transcription promoter in its 5'-portion. However, the use of a promoter primer comprising a dUMP nucleotide can only be used in embodiments of the invention which are performed in a stepwise manner, because the presence of UNG in a continuous reaction would cleave the transcription promoter portion of a promoter primer from the target-complementary portion of the promoter primer, thus destroying the ability of the promoter primer to generate more ssDNA transcription substrates. There are a number of other methods known in the art for linearizing a circular DNA molecule, which can be used in embodiments of the invention, and those with knowledge in the art will know or know how to find suitable methods for use in the invention. By way of example, but not of limitation, a number of such methods which can be used are described herein in the section entitled "Methods for Defining the 5'- and 3'-Ends of Target Sequences That Comprise Only a Portion of a Larger RNA or DNA Target Nucleic Acid."

Other embodiments of the invention comprise use of a promoter primer for synthesis of a second-strand cDNA as a transcription substrate of the invention. In those embodiments, a transcription promoter can be incorporated into the second-strand cDNA by, either (a) synthesizing first-strand cDNA using a promoter primer that has a sequence in its 5'-portion comprising a sequence that is complementary to a sense transcription promoter (i.e., it comprises an anti-sense promoter primer) or, (b) using a promoter primer comprising a sense transcription promoter for synthesis of second-strand cDNA. The promoter sequence used in a promoter primer can be determined based on knowledge of sequences of sense promoters for RNA polymerases of the invention and of the rules of nucleic acid base complementarity and the directionality of DNA and RNA synthesis by DNA and RNA polymerases. By way of example, if a sense transcription promoter is desired in a second-strand cDNA that is made by primer extension of first-strand cDNA, which is in turn made by reverse transcription of mRNA, one can work backwards from having a sense transcription promoter of known sequence in a transcription substrate at the 3'-end of a target nucleic acid sequence that is to be amplified by an RNA polymerase of the invention, in order to determine the appropriate sense or anti-sense sequence (and position of the sequence with respect to the target sequence) that is needed, respectively, for promoter primers that are used for first-strand cDNA synthesis, or for second-strand cDNA synthesis.

In some embodiments of the invention, more than one promoter can be present on the promoter primer. By way of example, but not of limitation, a promoter primer can encode two promoter sequences, both of which encode sense promoters on first-strand cDNA (e.g., for two different RNA polymerases of the invention). Alternatively, a first promoter sequence of the promoter primer and the resulting first-strand cDNA can comprise a sense promoter and a second promoter sequence can comprise an anti-sense promoter, in which case, the first promoter sequence will be anti-sense and the second promoter sequence will be sense in second-strand cDNA. In embodiments that include additional rounds of transcription by using RNA from the first round to obtain a second transcription substrate for transcription, it is necessary to take into account the fate of the promoter sequences through the subsequent rounds of transcription when designing the reaction.

In addition to the transcription promoter sequence and the target-complementary sequence, a promoter primer of the invention can also have additional nucleic acid sequences that are 5'-of and/or 3'-of the transcription promoter sequence, but a promoter primer is not required to have such additional other sequences. By way of example, but not of limitation, a promoter primer can have a transcription initiation site 5'-of the promoter sequence. In some embodiments of the invention, a promoter primer can have one or more transcription termination sequences, one or more sites for DNA cleavage, (such as, but not limited to, a dUMP residue that can be cleaved using uracil-N-glycosylase and endonuclease IV, or other cleavage methods discussed elsewhere herein) to permit controlled linearization of a circular first-strand cDNA that is a transcription substrate, one or more origins ("ori's") of replication (preferably an ori for a single-stranded replicon, such as, but not limited to, a phage M13 replicon), a selectable or screenable marker, such as, but not limited to an antibiotic-resistance gene or a beta-galactosidase gene, respectively, or one or more transposon recognition sequences (e.g., OE or ME sequences) that can be recognized and used by a transposase for in vitro or in vivo transposition, or one or more sites that are recognized by a recombinase (such as, but not limited to, the cre-lox system), and/or other sequences or genetic elements for a particular purpose. After reading the specification of the present invention, those with knowledge in the art will know that a sequence that is 5'-of a functional promoter will be transcribed by an RNA polymerase of the invention, and will therefore know where to position particular additional sequences or genetic elements relative to the promoter sequence in a promoter primer. In some embodiments of the invention, a promoter primer has a 5'-phosphate or is phosphorylated at its 5'-end using an enzyme, such as, but not limited to, a polynucleotide kinase (e.g., T4 PNK), during the processes of a method of the invention. A primary reason for providing a 5'-phosphate group on a promoter primer is to permit ligation of linear first-strand cDNA following reverse transcription or primer extension of a promoter primer on a target sequence in order to make a ssDNA transcription substrate comprising circular first-strand cDNA.

A number of examples of embodiments that use promoter primers of the invention are described below. The invention comprises all methods for using a promoter primer wherein the transcription promoter can be used by an RNA polymerase that can synthesize RNA using a ssDNA transcription substrate and is not limited to only the example embodiments presented.

With respect to methods that use a promoter primer, one embodiment of the invention comprises a method for obtaining a circular ssDNA transcription substrate of the invention for making a transcription product corresponding to a target sequence in a target nucleic acid, the method comprising:

a. obtaining a single-stranded promoter primer for synthesis of a first-strand cDNA, the promoter primer comprising a sequence at its 3'-end that is complementary to the 3'-end of the target sequence that is to be transcribed, and a 5'-portion comprising a single-stranded sense transcription promoter, wherein the promoter functions to direct transcription by an RNA polymerase that can use a ssDNA transcription substrate for synthesis of RNA or modified RNA that is complementary to the target sequence, and optionally, a phosphate group or a topoisomerase moiety on its 5'-end;

b. annealing the promoter primer to the target nucleic acid;

c. primer-extending or the promoter primer annealed to the target nucleic acid with a DNA polymerase under DNA synthesis conditions so as to obtain a linear first-strand cDNA that is complementary to the target sequence or sequences to which the promoter primer was annealed, and wherein, the linear first-strand cDNA comprises the transcription promoter at a position which is 5'-of the target sequence in the first-strand cDNA which is complementary to the target sequence;

d. optionally, removing the target nucleic acid that is annealed to the linear first-strand cDNA;

e. ligating the linear first-strand cDNA, wherein the 5'-end of the linear first-strand cDNA is covalently attached to the 3'-end of the linear first-strand cDNA so as to obtain circular first-strand cDNA, wherein the circular first-strand cDNA comprises a circular ssDNA transcription substrate; and f. obtaining the circular ssDNA transcription substrate.

Another embodiment of the invention comprises a method for obtaining a linear ssDNA transcription substrate for making a transcription product corresponding to a target sequence in a target nucleic acid, the method comprising:

a. obtaining a circular ssDNA transcription substrate by carrying out steps (a) through (f) of the method above; then b. linearizing the circular ssDNA transcription substrate at a site 3'-of the transcription promoter and 5'-of the cDNA target sequence that is complementary to the target nucleic acid sequence, wherein a linear ssDNA transcription substrate is obtained; and c. obtaining the linear ssDNA transcription substrate.

A general embodiment of the invention comprises a method for making a transcription product corresponding to a target sequence in a target nucleic acid, the method comprising:

a. obtaining a ssDNA transcription substrate, chosen from among a circular ssDNA transcription substrate and a linear ssDNA transcription substrate;

b. contacting the ssDNA transcription substrate with an RNA polymerase that transcribes the ssDNA transcription substrate using the single-stranded transcription promoter under transcription conditions so as to obtain transcription product; and c. obtaining the transcription product.

The target nucleic acid can be DNA or RNA. By way of example, but not of limitation, a target sequence can comprise a target nucleic acid comprising a single species of mRNA or a target sequence can comprise a target nucleic acid, which can comprise all of the mRNA in a sample.

Thus, one embodiment of the invention is a method for using a promoter primer for making a transcription product corresponding to a target sequence comprising a target nucleic acid comprising mRNA (FIG. 22), the method comprising a. obtaining a target nucleic acid comprising mRNA;

b. obtaining a single-stranded promoter primer for synthesis of a first-strand cDNA, the promoter primer comprising: (i) a sequence at its 3'-end that is complementary to the 3'-end of the target sequence that is to be transcribed, wherein the complementary sequence on the promoter primer is chosen from among (a) and oligo(dT) sequence, (b) an anchored oligo(dT) sequence, (c) a sequence that is complementary to a specific sequence at the 3'-end of an mRNA, and (d) a sequence of nucleotides, each of which nucleotides comprises a random nucleotide base that is complementary to any of the four canonical nucleotide bases in RNA; and (ii) a 5'-portion comprising a single-stranded sense transcription promoter, wherein the promoter functions to direct transcription by an RNA polymerase that can use a ssDNA transcription substrate for synthesis of RNA or modified RNA that is complementary to the target sequence; and (iii) optionally, a phosphate group or a topoisomerase moiety on its 5'-end;

c. annealing the promoter primer to the target nucleic acid;

d. primer-extending the promoter primer annealed to the target nucleic acid with a DNA polymerase under DNA synthesis conditions so as to obtain a linear first-strand cDNA that is complementary to the target sequence or sequences to which the promoter primer was annealed, and wherein, the linear first-strand cDNA comprises the transcription promoter at a position which is 5'-of the target sequence in the first-strand cDNA which is complementary to the target sequence;

e. optionally, removing the RNA that is annealed to the linear first-strand cDNA;

f. ligating the linear first-strand cDNA, wherein the 5'-end of the linear first-strand cDNA is covalently attached to the 3'-end of the linear first-strand cDNA so as to obtain circular first-strand cDNA, wherein the circular first-strand cDNA comprises a circular ssDNA transcription substrate;

g. optionally, linearizing the circular ssDNA transcription substrate at a site that is 3'-of the promoter sequence and 5'-of the cDNA target sequence that is complementary to the target sequence, wherein a linear ssDNA transcription substrate is obtained;

h. contacting the circular ssDNA transcription substrate from step f, or the linear ssDNA transcription substrate from step g with an RNA polymerase that transcribes the ssDNA transcription substrate using the promoter under transcription conditions so as to obtain transcription product; and i. obtaining the transcription product.

The methods for obtaining a ssDNA transcription substrate and for making a transcription product corresponding to a target sequence can be performed in a stepwise manner, or, under suitable reaction conditions, they can be performed continuously in a single reaction mixture.

Figure 23:
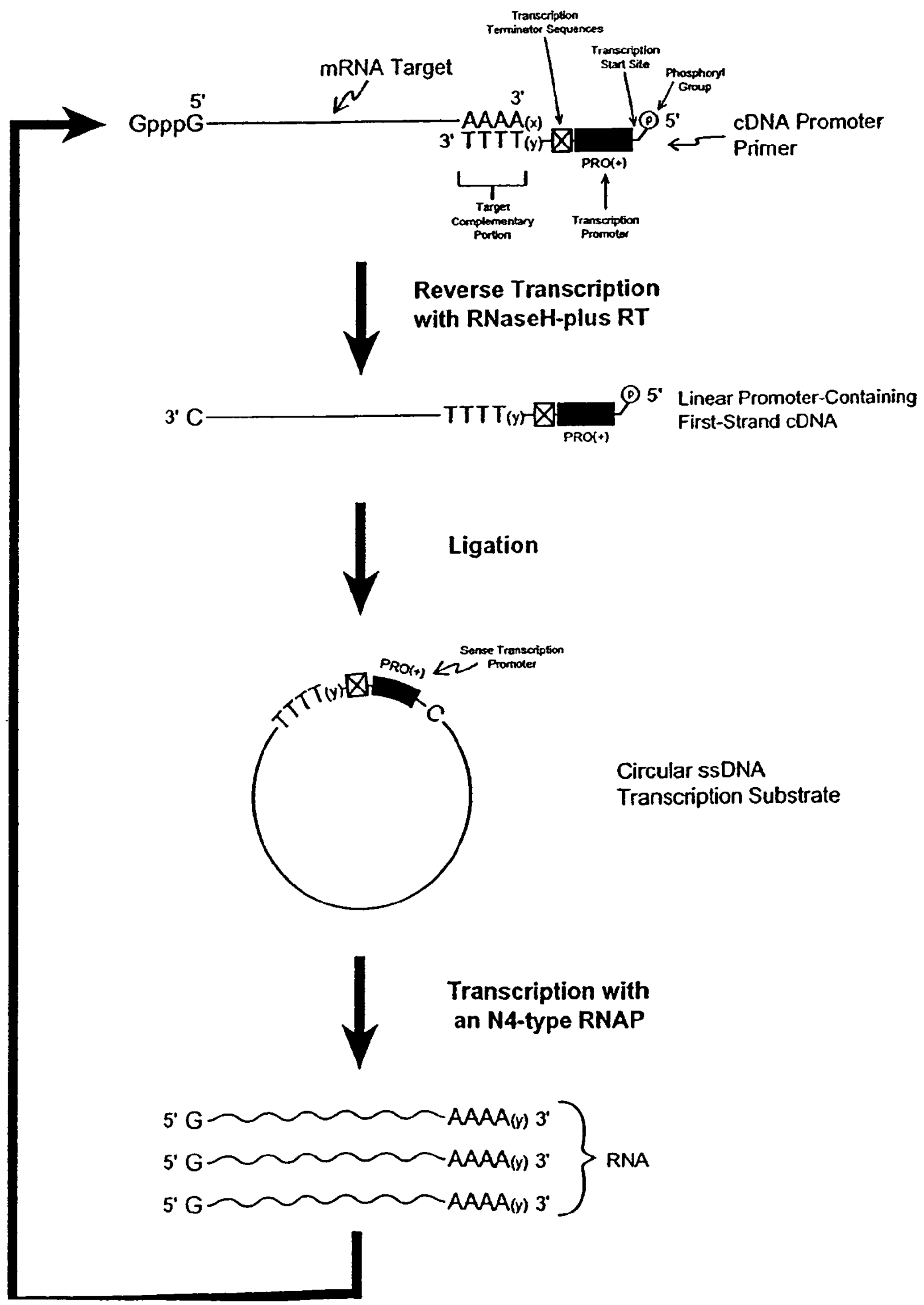
FIG. 23—Schematic of an embodiment of a continuous transcription assay that uses a promoter primer that also comprises transcription termination sequences to generate a circular ssDNA transcription substrate.

Thus, one embodiment of the invention comprises a method for obtaining additional rounds of transcription of a target sequence in a target nucleic acid (FIG. 23), the method comprising:

a. obtaining the transcription products from step c of the methods above (such as for example, a linear ssDNA transcription substrate for making a transcription product corresponding to a target sequence in a target nucleic acid);

b. obtaining a single-stranded promoter primer for synthesis of a first-strand cDNA, the promoter primer comprising: (i) a sequence at its 3'-end that is complementary to the 3'-end of the target sequence that is to be transcribed, and (ii) a 5'-portion comprising a single-stranded sense transcription promoter, wherein the promoter functions to direct transcription by an RNA polymerase that can use a ssDNA transcription substrate for synthesis of RNA or modified RNA that is complementary to the target sequence, and (iii) optionally, a phosphate group or a topoisomerase moiety on its 5-end;

c. annealing the promoter primer to the target nucleic acid;

d. primer-extending the promoter primer annealed to the target nucleic acid with a DNA polymerase under DNA synthesis conditions so as to obtain a linear first-strand cDNA that is complementary to the target sequence or sequences to which the promoter primer was annealed, and wherein, the linear first-strand cDNA comprises the transcription promoter at a position that is 5'-of the target sequence in the first-strand cDNA which is complementary to the target sequence;

e. optionally, removing the RNA that is annealed to the linear first-strand cDNA;

f. ligating the linear first-strand cDNA, wherein the 5'-end of the linear first-strand cDNA is covalently attached to the 3'-end of the linear first-strand cDNA so as to obtain circular first-strand cDNA, wherein the circular first-strand cDNA comprises a circular ssDNA transcription substrate;

g. optionally, linearizing the circular ssDNA transcription substrate at a site that is 3'-of the promoter sequence and 5'-of the cDNA target sequence that is complementary to the target sequence, wherein a linear ssDNA transcription substrate is obtained;

h. contacting the circular ssDNA transcription substrate from step f, or the linear ssDNA transcription substrate from step g with an RNA polymerase that transcribes the ssDNA transcription substrate using the promoter under transcription conditions so as to obtain transcription products; and i. obtaining the additional transcription products.

Different embodiments of methods of the invention can also be used to make a transcription product corresponding to target sequences that are internal to a target nucleic acid sequence. By way of example, some embodiments can be used to make a transcription product corresponding to sequences, such as, but not limited to, wild-type or mutated sequence in genomic DNA. In these embodiments, one or more processes, such as, but not limited to, annealing a blocking oligo to the target nucleic acid, are required to limit the 3'-end of the target sequence that is transcribed, as is discussed elsewhere herein. In general, the target nucleic acid must be single-stranded for use in a method of the invention. Thus, a double-stranded nucleic acid must be denatured.

Thus, one embodiment of the invention for using a promoter primer is a method for making a transcription product corresponding to a target sequence that comprises only a portion of a target nucleic acid comprising single-stranded DNA or RNA, the method comprising a. obtaining a target nucleic acid comprising single-stranded DNA or RNA; then b. obtaining a single-stranded promoter primer for synthesis of a first-strand cDNA, the promoter primer comprising: (i) a sequence at its 3'-end that is complementary to the 3'-end of the target sequence that is to be transcribed, and (ii) a 5'-portion comprising a single-stranded sense transcription promoter, wherein the promoter functions to direct transcription by an RNA polymerase that can use a ssDNA transcription substrate for synthesis of RNA or modified RNA that is complementary to the target sequence, and (iii) optionally, a phosphate group or a topoisomerase moiety on its 5-end;

c. obtaining a blocking oligo, the blocking oligo comprising a sequence that anneals tightly to a sequence on the target nucleic acid so as to delimit the 3'-end of a primer extension product of the promoter primer using the target nucleic acid as a template, wherein the blocking oligo is not displaced by the primer extension product, and wherein the blocking oligo is not itself capable of being primer extended by a DNA polymerase;

d. annealing the promoter primer and the blocking oligo to the target nucleic acid;

e. primer-extending the promoter primer annealed to the target nucleic acid with a DNA polymerase under DNA synthesis conditions so as to obtain a linear first-strand cDNA that is complementary to the target sequence to which the promoter primer was annealed and that is not complementary to the sequence where the blocking oligo is annealed, and wherein, the linear first-strand cDNA comprises the transcription promoter at a position which is 5'-of the target sequence in the first-strand cDNA which is complementary to the target sequence;

f. optionally, removing the target nucleic acid that is annealed to the linear first-strand cDNA;

g. ligating the linear first-strand cDNA, wherein the 5'-end of the linear first-strand cDNA is covalently attached to the 3'-end of the linear first-strand cDNA so as to obtain circular first-strand cDNA, wherein the circular first-strand cDNA comprises a circular transcription substrate;

h. optionally, linearizing the circular ssDNA transcription substrate at a site that is 3'-of the promoter sequence and 5'-of the cDNA target sequence that is complementary to the target sequence, wherein a linear ssDNA transcription substrate is obtained;

i. contacting the circular ssDNA transcription substrate from step g, or the linear ssDNA transcription substrate from step h with an RNA polymerase that transcribes the ssDNA transcription substrate using the promoter under transcription conditions so as to obtain transcription products; and j. obtaining the transcription products; and k. optionally, repeating steps b through k to obtain additional rounds of transcription to obtain transcription products.

In still other embodiments of the invention, which are preferred embodiments, the circular first-strand cDNA does not comprise a transcription substrate of the invention. Rather, in those embodiments, the circular first-strand cDNA is used as a template for DNA synthesis using a strand-displacing DNA polymerase and at least one strand displacement primer, and in some embodiments, multiple strand displacement primers. A "strand displacement primer," as used herein, is an oligonucleotide or polynucleotide that can be primer extended by a strand displacing DNA polymerase of the invention, wherein strand displacement DNA synthesis occurs. In general, strand displacement is more a property of the DNA polymerase and the reaction conditions used than of the primer. Thus, the composition and properties of a strand displacement primer can vary greatly. For example, in some embodiments of the invention, a strand displacement primer can be an oligonucleotide that is hybridizable to a circular DNA template, wherein the DNA synthesis product resulting from rolling circle replication by a strand displacing DNA polymerase results in displacement of the ssDNA strand displacement primer extension product, resulting in tandem complementary ssDNA copies of circular template. In other embodiments, it is preferred that the strand displacement primer has a 3'-portion that is complementary to a sequence in a circular DNA template and a 5'-portion that is non-complementary, and therefore has a "flap;" the protruding flap appears to facilitate displacement of the primer in some cases. When strand displacement is carried out on linear DNA templates, strand displacement primers can be designed to have particular nucleotide compositions and/or structures, and additional methods and reaction components can be used in order to facilitate strand displacement by liberating the strand displacement primer from the template. This is discussed further in the section of the present invention entitled "Methods of the Invention for Strand Displacement Replication on Linear Templates."

A strand-displacing DNA polymerase of the invention can be any DNA polymerase that results in strand displacement. Preferred strand-displacing DNA polymerases of the present invention lack 5'-exonuclease activity, including structure-dependent 5'-nuclease activity. Preferred strand-displacing DNA polymerases comprise rBst DNA polymerase large fragment, also called "IsoTherm™ DNA Polymerase" (Epicentre Technologies, Madison, Wis., USA), Bca DNA Polymerase (TAKARA Shuzo Company, Kyoto, Japan), ϕ29 DNA polymerase (U.S. Pat. Nos. 5,198,543 and 5,001,050, incorporated herein by reference), SequiTherm™ DNA Polymerase (Epicentre Technologies, Madison, Wis., USA), MMLV reverse transcriptase, and Sequenase® DNA Polymerase (USB, Cleveland, Ohio, USA). In these embodiments, a strand displacement primer is used to prime second-strand DNA synthesis using circular first-strand cDNA as a template. Once DNA synthesis has proceeded completely around the circular first-strand cDNA template, the second-strand cDNA is displaced so that the displaced single-stranded second DNA strand is released into the reaction medium. Since a transcription promoter is present at least once in every round of DNA synthesis of the circular first-strand cDNA template, this released single-stranded second-strand DNA can be used as a ssDNA transcription substrate by an RNA polymerase of the invention. However, in this case, the RNA that is synthesized using the single-stranded second-strand DNA as a ssDNA transcription substrate comprises anti-sense RNA, rather than sense RNA as in previous embodiments that used first-strand cDNA as a template. Anti-sense RNA can be used for many applications, such as, but not limited to, for use as probes for nucleic acid arrays. As the second DNA strand continues to grow, longer and longer concatemers of the anti-sense RNA are formed.

With respect to embodiments of the invention that use a promoter primer, some embodiments obtain a ssDNA transcription template for making a transcription product corresponding to a target sequence in a target nucleic acid by first obtaining a circular first-strand cDNA comprising an anti-sense transcription promoter, wherein the circular first-strand cDNA is then used as a template for strand displacement DNA synthesis of the linear ssDNA transcription substrate by a strand-displacing DNA polymerase.

Figure 24:
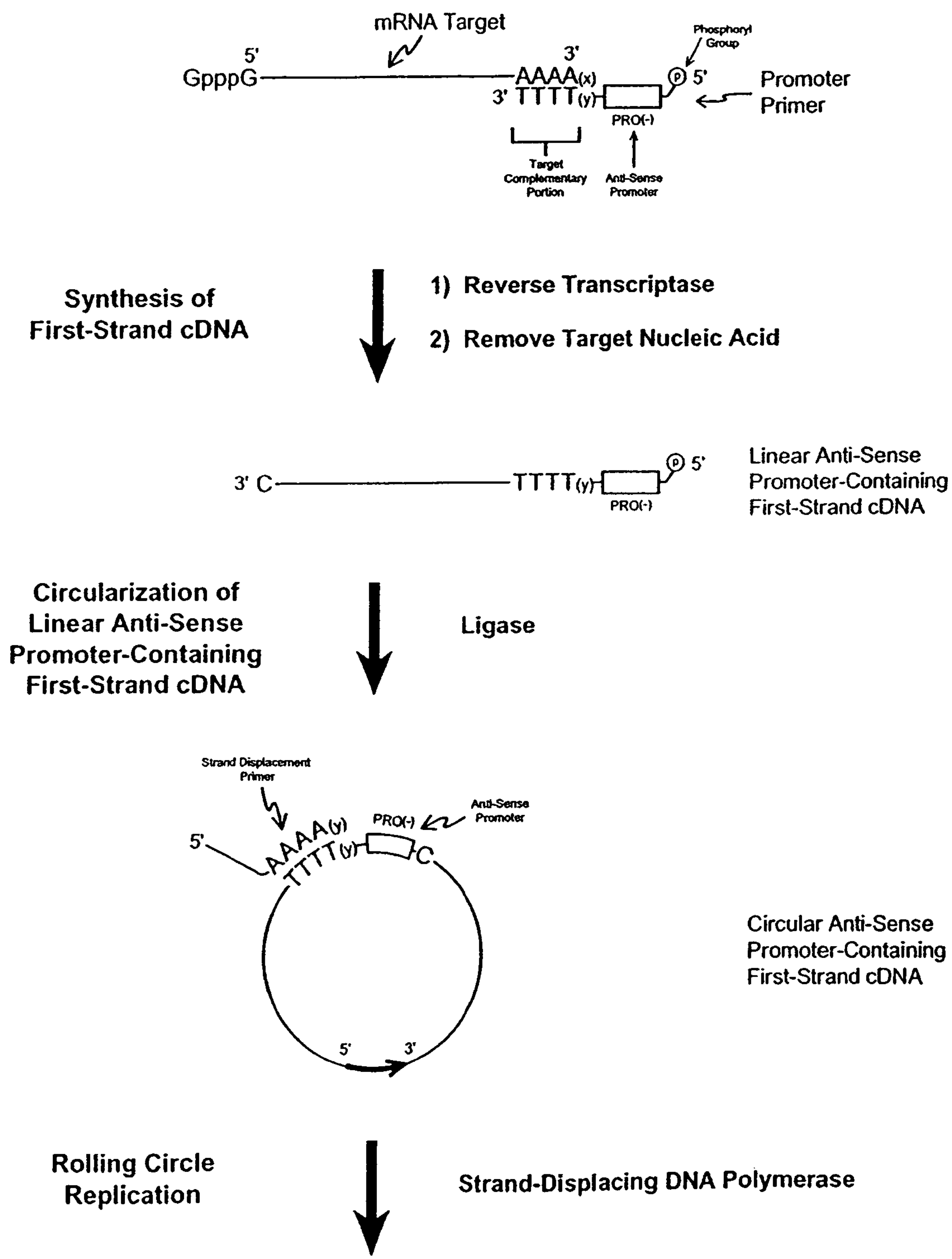
FIG. 24—Embodiment that uses a promoter primer comprising an anti-sense sequence of an N4 vRNAP promoter to make a circular anti-sense-promoter-containing first-strand cDNA that serves as a template for rolling circle replication, thereby synthesizing a linear second-strand ssDNA transcription substrate which can be used to synthesize more RNA.
Figure 24:
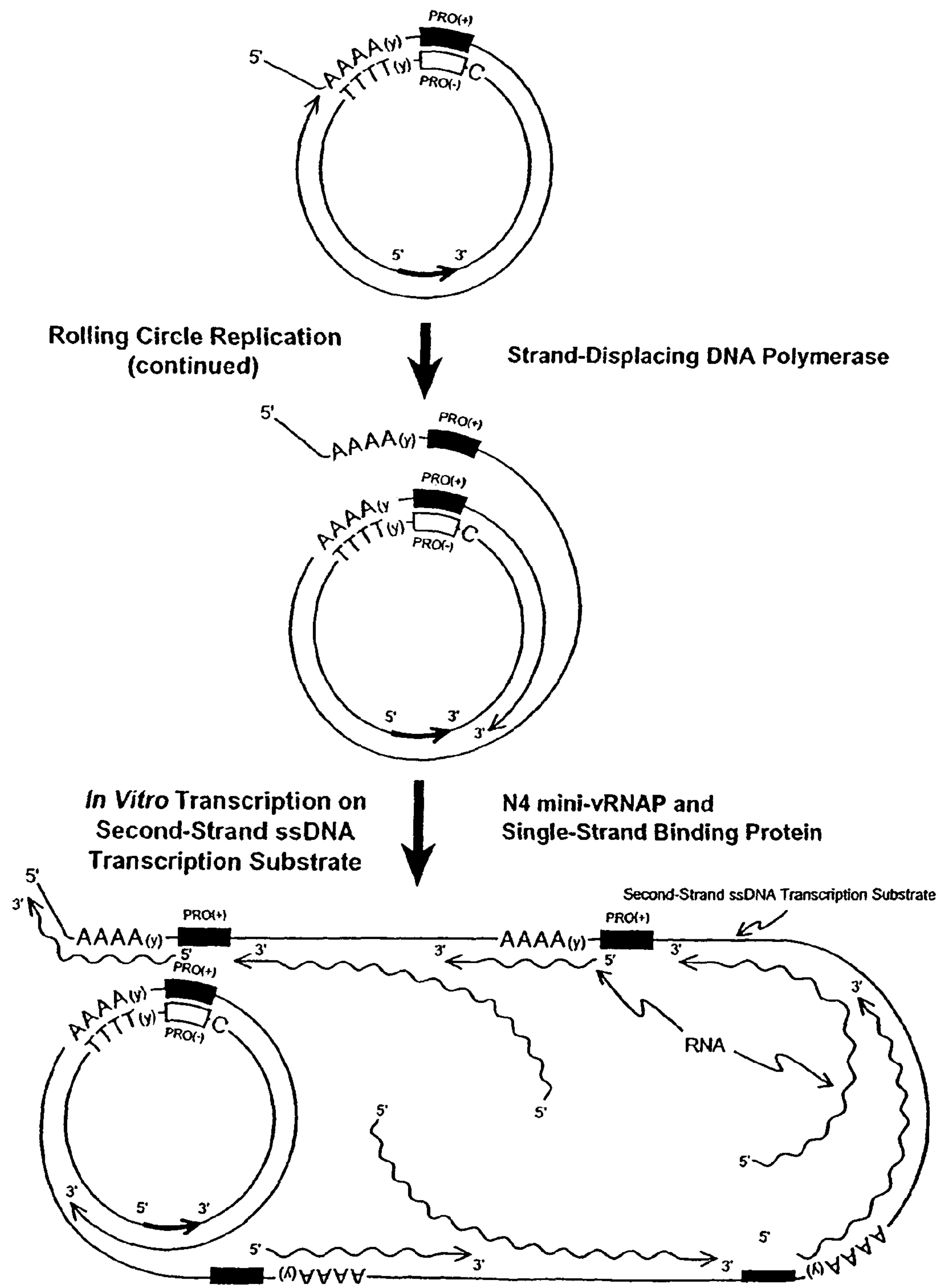

Thus, one embodiment of the invention that uses a promoter primer comprises a method for making a transcription product corresponding to a target sequence in a target nucleic acid (FIG. 24), the method comprising:

a. obtaining a target nucleic acid comprising single-stranded DNA or RNA;

b. obtaining a single-stranded anti-sense promoter primer for synthesis of a first-strand cDNA, the anti-sense promoter primer comprising: (i) a sequence at its 3'-end that is complementary to the 3'-end of the target sequence that is to be transcribed, and (ii) a 5'-portion comprising a single-stranded sequence that is complementary to a sense transcription promoter (i.e., an "anti-sense promoter), wherein the sense promoter functions to direct transcription by an RNA polymerase that can use a ssDNA transcription substrate for synthesis of RNA or modified RNA that is complementary to the target sequence, and (iii) optionally, a phosphate group or a topoisomerase moiety on its 5-end;

c. optionally, (if the 5'-end of the target sequence in the target nucleic acid is not a 5'-terminus or otherwise delimited,) obtaining a blocking oligo, the blocking oligo comprising a sequence that anneals tightly to a sequence on the target nucleic acid so as to delimit the 3'-end of a primer extension product of the promoter primer using the target nucleic acid as a template, wherein the blocking oligo is not displaced by the primer extension product, and wherein the blocking oligo is not itself capable of being primer extended by a DNA polymerase;

d. annealing the promoter primer and, optionally, the blocking oligo to the target nucleic acid;

e. primer-extending or the promoter primer annealed to the target nucleic acid with a DNA polymerase under DNA synthesis conditions so as to obtain a linear first-strand cDNA that is complementary to the target sequence to which the promoter primer was annealed and that is not complementary to the sequence where the blocking oligo is annealed (if used), and wherein, the linear first-strand cDNA comprises the anti-sense transcription promoter at a position which is 5'-of the target sequence in the first-strand cDNA which is complementary to the target sequence;

f. optionally, removing the target nucleic acid that is annealed to the linear first-strand cDNA; then, g. ligating the linear first-strand cDNA, wherein the 5'-end of the linear first-strand cDNA is covalently attached to the 3'-end of the linear first-strand cDNA so as to obtain circular first-strand cDNA;

h. obtaining a strand-displacement primer;

i. annealing the strand displacement primer to the circular first-strand cDNA;

j. obtaining a strand-displacing DNA polymerase;

k. contacting the circular first-strand cDNA to which the strand displacement primer is annealed with a strand-displacing DNA polymerase under DNA synthesis conditions so as to obtain linear second-strand cDNA, wherein the second-strand cDNA comprises a ssDNA transcription template comprising a sense transcription promoter;

l. obtaining the linear second-strand ssDNA transcription template;

m. obtaining an RNA polymerase that transcribes the ssDNA transcription substrate using the promoter under transcription conditions;

n. contacting the linear second-strand ssDNA transcription template with the RNA polymerase under transcription conditions so as to obtain anti-sense transcription products; and o. obtaining the anti-sense transcription products; and p. optionally, repeating steps b through p to obtain additional rounds of transcription of the anti-sense transcription products.

b. Composition of Promoter Primers of the Invention

In preferred embodiments of the invention, a promoter primer comprises DNA nucleotides. A promoter primer can also comprise one or more modified nucleotides for a particular purpose. By way of example, but not of limitation, a promoter primer can comprise one or more dUMP nucleotides 3'-of a sense transcription promoter and 5'-of the sequence that is complementary to a target nucleic acid sequence, which provides a site for linearizing a circular ssDNA transcription substrate using UNG and endo IV, as discussed elsewhere herein. However, the invention is not limited to promoter primers comprising DNA nucleotides or modified DNA nucleotides, and in some cases, a promoter primer can comprise RNA or modified RNA nucleotides or both DNA and RNA nucleotides or modified nucleotides.

The nucleic acid target-complementary portion of a promoter primer can be complementary to a specific known sequence in the RNA target in a sample, or it can comprise a mixture of all possible or many possible sequences, such as, but not limited to, random hexamer sequences. Random primer sequences can be made by including nucleotide reagents which are complementary to all four canonical bases during the chemical synthesis of each nucleotide position of the mRNA-complementary portion of the promoter primer. In embodiments of the invention using samples containing mRNA target nucleic acids, which are preferred embodiments, the 3'-end of a promoter primer comprises either a specific sequence that is complementary to a known sequence of a specific mRNA or, if the mRNA has a poly(A) tail at its 3'-end, the 3'-end of the promoter primer can comprise an oligo(dT) sequence. In still other embodiments of the invention for mRNA target nucleic acids, the 3'-end of a promoter primer can comprise a random sequence, such as, but not limited to a random hexamer sequence.

A promoter primer of the invention comprises a transcription promoter in its 5'-portion. In most embodiments, the transcription promoter comprises a sense promoter sequence that is capable of binding an RNA polymerase of the invention. However, those with knowledge in the art will understand that, due to the fact that the transcription promoter is 5'-of the linear first-strand cDNA that is synthesized by reverse transcription of the RNA target nucleic acid using the promoter primer, an RNA polymerase of the invention cannot use the transcription promoter to synthesize RNA complementary to first-strand cDNA that is complementary to the RNA target nucleic acid. However, if the 5'-end of the linear first-strand cDNA is ligated to its 3'-end so as to form circular first-strand cDNA, then an RNA polymerase of the invention can use the transcription promoter to synthesize RNA complementary to first-strand cDNA that is complementary to the RNA target nucleic acid; thus, a circular first-strand cDNA of this embodiment comprises a transcription substrate of the invention. Thus, a preferred promoter primer of these embodiments of the invention is phosphorylated at its 5'-end in order to facilitate ligation of linear first-strand cDNA by a ligase of the invention under ligation conditions. By means of example, but not of limitation, the 5'-end of the promoter primer can be phosphorylated using T4 polynucleotide kinase and ATP under suitable reaction conditions known in the art. In other embodiments, the promoter primer has a type 1 topoisomerase moiety at its 5'-end in order to facilitate topoisomerase-mediated ligation of linear first-strand cDNA under ligation conditions (e.g., U.S. Pat. No. 5,766,891, incorporated herein by reference).

D. Composition, Design and use of Promoter Splice Template Oligos, Splice Template Oligos, Promoter Ligation Oligos, Ligation Oligos, Promoter Primers, Primers, and Ligation Splint Oligos of the Invention Depending on the particular method and application, a promoter splice template oligo, a splice template, a promoter ligation oligo, a ligation oligo, a promoter primer, a primer, or a ligation splint oligo, or oligos used for other purposes can comprise unmodified or modified DNA, RNA or both DNA and RNA for various applications and embodiments of the invention, some of which are discussed in greater detail in individual sections related thereto. By way of example, but not of limitation, in some embodiments, these molecules can comprise DuraScript™ RNA made using the DuraScribe™ T7 Transcription Kit (Epicentre Technologies, Madison, Wis.). Similar types of modified RNA oligos that contain 2'-F-dCMP and 2'-F-dUMP can also be made using the N4 mini-vRNAP Y678F mutant enzyme, described herein in the section on "RNA Polymerases of the Invention." DNA oligos can be synthesized on an oligo synthesizer, which is usually preferred, or enzymatically, using methods discussed elsewhere herein.

In addition to the transcription promoter sequence and a target-complementary sequence, if present, the various promoter-containing oligos of the invention, including, but not limited to, promoter splice template oligos, promoter ligation oligos, or promoter primers, of the invention can also have additional nucleic acid sequences that are 5'-of and/or 3'-of the transcription promoter sequence, but a promoter-containing oligo is not required to have such additional other sequences. By way of example, but not of limitation, these oligos can have a transcription initiation site 5'-of the promoter sequence. In some embodiments of the invention, a promoter-containing oligo can have one or more primer sites, one or more transcription termination sequences, one or more sites for DNA cleavage, (such as, but not limited to, a dUMP residue that can be cleaved using uracil-N-glycosylase and endonuclease IV, or other cleavage methods discussed elsewhere herein) to permit controlled linearization of a circular first-strand cDNA that is a transcription substrate, one or more origins ("ori's") of replication (preferably an ori for a single-stranded replicon, such as, but not limited to, a phage M13 replicon), a selectable or screenable marker, such as, but not limited to an antibiotic-resistance gene or a beta-galactosidase gene, respectively, or one or more transposon recognition sequences (e.g., OE or ME sequences) that can be recognized and used by a transposase for in vitro or in vivo transposition, or one or more sites that are recognized by a recombinase (such as, but not limited to, the cre-lox system), and/or other sequences or genetic elements for a particular purpose. Similarly, other oligos used in a method of the invention, including those that lack a promoter sequence, such as splice template oligos, ligation oligos, or primers can have one or more of any of these additional sequences and/or genetic elements 5'-of the target-complementary or target-joining portion of each respective oligo.

The various methods of the invention, including, but not limited to the various processes for attaching one or more sense and/or anti-sense transcription promoter sequences to a target nucleic acid sequence, are not mutually exclusive of each other, and in some embodiments of the invention, more than one method can be used together. By way of example, but not of limitation, both an oligo(dT)-promoter primer and a splice template oligo that is used to primer-extend the 3'-end of a first-strand cDNA that is synthesized by reverse transcription of mRNA from a sample can be used. In some embodiments, the splice template oligo can be a promoter spice template oligo, which encodes a promoter sequence, and in other embodiments, a splice template oligo that does not encode a promoter sequence can be used. A splice template oligo that does not encode a promoter can be used, without limitation, to provide a primer binding site, a single-stranded origin of replication ("ori"), such as a phage M13 ori, a selectable or screenable marker, such as a sequence that encodes an antibiotic-resistance gene or a beta-galactosidase gene, respectively, and/or a transcription termination sequence. If the splice template oligo encodes a promoter sequence, it can encode a sequence that comprises a sense transcription promoter in the synthesized first-strand cDNA or it can encode a sequence that results in a sense promoter in a second cDNA strand that is synthesized by strand displacement DNA synthesis using first-strand cDNA as a template. In some embodiments of the invention, more than one sense transcription promoter, which can have the same DNA sequence or a different DNA sequence, can be present in first-strand cDNA and/or second-strand cDNA. The promoter sequence used in a promoter splice template oligo can be determined based on knowledge of sequences of sense promoters for RNA polymerases of the invention and of the rules of nucleic acid base complementarity and the directionality of DNA and RNA synthesis by DNA and RNA polymerases. By way of example, if a sense transcription promoter is desired in a second-strand cDNA that is made by primer extension of first-strand cDNA, which in turn is made by reverse transcription of mRNA, one can work backwards from having a sense transcription promoter of known sequence at the 3'-end of a target nucleic acid sequence that is to be transcribed by an RNA polymerase of the invention, in order to determine the anti-sense sequence (and directionality of transcription encoded by the sequence) that is needed in the first-strand cDNA, and then, what is needed in the promoter splice template oligo to which the primer-extended first-strand cDNA must be complementary in order for the promoter splice template oligo to serve as a template for primer extension of the first cDNA strand. Based on a reading of the disclosures herein, those with knowledge in the art will understand other methods of the invention which use processes with other different combinations or permutations of promoter splice template oligos, splice template oligos, promoter ligation oligos, promoter primers, and non-promoter primers to make ssDNA transcription substrates having ssDNA promoters that are recognized by RNA polymerases of the invention and that can be used to synthesize or make a transcription product corresponding to a target nucleic acid sequence for a particular purpose. All such methods are included in the invention.

E. Circularizing Linear ssDNA

1. Methods for Cloning ssDNA and Generating Libraries of ssDNA Clones, Including Expression Clones and Expressions Libraries In some embodiments, the methods of the invention for obtaining a circular ssDNA transcription substrate corresponding to a target sequence for a target nucleic acid comprise obtaining molecular clones of the target sequence. In still other embodiments, such as, but not limited to embodiments in which the target sequence comprises first-strand cDNA corresponding to all target mRNAs in a sample, the invention comprises methods for obtaining a library of clones comprising the target sequences of target nucleic acid. In embodiments that comprise obtaining a clone or a library of clones comprising target sequences, a promoter splice template oligo, a promoter ligation oligo, or a promoter primer that comprises a single-stranded origin of replication (ori), such as, but not limited to an M13 ori, is used, and in most embodiments, a sequence that encodes a selectable or screenable marker, such as, but not limited to an antibiotic-resistance gene or a beta-galactosidase gene, respectively, is also used, and, optionally, a transcription termination sequence or other sequences or genetic elements are also used. Methods, *E. coli* host cells, bacteriophage (including helper phage) strains, and vectors and sequences, including M13 ori sequences, that are needed or useful for working with M13 phages and M13 nucleic acids and vectors and sequences derived therefrom are available and well-known in the art (e.g., see Chapter 3, Volume 1 of Sambrook and Russell, Molecular Cloning, A Laboratory Manual, Third Edition, 2001, Cold Spring Harbor Laboratory Press, Cold Spring Harbor, N.Y., incorporated herein by reference) and these methods and compositions can be used for methods of the invention for obtaining replicable clones of single-stranded DNA corresponding to target sequences of target nucleic acid. Also, a number of selectable or screenable markers and selection and screening systems are known in the art, such as, but not limited to those described by Sambrook and Russell Molecular Cloning, A Laboratory Manual, Third Edition (Cold Spring Harbor Laboratory Press, Cold Spring Harbor, N.Y.; e.g., see Chapter 1, Volume 1), which is incorporated herein by reference, and any suitable marker or selection or screening system can be used for the present invention.

Thus, one embodiment of the invention is a method for cloning a target sequence, the method comprising:

a. obtaining a single-stranded promoter primer comprising a 3'-end portion that has a sequence that is complementary to the 3'-end of a target sequence and a 5'-portion, the 5'-portion comprising a sequence at or near the 5'-end that encodes a single-stranded sense transcription promoter for an RNA polymerase that can make a transcription product using a ssDNA transcription substrate and additional sequences 3'-of the promoter sequence, the additional sequences comprising a single-stranded origin of replication that can be replicated in a host cell, at least one gene for a selectable or screenable marker that is expressible in the host cell, and optionally, the 5'-end of the promoter primer can have a phosphate group or a topoisomerase moiety or a phosphate or topoisomerase moiety can be added to the 5'-end of linear first-strand cDNA as an additional step of the method prior to the ligation step;

b. annealing the promoter primer to the target nucleic acid;

c. obtaining a DNA polymerase;

d. primer-extending the promoter primer annealed to the target nucleic acid with the DNA polymerase under DNA synthesis conditions;

e. obtaining a linear first-strand cDNA comprising a sequence that is complementary to the target sequence;

f. optionally, removing the target nucleic acid that is annealed to the linear first-strand cDNA;

g. ligating the linear first-strand cDNA, wherein the 5'-end of the linear first-strand cDNA is covalently joined to the 3'-end of the linear first-strand cDNA so as to obtain circular first-strand cDNA, wherein the circular first-strand cDNA comprises a circular ssDNA transcription substrate;

h. obtaining the circular ssDNA transcription substrate;

i. obtaining host cells that can replicate a circular ssDNA comprising the single-stranded origin of replication and in which the selectable or screenable marker is expressible;

j. incubating the host cells with DNA comprising a circular ssDNA transcription substrate under conditions suitable to obtain transformation;

k. plating the host cells that were incubated with the DNA comprising a circular ssDNA transcription substrate on medium that contains a composition that permits selection or screening for cells that contain and express the gene for the selectable or screenable marker; and l. obtaining transformed host cells that contain replicable clones comprising the target sequence.

In some embodiments, the host cells that are used to obtain replicable clones comprising the target sequence are host cells that comprise an inducible gene for an RNAP, wherein the RNAP can binds to the single-strand promoter and initiate transcription of a single-strand template therefrom. In particularly suitable embodiments, the host cells comprise an inducible gene that encodes an N4 vRNAP. In other embodiments, the host cells comprise an inducible gene that encodes an RNA polymerase that can bind to a pseudopromoter that is on a ssDNA transcription substrate and initiate transcription from the pseudopromoter. Inducible promoters that can be used to express the RNAP in the host cells in the presence of an inducing substance are described elsewhere herein. When host cells comprising an inducible RNAP are used to obtain replicable clones according to this embodiment of the invention, the transformed host cells that contain replicable clones, when incubated in the presence of an inducing substance under inducing conditions, comprise expression clones. Still further, in embodiments of the invention in which the target sequence comprises target nucleic acid comprising all mRNAs in a sample, the collection of all transformed host cells that contain replicable clones comprises a library of replicable clones. In yet another embodiment, if the host cells contain an inducible gene that encodes an RNAP, wherein the RNAP can bind to a single-stranded promoter and initiate transcription of a single-strand template therefrom, the collection of all transformed host cells that contain replicable clones comprises a library of replicable expression clones.

The invention also comprises embodiments of methods for cloning a target sequence by using a promoter splice template oligo or a promoter ligation oligo that comprises sequences that encode a single-stranded origin of replication (ori), such as, but not limited to an M13 ori, that is replicable in a host cell, a selectable or screenable marker, such as, but not limited to an antibiotic-resistance gene or a beta-galactosidase gene, respectively, that is expressible in the host cell and, optionally, a transcription termination sequence. In these embodiments, the sequences that encode the ori, the selectable or screenable marker and the transcription termination sequence, if present, are 5'-of the promoter-complementary sequence (i.e., 5'-of the anti-sense promoter sequence) in the promoter splice template oligo or 3'-of the sense promoter sequence in the promoter ligation oligo, respectively. Initial steps of the methods for cloning a target sequence using a promoter splice template oligo or a promoter ligation oligo comprise steps that are identical to those described previously for using these respective oligos for obtaining a linear ssDNA transcription substrate of the invention. However, the next step of the methods for cloning a target sequence using a promoter splice template oligo or a promoter ligation oligo comprises obtaining a circular ssDNA transcription substrate by ligating the 5'-end of the linear ssDNA transcription substrate to the 3'-end under ligation conditions. Ligation conditions addition of a phosphate group to the 5'-end of the linear ssDNA transcription substrate, if it is not already present, using kinase, such as, but not limited to T4 polynucleotide kinase. Thereafter, the steps of the methods of the invention for using a promoter splice template oligo or a promoter ligation oligo for obtaining transformed host cells that contain replicable clones, replicable expression clones, libraries or expression libraries of a target sequence for target nucleic acid in a sample are the same as described above for methods that use a promoter primer.

Based on the above description of the invention for using promoter splice template oligos, promoter ligation oligos, and promoter primers for obtaining host cells that contain replicable clones or libraries of target sequences, those with knowledge in the art will understand that the invention also comprises similar methods for obtaining host cells that contain replicable clones or libraries of target sequences using splice template oligos, ligation oligos, and primers that lack a promoter sequence. Thus, provided an oligo encodes sequences that comprise a single-stranded origin of replication and a suitable selectable or screenable marker for the host cell used, the methods for making replicable clones using an oligo that lacks a promoter sequence, including a splice template oligo, a ligation oligo or a primer, are substantially the same as those methods used for making replicable clones using a promoter splice template oligo, a promoter ligation oligo or a promoter primer, respectively. Of course, replicable clones of a target sequence made using an oligo that lacks a promoter sequence cannot express the target sequence, and therefore, expression clones and expression libraries cannot be obtained using these oligos.

2. Ligases and Ligation Methods for Circularizing Linear ssDNA

It will be clear from the above descriptions of methods for obtaining ssDNA transcription substrates that it is useful in various embodiments to ligate linear ssDNA to obtain circular ssDNA, including, but not limited to circular ssDNA transcription substrates. The invention is not limited to a specific ligase for circularizing a linear ssDNA molecule and different ligases and ligation methods can be used in different embodiments in order to accomplish a particular purpose. In embodiments that use a ligase, the 5'-end of the linear ssDNA that is ligated to obtain a circular ssDNA must have a 5'-phosphate group or the 5'-end must be phosphorylated using a polynucleotide kinase, such as, but not limited to T4 polynucleotide kinase, during the processes of the method of the invention.

A ligase that catalyzes non-homologous intramolecular ligation, such as, but not limited to ThermoPhage™ RNA Ligase II (Prokaria, Ltd., Reykjavik, Iceland), is a suitable ligase for ligating linear ssDNA to form a circular ssDNA.

NAD-dependent DNA ligases that are not active on blunt ends, such as, but not limited to Ampligase® Thermostable DNA Ligase (Epicentre Technologies, Madison, Wis., USA), Tth DNA ligase, Tfl DNA ligase, and Tsc DNA Ligase (Prokaria Ltd., Reykjavik, Iceland) can be used to ligate the 5'-phosphate and 3'-hydroxyl termini of DNA ends that are adjacent to one another when annealed to a complementary DNA molecule, and are suitable ligases in embodiments of the invention that use a ligation splint oligo comprising DNA. However, the invention is not limited to the use of a particular ligase and any suitable ligase can be used. For example, T4 DNA ligase can be used in embodiments of the invention that use a ligation splint. Still further, Faruqui discloses in U.S. Pat. No. 6,368,801 that T4 RNA ligase can efficiently ligate DNA ends of nucleic acids that are adjacent to each other when hybridized to an RNA strand. Thus, T4 RNA ligase is a suitable ligase of the invention in embodiments in which DNA ends are ligated on a ligation splint oligo comprising RNA or modified RNA, such as, but not limited to modified RNA that contains 2'-F-dCTP and 2'-F-dUTP made using the DuraScribe™ T7 Transcription Kit (Epicentre Technologies, Madison, Wis. USA) or the N4 mini-vRNAP Y678F mutant enzyme described herein.

The invention is also not limited to the use of a ligase for covalently joining the 5'-end to the 3'-end of the same or different nucleic acid molecules in the various embodiments of the invention. By way of example, other ligation methods such as, but not limited to, topoisomerase-mediated ligation (e.g., U.S. Pat. No.5,766,891, incorporated herein by reference) can be used.

G. Modes of Performance of the Methods of the Invention

Depending on the application and its requirements and constraints, the methods of the invention can be performed in a stepwise fashion, with one set of reactions being performed, followed by purification of a reaction product or removal of reagents or inactivation of enzymes or addition of reagents before proceeding to the next set of reactions, or, in other embodiments for other applications, the methods can be performed as a continuous set of multiple reactions in a single reaction mixture. By way of example, but not of limitation, in some embodiments, each of the separate reactions for synthesis of a cDNA library and for transcription using promoter-containing first-strand cDNA as a template for transcription can be performed separately. Still by way of example, in some embodiments in which the methods of the invention are used as part of a diagnostic assay, all of the reactions can be carried out in a single reaction mixture and the products of the transcription reaction may be detected, without ever being isolated.

The invention also comprises parts or subsets of the methods and compositions of the invention. By way of example, but not of limitation, in addition to obtaining a method for making a transcription product corresponding to the mRNA molecules in a sample, the invention also comprises improved methods for making full-length first-strand cDNA with DNA sequences corresponding to the complete 5'-end of the mRNA in the sample, and cloning the single-stranded cDNA using a single-stranded origin of replication, such as a phage M13 ori. This method for making and cloning full-length cDNA corresponding to mRNA in a sample can be, but need not be, part of the method for making a transcription product. Thus, the invention comprises all of the individual steps of the methods of the invention that are enabled thereby, in addition to the overall methods.

G. Examples of the Scope of Applications of the Invention

Those with knowledge in the art will understand that the present invention is novel and very broad in scope and provides improvements in methods, processes, compositions and kits related to making transcription products corresponding to a target nucleic acid sequence comprising RNA, including mRNA, or DNA in a biological sample for many applications. These methods are useful for applications such as, but not limited to, making full-length cDNA and cDNA libraries, improving gene expression analysis, and detecting a target sequence. By way of further example, but not of limitation, the present invention comprises improved methods, processes, compositions and kits that improve upon methods and applications to:

1. amplify nucleic acid molecules in vitro
2. amplify nucleic molecules in vivo
3. amplify a DNA sequence in vitro
4. amplify a DNA sequence in vivo
5. amplify a genomic DNA sequence in vitro
6. amplify a genomic DNA sequence in vivo
7. amplify an RNA sequence in vitro
8. amplify an RNA sequence in vivo
9. amplify mRNA
10. amplify rRNA
11. make cDNA complementary to an RNA
12. make full-length first-strand cDNA complementary to mRNA
13. make a cDNA library complementary to mRNA in a sample
14. synthesize RNA
15. synthesize modified RNA, such as, but not limited to, RNA containing 2'-fluoro-nucleotides for various applications, including, but not limited to, other applications for modified RNA or dsRNA herein above or below.
16. synthesize DNA
17. detect the presence of a nucleic acid sequence in a sample
18. detect the presence of a target nucleic acid sequence in a sample that is indicative of the presence of a target organism
19. detect the presence of a target nucleic acid analyte in a sample
20. detect the presence of a DNA sequence in a sample
21. detect the presence of an RNA sequence in a sample
22. detect the presence (or absence at a detectable level) of a gene in a sample
23. detect the presence (or absence at a detectable level) of a mutated gene in a sample
24. detect the presence of a target organism in a sample
25. detect the presence of a virus in a sample
26. detect the presence of a bacterium in a sample
27. detect the presence of a pathogenic organism in a sample
28. detect the presence of a beneficial organism in a sample
29. identify and quantify nucleic acids associated with RNA and DNA binding proteins using a ssDNA transcription substrate of the invention and an RNA polymerase that can synthesize RNA using the ssDNA transcription substrate as an indirect signaling method similar to the IDAT and other methods that use a T7-type RNA polymerase, as disclosed by Zhang et al. (*Proc. Natl. Acad. Sci. USA* 98:5497-5502, 2001) and by Eberwine in PCT Publication No. WO 02/14476, both of which are incorporated herein by reference
30. detect an oncogene
31. detect an anti-oncogene
32. quantify the level of a virus, a microorganism, a gene, an mRNA, an rRNA, a nucleic acid analyte, or any other nucleic acid of whatever type for whatever purpose.
33. use as a probe
34. use as a probe for an array or microarray
35. make dsRNA or modified dsRNA that can be introduced into human, animal or other eukaryotic cells in serum and without use of a transfection agent.

36. synthesize dsRNA or modified dsRNA in vitro for use in RNAi
37. synthesize dsRNA or modified dsRNA in vivo for use in RNAi
38. synthesize dsRNA or modified dsRNA in vitro for use siRNA
39. synthesize dsRNA in vivo for use siRNA
40. make RNAi or modified RNAi that silences a gene encoded by a virus or other infectious agent.
41. make siRNAi or modified siRNA that silences a gene encoded by a virus or other infectious agent.
42. make RNAi or modified RNAi that silences a gene encoded by a plant, animal, human, fungal or other eukaryotic host gene that is involved with and/or interacts with a biological molecule encoded by a virus or other infectious agent.
43. make siRNAi or modified siRNA that silences a gene encoded by a plant, animal, human, fungal or other eukaryotic host gene that is involved with and/or interacts with a biological molecule encoded by a virus or other infectious agent.
44. make RNAi or modified RNAi that silences a non-essential disease-susceptibility gene encoded by a plant, animal, human, fungal or other eukaryotic host gene.
45. make siRNAi or modified siRNA that silences a non-essential disease-susceptibility gene encoded by a plant, animal, human, fungal or other eukaryotic host gene.
46. make RNAi or modified RNAi that silences a non-essential gene encoded by a plant, animal, human, fungal or other eukaryotic host gene, wherein the gene silencing results in a beneficial effect.
47. make siRNAi or modified siRNA that silences a non-essential gene encoded by a plant, animal, human, fungal or other eukaryotic host gene, wherein the gene silencing results in a beneficial effect.
48. make RNAi or modified RNAi that silences a non-essential gene encoded by a plant, animal, fungal or other eukaryotic host gene, wherein the gene silencing results in improved yield, production of a biological molecule, flavor, or other commercially beneficial effect, such as, but not limited to, cold-hardiness, salt-tolerance, shortened growing season, or increased efficiency of utilization of a nutrient.
49. make siRNAi or modified siRNA that silences a non-essential gene encoded by a plant, animal, fungal or other eukaryotic host gene, wherein the gene silencing results in improved yield, production of a biological molecule, flavor, or other commercially beneficial effect, such as, but not limited to, cold-hardiness, salt-tolerance, shortened growing season, or increased efficiency of utilization of a nutrient.
50. diagnose the presence and/or level of an infectious organism
51. diagnose a disease of any type
52. detect the presence of a nucleic acid in an environmental sample
53. differentiate, both qualitatively and quantitatively, between which mRNA molecules are present in different types of cells or in the same type of cells under different conditions or in the same or different types of cells under the same or different conditions or in response to specific stimuli or treatments
54. analyze, both qualitatively and quantitatively, gene expression profiles in cells under different defined conditions
55. analyze, both qualitatively and quantitatively, gene expression profiles in different types of cells under the same defined environmental conditions
56. analyze, both qualitatively and quantitatively, gene expression profiles in cells over time
57. analyze, both qualitatively and quantitatively, gene expression in response to specific stimuli
58. make a library or libraries of mRNA molecules and/or cDNA molecules that are present in one type of cell that are not present in another type of cell, or that are present in one type of cell under certain conditions but not under other conditions (i.e., a subtraction library).
59. map and clone sequences corresponding to the 5'-ends of mRNA's, including, but not limited to, those generated from a specific gene by alternative splicing and promoter usage
60. generate improved templates for more accurate rapid amplification of cDNA ends ("RACE") techniques (e.g., see Flouriot et al., *Nucleic Acids Res.* 27:e8 (I-iv), 1999, incorporated herein by reference).
61. make and/or amplify mRNA for in vitro or in vivo translation, including, but not limited to coupled or step-wise transcription and translation.
62. amplify RNA and/or DNA or modified RNA and/or DNA present in living cells, such as, but not limited to, tumor or cancer cells from a patient for introduction into dendritic cells (e.g., see U.S. Pat. Nos. 5,994,126 and 6,475,483 of Steinman et al., incorporated herein by reference) or other cells from the patient in order to boost or increase an in vivo response, such as, but not limited to, an immune response in the patient, with the goal of decreasing the size or the number of cells in the tumor or cancer in the patient.
63. make and/or amplify RNA and/or DNA or modified RNA and/or DNA from a patient and or present in a virus or other infectious agent, wherein the RNA and/or DNA is for use as an RNA vaccine and/or a DNA vaccine, respectively.
64. make RNA or modified RNA that can be introduced into human, animal or other eukaryotic cells in serum and without use of a transfection agent.
65. make modified RNA containing 2'-fluoro-2'deoxy-nucleotides, such as, but not limited to, 2'-F-dCMP and 2'-F-dUTP, in place of the corresponding canonical nucleotides.
66. produce arrays or microarrays of amplified nucleic acids by attaching the amplification products onto a solid substrate.
67. detect a mutation or a mutated form of a target nucleic acid sequence in a sample
68. quantify the amount of a target nucleic acid or target nucleic acids in a sample.

The mini-vRNAP Y678F mutant enzyme has improved ability to incorporate 2'-fluoro-dNTPs compared to the wild-type N4 vRNAP or mini-vRNAP (Kazmierczak, K. M., et al., *EMBO J.,* 21:5815-5823, 2002, incorporated herein by reference). Modified RNA molecules that contain 2'-F-dCMP and 2'-F-dUTP are resistant to RNase A-type ribonucleases (Sousa et al., U.S. Pat. No. 5,849,546), included herein by reference. Capodici et al., (*J. Immunology* 169:5196-5201, 2002), included herein by reference, showed that 2'-fluoro-containing dsRNA molecules made using the DuraScribe™ T7 Transcription Kit (Epicentre Technologies, Madison, Wis. USA) did not require transfection reagents for delivery into cells, even in the presence of serum. Kakiuchi et al. (*J. Biol. Chem.* 257:1924-1928, 1982), included herein by reference, showed that use of $[(2'\text{-F-dI})_n$: $(2'\text{-F-dC})_n]$ duplexes were 40-100 times less antigenic than [(rI).sub$_n$.: (rC$_n$.] duplexes, and did not induce an interferon response like [(rI)$_n$.: (rC)$_n$.] duplexes.

H. Use of Methods of the Present Invention for Making Double-Stranded RNA for RNA Interference 1. Combining Use of a ssDNA Transcription Substrate for N4 mini-vRNAP and a Substrate for dsDNA Substrate for a T7-Type RNAP to Synthesize Both RNA Strands of dsRNA for Use as RNAi The methods of the present invention can also be combined with methods in the art for a particular purpose. By way of example, but not of limitation, both N4 vRNAP-type promoters and T7 RNAP-type promoters can be combined for a method to make double-stranded RNA for use as RNAi or siRNA. Thus, in one embodiment, a primer comprising a T7 RNAP or other T7-type protopromoter at its 5'-end and a sequence that is complementary to the 3'-end of a target sequence can be used for reverse transcription or primer extension to synthesize first-strand cDNA that is complementary to a target sequence in a target nucleic acid. Then, the 3'-end of the first-strand cDNA can be primer-extended using a promoter splice template oligo, the promoter splice template oligo comprising a sequence at its 3'-end that is complementary to the 3'-end of the first-strand cDNA and a sequence at its 5'-end that is complementary to a sense promoter for an N4 vRNAP promoter. The resulting product has a sense N4 vRNAP promoter on its 3'-end and an anti-sense T7 RNAP protopromoter sequence on its 5'-end. Thus, an N4 mini-vRNAP can be used to synthesize is sense-strand RNA from this single-stranded first-strand cDNA template corresponding to the target sequence. Then, the first-strand cDNA can be made double stranded by primer extension using a primer complementary to the 3'-end of the first-strand cDNA (e.g., complementary to the N4 vRNAP promoter) and first-strand cDNA as a template. The resulting double-stranded cDNA can be used for transcription of RNA that is anti-sense with respect to the target sequence using T7 RNAP. The sense and anti-sense modified RNA strands can be annealed to produce double-stranded RNA that can be used for RNA interference, including, but not limited to, as siRNA. In other embodiments of the invention, N4 mini-vRNAP Y678F and T7 RNAP Y639F (Sousa et al., U.S. Pat. No. 5,849,546, incorporated herein by reference) mutant enzymes can be used in order to synthesize, respectively, sense and anti-sense modified RNA that contains 2'-fluoro-pyrimidine nucleotides in place of the canonical pyrimidine nucleotides.

2. Methods for Making Transcription Products for Use as RNAi by Obtaining a ssDNA Transcription Substrate Comprising a Hairpin Target Sequence The present invention is not limited to this particular method for making dsRNA for use as RNAi. Another method of the invention uses a target sequence comprising a hairpin in order to synthesize a ssDNA transcription substrate that encodes both strands of a dsRNA and a non-complementary region. Transcription of the transcription substrate using an N4 vRNAP or another RNAP that recognizes a single-stranded pseudopromoter, as described herein, yields a hairpin RNA structure for use as RNAi. According to this method, a sense transcription promoter for an N4 vRNAP or a sense single-stranded pseudopromoter is attached at the 3'-end of a DNA target sequence using a promoter splice template, a promoter ligation oligo or a promoter primer, as described elsewhere herein, in order to make a ssDNA transcription substrate. The target sequence in the ssDNA transcription substrate comprises: (a) a 3'-portion, wherein the 3'-portion encodes a sequence for a first strand of a dsRNA that is to be used as RNAi; (b) a middle portion, wherein the middle portion comprises a sequence that is not complementary to either strand of the dsRNA; and (c) a 5'-portion, wherein the 5'-portion encodes the sequence for a second strand of the dsRNA that is to be used as RNAi and wherein the RNA encoded by the 5'-portion that encodes the second strand is complementary to and can anneal to the RNA encoded by the 3'-portion that encodes the first strand so as to form a hairpin structure wherein the middle portion is a loop structure of the hairpin. This ssDNA transcription substrate is used for in vitro transcription by an RNA polymerase that can transcribe the ssDNA transcription substrate. Suitable RNA polymerases comprise N4 vRNAPs, such as mini-vRNAP or mini-vRNAP Y678F, for transcription substrates having an N4 vRNAP promoter. In other embodiments that use a transcription substrate comprising a single-stranded pseudopromoter, an RNAP that can bind to and synthesize RNA using the pseudopromoter can be used in order to synthesize a dsRNA hairpin that can be used as RNAi. In still other embodiments, a molecule that is identical to a ssDNA transcription substrate of the invention for synthesis of hairpin RNA for use as RNAi can be obtained by chemical synthesis using an oligonucleotide synthesizer using methods known in the art. The chemically synthesized ssDNA can be used as a substrate for in vitro transcription using an RNA polymerase of the present invention.

In some embodiments that use a hairpin substrate for in vitro transcription, 2'-fluoro-pyrimidine deoxynucleotides are used in place of canonical pyrimidine nucleotides when the mini-vRNAP Y678F (Kazmierczak, K. M., et al., *EMBO J.* 21:5815-5823, 2002, incorporated herein by reference) or a mutant T7-type RNAP, such as the T7 RNAP Y639F mutant enzyme (Sousa et al., U.S. Pat. No. 5,849,546, incorporated herein by reference), is used to synthesize dsRNA for use as RNAi.

I. KITS AND COMPOSITIONS OF THE INVENTION

The present invention also comprises kits and compositions for carrying out the methods of the invention. A kit of the invention comprises one or, preferably, multiple components for carrying out the various processes of a method. With respect to embodiments of the invention for making a transcription product corresponding to a target sequence of a target nucleic acid, a kit comprises an RNA polymerase of the invention that can synthesize RNA using a ssDNA transcription substrate and at least one oligonucleotide, and preferably multiple oligonucleotides, that encode a sequence for either a sense or an anti-sense transcription promoter of the invention, including a promoter splice template oligo, a promoter ligation oligo or a promoter primer for use in generating a transcription substrate of the invention. With respect to embodiments of the invention for obtaining host cells comprising replicable single-stranded clones or libraries of replicable single-stranded clones comprising target sequences of target nucleic acids in a sample, a kit comprises, at a minimum, at least one oligonucleotide, chosen from among a promoter splice template oligo, a splice template oligo, a promoter ligation oligo, a ligation oligo, or a promoter primer or primer, wherein the oligo comprises a single-stranded origin of replication (ori), such as, but not limited to an M13 ori, and a sequence that encodes a selectable or screenable marker, such as, but not limited to an antibiotic-resistance gene, or a beta-galactosidase gene, respectively, and a host cell that can replicate a circular ssDNA comprising the single-stranded origin of replication and in which the selectable or screenable marker is expressible. With respect to embodiments for obtaining host cells comprising replicable single-stranded expression clones or expression libraries comprising a target sequence of target nucleic acid, a kit of the invention comprises an oligonucleotide that comprises a promoter for an RNA polymerase of the invention that can synthesize RNA using a ssDNA transcription substrate and the host cell comprises an inducible gene for the RNA polymerase that recognizes the promoter.

Depending on the particular embodiment, a kit can also contain one or more other components. By way of example, but not of limitation, a kit can comprise one or more other oligos, including splice template oligos, ligation splint oligos, and/or primers, including, but not limited to strand-displacement primers. A kit of the invention can also contain one or more other enzymes, such as, but not limited to, a reverse transcriptase, a ligase, a DNA polymerase, which can be a strand displacing DNA polymerase, an RNaseH, and/or other enzymes for particular processes of the invention. Still further a kit can contain components or reagents for use with host cells, such as helper phages, inducing substances, or substances for making the cells competent for transformation.

A kit can be for a specific method, such as, but not limited to, a kit for the synthesis and cloning of full-length cDNA or cDNA libraries that correspond to the complete sequence of 5'-ends of mRNA molecules, a kit for generating templates for random amplification of cDNA ends (RACE), a kit for making a transcription product corresponding to mRNA from a particular type of cell or different cells, whether under the same conditions or different environmental conditions, for gene expression profiling, including generation of sense or anti-sense probes for microarrays, a kit for amplification of an RNA or DNA sequence, including a kit for performing multiple rounds of transcription of a target nucleic acid sequence in a single reaction mixture, a kit for making a transcription product corresponding to a particular target nucleic acid sequence, if present in a sample, that is diagnostic or indicative of a pathogen, a disease gene, a mutated allele, or the like, a kit for an analyte-specific assay, wherein the analyte is a nucleic acid, a kit for amplifying a target nucleic acid by strand displacement replication or rolling circle replication and/or transcription of a ssDNA transcription substrate, a kit for making RNAi, including siRNA, or modified RNAi or siRNA, including, but not limited to, 2'-F-dCMP- and 2'-F-dUMP-containing RNAi or siRNA, or any of a broad range of kits that will be understood by those with knowledge in the art by a reading of the description of the invention herein.

In general, a kit of the invention will also comprise a description of the components of the kit and instructions for their use in a particular process or method or methods of the invention. In general, a kit of the present invention will also comprise other components, such as, but not limited to, buffers, ribonucleotides and/or deoxynucleotides, including modified nucleotides in some embodiments, DNA polymerization or reverse transcriptase enhancers, such as, but not limited to betaine (trimethylglycine), and salts of monvalent or divalent cations, such as but not limited to potassium acetate or chloride and/or magnesium chloride, enzyme substrates and/or cofactors, such as, but not limited to, ATP or NAD, and the like which are needed for optimal conditions of one or more reactions or processes of a method or a combination of methods for a particular application. A kit of the invention can comprise a a set of individual reagents for a particular process or a series of sets of individual reagents for multiple processes of a method that are performed in a stepwise or serial manner, or a kit can comprise a multiple reagents combined into a single reaction mixture or a small number of mixtures of multiple reagents, each of which perform multiple reactions and/or processes in a single tube. In general, the various components of a kit for performing a particular process of a method of the invention or a complete method of the invention will be optimized so that they have appropriate amounts of reagents and conditions to work together in the process and/or method.

Components of a kit may be provided as solutions or as dried powder(s). When reagents and/or components are provided as a dry powder, the powder can be reconstituted by the addition of a suitable solvent, in which case, the solvent may also be provided in another container.

As used herein in the specification, "a" or "an" may mean one or more. As used herein in the claim(s), when used in conjunction with the word "comprising," the words "a" or "an" may mean one or more than one. As used herein "another" may mean at least a second or more.

IX. USE OF RNA POLYMERASES OF THE INVENTION IN SIGNALING SYSTEMS

With respect to this aspect of the invention, a "signaling system" means and comprises the multitude of substances, compositions and environmental conditions comprising a method for detecting the presence or quantity of an analyte in a sample by detecting a transcript that results from transcription of a ssDNA polynucleotide that is operably joined to an analyte-binding substance. An important composition of a method comprising a signaling system of the invention is an analyte-binding substance that is operably joined to a ssDNA polynucleotide, wherein the ssDNA polynucleotide comprises a sequence that encodes a detectable transcript, wherein the sequence is operably joined to a single-stranded promoter for an RNA polymerase that can bind the promoter of the ssDNA polynucleotide and transcribe the sequence thereof, thereby making the detectable transcript under transcription conditions.

Other methods for detecting an analyte using transcription are known in the art, including the methods described by Zhang et al. (*Proc. Natl. Acad. Sci. USA* 98: 5497-5502, 2001), by Eberwine in PCT Patent Application No. WO 02/14476, and by Hudson et al. in U.S. Pat. No. 6,100,024, all of which are incorporated herein by reference. In contrast to the present invention, all of the methods of the prior art require, at a minimum, making a composition comprising a double-stranded promoter, and in most cases, the methods in the art also require preparation of double-stranded templates.

The signaling systems of the present invention differ from methods in the prior art in that they use a single-stranded DNA polynucleotide that is operably joined to an analyte-binding substance (ABS), wherein the single-stranded DNA polynucleotide comprises a single-stranded promoter that is operably joined to a single-stranded template that encodes a transcription product, and wherein the ABS is detected by making the transcription product using an RNA polymerase that binds to the single-stranded promoter comprising the single-stranded DNA polynucleotide.

The invention comprises methods, compositions and kits for using the RNA polymerases of the invention as a signaling system for an analyte of any type, including analytes such as, but not limited to, antigens, antibodies or other substances, in addition to an analyte that is a target nucleic acid.

Thus, the invention comprises a method for detecting an analyte in or from a sample, the method comprising:

1. obtaining a transcription signaling system, the transcription signaling system comprising a ssDNA comprising: (a) a sequence for a promoter for an RNA polymerase chosen from among N4 vRNAP, N4 mini-vRNAP, and N4 mini-vRNAP Y678F enzymes or another enzyme that binds a single-stranded promoter and transcribes a single-stranded template to which it is operably joined; and (b) a signal sequence that is operably joined to the promoter sequence, wherein the signal sequence, when transcribed by the RNA polymerase, is detectable in some manner; and 2. joining the transcription signaling system, either covalently or non-covalently, to an analyte-binding substance, wherein the joining to the analyte-binding substance is not affected by the conditions of the assay and wherein the joining to the analyte-binding substance does not affect the ability of the transcription signaling system to be transcribed using the RNA polymerase under transcription conditions;

3. contacting the analyte-binding substance to which the transcription signaling system is joined with a sample under binding conditions, wherein the analyte, if present in the sample, binds to the analyte-binding substance so as to form a specific binding pair; and 4. removing the specific binding pair from the sample so as to separate it from other components in the sample; and 5. incubating the specific-binding pair under transcription conditions with an RNA polymerase, wherein the RNA polymerase can synthesize a transcription product that is complementary to the signal sequence in the ssDNA transcription signaling system under the transcription conditions;

6. obtaining a transcription product that is complementary to the signal sequence in the ssDNA transcription signaling system; and 7. detecting the transcription product or a substance that results from the transcription product.

This method of the invention can be used for a broad range of analytes and analyte-binding substances. By way of example, but not of limitation, the analyte can be an antigen and the analyte-binding substance can be antibody, or the analyte can be a nucleic acid and the analyte-binding substance can be another complementary nucleic acid. As discussed below, a large number of other substances exist for which a specific-binding pair can be found, all of which are within the scope of the invention.

In order to detect an analyte in a sample, an assay of this aspect of the invention uses an analyte-binding substance that "binds" to the analyte under "binding conditions." The analyte-binding substance, which can also be referred to as an "affinity molecule," an "affinity substance," a "specific binding substance," or a "binding molecule" for the analyte, is in turn detected by making a transcription product using a transcription signaling system that is joined to the analyte-binding substance. The transcription signaling system comprises a single-stranded promoter that is operably joined to a single-stranded signal sequence, wherein transcription of the signal sequence by an RNA polymerase that can use the single-stranded signaling system results in a transcription product that is detectable by some means, as discussed below.

1. Analytes and Analyte-Binding Substances for Assays in which an RNA Polymerase that Recognizes a Single-Stranded Promoter Is Used as a Signaling System An "analyte" or an "analyte-binding substance" of this aspect of the invention can be any of those described in U.S. Pat. No.6,562,575 of one of the present inventors, which is entitled "Analyte-Specific Assays Based on Formation of a Replicase Substrate," and which is incorporated herein in its entirety by reference so as to be made part of the present invention. An analyte can be any substance whose presence, concentration or amount in a sample is determined in an assay. By way of example, but not of limitation, an analyte can be a biochemical molecule or a biopolymer or a segment of a biopolymer, such as a protein or peptide, including a glycoprotein or lipoprotein, an enzyme, hormone, receptor, antigen or antibody, nucleic acid (DNA or RNA), polysaccharide, or lipid.

An analyte-binding substance that is a nucleic acid, polynucleotide, oligonucleotide or a segment of a nucleic acid or polynucleotide, including nucleic acids composed of either DNA or RNA, or both DNA and RNA mononucleosides, including modified DNA or RNA mononucleosides, can also be used according to the invention to detect an analyte that does not comprise nucleic acid. For example, a method termed "SELEX," as described by Gold and Tuerk in U.S. Pat. No. 5,270,163, can be used to select a nucleic acid for use as an analyte-binding substance according to the invention. SELEX permits selection of a nucleic acid molecule that has high affinity for a specific analyte from a large population of nucleic acid molecules, at least a portion of which have a randomized sequence. For example, a population of all possible randomized 25-mer oligonucleotides (i.e., having each of four possible nucleic acid bases at every position) will contain $4^{25}$ (or $10^{15}$) different nucleic acid molecules, each of which has a different three-dimensional structure and different analyte binding properties. SELEX can be used, according to the methods described in U.S. Pat. Nos. 5,270,163; 5,567,588; 5,580,737; 5,587,468; 5,683,867; 5,696,249; 5723,594; 5,773,598; 5,817,785; 5,861,254; 5,958,691; 5,998,142; 6,001,577; 6,013,443; and 6,030,776, incorporated herein by reference, in order to select an analyte-binding nucleic acid with high affinity for a specific analyte that is not a nucleic acid or polynucleotide. Once selected using SELEX, nucleic acid affinity molecules can be made by any of numerous known in vivo or in vitro techniques, including, by way of example, but not of limitation, automated nucleic acid synthesis techniques, PCR, or in vitro transcription.

Naturally occurring nucleic acid or polynucleotide sequences that have affinity for other naturally occurring molecules such as, but not limited to, protein molecules, are also known in the art. Examples include, but are not limited to certain nucleic acid sequences such as operators, promoters, origins of replication, sequences recognized by steroid hormone-receptor complexes, restriction endonuclease recognition sequences, ribosomal nucleic acids, and so on, which are known to bind tightly to certain proteins. For example, in two well-known systems, the lac repressor and the bacteriophage lambda repressor each bind to their respective specific nucleic acid sequences called "operators" to block initiation of transcription of their corresponding mRNA molecules. Nucleic acids containing such specific sequences can be used in the invention as analyte-binding substances for the respective proteins or other molecules for which the nucleic acid has affinity. In these cases, the nucleic acid with the specific sequence can be used according to this aspect of the invention as the analyte-binding substance for the respective specific protein, glycoprotein, lipoprotein, small molecule or other analyte that it binds. One of several techniques which are generally called "footprinting" (e.g., see Galas, D. and Schmitz, A, *Nucleic Acids Res.* 5:3161, 1978) can be used to identify sequences of nucleic acids which bind to a protein. Other methods are also known to those with skill in the art and can be used to identify nucleic acid sequences for use as specific analyte-binding substances for use in the invention.

A peptide nucleic acid (PNA) or a molecule comprising both a nucleic acid and a PNA can also be used according to the invention as an analyte-binding substance for an analyte that is a nucleic acid or polynucleotide. PNA as an analyte-binding substance of the invention provides tighter binding (and greater binding stability) in assays for a nucleic acid analyte (e.g., see U.S. Pat. No. 5,985,563). Also, since PNA is not naturally occurring, PNA molecules are highly resistant to protease and nuclease activity. Antibodies to PNA/DNA or PNA/RNA complexes can be used in the invention for capture, recognition, detection, identification, or quantitation of nucleic acids in biological samples, via their ability to bind specifically to the respective complexes without binding the individual molecules (U.S. Pat. No. 5,612,458).

The invention also contemplates that a combinatorial library of randomized peptide nucleic acids prepared by a method such as, but not limited to, the methods described in U.S. Pat. Nos. 5,539,083; 5,831,014; and 5,864,010, can be used to prepare analyte-binding substances for use in assays for analytes of all types, including analytes that are nucleic acids, proteins, or other analytes, without limit. As is the case for the SELEX method with nucleic acids, randomized peptide or peptide nucleic acid libraries are made to contain molecules with a very large number of different binding affinities for an analyte. After selection of an appropriate affinity molecule for an analyte from a library, the selected affinity molecule can be used in the invention as an analyte-binding substance.

An analyte-binding substance can also be an oligonucleotide or polynucleotide with a modified backbone that is not an amino acid, such as, but not limited to modified oligonucleotides described in U.S. Pat. Nos. 5,602,240; 6,610,289; 5,696,253; or 6,013,785.

The invention also contemplates that an analyte-binding substance can be prepared from a combinatorial library of randomized peptides (i.e., comprising at least four naturally-occurring amino acids). One way to prepare the randomized peptide library is to place a randomized DNA sequence, prepared as for SELEX, downstream of a phage T7 RNA polymerase promoter, or a similar promoter, and then use a method such as, but not limited to, coupled transcription-translation, as described in U.S. Pat. Nos. 5,324,637; 5,492,817; or 5,665,563, or stepwise transcription, followed by translation. Alternatively, a randomized DNA sequence, prepared as for SELEX, can be cloned into a site in a DNA vector that, once inserted, encodes a recombinant MDV-1 RNA containing the randomized sequence that is replicatable by Q-beta replicase (e.g., between nucleotides 63 and 64 in MDV-1 (+) RNA; see U.S. Pat. No. 5,620,870). The recombinant MDV-1 DNA containing the randomized DNA sequence is downstream from a T7 RNA polymerase promoter or a similar promoter in the DNA vector. Then, following transcription, the recombinant MDV-1 RNA, containing the randomized sequence can be used to make a randomized peptide library comprising at least four naturally-occurring amino acids by coupled replication-translation as described in U.S. Pat. No. 5,556,769. An analyte-binding substance can be selected from the library by binding peptides in the library to an analyte, separating the unbound peptides, and identifying one or more peptides that is bound to analyte by means known in the art. Alternatively, high throughput screening methods can be used to screen all individual peptides in the library to identify those which can be used as analyte-binding substances. Although the identification of an analyte-binding peptide by these methods is difficult and tedious, the methods in the art are improving for doing so, and the expenditure of time and effort required may be warranted for identifying analyte-binding substances for use in assays of the invention that will be used routinely in large numbers.

A variety of other analyte-binding substances can also be used in methods for this aspect of the invention.

For an antigen analyte (which itself may be an antibody), antibodies, including monoclonal antibodies, are available as analyte-binding substances. For certain antibody analytes in samples which include only one antibody, an antibody binding protein such as *Staphylococcus aureus* Protein A can be employed as an analyte-binding substance.

For an analyte, such as a glycoprotein or class of glycoproteins, or a polysaccharide or class of polysaccharides, which is distinguished from other substances in a sample by having a carbohydrate moiety which is bound specifically by a lectin, a suitable analyte-binding substance is the lectin.

For an analyte which is a hormone, a receptor for the hormone can be employed as an analyte-binding substance. Conversely, for an analyte which is a receptor for a hormone, the hormone can be employed as the analyte-binding substance.

For an analyte which is an enzyme, an inhibitor of the enzyme can be employed as an analyte-binding substance. For an analyte which is an inhibitor of an enzyme, the enzyme can be employed as the analyte-binding substance.

Usually, an analyte molecule and an affinity molecule for the analyte molecule are related as a specific "binding pair", i.e., their interaction is only through non-covalent bonds such as hydrogen-bonding, hydrophobic interactions (including stacking of aromatic molecules), van der Waals forces, and salt bridges. Without being bound by theory, it is believed in the art that these kinds of non-covalent bonds result in binding, in part due to complementary shapes or structures of the molecules involved in the binding pair.

The term "binding" according to this aspect of the invention refers to the interaction between an analyte-binding substance or affinity molecule and an analyte as a result of non-covalent bonds, such as, but not limited to, hydrogen bonds, hydrophobic interactions, van der Waals bonds, and ionic bonds.

Based on the definition for "binding," and the wide variety of affinity molecules and analytes which can be used in the invention, it is clear that "binding conditions" vary for different specific binding pairs. Those skilled in the art can easily determine conditions whereby, in a sample, binding occurs between affinity molecule and analyte that may be present. In particular, those skilled in the art can easily determine conditions whereby binding between affinity molecule and analyte, which would be considered in the art to be "specific binding," can be made to occur. As understood in the art, such specificity is usually due to the higher affinity of affinity molecule for analyte than for other substances and components (e.g., vessel walls, solid supports) in a sample. In certain cases, the specificity might also involve, or might be due to, a significantly more rapid association of affinity molecule with analyte than with other substances and components in a sample.

"Hybridization" is the term used to refer to the process of incubating an affinity molecule comprising a nucleic acid, or a peptide nucleic acid (PNA) molecule, or a covalently linked, joined or attached nucleic acid-PNA molecule with an analyte comprising a nucleic acid under "binding conditions," which are also called "hybridization conditions." The ability of two polymers of nucleic acid containing complementary sequences to find each other and anneal through base pairing interaction is a well-recognized phenomenon. The initial observations of the "hybridization" process by Marmur and Lane (*Proc. Nat. Acad. Sci. USA* 46:453, 1960) and Doty, et al. (*Proc. Nat. Acad. Sci. USA* 46:461, 1960) have been followed by the refinement of this process into an essential tool of modern biology. "Hybridization" also refers to the "binding" or "pairing" of complementary nucleic acid bases in a single-stranded nucleic acid, PNA, or linked nucleic acid-PNA affinity molecule with a single-stranded nucleic acid analyte, which occurs according to base pairing rules (e.g., adenine pairs with thymine or uracil and guanine pairs with cytosine). Those with skill in the art will be able to develop and make conditions which comprise binding conditions or hybridization conditions for particular nucleic acid analytes of an assay. In developing and making binding conditions for particular nucleic acid analytes analyte-binding substances, as well as in developing and making hybridization conditions for particular analytes and capture probes, certain additives can be added in the hybridization solution. By way of example, but not of limitation, dextran sulfate or polyethylene glycol can be added to accelerate the rate of hybridization (e.g., Chapter 9, Sambrook, et al., Molecular Cloning: A Laboratory Manual, 2nd Edition, Cold Spring Harbor Laboratory Press, 1989), or betaine can be added to the hybridization solution to eliminate the dependence of $T_m$ on basepair composition (Rees, W. A., et al., *Biochemistry* 32:137-144, 1993).

The terms "degree of homology" or "degree of complementarity" are used to refer to the extent or frequency at which the nucleic acid bases on one strand (e.g., of the affinity molecule) are "complementary with" or "able to pair" with the nucleic acid bases on the other strand (e.g., the analyte). Complementarity may be "partial," meaning only some of the nucleic acid bases are matched according to base pairing rules, or complementarity may be "complete" or "total." The length (i.e., the number of nucleic acid bases comprising the nucleic acid and/or PNA affinity molecule and the nucleic acid analyte), and the degree of "homology" or "complementarity" between the affinity molecule and the analyte have significant effects on the efficiency and strength of binding or hybridization when the nucleic acid bases on the affinity molecule are maximally "bound" or "hybridized" to the nucleic acid bases on the analyte. The terms "melting temperature" or "$T_m$" are used as an indication of the degree of complementarity. The $T_m$ is the temperature at which a population of double-stranded nucleic acid molecules becomes half dissociated into single strands under defined conditions. Based on the assumption that a nucleic acid molecule that is used in hybridization will be approximately completely homologous or complementary to a target polynucleotide, equations have been developed for estimating the $T_m$ for a given single-stranded sequence that is hybridized or "annealed" to a complementary sequence. For example, a common equation used in the art for oligodeoxynucleotides is: $T_m$=81.5° C.+0.41 (% G+C) when the nucleic acid is in an aqueous solution containing 1 M NaCl (see e.g., Anderson and Young, Quantitative Filter Hybridization, in Nucleic Acid Hybridization, 1985). Other more sophisticated equations available for nucleic acids take nearest neighbor and other structural effects into account for calculation of the $T_m$. Binding is generally stronger for PNA affinity molecules than for nucleic acid affinity molecules. For example the $T_m$ of 10-mer homothymidine PNA binding to its complementary 10-mer homoadenosine DNA is 73° C., whereas the $T_m$ for the corresponding 10-mer homothymidine DNA to the same complementary 10-mer homoadenosine DNA is only 23° C. Equations for calculating the $T_m$ for a nucleic acid are not appropriate for PNA. Preferably, a $T_m$ that is calculated using an equation in the art, is checked empirically and the hybridization or binding conditions are adjusted by empirically raising or lowering the stringency of hybridization as appropriate for a particular assay. As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids that are not completely complementary to one another be hybridized or annealed together.

With regard to complementarity, it is important for some assays of the invention to determine whether the hybridization represents complete or partial complementarity. For example, where it is desired to detect simply the presence or absence of pathogen DNA (such as from a virus, bacterium, fungi, mycoplasma, protozoan), it is only important that the hybridization method ensures hybridization when the relevant sequence is present. In those embodiments of the invention, conditions can be selected where both partially complementary probes and completely complementary probes will hybridize.

2. Signal Sequences for Use in Signaling Systems

The methods for using RNA polymerases of the invention as a signaling system are also not limited to the signal sequences, which can vary greatly. By way of example, but not of limitation, a signal sequence can comprise a substrate for Q-beta replicase, which is detectable in the presence of the replicase under replication conditions. It can also comprise a sequence that encodes a protein, such as green fluorescent protein, that is detectable following translation of the signal sequence. Without limitation, it can also comprise a sequence that is detectable by a probe, such as, but not limited to a molecular beacon, as described by Tyagi et al. (U.S. Pat. Nos. 5,925,517 and 6,103,476 of Tyagi et al. and U.S. Pat. No. 6,461,817 of Alland et al., all of which are incorporated herein by reference).

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of a Transcriptionally Active Domain of N4 Virion RNA Polymerase To determine the minimal domain possessing RNA polymerase activity, controlled proteolysis was performed followed by catalytic (transcriptional) autolabeling (Hartmann, et al., 1988). Upon incubation of RNA polymerase with a benzaldehyde derivative of the initiating nucleotide, the benzaldehyde group forms a Schiff-base with the ϵ-amino group of lysines located within 12 Å of the nucleotide-binding site. The crosslinking step was performed in the presence of DNA template because it stimulates binding of the initiating nucleotide. The unstable Schiff-base is converted to a stable secondary amine by reduction under mild conditions with sodium borohydride, with concomitant reduction of any non-reacted benzaldehyde derivative. Addition of the next template-directed $\alpha$-$^{32}$P labeled NTP leads to phosphodiester bond formation and catalytic autolabeling of the transcriptionally active polypeptide. Controlled trypsin proteolysis of vRNAP was performed, followed by catalytic autolabeling and analysis on SDS-PAGE (FIG. 3A). Initially, three proteolytic fragments are generated, of which the smaller two are catalytically active. Upon further incubation with trypsin, a single stable, transcriptionally active product approximately 1,100 amino acids in length remains. N-terminal sequencing of the three initial proteolytic fragments (FIG. 3B) indicated that the stable active polypeptide (mini-vRNAP) corresponds to the middle ⅓ of vRNAP, the region containing the three motifs described above (FIG. 2A, SEQ ID NOS:3-4).

Example 2

Cloning and Purification of N4 mini-vRNAP

Figure 4:
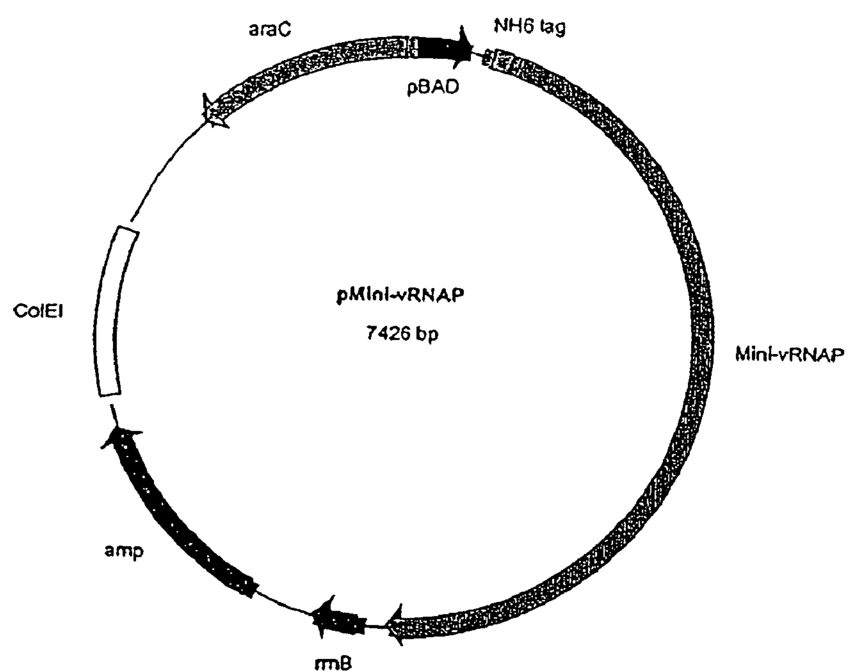
FIG. 4—ORFs for full length polymerase, mini-vRNAP and mutants thereof were cloned under pBAD control with an N-terminal hexahistidine tag. In other experiments, ORFs for mini-vRNAP and the Y678F mutant thereof, both of which lacked an N-terminal hexahistidine tag, were cloned in *E. coli* under pT7 control in cells which inducibly express T7 RNAP; the polypeptides obtained showed similar activities to the polypeptides with hexahistidine tags shown in this figure.
Figure 5:
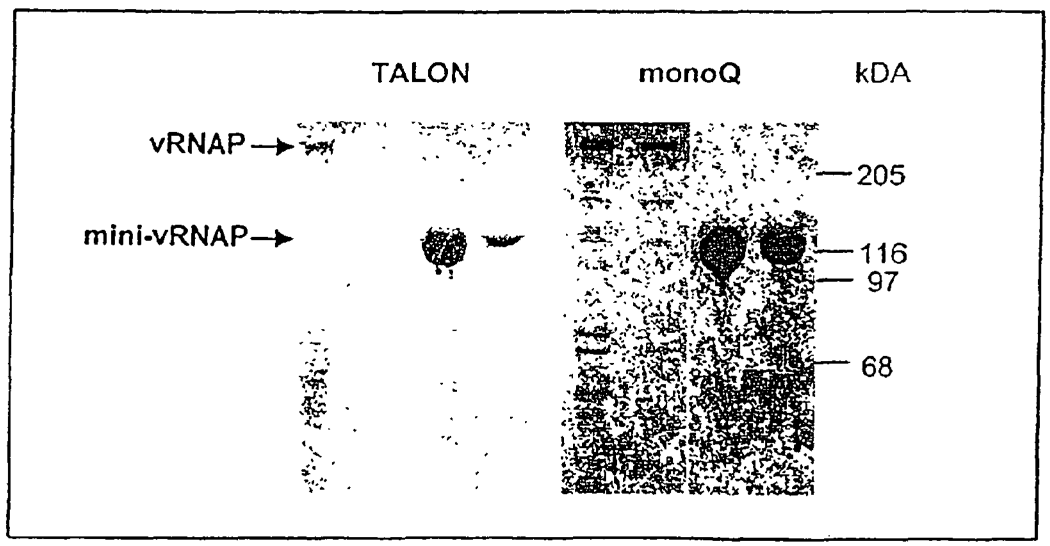
FIG. 5—Purification of cloned vRNAP and mini-vRNAP. The left hand side shows the relative amounts of full size and mini-vRNAP proteins purified on TALON columns from the same volume of induced cells. Further concentration on a monoQ column reveals that, in contrast to full size vRNAP, mini-vRNAP is stable after induction (right).

The full-size vRNAP and the mini-vRNAP (SEQ ID NOS:6 and 15) ORFs were cloned under pBAD control with an N-terminal hexahistidine tag (FIG. 4). The mini-vRNAP domain was cloned into the pBAD B expression plasmid, which was purchased from Invitrogen. Five restriction enzyme sites within pBAD B have been altered; the SnaI site was converted to a HpaI site, and the PflMI and EcoRV sites were destroyed, all by site-directed mutagenesis. The BstBI and HindIII sites were destroyed by enzyme digestion followed by Klenow treatment and re-ligation. FIG. 5 (left) shows the relative amounts of full-length and mini-vRNAP proteins purified on TALON columns from the same volume of *E. coli* BL21 induced cells. Cloned mini-vRNAP is expressed at 100-fold higher levels than cloned full size vRNAP. Further concentration on a MonoQ column reveals that, in contrast to full size vRNAP, mini-vRNAP is stable after induction (FIG. 5, right). At least 10 mg of mini-vRNAP at a 20 mg/ml concentration are obtained from 1 L of induced cells in just two purification steps: TALON and MonoQ mini-columns. A non-histagged version of mini-vRNAP has also been cloned (SEQ ID NO:4). In this case, the enzyme is purified from a crude extract of induced cells in two steps: a promoter DNA-affinity column and MonoQ.

Mini-vRNAP possesses a high binding affinity (Kd=1 nM) for N4 promoter-containing DNA oligonucleotides. This property was used for purification of non-his tagged mini-vRNAP (SEQ ID NO:4) on a DNA-affinity column. The column was prepared by adsorbing a 5' biotinylated N4 promoter-containing DNA oligonucleotide onto the matrix of a 1 ml HiTrap Streptavidin column (Pharmacia/Amersham Cat.#17-5112-01) according to the manufacturer's instructions. A debris-free sonicate of bacterial cells expressing mini-vRNAP was passed through the column. To bind mini vRNAP to the DNA-affinity column, the pH in the extract and binding/washing buffer should be between 5 to 9, and the NaCl concentration should be between 50 mM and 2M. Nucleases in the extract are inhibited by addition of 2 mM EDTA. After washing the column, mini-vRNAP was eluted with warm (25° C.) water; the elution temperature was raised from 4° C. to 25° C. to increase mini-vRNAP recovery. For complete elution, the temperature can be raised up to 43° C. without significant change in the quality of the preparation. Elution under these conditions occurs due to the removal of metal ions and consequent melting of the promoter hairpin and dissociation of mini-vRNAP. Different DNA oligonucleotides containing variants of the P2 promoter (SEQ ID NOS: 16-19), were used in DNA-affinity columns and tested in mini-vRNAP affinity purification. The best yield was achieved using the DNA oligonucleotide of SEQ ID NO:16. However, the DNA oligonucleotides of SEQ ID NOS:19-20 require a lower temperature than the DNA oligonucleotide of SEQ ID NO:16 for complete elution of the protein, in agreement with the lower thermal stability of the respective promoter hairpins.

Up to 1 mg of mini-vRNAP of 90% purity is obtained from a crude extract of 100 ml *E. coli* culture expressing mini-vRNAP in a single purification step using a 1 ml DNA-affinity column. The binding capacity of the DNA-affinity column was not detectably decreased by multiple use.

Example 3

Effect of EcoSSB on Transcription of Single-Stranded Templates

Figure 6:
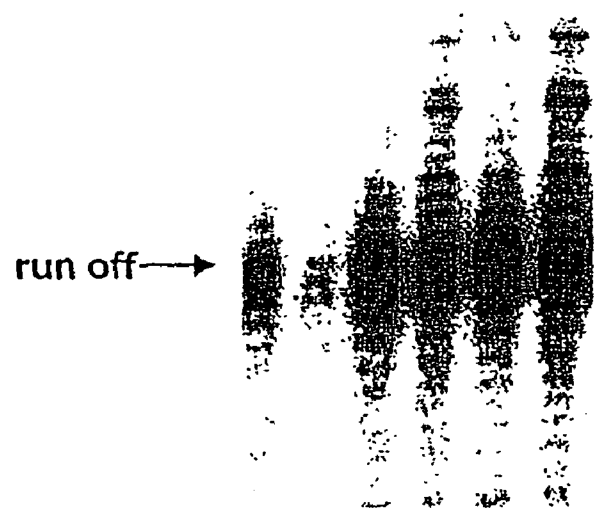
FIG. 6—Activation of N4 vRNAP transcription by EcoSSB at three different ssDNA concentrations. The extent of EcoSSB activation is template-concentration dependent, with highest activation at low DNA template concentration.

Inventors have previously shown that EcoSSB is required for N4 vRNAP transcription in vivo (Glucksmann, et al., Cell 70:491-500, 1992). EcoSSB is unique in that, unlike other SSBs whose effect on vRNAP transcription was tested, it does not melt the promoter hairpin structure (Glucksmann-Kuis, et al., Cell 84:147-154, 1996). Recently, inventors have reinvestigated the effect of EcoSSB on vRNAP transcription of single-stranded templates. FIG. 6 shows transcription in the absence and presence of Eco SSB at three different ssDNA template concentrations. The extent of EcoSSB activation is template-concentration dependent, with highest activation at low DNA template concentration. These results suggest that EcoSSB overcomes template limitation on ssDNA templates.

Figure 7:
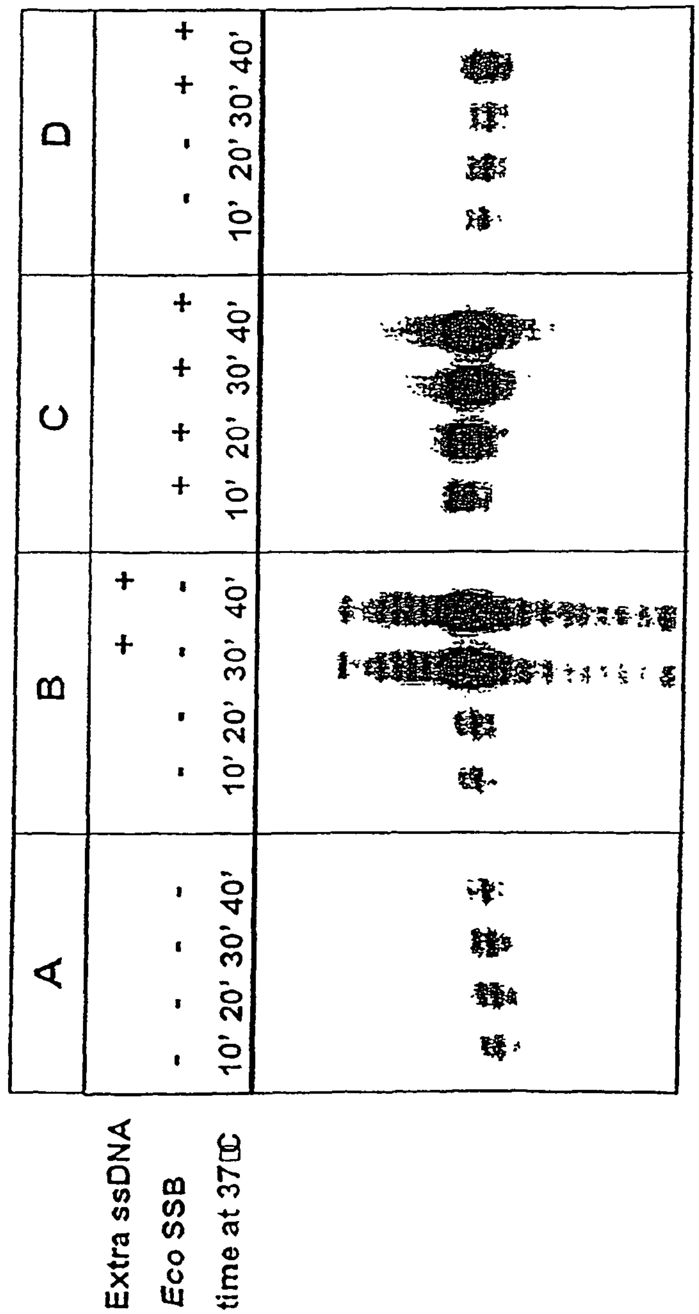
FIG. 7A, FIG. 7B, FIG. 7C, and FIG. 7D—Effect of EcoSSB on ssDNA template recycling. In the absence of EcoSSB, no increase in transcription was observed beyond 10 min of incubation (FIG. 7A). Addition of template at 20 min to the reaction carried out in the absence of EcoSSB led to a dramatic increase in RNA synthesis (FIG. 7B). RNA synthesis increased linearly throughout the period of incubation (FIG. 7C). Addition of EcoSSB at 20 min led to a slow rate of transcriptional recovery (FIG. 7D).

To further explore this hypothesis, the effect of addition of template or EcoSSB to transcription reactions after 20 min incubation in the absence of EcoSSB was tested. The transcription reaction mixtures (5-50 μl) contained 20 mM Tris-HCl (pH 7.9 at 25° C.), 10 mM $MgCl_2$, 50 mM NaCl, 1 mM dithiothreitol, 0.01-1 μM mini-vRNAP, 1-100 nM ssDNA template (30-100 nt long, synthesized by Integrated DNA Technologies), 1 mM each of 3 non-labeled NTPs, 0.1 mM $\alpha$-$^{32}$P NTP (1-2 Ci/mmol, NEN), and 1-10 μM *E. coli* SSB. Incubation was for 1 to 80 min at 37° C. at the indicated temperature. In the presence of EcoSSB, RNA synthesis increased linearly throughout the period of incubation (FIG. 7C). In the absence of EcoSSB, no increase in transcription was observed beyond 10 min of incubation (FIG. 7A). Addition of template at 20 min to the reaction carried out in the absence of EcoSSB led to a dramatic increase in RNA synthesis (FIG. 7B). Addition of EcoSSB at 20 min led to a slow rate of transcriptional recovery (FIG. 7D). These results suggest that EcoSSB converts the template from a transcriptionally inactive RNA:DNA hybrid to transcriptionally active single-stranded DNA.

To test this hypothesis, the physical states of the DNA template and the RNA product were analyzed by native gel electrophoresis in the absence and in the presence of EcoSSB. In order to have effective transcription in the absence of EcoSSB, transcription was performed at an intermediate (5 nM) DNA concentration, at which only a 2-fold effect of EcoSSB is observed.

Figure 8:
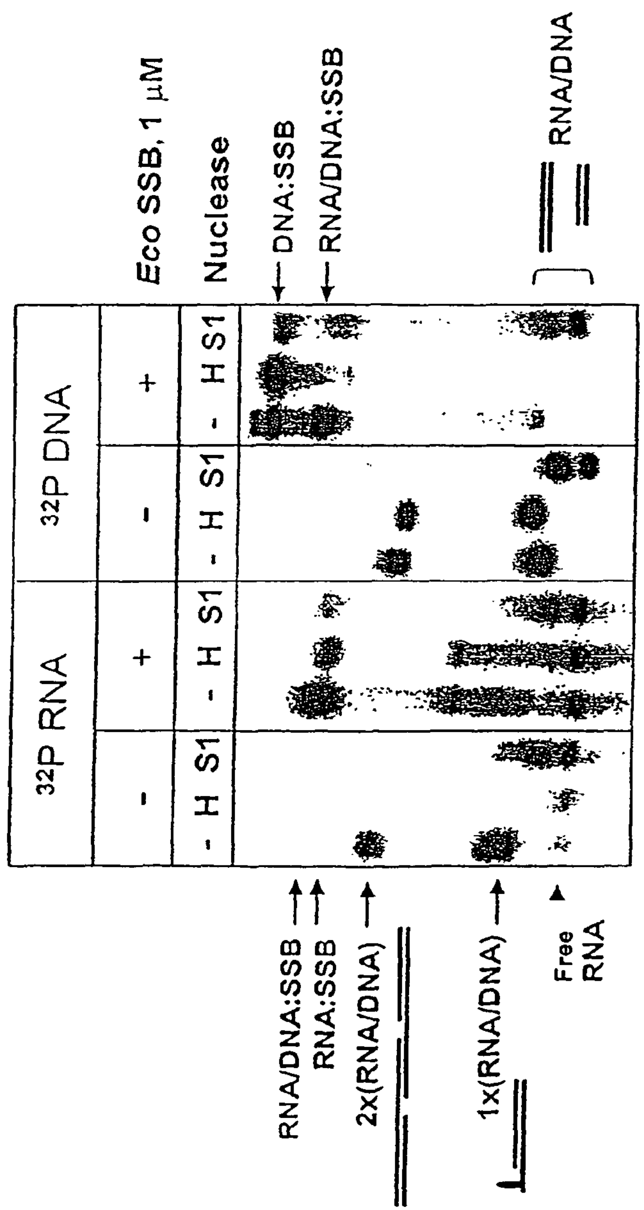
FIG. 8—Effect of EcoSSB on the state of template DNA and product RNA in vRNAP transcription. Native gel electrophoresis was carried out in the absence and in the presence of EcoSSB. Transcription was performed at an intermediate (5 nM) DNA concentration, at which only a 2-fold effect of EcoSSB is observed. Either $^{32}P$-labeled template (right panel) or labeled NTPs (left panel) were used to analyze the state of the template (right panel) or RNA product (left panel) in the absence or presence of EcoSSB.

The results of this experiment are shown in FIG. 8. Either $^{32}$P-labeled template (right panel) or labeled NTPs (left panel) were used to analyze the state of the template (right panel) or RNA product (left panel) in the absence or presence of EcoSSB. After transcription, the mixtures were split further into 3 samples: a control sample with no additions, a sample to which RNase H was added to specifically degrade RNA in RNA:DNA hybrids, and a third sample to which Nuclease S1 was added to degrade single-stranded nucleic acids. In the absence of EcoSSB, both the DNA template and the RNA product are in RNA:DNA hybrids, since the RNA product is RNase H sensitive while the DNA-containing bands show altered mobility after RNase H treatment. In the presence of EcoSSB, a significant portion of the RNA product is RNase H resistant and therefore free, although an RNase sensitive band is present that corresponds to an intermediate RNA:DNA:SSB complex. Under these conditions, the DNA is in an SSB:DNA complex. These results indicate that EcoSSB stimulates transcription through template recycling.

To define regions of EcoSSB essential for vRNAP transcription activation on single-stranded templates, the inventors have tested the effect of human mitochondrial SSB (HmtSSB), which shows extensive sequence and structural homology to EcoSSB. The N-terminus of EcoSSB contains DNA binding and tetramerization determinants while the C-terminus is involved in interaction with other replication proteins. Hmt SSB has no effect on vRNAP transcription although it does not melt the promoter hairpin. Interestingly, preliminary results using mutant EcoSSBs and EcoSSB-Hmt SSB chimeras suggest that the C-terminal region of EcoSSB is essential for vRNAP transcriptional activation.

Example 4

Characterization of mini-vRNAP Transcription Properties

Figure 9:
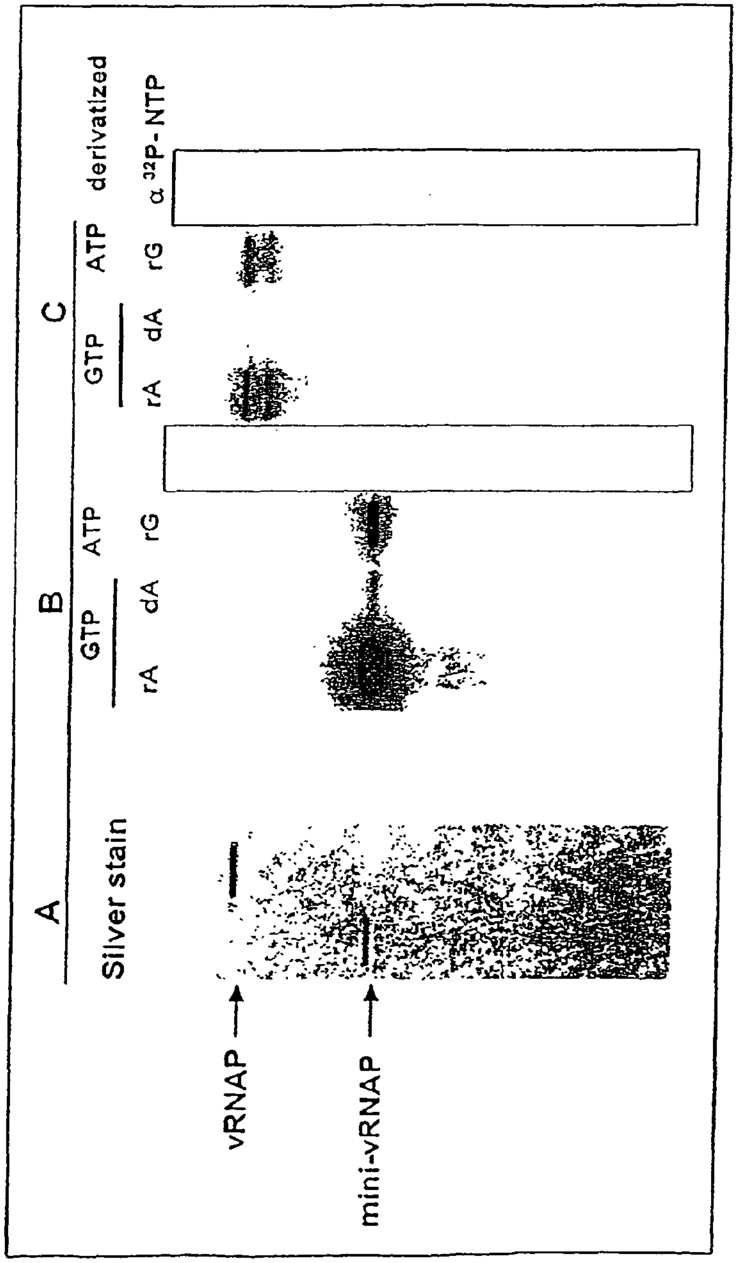
FIG. 9A, FIG. 9B, and FIG. 9C—Transcription initiation by vRNAP and mini-vRNAP. The initiation properties of the full length and mini-vRNA polymerases were compared at similar molar concentrations (FIG. 9A) using the catalytic autolabeling assay and two reaction conditions: using a template containing +1C, the benzaldehyde derivative of GTP and $\alpha$-$^{32}P$-ATP, or a template containing +1T, the benzaldehyde derivative of ATP and $\alpha$-$^{32}P$-GTP. Comparison of the results in FIGS. 9B and 9C demonstrates that mini-vRNAP exhibits initiation properties similar to full size vRNAP.

The initiation properties of the full length RNA polymerase and mini-vRNAP were compared at similar molar concentrations (FIG. 9A) using the catalytic autolabeling assay and two reaction conditions: 1-using a template containing +1C, the benzaldehyde derivative of GTP and $\alpha^2$P-ATP, or 2-a template containing +1T, the benzaldehyde derivative of ATP and $\alpha^2$P-GTP. Comparison of the results in FIGS. 9B and 9C demonstrates that mini-vRNAP exhibits initiation properties similar to full-length vRNAP. In addition, both enzymes discriminate against dATP incorporation to the same extent. Mini-vRNAP does not synthesize abortive products when the first four nucleotides of the transcript are comprised of 50% or more G or C nucleotides.

Figure 10:
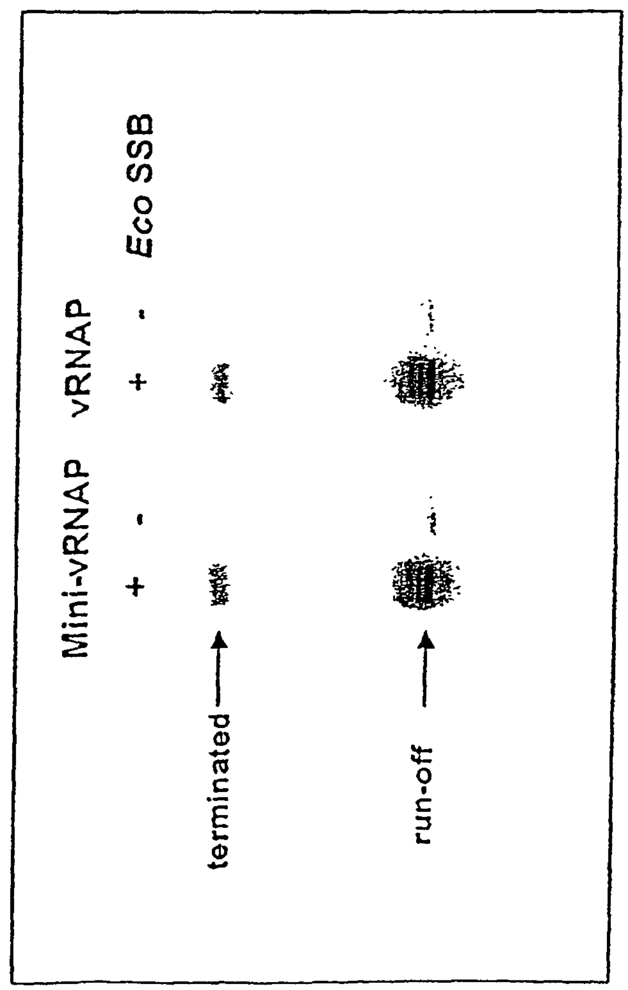
FIG. 10—Effect of EcoSSB on transcription of vRNAP and mini-vRNAP. The elongation and termination properties of vRNAP and mini-vRNAP are compared.

The elongation and termination properties of both enzymes are compared in FIG. 10. Similar run-off and terminated transcripts are synthesized. Moreover, EcoSSB activates transcription by both enzymes to the same levels. This result indicates that, if there are any sites of specific contact between vRNAP and EcoSSB, they reside in the mini-vRNAP domain.

The sequence of the terminator signals for vRNAP present in the N4 genome include SEQ ID NOS:21-26. The signals of SEQ ID NO:21 and 22 have been tested in vitro on single-stranded templates.

The rate of mini-vRNAP transcription has been compared to the rate of T7 RNA polymerase under the same conditions using the same DNA template. The template used was linearized pET11 containing the original T7 promoter and the N4 vRNAP P2 promoter that was introduced through cloning. The DNA template was denatured before performing transcription using N4 mini-vRNAP. The concentrations of T7 RNAP (Promega, Cat.#P2075) and mini-vRNAP were compared using SDS-PAGE. Transcription reactions contained 50 nM of polymerase, 100 nM of DNA template, 5× transcription buffer provided with the T7 RNAP, and 1 mM of each ATP, GTP and CTP and 0.1 mM of [$^{32}$P]-UTP (1 Ci/mmol). Each reaction mixture was split in two, and *E. coli* SSB was added to one half. The mixtures were incubated at 37° C. and aliquots were taken at different time points. Transcription products were electrophoresed on a 6% sequencing gel and the amount of radioactively-labeled RNA was quantitated by phosphoimaging. The results showed that: (a) transcription of T7 RNAP was not affected by the presence of *E. coli* SSB and (b) N4 mini-vRNAP synthesized 1.5 to 5 fold more RNA in the presence of EcoSSB than T7 RNAP at different time points of incubation.

The optimal temperature for mini-vRNAP transcription is 37° C. It exhibits 70% activity at 30° C., 65% at 45° C., and only 20% at 50° C.

The average error frequency was estimated by determining the misincorporation frequency of each of four [$^{32}$P]-α NTPs into RNA products using template ssDNAs missing the corresponding template nucleotide in the transcribed region. The following values were obtained: $1/5\times10^4$ for misincorporation of G and U using "no C" (SEQ ID NO:10) and "no A" (SEQ ID NO:11) ssDNA templates, respectively; $1/4\times10^4$ for misincorporation of C using the "no G" (SEQ ID NO: 12) template, and $1/2\times.\ 10^4$ for misincorporation of A using the "no T" (SEQ ID NO:13) template. For comparison, the average error frequency for T7 RNAP is $1/2\times10^4$ (Huang, et al., 2000). Using the method for detection of mispair formation described by Huang, et al. (2000), no misincorporation by mini-vRNAP was detected.

The ability of mini-vRNAP to incorporate derivatized nucleotides was measured. Transcription by mini-vRNAP in the presence of 0.1-1 mM Digoxigenin-11-UTP (cat#1209256, Roche), Biotin-16-UTP (cat#1388908, Roche) or underivatized UTP, yielded comparable amounts of product RNA using "control" ssDNA (SEQ ID NO:9) as a transcription template. The product RNAs synthesized in the presence of derivatized UTP have higher molecular mass than those synthesized in the presence of underivatized UTP, and the difference corresponds to the mass difference of the UTPs used. Several derivatives (i.e. 2'Fluoro-ribonucleoside triphosphates, dideoxynucleoside triphosphates) are being tested. The fluorescent analog Fluorescein-12-UTP (Roche catalog #1427857) has been tested using a template which encodes a 51 nucleotide transcript containing a run of 4 Us, and a nucleotide mix containing ATP, CTP, GTP and Fluorescein-12-UTP only. Transcription was only 3% of that achieved with UTP, biotin-6-UTP or digoxigenin-1 1-UTP under the same reaction conditions. However, incorporation of the fluorescent analog at higher yields is expected to occur in the presence of underivatized UTP or on templates with other sequence compositions.

Example 5

Sequence Determinants of mini-vRNAP Promoter Binding

The three N4 early promoters present in the N4 genome contain a pair of Cs separated by 4 nucleotides from the base of the 5 bp promoter stem. In the preferred promoter P2, these 4 bases are As and the Cs are followed by a T. Preferably, mini-vRNAP uses a 17 nucleotide promoter sequence located immediately upstream of the transcription initiation site. Promoters for N4 vRNA polymerase are described by Haynes et al., Cell 41:597-605 (1985) and Dai et al., Genes Devepmnt. 12:2782-2790 (1998), herein incorporated by reference. vRNAP-promoter recognition and activity require specific sequences and a hairpin structure on the template strand. The vRNAP promoters of SEQ ID NOS:27-29 assume a hairpin structure comprised of a 5-7 bp stem and 3 b purine-containing loop. The −11 position corresponds to the center of the loop; +1 indicates the transcription start site. Thus, promoter sequences of the invention include, but are not limited to:

```
                                SEQ ID NO: 27
-11 +1 P1   3'-CAACGAAGCGTTGAATACCT-5'

                                SEQ ID NO: 28
-11 +1 P2   3'-TTCTTCGAGGCGAAGAAAACCT-5', and

                                SEQ ID NO: 29
-11 +1 P3   3'-CGACGAGGCGTCGAAAACCA-5'
```

Other possible vRNAP promoters of the current invention include a set of any inverted repeats forming a hairpin with a 2-7 bp long stem and 3-5 b loop having purines in the central and/or next to the central position of the loop.

Figure 11:
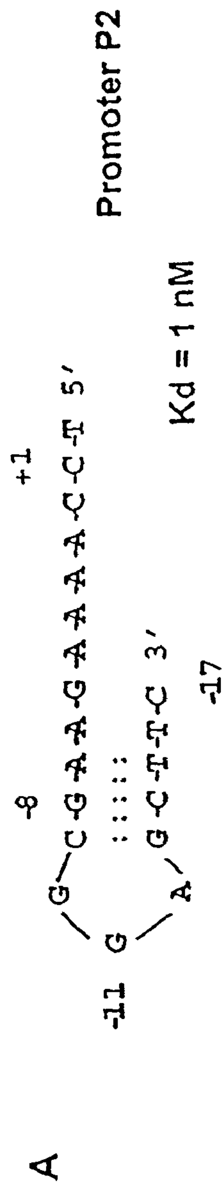
FIG. 11A and FIG. 11B—Determination of mini-vRNAP promoter contacts. A 20-base oligonucleotide (SEQ ID NO:30) containing wild type promoter P2 sequence binds with a 1 nM Kd (FIG. 11A). Most oligonucleotides substituted with 5-Iodo-dU at specific positions showed close to wild type affinity except for the oligonucleotides substituted at positions −11 (at the center of the loop) and −8, indicating that these positions are essential for promoter recognition (FIG. 11B). UV crosslinking indicates that mini-vRNAP primarily contacts the −11 position.
Figure 11:
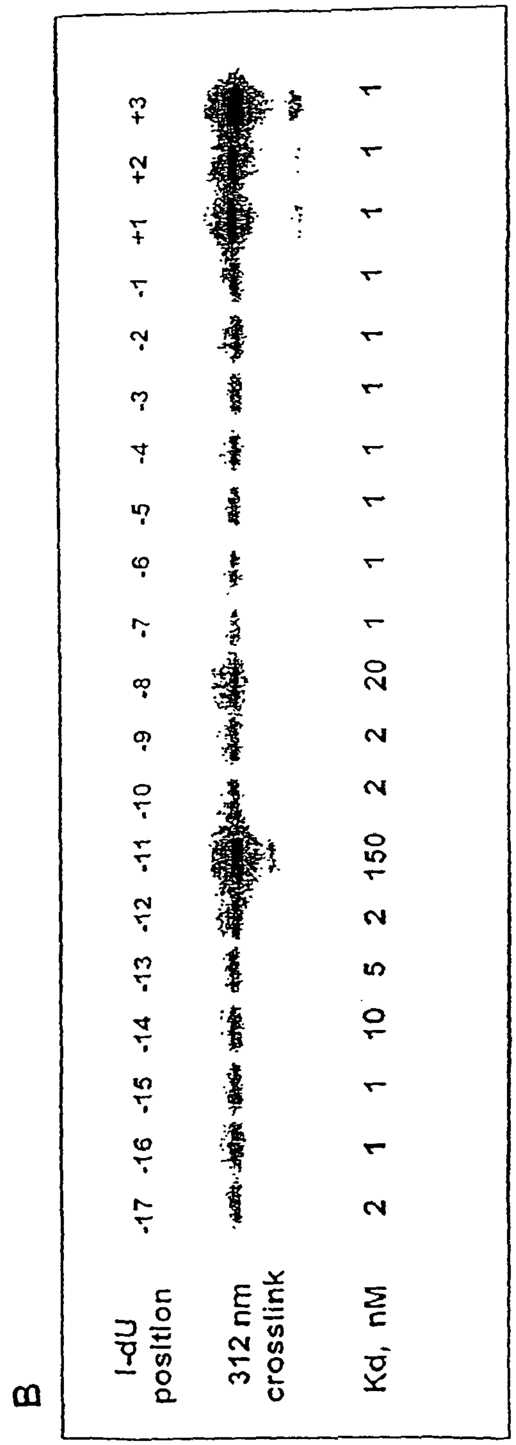

To study the sequence determinants of promoter binding, 20 base-long promoter oligonucleotides, containing the wild-type vRNAP promoter P2 sequence and substituted at every position with a single 5-Iodo-dU, were used. Whenever substitutions were made in the stem, the corresponding pairing base was changed to A. These oligonucleotides were $^{32}P$ end-labeled and used to determine the enzyme's affinity for promoter DNAs by a filter binding assay and the ability to crosslink to mini-vRNAP upon UV irradiation at 320 nm. A 20-base oligonucleotide with wild type promoter P2 sequence binds with a 1 nM Kd. Most oligonucleotides showed close to wild type affinity except for the oligonucleotides substituted at positions −11 (at the center of the loop) and −8, indicating that these positions are essential for promoter recognition (FIG. 11). Surprisingly, UV crosslinking was most effective at position −11, in spite of the low binding affinity, indicating a specific contact at this position to mini-vRNAP. Crosslinking was also observed to positions +1, +2 and +3, indicating non-specific contacts with this region of the template, since 5-Iodo-dU substituted oligonucleotides at these positions showed wild-type binding affinity.

Figure 12:
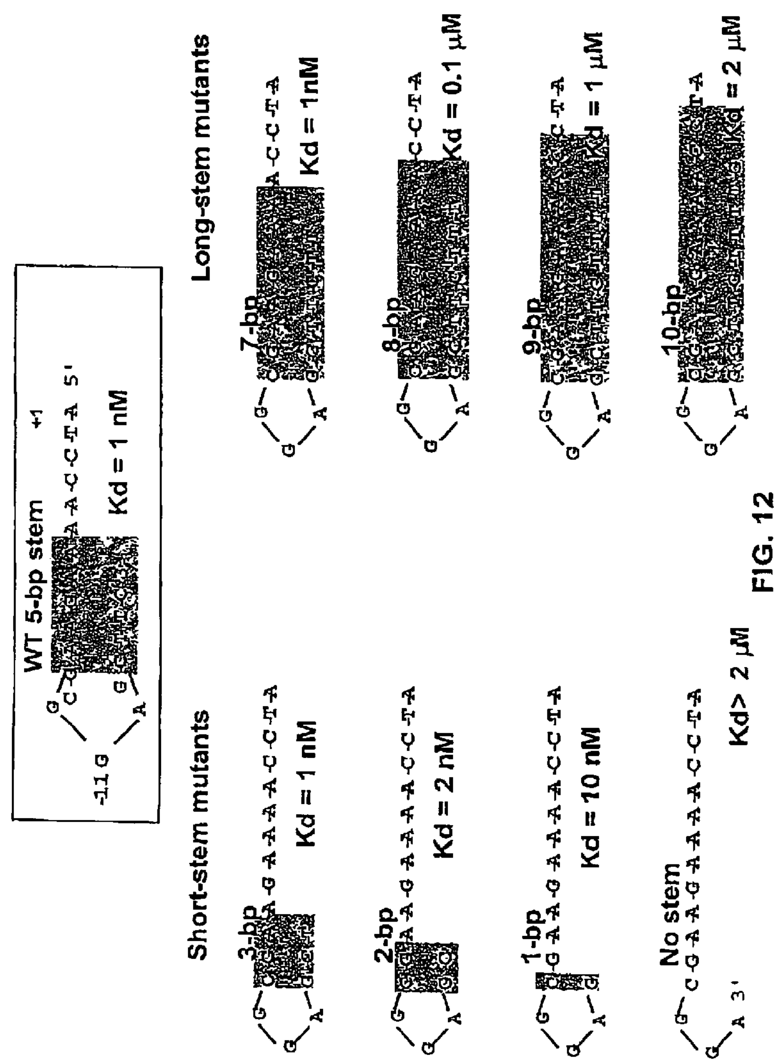
FIG. 12—Binding affinities of stem-length promoter mutants. Wild type promoter P2 with a 5 bp stem has a Kd of 1 nM (top) (SEQ ID NO:31). The stem was shortened by removal of 3' bases (left) (SEQ ID NO:32-35). The stem can be shortened by two base pairs without change in the binding affinity. The effect of lengthening the stem by addition of 3' bases is shown (right) (SEQ ID NO:36-39). The stem can be lengthened by two base pairs without change in the binding affinity.

The effect of changes in the stem length of the hairpin on the ability of mini-vRNAP to bind P2 promoter DNA was analyzed. As shown above, wild type promoter P2 with a 5 bp stem has a Kd of 1 nM (FIG. 12, top). The stem was shortened by removal of 3' bases as shown in FIG. 12 (left). The stem can be shortened by two base pairs without change in the binding affinity. If two or one loop-closing base pairs remain, the binding affinity of templates is still substantial (2-10 nM). This result, although surprising, is not unexpected since it has been shown that the oligonucleotide 3'd(CGAGGCG)5' forms an unusually stable minihairpin (Yoshizawa, et al., Biochemistry 36, 4761-4767, 1997). No binding is observed if one more nucleotide is removed and the loop cannot form. These results indicate that formation of a loop is essential for vRNAP-promoter recognition.

The effect of lengthening the stem by addition of 3' bases is shown in FIG. 12 (right). The stem can be lengthened by two base pairs without change in the binding affinity. On the other hand, base pairing at −2 reduces binding affinity by two orders of magnitude, with a further one order of magnitude reduction caused by base pairing at −1 and +1. These results indicate that single-strandedness of the template at positions −2, −1 and +1 is required for efficient template binding.

Figure 13:
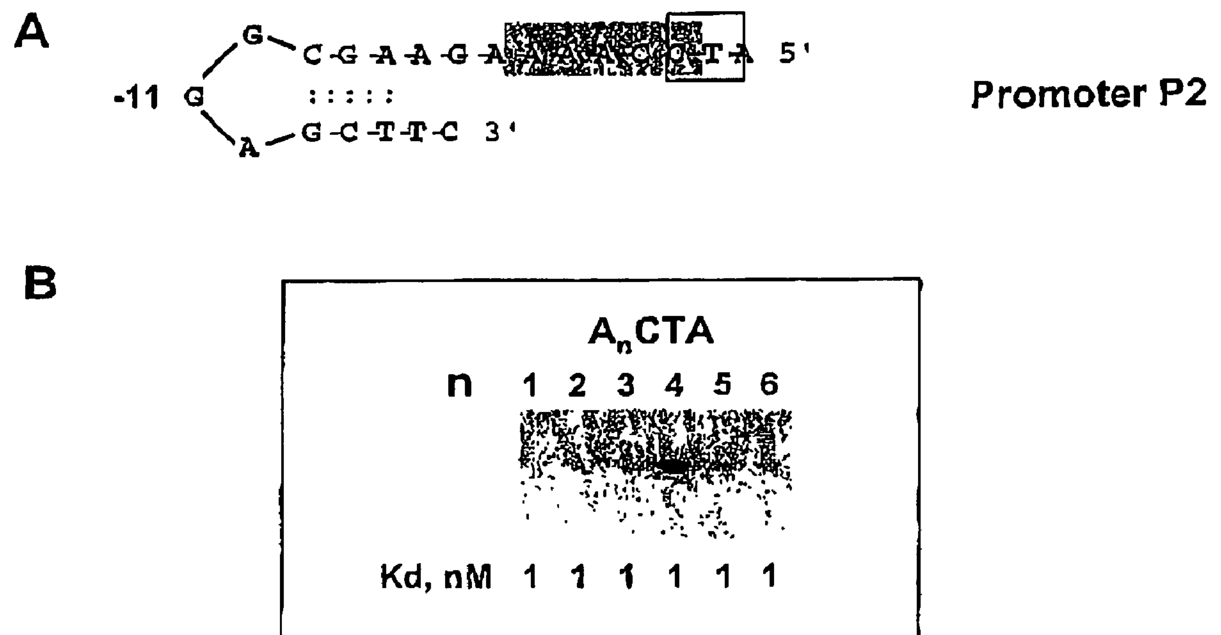
FIG. 13A and FIG. 13B—Identification of the transcription start site by catalytic autolabeling. A series of templates were constructed with a single C placed at different distances from the center of the hairpin (position −11) by addition or deletion of the tract of As present at promoter P2 (FIG. 13A) (SEQ ID NO:31). The affinity of mini-vRNAP for these promoters was measured by filter binding, and transcription initiation was measured by catalytic autolabeling of mini-vRNAP. All templates showed similar binding affinities. However, only the template with a C positioned 12 bases downstream from the center of the hairpin was able to support transcription initiation (FIG. 13B).

All three N4 early promoters present in the N4 genome contain a pair of Cs separated by 4 nucleotides from the base of the 5 bp promoter stem. In promoter P2, these 4 bases are As and the Cs are followed by a T. To identify the determinants of the site of transcription initiation, a series of templates were constructed with a single C placed at different distances from position −11 of the hairpin by addition or deletion of the tract of As present at promoter P2 (FIG. 13). The affinity of mini-vRNAP for these promoters was measured by filter binding and transcription initiation was measured by catalytic autolabeling of mini-vRNAP. All templates showed similar binding affinities. However, only the template with a C positioned 12 bases downstream from the center of the hairpin was able to support transcription initiation. This result indicates that mini-vRNAP utilizes this position as the transcription start site (+1).

Example 6

Identification of Sequence Motifs Essential for mini-vRNAP Activity

Figure 3:
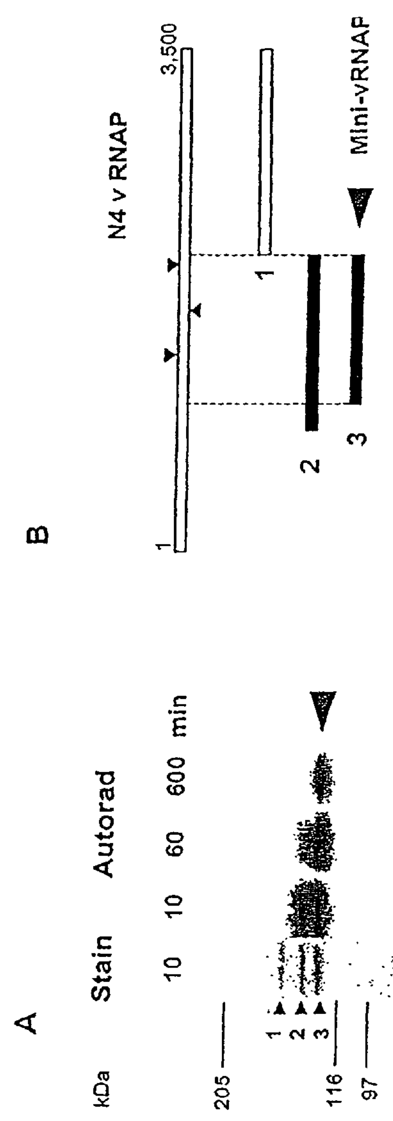
FIG. 3A and FIG. 3B—Identification of the minimal transcriptionally active domain of N4 vRNAP by proteolytic cleavage.

As shown in FIG. 2A, vRNAP contains the sequence $Rx_3Kx_6YG$, designated Motif B in the Pol I and Pol αDNA polymerases and the T7-like RNA polymerases. To determine the relevance of this motif to vRNAP activity, two mutants K670A and Y678F (SEQ ID NO:8) (position numbers in mini-vRNAP) were constructed by site-specific mutagenesis of mini-vRNAP. These two positions were chosen because, in T7-like RNA polymerases, the lysine is involved in nucleotide binding and the tyrosine in discrimination against deoxynucleoside triphosphates (Maksimova, et al., Eur. J Biochem. 195:841-847, 1991; Bonner, et al., EMBO J. 11:3767-3775, 1992; Osumi-Davis, et al., J. Mol Biol. 226: 37-45, 1992). The His-tagged Y678F mini-vRNAP gene (SEQ ID NO:7) differs from that of the mini-vRNAP domain sequence (SEQ ID NO:3) at two positions: nucleotide 2033 (A) was changed to a T, and nucleotide 2034 (T) was changed to a C.

Figure 14:
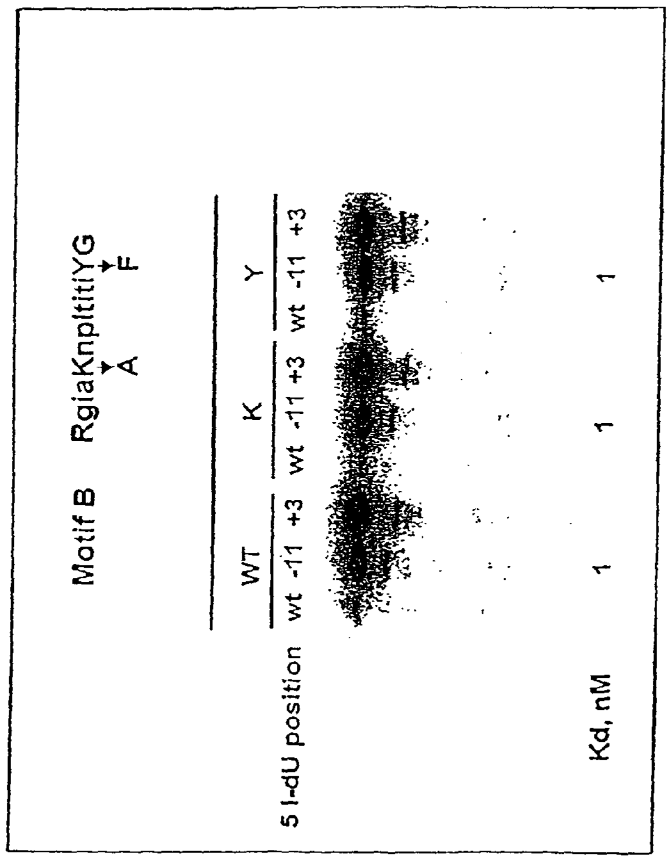
FIG. 14—UV crosslinking of mutant mini-vRNAPases to promoter Oligonucleotides (SEQ ID NO:40-41). Two mutants (K670A and Y678F) were tested for their ability to bind to wild type promoters. Both mutant RNA polymerases bound to promoter DNA with wild type affinities and crosslinked to 5-Iodo-dU substituted P2 DNA templates at positions −11 and +3 as well as the wild type enzyme, indicating that these polymerase mutations do not affect promoter binding.

These RNA polymerase mutants were cloned under pBAD control, purified and tested for their ability to bind to wild type promoters. Both mutant polymerases bound to promoter DNA with wild type affinities and crosslinked to 5-Iodo-dU substituted P2 DNA templates at positions −11 and +3 with wild-type affinities (FIG. 14), indicating that these mutations do not affect promoter binding.

Figure 15:
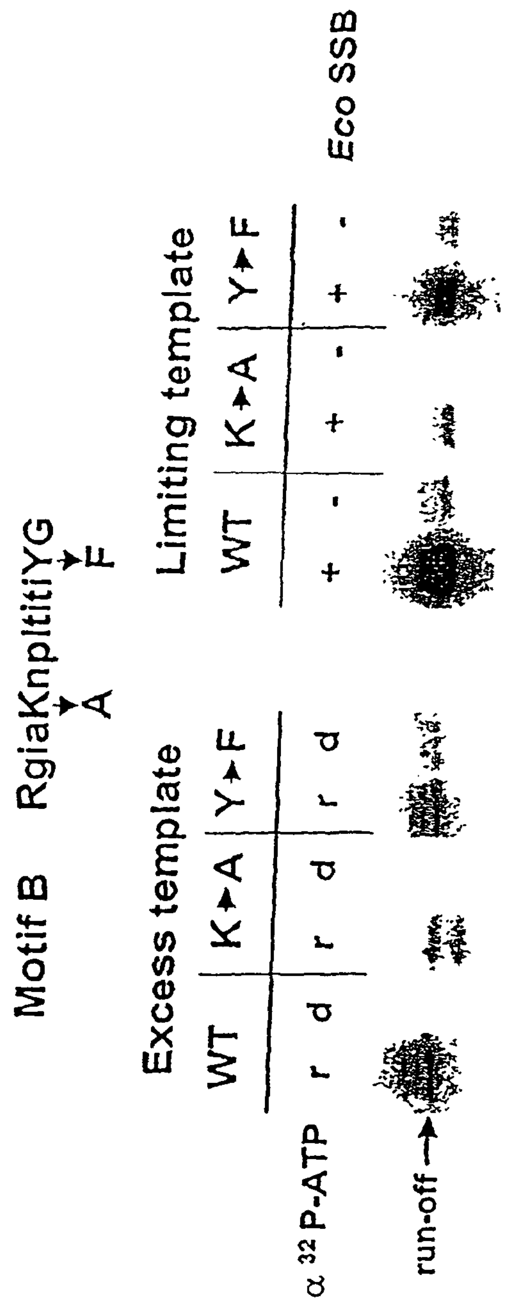
FIG. 15—Run-off transcription by mutant mini-vRNAPases (SEQ ID NO:40-41). The wild type and Y678F (SEQ ID NO:8) enzymes displayed similar activities at both template excess and template-limiting conditions, while the K670A enzyme exhibited decreased activity under both conditions. Under limiting template conditions, all three enzymes were activated by EcoSSB (right panel). However, the Y678F enzyme showed reduced discrimination between incorporation of ribo- and deoxyribonucleoside triphosphates.

The mutant enzymes were tested for their ability to support run-off transcription. The wild-type enzyme and Y678F enzyme (SEQ ID NO:8) displayed similar activities at both template excess and template-limiting conditions, while the K670A enzyme exhibited decreased activity under both conditions (FIG. 15). Under limiting template conditions, all three enzymes were activated by Eco SSB (right panel). However, the Y678F enzyme showed reduced discrimination between ribo- and deoxyribonucleoside triphosphates.

Figure 16:
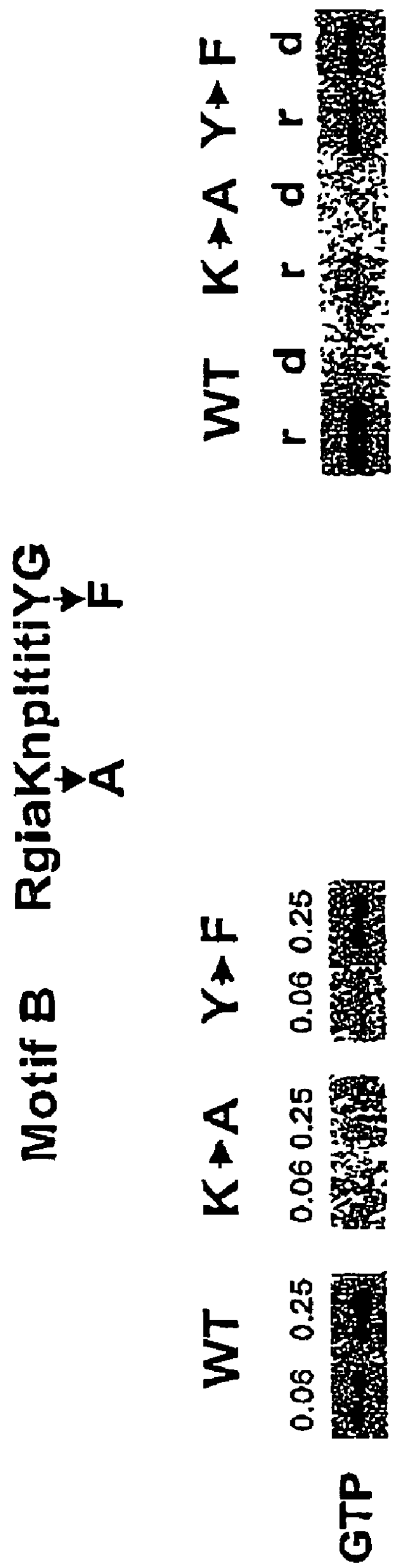
FIG. 16—Mutant mini-vRNAPases in transcription initiation (SEQ ID NO:40-41). The initiation properties of the three enzymes were compared using catalytic autolabeling. The K670A enzyme displays significantly reduced activity with the GTP derivative. The Y678F enzyme, in contrast to wild type polymerase, incorporates dATP as efficiently as rATP in a single round of phosphodiester bond formation.

The initiation properties of the three enzymes were compared using catalytic autolabeling (FIG. 16). The K670A enzyme displays significantly reduced activity with the GTP derivative. The Y678F enzyme, in contrast to wild-type polymerase, incorporates dATP as efficiently as rATP in a single round of phosphodiester bond formation.

Therefore, the behavior of the K670A and Y678F mutant enzymes indicates that Motif B is involved in catalysis, with the lysine probably required for NTP binding and the tyrosine responsible for dNTP discrimination. These results suggest that, despite its lack of extensive sequence similarity, vRNAP is a Class II T7-like RNA polymerase. Results of recent experiments revealed the location of the two carboxylates (aspartates) involved in catalysis.

Example 7

Figure 17:
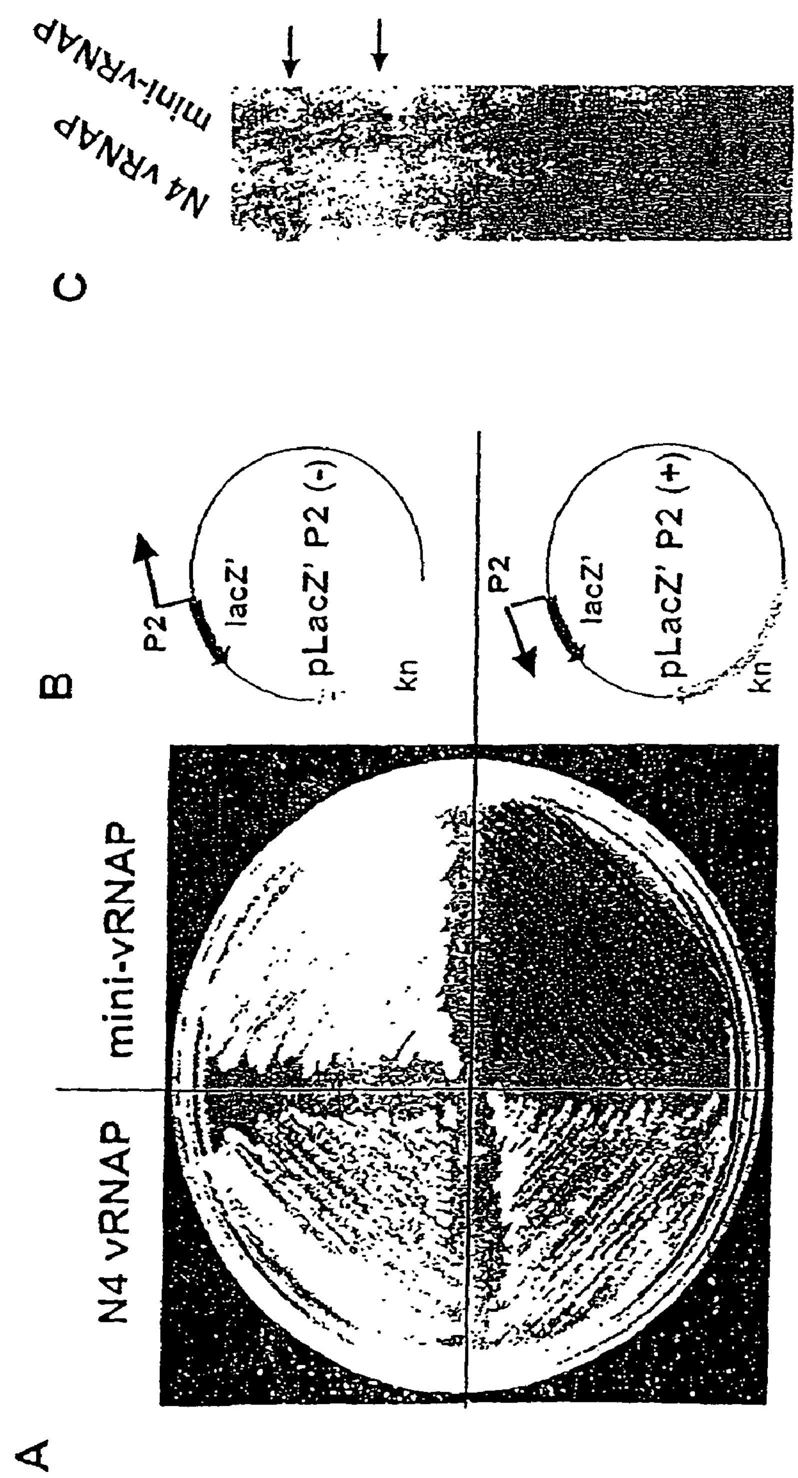
FIG. 17A, FIG. 17B, and FIG. 17C—Detection of in vivo activities of N4 vRNAP and mini-vRNAP. Transcription of β-galactosidase α-peptide by fill size and mini-vRNAP was assayed on inducing-Xgal media (FIG. 17A). Plasmid (pACYC) templates were constructed with a reporter gene (α-peptide of β-galactosidase) under the control of vRNAP promoter P2 cloned in either of two orientations (FIG. 17B). Induction of mini-vRNAP led to production and accumulation of detectable levels of the protein, whereas full-length vRNAP was degraded (FIG. 17C).

Development of an In Vivo System Using Mini-vRNAP and N4 vRNAP Promoters for in vivo Expression of RNAs and Proteins Plasmid templates were constructed with a reporter gene (α-peptide of β-galactosidase) cloned under the control of vRNAP promoter P2 present in either of two orientations (FIG. 17B). The reporter construct was generated by cloning a cassette into plasmid pACYC 177, which was obtained from New England Biolabs. The cassette contains an approximately 30 bp long fragment originating from pT7Ac (purchased from United States Biochemical), a N4 promoter, and sequence encoding the alpha fragment of lacZ (lacZ'). The N4 promoter and lacZ' were generated by oligonucleotide annealing and PCR amplification, respectively. This cassette replaces the pACY177 sequence located between the cleavage sites for restriction enzymes ApaLI and BamHI. These reporter plasmids and recombinant full-length or mini-vRNAP expressing plasmids were introduced into *E. coli* DH5═ (ΔM15), a strain that encodes the β-galactosidase θ-peptide. Expression of the reporter gene a-peptide) in this strain results in the synthesis of active β-galactosidase and consequent production of blue colonies on X-gal plates. Transcription of α-peptide by full-length and mini-vRNAP was assayed on inducing-Xgal media and shown in FIG. 17A. Induction of full-length polymerase results in small colonies with no β-galactosidase activity. This is not surprising since full-length vRNAP is degraded in these cells (FIG. 17C). In contrast, induction of mini-vRNAP led to detectable levels of the protein (FIG. 17C) and to β-galactosidase activity only from the plasmid containing promoter P2 in the proper orientation (FIG. 17A). These results indicate that this system will be suitable for in vivo expression of RNAs and proteins under mini-N4 vRNAP promoter control.

Example 8

Rolling Circle Transcription of Model ssDNA Transcription Substrates

Each oligonucleotides (50 picomoles), comprising a sense P2 promoter sequence (or, in control reactions, an anti-sense sequence to the P2 promoter or no promoter) at its 5'-end, which was phosphorylated, and up to 52 additional nucleotides corresponding to a model target sequence (e.g., for the human beta actin gene) in its 3'-portion, was ligated in a reaction mixture containing 0.2 mM ATP, 1 mM DTT, and 50 micrograms per ml of BSA for 2 hours at 60° C. using 200 units of ThermoPhage™ RNA Ligase II (Prokaria, Rejkjavik, Iceland, #Rlig122) in 1× ThermoPhage RNA Ligase II Buffer comprising 50 mM MOPS, pH 7.5, 5 mM MgCl2, and 10 mM KCl. Then, linear oligos were removed by digestion with Exonuclease I (EPICENTRE Technologies, Madison, Wis.), the Exo I was heat-inactivated, and the circular ssDNA oligos were ethanol precipitated using standard techniques.

One picomole of circular ssDNA oligonucleotide, prepared as just described, was then incubated for four hours at 37° C. in a 60-microliter reaction mixture comprising one microgram of mini-vRNAP (EPICENTRE), 1 mM each NTP, 1 mM DTT, and 5 micromolar *E. coli* SSB Protein (EPICENTRE), in 1× Transcription Buffer comprising 40 mM Tris HCl, pH 7.5, 10 mM NaCl, 6 mM MgCl2, and 1 mM spermidine. The resulting mini-vRNAP transcription products were then analyzed by electrophoresis in a 1% agarose gel containing 0.22 M formaldehyde. Transcription products, including products having a length many-fold greater than the starting oligonucleotide, were observed on the the gel, indicating efficient rolling circle transcription. No transcription products were observed if the oligo did not contain a P2 promoter, if an anti-sense sequence to the P2 promoter was used instead of the sense P2 promoter, or if an unligated linear oligo with a sense P2 promoter was used.

Example 9

Use of a Random Hexamer Promoter Primer to Obtain a Circular ssDNA Transcription Substrate for Making Transcription Product Corresponding to a Target Nucleic Acid Sequence Comprising mRNA Messenger RNA is obtained from a sample using techniques known in the art for isolating polyadenylated RNA. A suitable amount of mRNA, such as about 1-10 micrograms of mRNA, is then used for reverse transcription using MMLV reverse transcriptase (EPICENTRE) and a large excess of a random hexamer promoter primer comprising a P2 sense promoter in its 5'-portion, which is phosphorylated at the 5'-end, and a random hexamer sequence at its 3'-end. Following reverse transcription according to the directions supplied with the MMLV reverse transcriptase, the resulting first-strand cDNA is treated with *E. coli* RNase H (EPICENTRE) to digest the RNA, the RNaseH is inactivated with heat, and the first-strand cDNA is purified and ethanol precipitated. Then, the first-strand cDNA is circularized using ThermoPhage™ RNA Ligase II (Prokaria) as described in Example 8. Preferably, circular ssDNA molecules are obtained which comprise from 20 to about 200 nucleotides of cDNA complementary to the target mRNA, which is operably joined to the P2 promoter.

In vitro transcription of the resulting circular ssDNA molecules, which comprise circular ssDNA transcription substrates of the invention, as described in Example 8, yields transcription products corresponding to the mRNA in the sample. In some transcription reactions, an inorganic pyrophosphatase and high NTP concentrations are used to increase the yield of transcription product obtained. The concentrations of N4 mini-vRNAP enzyme, NTPs and pyrophosphatase can be titrated to determine the levels of each component that results in maximum yield of transcription product.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for making a transcription product having a sequence that is identical to at least a portion of a target sequence in a target nucleic acid consisting of RNA, the method comprising the steps of:

(a) providing a sense promoter primer, the sense promoter primer exhibiting, at its 3'-end, a sequence complementary to the 3'-end of the target sequence, the sense promoter primer further exhibiting, at its 5'-end, a sense transcription promoter sequence;

(b) annealing the sense promoter primer to the target nucleic acid and primer-extending the sense promoter primer with an RNA-dependent DNA polymerase using target nucleic acid as a template to generate linear sense-promoter-containing first-strand cDNA;

(c) removing the target nucleic acid;

(d) ligating the first-strand cDNA to itself with a ligase, whereby the 5'-end is covalently joined to the 3'-end to obtain circular first-strand cDNA containing the sense transcription promoter sequence;

(e) obtaining a circular transcription substrate; and (f) admixing the transcription substrate with an RNA polymerase and NTPs and incubating under conditions wherein a transcription product having a sequence that is identical to at least a portion of a target sequence is synthesized.

2. The method of claim 1, additionally comprising the step of cleaving the circular transcription substrate at a site that is 3'-of the promoter sequence and 5'-of the target-complementary sequence to generate a linear transcription substrate.

3. The method of claim 1, wherein the target nucleic acid in the sample is mRNA.

4. The method of claim 1, wherein the sense promoter primer is selected from the group consisting of:

(i) an oligo(dT) promoter primer;

(ii) an anchored oligo(dT) promoter primer;

(iii) a specific-sequence promoter primer that is complementary to a specific sequence in the target nucleic acid sequence; and (iv) a random sequence promoter primer that exhibits a random sequence at its 3'-end.

5. The method of claim 1, wherein the sense promoter primer additionally comprises one or more transcription termination sequences between the target-complementary sequence at its 3'-end and the sense promoter sequence in its 5'-end portion.

6. The method of claim 1, wherein the sense promoter primer additionally comprises a transcription initiation sequence 5'-of the sense promoter sequence.

7. The method of claim 1, wherein, between the target-complementary sequence at its 3'-end and the sense promoter sequence in its 5'-end portion, the sense promoter primer additionally comprises one or more sequences or genetic elements selected from among one or more origins of replication, one or more sequences that encode a selectable or screenable marker, one or more sequences that can be recognized and used by a transposase for in vitro or in vivo transposition, and one or more sites that are recognized by a recombinase.

8. The method of claim 2, wherein the sense promoter primer has a dUMP nucleotide between the target-complementary sequence at its 3'-end and the sense promoter sequence in its 5'-end portion.

9. The method of claim 8, wherein the circular transcription substrate is linearized by treatment with uracil-N-glycosylase (UNG) and endonuclease IV (endo IV).

10. The method of claim 1, wherein the ligase used in step (d) for said joining is a thermostable RNA ligase derived from phage TS2126.

11. The method of claim 1, wherein the method is performed in a stepwise fashion by purifying the reaction products by removing reaction components and/or inactivating enzymes from one set of reactions prior to proceeding to the next set of reactions.

12. The method of claim 11, wherein the linear sense promoter-containing first-strand cDNA reaction product is purified prior to the step of circularizing with a ligase.

13. A method for generating linear first-strand cDNA complementary to a target sequence in a target nucleic acid wherein its 3' and 5' ends exhibit sequences that are not complementary to the target sequence, the method comprising:

(1) primer extending a primer with a DNA polymerase using target nucleic acid as a template to generate linear first-strand cDNA that is complementary to the target sequence, wherein the primer comprises
  (i) a 5'-end portion that is not complementary to the target nucleic acid,
  (ii) a 3'-end portion that is complementary to the target nucleic acid, and
  (iii) a cleavage site within its 5'-end portion;

(2) purifying the linear first-strand cDNA reaction products by removing reaction components and/or inactivating enzymes from the DNA polymerase primer extension reaction of step (1);

(3) circularizing the linear first-strand cDNA generated in step (1) with a ligase under ligation conditions to generate circular first-strand cDNA;

(4) purifying the circular first-strand cDNA by removing reaction components and/or inactivating enzymes from the ligase reaction of step (3);

(5) linearizing the circular first-strand cDNA generated in step (3) at the cleavage site to generate linear first-strand cDNA that exhibits the sequence 3'-of the cleavage site of the primer in its 5'-end portion and the sequence 5'-of the cleavage site of the primer in its 3'-end portion; and (6) using the linear first-strand cDNA generated in step (5) for sequencing of the target nucleic acid.

14. The method of claim 13, wherein the ligase for circularizing is the RNA ligase derived from phage TS2126.

15. The method of claim 13, wherein the cleavage site in the primer comprises a dUMP nucleotide.

16. The method of claim 15, wherein said step of linearizing the circular first-strand cDNA comprises treating with uracil-N-glycosylase (UNG) and endonuclease IV (endo IV).

17. The method of claim 13, wherein the target nucleic acid is RNA and the primer is selected from the group consisting of:

(i) an oligo(dT) primer;

(ii) an anchored oligo(dT) primer;

(iii) a specific-sequence primer that is complementary to a specific sequence in the target nucleic acid sequence; and (iv) a random sequence primer that exhibits a random sequence at its 3'-end.

18. A method comprising:

(a) providing a sample that contains RNA target nucleic acid;

(b) providing a primer, the primer comprising a 5'-end portion that exhibits a sequence that is not complementary to the target nucleic acid and a 3'-end portion that is complementary to the target nucleic acid, wherein the primer contains a cleavage site between the 5'-end portion and the 3'-end portion;

(c) annealing the primer to the target nucleic acid so as to form a target nucleic acid-primer complex;

(d) contacting the target nucleic acid-primer complex with a DNA polymerase under polymerization reaction conditions so as to synthesize first-strand cDNA that is complementary to a sequence in the target nucleic acid;

(e) obtaining the first-strand cDNA by removing the target nucleic acid;

(f) ligating the first-strand cDNA under ligation conditions in the absence of a ligation splint using the RNA ligase derived from phage TS2126, which catalyzes non-homologous ligation of ssDNA, to obtain circular first-strand cDNA that exhibits the sequences of the 5'-end portion and of the 3'-end portion of the primer; and (g) linearizing the circular first-strand cDNA at the cleavage site to obtain linear first-strand cDNA that exhibits the sequence of the 3'-end portion of the primer at its 5' end and the 5'-end portion of the primer at its 3' end.

19. The method of claim 18, wherein the cleavage site is a dUMP residue that can be cleaved using uracil-N-glycosylase and endonuclease IV.

20. The method of claim 18, further comprising sequencing the linear first-strand cDNA that exhibits the sequence of the 3'-end portion of the primer at its 5' end and the 5'-end portion of the primer at its 3' end.

21. The method of claim 18, further comprising detecting the linear first-strand cDNA that exhibits the sequence of the 3'-end portion of the primer at its 5' end and the 5'-end portion of the primer at its 3' end, which detecting is indicative of the presence of the target nucleic acid.

22. The method of claim 18, further comprising quantifying the amount of target nucleic acid in the sample by comparing the amount of the linear first-strand cDNA that exhibits the sequence of the 3'-end portion of the primer at its 5-end and the 5'-end portion of the primer at its 3'-end which is amplified from the sample to the amount of product which is amplified from of a reference sample that has a known quantity of the target nucleic acid.

23. The method of claim 1, wherein said sense promoter primer provided in step (a) exhibits a sense transcription promoter sequence of a double-stranded transcription promoter and said obtaining a circular transcription substrate in step (e) further comprises annealing an oligonucleotide to the circular first-strand cDNA containing the sense transcription promoter sequence under conditions wherein a circular transcription substrate having a double-stranded promoter is obtained.

24. The method of claim 1, wherein said sense promoter primer provided in step (a) exhibits a sense transcription promoter sequence of a single-stranded transcription promoter and the circular first-strand cDNA containing the sense transcription promoter sequence obtained in step (d) is a circular transcription substrate.

* * * * *